(12) United States Patent
Shen et al.

(10) Patent No.: US 6,770,658 B2
(45) Date of Patent: Aug. 3, 2004

(54) SUBSTITUTED γ-PHENYL-Δ-LACTAMS AND USES RELATED THERETO

(75) Inventors: Yaping Shen, Port Coquitlam (CA); David L. Burgoyne, Delta (CA); Ronald W. Lauener, New Westminster (CA); Yuanlin Zhou, Richmond (CA); Patrick J. Rebstein, Vancouver (CA); Samuel D. M. Abraham, Vancouver (CA)

(73) Assignee: Inflazyme Pharmaceuticals Ltd., Richmond (CA)

( * ) Notice: Subject to any disclaimer, the term of this patent is extended or adjusted under 35 U.S.C. 154(b) by 21 days.

(21) Appl. No.: 10/263,336

(22) Filed: Oct. 1, 2002

(65) Prior Publication Data

US 2003/0186943 A1 Oct. 2, 2003

Related U.S. Application Data

(63) Continuation-in-part of application No. 09/786,949, filed as application No. PCT/CA99/00819 on Sep. 9, 1999, now Pat. No. 6,458,829, application No. 10/263,336, which is a continuation-in-part of application No. 10/081,993, filed on Feb. 22, 2002, which is a continuation of application No. 09/527,699, filed on Mar. 16, 2000, now abandoned, which is a continuation of application No. 09/393,445, filed on Sep. 8, 1999, now abandoned.

(60) Provisional application No. 60/149,517, filed on Aug. 17, 1999, provisional application No. 60/121,507, filed on Feb. 23, 1999, and provisional application No. 60/099,637, filed on Sep. 9, 1998.

(51) Int. Cl.[7] ............................................. A61K 31/445
(52) U.S. Cl. ........................................ 514/315; 546/243
(58) Field of Search ........................... 546/243; 514/315

(56) References Cited

U.S. PATENT DOCUMENTS

| 3,565,904 A | 2/1971 | Juby et al. .................. 260/294 |
|---|---|---|
| 3,607,885 A | 9/1971 | Dombro .................. 260/343.5 |
| 3,718,743 A | 2/1973 | Shen et al. .................. 424/267 |
| 3,814,771 A | 6/1974 | Shen et al. ............. 260/293.73 |
| 4,391,978 A | 7/1983 | Imhof et al. ................. 546/138 |
| 4,616,089 A | 10/1986 | Jacobs et al. ................ 549/323 |
| 4,838,925 A | 6/1989 | Tseng ............................ 71/90 |
| 5,292,884 A | 3/1994 | Honn et al. .................. 546/216 |
| 5,338,861 A | 8/1994 | Botta et al. .................. 548/552 |
| 5,416,224 A | 5/1995 | Rebrovic ..................... 549/273 |
| 5,441,978 A | 8/1995 | Suga .......................... 514/460 |
| 5,462,947 A | 10/1995 | Svensson et al. ............ 514/317 |
| 5,478,356 A | 12/1995 | Kaaret ............................ 8/111 |
| 5,629,429 A | 5/1997 | Kronenthal et al. ...... 548/311.4 |
| 6,458,829 B1 | 10/2002 | Shen et al. .................. 514/460 |

FOREIGN PATENT DOCUMENTS

| DE | 4207301 C1 | 6/1993 |
|---|---|---|
| DE | 19603477 A1 | 8/1997 |
| EP | 062 018 A1 | 10/1982 |
| EP | 157 364 B1 | 10/1985 |
| EP | 564 193 A1 | 10/1993 |
| GB | 2 228 481 A | 8/1990 |
| GB | 2 228 482 A | 8/1990 |
| JP | 06-157459 | 6/1994 |
| WO | WO 92/09590 | 6/1992 |
| WO | WO 92/10487 | 6/1992 |
| WO | WO 92/18475 | 10/1992 |
| WO | WO 92/20738 | 11/1992 |
| WO | WO 93/08803 | 5/1993 |
| WO | WO 97/17420 | 5/1997 |
| WO | WO 97/20822 | 6/1997 |

OTHER PUBLICATIONS

Fadel and Arzel, "Asymmetric Construction of Bensylic Quaternary Carbons from Chiral Malonates: Formal Synthesis of Natural (−)Aphanorphine," *Tetrahedron: Asymmetry* 6(4):893–900, 1995.

*Primary Examiner*—Amelia Owens
(74) *Attorney, Agent, or Firm*—Seed IP Law Group PLLC

(57) ABSTRACT

γ-Phenyl-substituted Δ-lactams are disclosed. They may be formulated into pharmaceutical compositions, and/or used in the treatment or prevention of inflammation or other conditions or disease states.

50 Claims, No Drawings

SUBSTITUTED γ-PHENYL-Δ-LACTAMS AND USES RELATED THERETO

TECHNICAL FIELD

This invention is directed towards Δ-lactam compounds, and in particular to γ-Phenyl-substituted Δ-lactams, and therapeutic uses related thereto.

BACKGROUND OF THE INVENTION

The Inflammatory Response (Inflammation)

Inflammation is an essential localized host response to invading microorganisms or tissue injury which involves cells of the immune system. The classic signs of inflammation include redness (erythema), swelling (edema), pain and increased heat production (pyrema) at the site of injury. The inflammatory response allows the body to specifically recognize and eliminate an invading organism and/or repair tissue injury. Many of the acute changes at the site of inflammation are either directly or indirectly attributable to the massive influx of leukocytes (e.g., neutrophils, eosinophils, lymphocytes, monocytes) which is intrinsic to this response. Leukocytic infiltration and accumulation in tissue results in their activation and subsequent release of inflammatory mediators such as $LTB_4$, prostaglandins, TNF-α, IL-1β, IL-8, IL-5, IL-6, histamine, proteases and reactive oxygen species for example.

Normal inflammation is a highly regulated process that is tightly controlled at several levels for each of the cell types involved in the response. For example, expression of the pro-inflammatory cytokine TNF-α is controlled at the level of gene expression, translation, post-translational modification and release of the mature form from the cell membrane. Many of the proteins up-regulated during inflammation are controlled by the transcription factor, NF-κB. Pro-inflammatory responses are normally countered by endogenous anti-inflammatory mechanisms such as generation of IL-10 or IL-4. A characteristic of a normal inflammatory response is that it is temporary in nature and is followed by a resolution phase which brings the state of the tissue back to its prior condition. The resolution phase is thought to involve up-regulation of anti-inflammatory mechanisms, such as IL-10, as well as down-regulation of the pro-inflammatory processes.

Inflammatory Disease

Inflammatory disease occurs when an inflammatory response is initiated that is inappropriate and/or does not resolve in the normal manner but rather persists and results in a chronic inflammatory state. Inflammatory disease may be systemic (e.g. lupus) or localized to particular tissues or organs and exerts an enormous personal and economic burden on society. Examples of some of the most common and problematic inflammatory diseases are rheumatoid arthritis, inflammatory bowel disease, psoriasis, asthma, emphysema, colitis and ischemia-reperfusion injury.

A common underlying theme in inflammatory disease is a perturbation of the cellular immune response that results in recognition of host proteins (antigens) as foreign. Thus the inflammatory response becomes misdirected at host tissues with effector cells targeting specific organs or tissues often resulting in irreversible damage. The self-recognition aspect of auto-immune disease is often reflected by the clonal expansion of T-cell subsets characterized by a particular T-cell receptor (TCR) subtype in the disease state. Often inflammatory disease is also characterized by an imbalance in the levels of T-helper (Th) subsets (i.e., Th1 cells vs. Th2 cells).

Therapeutic strategies aimed at curing inflammatory diseases usually fall into one of two categories: (a) down-modulation of processes that are up-regulated in the disease state or (b) up-regulation of anti-inflammatory pathways in the affected cells or tissues. Most regimes currently employed in the clinic fall into the first category. Some examples of which are corticosteroids and non-steroidal anti-inflammatory drugs (NSAIDs).

Many of the tissue, cellular and biochemical processes which are perturbed in inflammatory disease have been elucidated and this has allowed the development of experimental models or assays to mimic the disease state. These in-vitro assays enable selection and screening of compounds with a high probability of therapeutic efficacy in the relevant inflammatory disease. Thus, currently employed assays used to model the importance of the activated leukocytes in the development of acute inflammation and maintenance of the chronic inflammatory state are assays monitoring leukocyte chemotaxis and cellular degranulation and cytokine synthesis and reactive oxygen species (ROS) production assays in vitro. Since a result of acute or chronic neutrophil activation is release of ROS with resultant tissue damage, an assay for scavengers of ROS allows detection of compounds with potential therapeutic efficacy. Cellular assays to detect inhibitors of TNF-α release from stimulated macrophage or monocytic cells are an important component of an in vitro model for inflammation as this cytokine is upregulated and has been shown to contribute to the pathology in many inflammatory diseases. Since elevated cAMP in affected cells has been shown to modulate or dampen the inflammatory response, monitoring cellular cyclic AMP (cAMP) levels, and the activity of pathways controlling cAMP levels allows for the detection of potential anti-inflammatory compounds. Assays may include monitoring the level of cAMP itself, phosphodiesterase activity, or changes in cAMP response element (CRE)-luciferase activity.

Rheumatoid Arthritis

Rheumatoid arthritis (RA), the most common form of inflammatory arthritis, is an auto-immune disorder of unknown etiology which affects 1% of the adult population and is characterized by symmetric, chronic, erosive synovitis (inflammation of the joint synovial lining) and frequent multisystem involvement. Interestingly, it is 3–6 times more prevalent in women than men. Most patients exhibit a chronic fluctuating course of disease that, if left untreated, results in progressive joint destruction, deformity, disability, and premature death. Symptoms indicative of RA include pain and swelling of the joints (usually symmetrical), morning stiffness of joints and muscles, general weakness/fatigue and fever and weight loss. RA results in more than 9 million physician visits and more than 250,000 hospitalizations per year in the U.S. each year. It frequently affects patients in their most productive years, and thus, disability results in major economic loss.

Recent insights have established that the genetic background, especially the structure of the class II major histocompatibilty (MHC) genes, plays a critical role in an individual's susceptibility and the severity of the disease. The current understanding of cytokine networks, chemokines, growth factors and adhesion molecules have led to the appreciation that T cell-dependent and T cell-independent pathways contribute to the initiation and perpetuation of rheumatoid arthritis. Furthermore, much has been learned about the specific cellular and biochemical events responsible for the bone and cartilage destruction that characterizes this disorder. At the tissue level, RA is characterized by synovial hyperplasia, hypertrophy, angiogenesis and attachment and invasion of synovial fibroblasts into adjacent cartilage and bone. In active RA there are increased levels of the pro-inflammatory cytokines TNF-α, IL-1 and IL-6 relative to the anti-inflammatory cytokines in affected joints.

Current Treatments for Rheumatoid Arthritis and Other Inflammatory Diseases

At present there is no cure or prevention (prophylactic) available for rheumatoid arthritis, only regimes that address symptoms such as pain and stiffness. The five major treatment modalities for this disease include medication (pharmacological), physical (exercise), joint protection and lifestyle changes and surgery.

Therapeutics for rheumatoid arthritis can be divided into three groups: nonsteroidal anti-inflammatory drugs (NSAIDs), disease modifying anti-rheumatic drugs (DMARDs) also known as second line agents and corticosteroids.

NSAIDs reduce pain at low doses and relieve some of the inflammatory symptoms (swelling and stiffness) at higher doses through inhibition of prostaglandin synthesis. Examples of non-prescription NSAIDs include acetylsalicylic acid (ASA®, Aspirin®, Anacin®, etc.) and ibuprofen (Motrin®, Advil®, etc.). Examples of NSAIDs requiring a prescription include Naprosyn®, Relafen®, Indocid®, Voltaren®, Feldene® and Clinoril®. Although these medications effectively address the acute inflammatory component of rheumatoid arthritis, they only treat the symptoms of and do not change the progression of the underlying disease. The deleterious side effects of NSAIDs can be serious with prolonged administration and are mainly gastrointestinal (heartburn, bleeding or ulcers).

DMARDs are often prescribed if inflammation persists for more than 6 weeks or when the arthritis affects many joints simultaneously. They are usually administered in addition to a NSAID or steroid. Many DMARDs work by suppressing immune cells involved in the inflammatory response thus slowing progression of the disease. However, they are unable to reverse permanent joint damage. The most common drugs of this class are gold salts, methotrexate, azathioprine, sulphasalazine, hydroxychloroquine, penicillamine and chloroquine. DMARDs often take several weeks for beneficial effects to be seen and in many cases the exact mode of efficacy in rheumatoid arthritis is unknown. Side effects are numerous including mouth sores, rashes, diarrhea and nausea. More serious side effects which necessitate careful monitoring through regular blood and urine tests include liver and kidney damage, excessive lowering of the white blood cell count (immune suppression) and platelet count (blood clotting).

Corticosteroids are frequently prescribed in RA patients with extreme inflammation accompanied by severe pain, swelling and stiffness in the joints. They are also used to treat systemic rheumatoid arthritis which can affect the lining of the lungs and blood vessels. The route of administration is usually oral (i.e., prednisone) but the drug can also be injected directly into the affected joint, vein, muscle or alternative site of inflammation. Side effects from long-term use of steroids in rheumatoid arthritis are serious and include cataracts, high blood pressure, muscle wasting, bruising, thinning of skin and bones, weight gain, diabetes and susceptibility to infection.

Even though only 5% of patients diagnosed with rheumatoid arthritis will go on to develop more severe disease (involving debilitating and irreversible joint damage) those that do certainly do not have an ideal set of therapeutics available to satisfactorily manage and/or cure the disease. The currently available NSAIDs (even selective COX-2 inhibitors) can successfully ameliorate the acute symptoms of rheumatoid arthritis such as swelling, pain and joint stiffness. However they do not affect either progression of joint destruction or effect any reversal of articular or bone erosion. Second line drugs such as DMARD's or corticosteroids may temporarily slow progression of the disease and reduce symptoms, but usually suffer from an unacceptable side-effect profile or variable patient response and cannot reverse existing joint damage. There is a significant need for therapeutic agents that effectively arrest or reverse disease progression in rheumatoid arthritis.

SUMMARY OF THE INVENTION

In one aspect, the present invention provides a composition comprising a compound according to formula (1) and salts, solvates, isolated stereoisomers, and mixtures thereof, and a pharmaceutically acceptable carrier, diluent, or excipient,

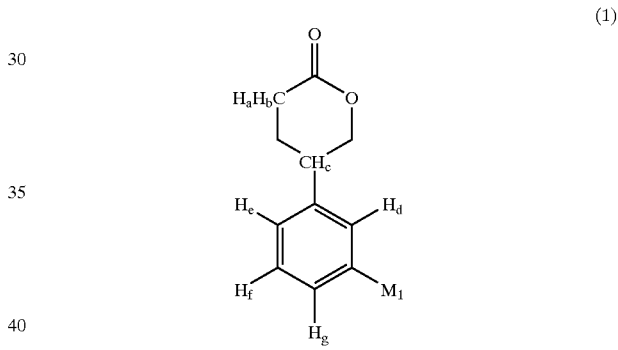

(1)

wherein each of hydrogens $H_a$, $H_b$, $H_c$, $H_d$, $H_e$, $H_f$ and $H_g$ may independently be replaced with a group selected from —W and —$R^7(W)_n$, and $M_1$ represents —W or —$R^7(W)_n$, wherein W is selected from —$NH_2$, —$CONH_2$, —COOH, —CN, —CHO, —OCHO, —X, —OH, —$NO_2$, —SH, —COX, —$NHR^8$, —$NR^8R^8$, —$CONHR^8$, —$CONR^8R^8$, —$COOR^8$, —$COR^8$, —$OCOR^8$, —$OR^8$, —$BH_2$, —$BHR^8$, —$BR^8R^8$, —$BO_2H_2$, —$BO_2R^8R^8$, —$PH_2$, —$PHR^8$, —$PR^8R^8$, —$POR^8$, —$PO_2R^8$, —$PO_3R^8$, —$SR^8$; —$SOR^8$, —$SO_2R^8$, —$SONH_2$, —$SONHR^8$, —$SONR^8R^8$, —$SO_2NH_2$, —$SO_2NHR^8$ and —$SO_2NR^8R^8$;

$R^7$ is a $C_1$–$C_{30}$ hydrocarbyl, halocarbyl or hydrohalocarbyl group wherein n of the hydrogen or halogen atoms of $R^7$ are substituted by an equal number of W groups independently selected at each location;

$R^8$ is a $C_1$–$C_{30}$ hydrocarbyl, halocarbyl or hydrohalocarbyl group;

n is selected from 0, 1, 2, 3, 4 and 5; and

X is selected from —Br, —Cl, —F, —I.

In other aspects of the composition comprising a compound of formula (1): $H_a$ and $H_b$ are hydrogen; $H_a$ is hydrogen and $H_b$ is —W; $H_a$ is hydrogen, $H_b$ is —W and the carbon to which $H_b$ is bound has an S configuration; $H_a$ is hydrogen, $H_b$ is —W, and the carbon to which $H_b$ is bound has an R configuration; $H_a$ is hydrogen and $H_b$ is —$R^7(W)_n$; $H_a$ is hydrogen, $H_b$ is —$R^7(W)_n$, and the carbon to which $H_b$ is bound has an S configuration; $H_a$ is hydrogen, $H_b$ is —$R^7(W)_n$, and the carbon to which $H_b$ is bound has an R configuration; $H_a$ is hydrogen, $H_b$ is —$R^7(W)_n$, $H_b$ is —$CH_2$-phenyl, and phenyl has 0, 1 or 2 W substitutions; $H_c$ is W; $H_d$ and $H_e$ are both hydrogen; $H_f$ is W; $H_f$ is selected from —OH and —$OR^8$; $H_f$ is selected from methoxy, ethoxy, propoxy, cyclopentyloxy, cyclohexyloxy, and benzyloxy; $H_f$ is selected from —$NH_2$, —$NHR^8$, and —$NR^8R^8$; $H_g$ is —$R^7(W)_n$; $M_1$ is —W; $M_1$ is selected from methoxy, ethoxy, propoxy, cyclopentyloxy, cyclohexyloxy, and benzyloxy; $M_1$ is selected from —$NH_2$, —$NHR^8$, and —$NR^8R^8$; $M_1$ is selected from —OH and —$OR^8$; and/or $M_1$ is —$R^7(W)_n$. In one embodiment, none of $H_a$, $H_b$, $H_c$, $H_d$, $H_e$, $H_f$ or $H_g$ is a heterocyclic ring.

The compound of formula (1) may have the stereochemistry of formula (1a)

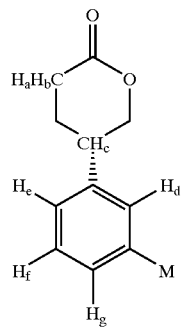

(1a).

The compound of formula (1) may have the stereochemistry of formula (1b)

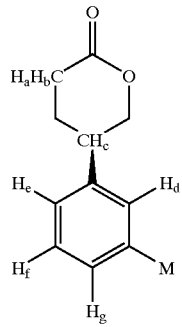

(1b).

A reference herein to compounds of formula (1) includes compounds of formulae (1a) and (1b).

In another aspect, the present invention provides a composition comprising a compound according to formula (2) and salts, solvates, isolated stereoisomers, and mixtures thereof, and a pharmaceutically acceptable carrier, diluent, or excipient,

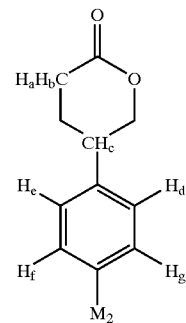

(2)

wherein each of hydrogens $H_a$, $H_b$, $H_c$, $H_d$, $H_e$, $H_f$ and $H_g$ may independently be replaced with a group selected from —W and —$R^7(W)_n$, and $M_2$ represents —W, wherein W is selected from —$NH_2$, —$CONH_2$, —COOH, —CN, —CHO, —OCHO, —X, —OH, —$NO_2$, —SH, —COX, —$NHR^8$, —$NR^8R^8$, —$CONHR^8$, —$CONR^8R^8$, —$COOR^8$, —$COR^8$, —$OCOR^8$, —$OR^8$, —$BH_2$, —$BHR^8$, —$BR^8R^8$, —$BO_2H_2$, —$BO_2R^8R^8$, —$PH_2$, —$PHR^8$, —$PR^8R^8$, —$POR^8$, —$PO_2R^8$, —$PO_3R^8$, —$SR^8$; —$SOR^8$, —$SO_2R^8$, —$SONH_2$, —$SONHR^8$, —$SONR^8R^8$, —$SO_2NH_2$, —$SO_2NHR^8$ and —$SO_2NR^8R^8$;

$R^7$ is a $C_1$–$C_{30}$ hydrocarbyl, halocarbyl or hydrohalocarbyl group wherein n of the hydrogen or halogen atoms of $R^7$ are substituted by an equal number of W groups independently selected at each location;

$R^8$ is a $C_1$–$C_{30}$ hydrocarbyl, halocarbyl or hydrohalocarbyl group;

n is selected from 0, 1, 2, 3, 4 and 5; and

X is selected from —Br, —Cl, —F, —I.

In other aspects of compositions comprising a compound of formula (2): $H_a$ and $H_b$ are hydrogen; $H_a$ is hydrogen and $H_b$ is —W; $H_a$ is hydrogen, $H_b$ is —W, and the carbon to which $H_b$ is bound has an S configuration; $H_a$ is hydrogen, $H_b$ is —W, and the carbon to which $H_b$ is bound has an R configuration; $H_a$ is hydrogen and $H_b$ is —$R^7(W)_n$; $H_a$ is hydrogen, $H_b$ is —$R^7(W)_n$, and the carbon to which $H_b$ is bound has an S configuration; $H_a$ is hydrogen, $H_b$ is —$R^7$ $(W)_n$, and the carbon to which $H_b$ is bound has an r configuration; $H_a$ is hydrogen, and $H_b$ is —$CH_2$-phenyl, where phenyl has 0, 1 or 2 W substitutions; $H_c$ is W; $H_d$ and $H_e$ are both hydrogen; $H_f$ is hydrogen and $H_g$ is W; $H_g$ is selected from —OH and —$OR^8$; $H_g$ is selected from methoxy, ethoxy, propoxy, cyclopentyloxy, cyclohexyloxy, and benzyloxy; $H_g$ is selected from —$NH_2$, —$NHR^8$, and —$NR^8R^8$; $H_f$ is hydrogen and $H_g$ is —$R^7(W)_n$; $M_2$ is selected from —$NH_2$, —$CONH_2$, —COOH, —CN, —CHO, —OCHO, —X, —OH, —$NO_2$, —SH, —COX, —$NHR^8$, —$NR^8R^8$, —$CONHR^8$, —$CONR^8R^8$, —$COOR^8$, —$COR^8$, —$OCOR^8$, and —$OR^8$; and/or $M_2$ is selected from —$NH_2$, —$NHR^8$, —$NR^8R^8$, —OH, and —$OR^8$. In a preferred embodiment, none of $H_a$, $H_b$, $H_c$, $H_d$, $H_e$, $H_f$ or $H_g$ may be replaced with a heterocyclic ring system.-

The compound of formula (2) may have the stereochemistry of formula (2a)

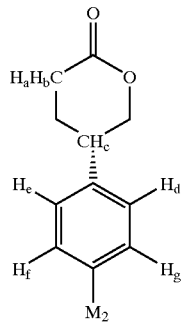

(2a).

The compound of formula (2) may have the stereochemistry of formula (2b)

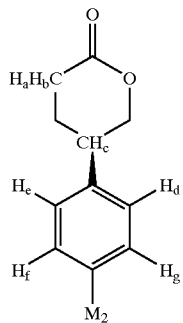

(2b).

A reference herein to compounds of formula (2) includes reference to compounds of formulae (2a) and (2b).

In another aspect, the present invention provides a compound according to formula (3) and salts, solvates, isolated stereoisomers, and mixtures thereof,

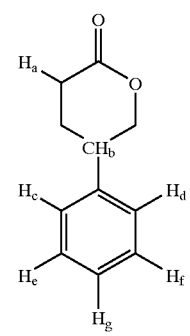

(3)

wherein each of hydrogens $H_a$, $H_c$, $H_d$, $H_e$, $H_f$ and $H_g$ may independently be replaced with a group selected from —W and —$R^7(W)_n$, and $H_b$ may be replaced with —W, wherein W is selected from —$NH_2$, —$CONH_2$, —COOH, —CN, —CHO, —OCHO, —X, —OH, —$NO_2$, —SH, —COX, —$NHR^8$, —$NR^8R^8$, —$CONHR^8$, —$CONR^8R^8$, —$COOR^8$, —$COR^8$, —$OCOR^8$, —$OR^8$, —$BH_2$, —$BHR^8$, —$BR^8R^8$, —$BO_2H_2$, —$BO_2R^8R^8$, —$PH_2$, —$PHR^8$, —$PR^8R^8$, —$POR^8$, —$PO_2R^8$, —$PO_3R^8$, —$SR^8$; —$SOR^8$, —$SO_2R^8$, —$SONH_2$, —$SONHR^8$, —$SONR^8R^8$, —$SO_2NH_2$, —$SO_2NHR^8$ and —$SO_2NR^8R^8$;

$R^7$ is a $C_1$–$C_{30}$ hydrocarbyl, halocarbyl or hydrohalocarbyl group wherein n of the hydrogen or halogen atoms of $R^7$ are substituted by an equal number of W groups independently selected at each location;

$R^8$ is a $C_1$–$C_{30}$ hydrocarbyl, halocarbyl or hydrohalocarbyl group;

n is selected from 0, 1, 2, 3, 4 and 5; and

X is selected from —Br, —Cl, —F, —I.

In a preferred embodiment, at least two of $H_e$, $H_f$, and $H_g$ are not hydrogen. In another preferred embodiment, $H_g$ is not $R^7(W)_n$. In another preferred embodiment, $H_g$ is neither hydrogen nor $R^7(W)_n$. In another preferred embodiment, none of $H_a$, $H_b$, $H_c$, $H_d$, $H_e$, $H_f$ or $H_g$ is a heterocyclic ring.

In other aspects, in the compound of formula (3): $H_a$ is hydrogen; $H_a$ is not hydrogen, and the carbon to which $H_a$ is bound has an S configuration; $H_a$ is not hydrogen and the carbon to which $H_a$ is bound has an R configuration; $H_a$ is —W; $H_a$ is —$R^7(W)_n$; $H_a$ is —$CH_2$-phenyl, and phenyl has 0, 1 or 2 W substitutions; $H_b$ is W; $H_b$ is —CN; $H_c$ and $H_d$ are both hydrogen; $H_e$ is hydrogen; $H_e$ is hydrogen and $H_f$ is W; $H_e$ is hydrogen and $H_f$ is selected from —OH and —$OR^8$; $H_e$ is hydrogen and $H_f$ is selected from methoxy, ethoxy, propoxy, cyclopentyloxy, cyclohexyloxy, and benzyloxy; $H_e$ is hydrogen and $H_f$ is selected from —$NH_2$, —$NHR^8$, and —$NR^8R^8$; $H_g$ is hydrogen; $H_g$ is —W; $H_g$ is selected from —OH and —$OR^8$; $H_g$ is selected from methoxy, ethoxy, propoxy, cyclopentyloxy, cyclohexyloxy, and benzyloxy; wherein $H_g$ is selected from —$NH_2$, —$NHR^8$, and —$NR^8R^8$; $H_g$ is —$R^7(W)_n$; and/or $H_g$ is $C_1$–$C_{30}$alkyl and n=0.

The compound of formula (3) may have the stereochemistry of formula (3a)

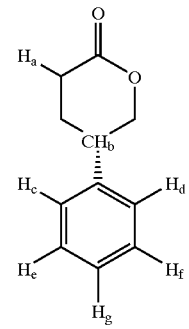

(3a).

The compound of formula (3) may have the stereochemistry of formula (3b)

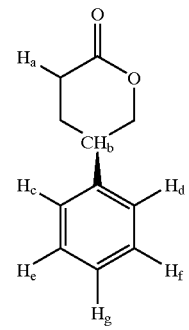

(3b).

A reference herein to compounds of formula (3) includes reference to compounds of formulae (3a) and (3b).-

In another aspect, the present invention provides compounds of formula (4)

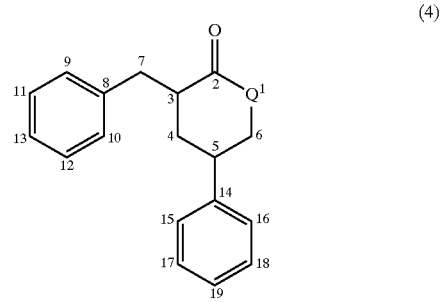

(4)

wherein, Q represents a multivalent atom other than carbon; and each of the carbons at positions 3, 4, 5, 6, 7, 9, 10, 11, 12, 13, 15, 16, 17, 18, and 19 in formula (4), as well as Q to the extent that it may be substituted, is independently substituted at each occurrence with H, —W or —$R^7$(W)$_n$, wherein W is selected from —$NH_2$, —$CONH_2$, —COOH, —CN, —CHO, —OCHO, —X, —OH, —$NO_2$, —SH, —COX, —$NHR^8$, —$NR^8R^8$, —$CONHR^8$, —$CONR^8R^8$, —$COOR^8$, —$COR^8$, —$OCOR^8$, —$OR^8$, —$BH_2$, —$BHR^8$, —$BR^8R^8$, —$BO_2H_2$, —$BO_2R^8R^8$, —$PH_2$, —$PHR^8$, —$PR^8R^8$, —$POR^8$, —$PO_2R^8$, —$PO_3R^8$, —$SR^8$; —$SOR^8$, —$SO_2R^8$, —$SONH_2$, —$SONHR^8$, —$SONR^8R^8$, —$SO_2NH_2$, —$SO_2NHR^8$ and —$SO_2NR^8R^8$;

$R^7$ is a $C_1$–$C_{30}$ hydrocarbyl, halocarbyl or hydrohalocarbyl group wherein n of the hydrogen or halogen atoms of $R^7$ are substituted by an equal number of W groups independently selected at each location;

$R^8$ is a $C_1$–$C_{30}$ hydrocarbyl, halocarbyl or hydrohalocarbyl group;

n is selected from 0, 1, 2, 3, 4 and 5; and

X is selected from —Br, —Cl, —F, —I.

In one aspect, the compound of formula (4) has the S configuration at carbon 3. In another aspect, the compound of formula (4) has the R configuration at carbon 3. In another aspect, the compound of formula (4) has the S configuration at carbon 5. In another aspect, the compound of formula (4) has the R configuration at carbon 5. In another aspect, none of the carbons at positions 3, 4, 5, 6, 7, 9, 10, 11, 12, 13, 15, 16, 17, 18, or 19 in formula (4) is substituted with a heterocyclic moiety.

In other aspects, in the compound of formula (4), as well as in compositions comprising the compound of formula (4) and a pharmaceutically acceptable carrier, diluent or excipient: Q is O; Q is S; Q is NH; and/or Q is N($R^7$(W)$_n$). In other aspects, the carbon(s) at position 4, or 6, and preferably both of positions 4 and 6, are substituted exclusively with hydrogen; the carbon at position 19 is substituted with —W; the carbon at position 19 is substituted with —$NH_2$, —$NHR^8$, or —$NR^8R^8$; the carbon at position 19 is substituted with —CN, —X, —OH, —$NO_2$, —SH, or —$OR^8$; one carbon at positions 17 and 18 is substituted with hydrogen; at least one carbon at positions 17 and 18 is substituted with —W; at least one carbon at positions 17 and 18 is substituted with —$NH_2$, —$CONH_2$, —COOH, —CN, —CHO, —OCHO, —X, —OH, —$NO_2$, —SH, —COX, —$NHR^8$, —$NR^8R^8$, —$CONHR^8$, —$CONR^8R^8$, —$COOR^8$, —$COR^8$, —$OCOR^8$, or —$OR^8$; at least one carbon at positions 17 and 18 is substituted with —$NH_2$, —$NHR^8$, or —$NR^8R^8$; and/or at least one carbon at positions 17 and 18 is substituted with —CN, —X, —OH, —$NO_2$, —SH, or —$OR^8$. In another aspect, only one of the carbons at positions 17, 18 and 19 is substituted with hydrogen. In another aspect, exactly two of the carbons at positions 17, 18 and 19 are substituted with hydrogen. In another aspect, none of the carbons at positions 17, 18 and 19 are substituted with hydrogen. In another aspect, no more than one of the carbons at positions 17, 18 and 19 are substituted with hydrogen.

In other aspects, in the compound of formula (4), as well as in compositions comprising the compound of formula (4) and a pharmaceutically acceptable carrier, diluent or excipient: the carbon at position 7 is substituted exclusively with hydrogen; the carbon at position 3 is substituted with hydrogen; the carbon at position 3 is substituted with —W; the carbon at position 3 is substituted with halogen; the carbon at position 3 is substituted with —$R^7$(W)$_n$; the carbon at position 3 is substituted with $C_1$–$C_6$hydrocarbyl; the carbons at positions 9 and 10 are substituted with hydrogen; the carbons at positions 11, 12, and 13 are independently substituted with hydrogen and —W; only one of the carbons at positions 11 and 12 is substituted with hydrogen; the carbon at position 11 and/or 12 is substituted with —$NH_2$, —$CONH_2$, —COOH, —CN, —CHO, —OCHO, —X, —OH, —$NO_2$, —SH, —COX, —$NHR^8$, —$NR^8R^8$, —$CONHR^8$, —$CONR^8R^8$, —$COOR^8$, —$COR^8$, —$OCOR^8$, or —$OR^8$; the carbon at position 11 and/or 12 is substituted with —$NH_2$, —$NHR^8$, or —$NR^8R^8$; the carbon at position 11 and/or 12 is substituted with —CN, —X, —OH, —$NO_2$, —SH, or —$OR^8$; the carbon at position 13 is substituted with —$NH_2$, —$CONH_2$, —COOH, —CN, —CHO, —OCHO, —X, —OH, —$NO_2$, —SH, —COX, —$NHR^8$, —$NR^8R^8$, —$CONHR^8$, —$CONR^8R^8$, —$COOR^8$, —$COR^8$, —$OCOR^8$, or —$OR^8$; the carbon at position 13 is substituted with —$NH_2$, —$NHR^8$, or —$NR^8R^8$; the carbon at position 13 is substituted with —CN, —X, —OH, —$NO_2$, —SH, or —$OR^8$; at least one carbon from positions 11, 12, and 13 is substituted with —$R^7$(W)$_n$; and/or at least one carbon from positions 11, 12, and 13 is substituted with $C_1$–$C_6$hydrocarbyl or $C_1$–$C_6$halocarbyl or $C_1$–$C_6$hydrohalocarbyl.

In another aspect, only one of the carbons at positions 11, 12, and 13 is substituted with hydrogen. In another aspect, exactly two of the carbons at positions 11, 12, and 13 are substituted with hydrogen. In another aspect, none of the carbons at positions 11, 12, and 13 are substituted with hydrogen. In another aspect, no more than one of the carbons at positions 11, 12, and 13 are substituted with hydrogen.

In compounds of formula (4), and compositions comprising one or more compounds of formula (4) and a pharmaceutically acceptable carrier, diluent or excipient, the carbon at position 6 is preferably not substituted with either =O or =S; the carbon at position 4 is preferably not substituted with =O; the phenyl ring bonded to the carbon at position 5 is preferably substituted with no more than 4 hydrogen atoms; the phenyl ring bonded to the carbon at position 5 is preferably substituted with no more than 4 $R^7$(W)$_n$ groups, and/or the compounds of formula (4) preferably exclude massonianalactone.

Thus, in a preferred compound of formula (4), Q is O or NH, the carbon at position 6 is substituted with not substituted with either =O or =S; the carbon at position 4 is not substituted with =O; the phenyl ring bonded directly to carbon 5 is directly substituted in at least one position with an atom other than carbon or hydrogen; and massonianalactone is excluded. Massonianalactone, which has the CAS Registry No. of 150270-05-6, is also known as 2H-pyran-2-one, tetrahydro-3-hydroxy-5-(4-hydroxy-3-methoxyphenyl)-3-[(4-hydroxy-3-methoxyphenyl)methyl]-, (3R-trans).

In a preferred embodiment, in compounds of formula (4), and compositions comprising a compound of formula (4), Q is NH, and not both of positions 17 and 18 are substituted with hydrogen.

For example, the present invention provides a Δ-lactam compound, and in particular a γ-Phenyl-substituted Δ-lactam compound of the formula (4) wherein Q is N or substituted N, as follows:

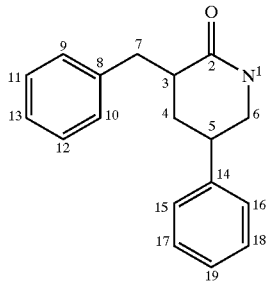

wherein each of the carbons at positions 3, 4, 5, 6, 7, 9, 10, 11, 12, 13, 15, 16, 17, 18, and 19, as well as the nitrogen at position 1, is independently substituted at each occurrence with H, —W or —$R^7(W)_n$, W is selected from —$NH_2$, —$CONH_2$, —COOH, —CN, —CHO, —OCHO, —X, —OH, —$NO_2$, —SH, —COX, —$NHR^8$, —$NR^8R^8$, —$CONHR^8$, —$CONR^8R^8$, —$COOR^8$, —$COR^8$, —$OCOR^8$, —$OR^8$, —$BH_2$, —$BHR^8$, —$BR^8R^8$, —$BO_2H_2$, —$BO_2R^8R^8$, —$PH_2$, —$PHR^8$, —$PR^8R^8$, —$POR^8$, —$PO_2R^8$, —$PO_3R^8$, —$SR^8$, —$SOR^8$, —$SO_2R^8$, —$SONH_2$, —$SONHR^8$, —$SONR^8R^8$, —$SO_2NH_2$, —$SO_2NHR^8$ and —$SO_2NR^8R^8$;

$R^7$ is a $C_1$–$C_{30}$ hydrocarbyl, halocarbyl or hydrohalocarbyl group wherein n of the hydrogen or halogen atoms of $R^7$ are substituted by an equal number of W groups independently selected at each location;

$R^8$ is a $C_1$–$C_{30}$ hydrocarbyl, halocarbyl or hydrohalocarbyl group;

n is selected from 0, 1, 2, 3, 4 and 5; and

X is selected from —Br, —Cl, —F, and —I.

In various embodiments of the aspect of the present invention that provides a γ-Phenyl-substituted Δ-lactam compound of the formula (4) wherein Q is N or substituted N, the following criteria may be used alone or in any combination in further describing the compound of the invention, where these criteria are exemplary only and other criteria may be found elsewhere herein: positions 4 and 6 are substituted exclusively with hydrogen; position 19 is substituted with —W; position 19 is substituted wit; —CN, —X, —OH, —$NO_2$, —SH, or —$OR^8$; one carbon at positions 17 and 18 is substituted with hydrogen; at least one carbon at positions 17 and 18 is substituted with —W; at least one carbon at positions 17 and 18 is substituted with —$NH_2$, —$CONH_2$, —COOH, —CN, —CHO, —OCHO, —X, —OH, —$NO_2$, —SH, —COX, —$NHR^8$, —$NR^8R^8$, —$CONHR^8$, —$CONR^8R^8$, —$COOR^8$, —$COR^8$, —$OCOR^8$, or —$OR^8$; at least one carbon at positions 17 and 18 is substituted with —CN, —X, —OH, —$NO_2$, —SH, or —$OR^8$; only one of the carbons at positions 17, 18 and 19 is substituted with hydrogen; the carbon at position 7 is substituted exclusively with hydrogen; the carbon at position 3 is substituted with hydrogen, $R^8$ or X; the carbons at positions 9 and 10 are substituted with hydrogen; the carbons at positions 11, 12, and 13 are independently substituted with hydrogen and —W; only one of the carbons at positions 11 and 12 is substituted with hydrogen; a carbon selected from positions 11 and 12 is substituted with —CN, —X, —OH, —$NO_2$, —SH, or —$OR^8$; at least one carbon from positions 11, 12, and 13 is substituted with —$R^7(W)_n$; at least one carbon from positions 11, 12, and 13 is substituted with $C_1$–$C_6$hydrocarbyl, $C_1$–$C_6$halocarbyl or $C_1$–$C_6$hydrohalocarbyl; exactly two of the carbons at positions 11, 12 and 13 are substituted with hydrogen; W is selected from, —OCHO, —OH, —$OCOR^8$, and —$OR^8$; W is selected from —$NH_2$, —CN, —X, —OH, —$NO_2$, —SH, —$NHR^8$, —$NR^8R^8$, —$OR^8$, and —$SR^8$; W is —$OR^8$; $R^7$ is a $C_1$–$C_{10}$ hydrocarbyl group wherein n of the hydrogen or halogen atoms of $R^7$ are substituted by an equal number of W groups independently selected at each location; $R^7$ is selected from the group consisting of alkyl, alkenyl, alkynyl, aryl, aralkyl, alkylaryl, alkenyl-substituted aryl, aryl-substituted alkenyl, alkynyl-substituted aryl, aryl-substituted alkynyl, biaryl, cycloalkyl, cycloalkenyl, bicycloalkyl, bicycloalkenyl, alkylcycloalkyl, alkenylcycloalkyl, alkynylcycloalkyl, aryl-substituted cycloalkyl, cycloalkyl-substituted aryl, aryl-substituted cycloalkenyl, cycloalkenyl-substituted aryl, aryl-fused cycloalkyl and polycycloalkyl; $R^8$ is a $C_1$–$C_{10}$ hydrocarbyl group; $R^8$ is a $C_1$–$C_{10}$ cyclohydrocarbyl group; $R^8$ is selected from the group consisting of alkyl, alkenyl, alkynyl, aryl, aralkyl, alkylaryl, alkenyl-substituted aryl, aryl-substituted alkenyl, alkynyl-substituted aryl, aryl-substituted alkynyl, biaryl, cycloalkyl, cycloalkenyl, bicycloalkyl, bicycloalkenyl, alkylcycloalkyl, alkenylcycloalkyl, alkynylcycloalkyl, aryl-substituted cycloalkyl, cycloalkyl-substituted aryl, aryl-substituted cycloalkenyl, cycloalkenyl-substituted aryl, aryl-fused cycloalkyl and polycycloalkyl; n is 0; position 1 is substituted with hydrogen; carbon 3 has the S configuration; carbon 3 has the R configuration; carbon 5 has the S configuration; carbon 5 has the the R configuration; wherein positions 3, 4, 6, 7, 9 and 10 are substituted with hydrogen, one of positions 11 and 12 is substituted with hydrogen, and one of positions 17 and 18 is substituted with hydrogen; at least one carbon from positions 11, 12, and 13 is substituted with $C_1$–$C_6$hydrocarbyl, $C_1$–$C_6$halocarbyl or $C_1$–$C_6$hydrohalocarbyl, and exactly two of the carbons at positions 11, 12 and 13 are substituted with hydrogen; position 19 is substituted with —CN, —X, —OH, —$NO_2$, —SH, or —$OR^8$ and one carbon at positions 17 and 18 is substituted with hydrogen and at least one carbon at positions 17 and 18 is substituted with —CN, —X, —OH, —$NO_2$, —SH, or —$OR^8$; positions 3, 4, 6, 7, 9 and 10 are substituted with hydrogen, and exactly two of the carbons at positions I1, 12 and 13 are substituted with hydrogen, and at least one carbon from positions 11, 12, and 13 is substituted with $C_1$–$C_6$hydrocarbyl, $C_1$–$C_6$halocarbyl or $C_1$–$C_6$hydrohalocarbyl, and one of positions 17 and 18 is substituted with hydrogen, and position 19 is substituted with —CN, —X, —OH, —$NO_2$, —SH, or —$OR^8$, and at least one carbon at positions 17 and 18 is substituted with —CN, —X, —OH, —$NO_2$, —SH, or —$OR^8$, and one carbon at positions 17 and 18 is substituted with hydrogen; positions 1, 3, 4, 6, 7, 9, 10, 11 and 18 are substituted with hydrogen, and positions 17 and 19 are substituted with $OR^8$ where $R^8$ is a $C_1$–$C_{10}$ hydrocarbyl group, and position 12 is substituted with $C_1$–$C_6$hydrocarbyl, $C_1$–$C_6$halocarbyl or $C_1$–$C_6$hydrohalocarbyl; positions 1, 3, 4, 5, 6, 7, 9, 10, 11, 13, 15, 16, and 18 are substituted with hydrogen, and position 12 is substituted with $C_1$ hydrocarbyl, and position 17 is substituted with —O-cyclopentyl, and position 19 is substituted with —O-methyl, where optionally positions 3 and 5 both have the S stereochemistry. Any of these compounds may be in the form of a salt or solvate according to the present invention.

The compounds disclosed herein of formulae 1, 2, 3 or 4 (i.e., compounds of formulae (1–4), or compounds of the present invention), or compositions comprising one of more of these compounds and a pharmaceutically acceptable carrier, diluent or excipient, may be used in a method for treating or preventing an inflammatory condition or disease in a patient, where the method comprises administering to the patient in need thereof an amount of a compound or composition according to the present invention, where the amount is effective to treat or prevent the inflammatory condition or disease of the patient.

The inflammatory condition or disease may be an autoimmune condition or disease; the inflammatory condition or disease may involve acute or chronic inflammation of bone and/or cartilage compartments of joints; the inflammatory condition or disease may be an arthritis selected from rheumatoid arthritis, gouty arthritis or juvenile rheumatoid arthritis; the inflammatory condition or disease may be asthma; the condition or disease may be associated with the disregulation of T-cells; the condition or disease may be associated with elevated levels of inflammatory cytokines (e.g., wherein the inflammatory cytokine is IL-2, or wherein the inflammatory cytokine is IFN-γ, or wherein the inflammatory cytokine is TNF-α); the inflammatory condition or disease may be multiple sclerosis; the inflammatory condition or disease may be pulmonary sarcadosis; the inflammatory condition or disease may be ocular inflammation or allergy; the inflammatory condition or disease may be an inflammatory bowel disease (e.g., Crohn's disease or ulcerative colitis); and the inflammatory condition or disease may be an inflammatory cutaneous disease (e.g., psoriasis or dermatitis).

Furthermore, the present invention provides a method for modulating intracellular cyclic adenosine 5'-monophosphate levels within a patient, comprising administering to a patient in need thereof an amount of a compound or composition according to the present invention, wherein the amount is effective to modulate the intracellular cyclic adenosine 5'-monophosphate levels of the patient. The patient may have an inflammatory condition or disease.

Furthermore, the present invention provides a method for treating or preventing a disease or condition in a patient, where the disease or condition is associated with pathological conditions that are modulated by inhibiting enzymes associated with secondary cellular messengers, the method comprising administering to a patient in need thereof an amount of a compound or a composition of the present invention, wherein the amount is effective to treat or prevent a disease or condition associated with pathological conditions that are modulated by inhibiting enzymes associated with secondary cellular messengers. The enzyme may be a cyclic AMP phosphodiesterase; or the enzyme may be a phosphodiesterase 4; or the enzyme may be a phosphodiesterase 3; or the enzymes may be both of phosphodiesterase 4 and phosphodiesterase 3; or the enzyme may be a cyclic GMP phosphodiesterase.

Furthermore, the present invention provides a method of treating or preventing transplant rejection in a patient, comprising administering to a patient in need thereof an amount of a compound or composition of the present invention, where the amount is effective to treat or prevent transplant rejection in the patient. The rejection may be due to graft versus host disease.

Furthermore, the present invention provides a method of treating or preventing uncontrolled cellular proliferation in a patient, comprising administering to a patient in need thereof an amount of a compound or composition according to the present invention, where the amount is effective to treat or prevent uncontrolled cellular proliferation in the patient. The uncontrolled cellular proliferation may be caused by a cancer selected from leukemia and solid tumors.

Furthermore, the present invention provides a method of treating or preventing conditions associated with the central nervous system (CNS) in a patient, comprising administering to a patient in need thereof an amount of a compound or composition according to the present invention, where the amount is effective to treat or prevent conditions associated with the central nervous system (CNS) in the patient. The condition associated with the central nervous system (CNS) may be depression.

In a method of the present invention, a compound of formulae (1–4), or a composition comprising one or more compounds of formulae (1–4) and a pharmaceutically acceptable carrier, diluent or excipient, may, although need not, achieve one or more of the following desired results in the subject to whom has been administered a compound of formulae (1–4) as defined above, or a composition containing one of these compounds and a pharmaceutically acceptable carrier, diluent or excipient:

1. Inhibition of reactive oxygen species generation from primary neutrophils;
2. Inhibition of neutrophil chemotaxis;
3. Inhibition of TNF-α production;
4. Inhibition of edema;
5. Oxygen radical scavenging;
6. Inhibition of cyclic-AMP phosphodiesterases 1, 3 and/or 4, and related PDEs such as PDE7;
7. Potentiate induction of CRE-mediated transcription activity in human monocytic cells;
8. Inhibition of PDE, preferably PDE4, PDE3, or PDE3 and PDE4;
9. Inhibition of cytokine production by activated T-cell subsets;
10. Inhibition of neutrophil myeloperoxidase release;
11. Low ratio of $IC_{50}PDE4(cat):IC_{50}PDE4(HARBS)$;
12. Inhibition of graft rejection;
13. Inhibition of clinical and histopathological parameters of disease in inflammatory bowel disease; and
14. Inhibition of clinical and histopathological parameters of arthritis in a murine collage-induced arthritis model.

These and other aspects and embodiments of the present invention will be apparent upon reference to the following detailed description. To this end, various references are set forth herein which describe in more detail certain procedures, compounds and/or compositions, and are hereby incorporated by reference in their entirety.

DETAILED DESCRIPTION OF THE INVENTION

The present invention provides compounds, compositions and methods useful in the treatment and/or prevent of various disease conditions. For example, in one aspect, the present invention provides a method of treating and/or preventing an inflammatory disease. The method includes administering to a subject in need thereof a therapeutically-effective amount of a compound or a pharmaceutically acceptable salt thereof, or a therapeutically effective amount of a composition containing a compound of formulae or a pharmaceutically acceptable salt thereof, of any of the compounds of formulae (1–4) as defined herein.

In one aspect, the present invention provides a composition comprising a compound according to formula (1) and salts, solvates, isolated stereoisomers, and mixtures thereof, and a pharmaceutically acceptable carrier, diluent, or excipient,

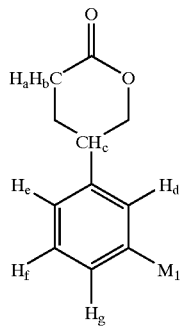

(1)

wherein each of hydrogens $H_a$, $H_b$, $H_c$, $H_d$, $H_e$, $H_f$ and $H_g$ may independently be replaced with a group selected from —W and —$R^7(W)_n$, and $M_1$ represents —W or —$R^7(W)_n$, wherein W is selected from —$NH_2$, —$CONH_2$, —COOH, —CN, —CHO, —OCHO, —X, —OH, —$NO_2$, —SH, —COX, —$NHR^8$, —$NR^8R^8$, —$CONHR^8$, —$CONR^8R^8$, —$COOR^8$, —$COR^8$, —$OCOR^8$, —$OR^8$, —$BH_2$, —$BHR^8$, —$BR^8R^8$, —$BO_2H_2$, —$BO_2R^8R^8$, —$PH_2$, —$PHR^8$, —$PR^8R^8$, —$POR^8$, —$PO_2R^8$, —$PO_3R^8$, —$SR^8$; —$SOR^8$, —$SO_2R^8$, —$SONH_2$, —$SONHR^8$, —$SONR^8R^8$, —$SO_2NH_2$, —$SO_2NHR^8$ and —$SO_2NR^8R^8$;

$R^7$ is a $C_1$–$C_{30}$ hydrocarbyl, halocarbyl or hydrohalocarbyl group wherein n of the hydrogen or halogen atoms of $R^7$ are substituted by an equal number of W groups independently selected at each location;

$R^8$ is a $C_1$–$C_{30}$ hydrocarbyl, halocarbyl or hydrohalocarbyl group;

n is selected from 0, 1, 2, 3, 4 and 5; and

X is selected from —Br, —Cl, —F, —I.

In other aspects of the composition comprising a compound of formula (1): $H_a$ and $H_b$ are hydrogen; $H_a$ is hydrogen and $H_b$ is —W; $H_a$ is hydrogen, $H_b$ is —W and the carbon to which $H_b$ is bound has an S configuration; $H_a$ is hydrogen, $H_b$ is —W, and the carbon to which $H_b$ is bound has an R configuration; $H_a$ is hydrogen and $H_b$ is —$R^7(W)_n$; $H_a$ is hydrogen, $H_b$ is —$R^7(W)_n$, and the carbon to which $H_b$ is bound has an S configuration; $H_a$ is hydrogen, $H_b$ is —$R^7(W)_n$, and the carbon to which $H_b$ is bound has an R configuration; $H_a$ is hydrogen, $H_b$ is —$R^7(W)_n$, $H_b$ is —$CH_2$-phenyl, and phenyl has 0, 1 or 2 W substitutions; $H_c$ is W; $H_d$ and $H_e$ are both hydrogen; $H_f$ is W; $H_f$ is selected from —OH and —$OR^8$; $H_f$ is selected from methoxy, ethoxy, propoxy, cyclopentyloxy, cyclohexyloxy, and benzyloxy; $H_f$ is selected from —$NH_2$, —$NHR^8$, and —$NR^8R^8$; $H_g$ is —$R^7(W)_n$; $M_1$ is —W; $M_1$ is selected from methoxy, ethoxy, propoxy, cyclopentyloxy, cyclohexyloxy, and benzyloxy; $M_1$ is selected from —$NH_2$, —$NHR^8$, and —$NR^8R^8$; $M_1$ is selected from —OH and —$OR^8$; and/or $M_1$ is —$R^7(W)_n$. In one embodiment, none of $H_a$, $H_b$, $H_c$, $H_d$, $H_e$, $H_f$ or $H_g$ is a heterocyclic ring.

The compound of formula (1) may have the stereochemistry of formula (1a)

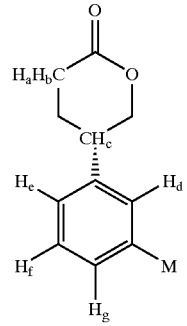

(1a).

The compound of formula (1) may have the stereochemistry of formula (1b)

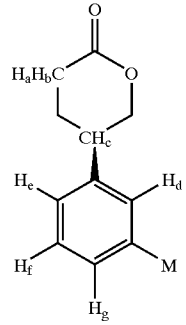

(1b).

A reference herein to compounds of formula (1) includes compounds of formulae (1a) and (1b).

In another aspect, the present invention provides a composition comprising a compound according to formula (2) and salts, solvates, isolated stereoisomers, and mixtures thereof, and a pharmaceutically acceptable carrier, diluent, or excipient,

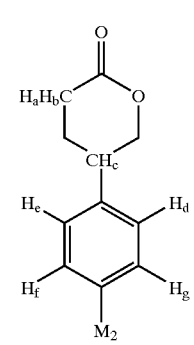

(2)

wherein each of hydrogens $H_a$, $H_b$, $H_c$, $H_d$, $H_e$, $H_f$ and $H_g$ may independently be replaced with a group selected from —W and —$R^7(W)_n$, and $M_2$ represents —W, wherein W is selected from —$NH_2$, —$CONH_2$, —COOH, —CN, —CHO, —OCHO, —X, —OH, —$NO_2$, —SH, —COX, —$NHR^8$, —$NR^8R^8$, —$CONHR^8$, —$CONR^8R^8$, —$COOR^8$, —$COR^8$, —$OCOR^8$, —$OR^8$, —$BH_2$, —$BHR^8$, —$BR^8R^8$, —$BO_2H_2$, —$BO_2R^8R^8$, —$PH_2$, —$PHR^8$, —$PR^8R^8$, —$POR^8$, —$PO_2R^8$, —$PO_3R^8$, —$SR^8$; —$SOR^8$, —$SO_2R^8$, —$SONH_2$, —$SONHR^8$, —$SONR^8R^8$, —$SO_2NH_2$, —$SO_2NHR^8$ and —$SO_2NR^8R^8$;

$R^7$ is a $C_1$–$C_{30}$ hydrocarbyl, halocarbyl or hydrohalocarbyl group wherein n of the hydrogen or halogen atoms of $R^7$ are substituted by an equal number of W groups independently selected at each location;

$R^8$ is a $C_1$–$C_{30}$ hydrocarbyl, halocarbyl or hydrohalocarbyl group;

n is selected from 0, 1, 2, 3, 4 and 5; and

X is selected from —Br, —Cl, —F, —I.

In other aspects of compositions comprising a compound of formula (2): $H_a$ and $H_b$ are hydrogen; $H_a$ is hydrogen and $H_b$ is —W; $H_a$ is hydrogen, $H_b$ is —W, and the carbon to which $H_b$ is bound has an S configuration; $H_a$ is hydrogen, $H_b$ is —W, and the carbon to which $H_b$ is bound has an R configuration; $H_a$ is hydrogen and $H_b$ is —$R^7(W)_n$; $H_a$ is hydrogen, $H_b$ is —$R^7(W)_n$, and the carbon to which $H_b$ is bound has an S configuration; $H_a$ is hydrogen, $H_b$ is —$R^7(W)_n$, and the carbon to which $H_b$ is bound has an r configuration; $H_a$ is hydrogen, and $H_b$ is —$CH_2$-phenyl, where phenyl has 0, 1 or 2 W substitutions; H, is W; $H_d$ and $H_e$ are both hydrogen; $H_f$ is hydrogen and $H_g$ is W; $H_g$ is selected from —OH and —$OR^8$; $H_g$ is selected from methoxy, ethoxy, propoxy, cyclopentyloxy, cyclohexyloxy, and benzyloxy; $H_g$ is selected from —$NH_2$, —$NHR^8$, and —$NR^8R^8$; $H_f$ is hydrogen and $H_g$ is —$R^7(W)_n$; $M_2$ is selected from —$NH_2$, —$CONH_2$, —COOH, —CN, —CHO, —OCHO, —X, —OH, —$NO_2$, —SH, —COX, —$NHR^8$, —$NR^8R^8$, —$CONHR^8$, —$CONR^8R^8$, —$COOR^8$, —$COR^8$, —$OCOR^8$, and —$OR^8$; and/or $M_2$ is selected from —$NH_2$, —$NHR^8$, —$NR^8R^8$, —OH, and —$OR^8$. In a preferred embodiment, none of $H_a$, $H_b$, $H_c$, $H_d$, $H_e$, $H_f$ or $H_g$ may be replaced with a heterocyclic ring system.

The compound of formula (2) may have the stereochemistry of formula (2a)

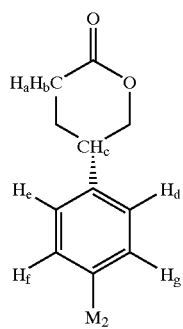

(2a).

The compound of formula (2) may have the stereochemistry of formula (2b)

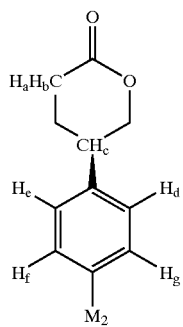

(2b).

A reference herein to compounds of formula (2) includes reference to compounds of formulae (2a) and (2b).

In another aspect, the present invention provides a compound according to formula (3) and salts, solvates, isolated stereoisomers, and mixtures thereof,

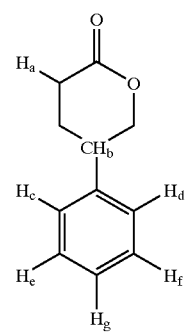

(3)

wherein each of hydrogens $H_a$, $H_c$, $H_d$, $H_e$, $H_f$ and $H_g$ may independently be replaced with a group selected from —W and —$R^7(W)_n$, and $H_b$ may be replaced with —W, wherein W is selected from —$NH_2$, —$CONH_2$, —COOH, —CN, —CHO, —OCHO, —X, —OH, —$NO_2$, —SH, —COX, —$NHR^8$, —$NR^8R^8$, —$CONHR^8$, —$CONR^8R^8$, —$COOR^8$, —$COR^8$, —$OCOR^8$, —$OR^8$, —$BH_2$, —$BHR^8$, —$BR^8R^8$, —$BO_2H_2$, —$BO_2R^8R^8$, —$PH_2$, —$PHR^8$, —$PR^8R^8$, —$POR^8$, —$PO_2R^8$, —$PO_3R^8$, —$SR^8$; —$SOR^8$, —$SO_2R^8$, —$SONH_2$, —$SONHR^8$, —$SONR^8R^8$, —$SO_2NH_2$, —$SO_2NHR^8$ and —$SO_2NR^8R^8$;

$R^7$ is a $C_1$–$C_{30}$ hydrocarbyl, halocarbyl or hydrohalocarbyl group wherein n of the hydrogen or halogen atoms of $R^7$ are substituted by an equal number of W groups independently selected at each location;

$R^8$ is a $C_1$–$C_{30}$ hydrocarbyl, halocarbyl or hydrohalocarbyl group;

n is selected from 0, 1, 2, 3, 4 and 5; and

X is selected from —Br, —Cl, —F, —I.

In a preferred embodiment, at least two of $H_e$, $H_f$, and $H_g$ are not hydrogen. In another preferred embodiment, $H_g$ is not $R^7(W)_n$. In another preferred embodiment, $H_g$ is neither hydrogen nor $R^7(W)_n$. In another preferred embodiment, none of $H_a$, $H_b$, $H_c$, $H_d$, $H_e$, $H_f$ or $H_g$ is a heterocyclic ring.

In other aspects, in the compound of formula (3): $H_a$ is hydrogen; $H_a$ is not hydrogen, and the carbon to which $H_a$ is bound has an S configuration; $H_a$ is not hydrogen and the carbon to which $H_a$ is bound has an R configuration; $H_a$ is —W; $H_a$ is —$R^7(W)_n$; $H_a$ is —$CH_2$-phenyl, and phenyl has 0, 1 or 2 W substitutions; $H_b$ is W; $H_b$ is —CN; $H_c$ and $H_d$ are both hydrogen; $H_e$ is hydrogen; $H_e$ is hydrogen and $H_f$ is W; $H_e$ is hydrogen and $H_f$ is selected from —OH and —$OR^8$; $H_e$ is hydrogen and $H_f$ is selected from methoxy, ethoxy, propoxy, cyclopentyloxy, cyclohexyloxy, and benzyloxy; $H_e$ is hydrogen and $H_f$ is selected from —$NH_2$, —$NHR^8$, and —$NR^8R^8$; $H_g$ is hydrogen; $H_g$ is —W; $H_g$ is selected from —OH and —$OR^8$; $H_g$ is selected from methoxy, ethoxy, propoxy, cyclopentyloxy, cyclohexyloxy, and benzyloxy; wherein $H_g$ is selected from —$NH_2$, —$NHR^8$, and —$NR^8R^8$; $H_g$ is —$R^7(W)_n$; and/or $H_g$ is $C_1$–$C_{30}$alkyl and n=0.

The compound of formula (3) may have the stereochemistry of formula (3a)

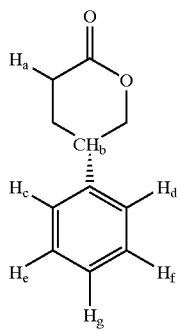

(3a).

The compound of formula (3) may have the stereochemistry of formula (3b)

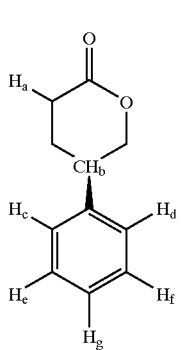

(3b).

A reference herein to compounds of formula (3) includes reference to compounds of formulae (3a) and (3b).

In another aspect, the present invention provides compounds of formula (4)

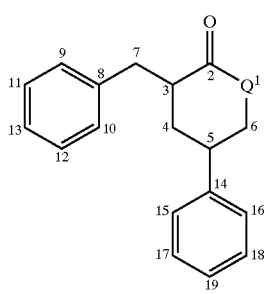

(4)

wherein, Q represents a multivalent atom other than carbon; and each of the carbons at positions 3, 4, 5, 6, 7, 9, 10, 11, 12, 13, 15, 16, 17, 18, and 19 in formula (4), as well as Q to the extent that it may be substituted, is independently substituted at each occurrence with H, —W or —R$^7$(W)$_n$, wherein W is selected from —NH$_2$, —CONH$_2$, —COOH, —CN, —CHO, —OCHO, —X, —OH, —NO$_2$, —SH, —COX, —NHR$^8$, —NR$^8$R$^8$, —CONHR$^8$, —CONR$^8$R$^8$, —COOR$^8$, —COR$^8$, —OCOR$^8$, —OR$^8$, —BH$_2$, —BHR$^8$, —BR$^8$R$^8$, —BO$_2$H$_2$, —BO$_2$R$^8$R$^8$, —PH$_2$, —PHR$^8$, —PR$^8$R$^8$, —POR$^8$, —PO$_2$R$^8$, —PO$_3$R$^8$, —SR$^8$; —SOR$^8$, —SO$_2$R$^8$, —SONH$_2$, —SONHR$^8$, —SONR$^8$R$^8$, —SO$_2$NH$_2$, —SO$_2$NHR$^8$ and —SO$_2$NR$^8$R$^8$;

R$^7$ is a C$_1$–C$_{30}$ hydrocarbyl, halocarbyl or hydrohalocarbyl group wherein n of the hydrogen or halogen atoms of R$^7$ are substituted by an equal number of W groups independently selected at each location;

R$^8$ is a C$_1$–C$_{30}$ hydrocarbyl, halocarbyl or hydrohalocarbyl group;

n is selected from 0, 1, 2, 3, 4 and 5; and

X is selected from —Br, —Cl, —F, —I.

In one aspect, the compound of formula (4) has the S configuration at carbon 3. In another aspect, the compound of formula (4) has the R configuration at carbon 3. In another aspect, the compound of formula (4) has the S configuration at carbon 5. In another aspect, the compound of formula (4) has the R configuration at carbon 5. In another aspect, none of the carbons at positions 3, 4, 5, 6, 7, 9, 10, 11, 12, 13, 15, 16, 17, 18, or 19 in formula (4) is substituted with a heterocyclic moiety.

In other aspects, in the compound of formula (4), as well as in compositions comprising the compound of formula (4) and a pharmaceutically acceptable carrier, diluent or excipient: Q is O; Q is S; Q is NH; and/or Q is N(R$^7$(W)$_n$). In other aspects, the carbon(s) at position 4, or 6, and preferably both of positions 4 and 6, are substituted exclusively with hydrogen; the carbon at position 19 is substituted with —W; the carbon at position 19 is substituted with —NH$_2$, —NHR$^8$, or —NR$^8$R$^8$; the carbon at position 19 is substituted with —CN, —X, —OH, —NO$_2$, —SH, or —OR$^8$; one carbon at positions 17 and 18 is substituted with hydrogen; at least one carbon at positions 17 and 18 is substituted with —W; at least one carbon at positions 17 and 18 is substituted with —NH$_2$, —CONH$_2$, —COOH, —CN, —CHO, —OCHO, —X, —OH, —NO$_2$, —SH, —COX, —NHR$^8$, —NR$^8$R$^8$, —CONHR$^8$, —CONR$^8$R$^8$, —COOR$^8$, —COR$^8$, —OCOR$^8$, or —OR$^8$; at least one carbon at positions 17 and 18 is substituted with —NH$_2$, —NHR$^8$, or —NR$^8$R$^8$; and/or at least one carbon at positions 17 and 18 is substituted with —CN, —X, —OH, —NO$_2$, —SH, or —OR$^8$. In another aspect, only one of the carbons at positions 17, 18 and 19 is substituted with hydrogen. In another aspect, exactly two of the carbons at positions 17, 18 and 19 are substituted with hydrogen. In another aspect, none of the carbons at positions 17, 18 and 19 are substituted with hydrogen. In another aspect, no more than one of the carbons at positions 17, 18 and 19 are substituted with hydrogen.

In other aspects, in the compound of formula (4), as well as in compositions comprising the compound of formula (4) and a pharmaceutically acceptable carrier, diluent or excipient: the carbon at position 7 is substituted exclusively with hydrogen; the carbon at position 3 is substituted with hydrogen; the carbon at position 3 is substituted with —W; the carbon at position 3 is substituted with halogen; the carbon at position 3 is substituted with —R$^7$(W)$_n$; the carbon at position 3 is substituted with C$_1$–C$_6$ hydrocarbyl; the carbons at positions 9 and 10 are substituted with hydrogen; the carbons at positions 11, 12, and 13 are independently substituted with hydrogen and —W; only one of the carbons at positions 11 and 12 is substituted with hydrogen; the carbon at position 11 and/or 12 is substituted with —NH$_2$, —CONH$_2$, —COOH, —CN, —CHO, —OCHO, —X, —OH, —NO$_2$, —SH, —COX, —NHR$^8$, —NR$^8$R$^8$, —CONHR$^8$, —CONR$^8$R$^8$, —COOR$^8$, —COR$^8$, —OCOR$^8$, or —OR$^8$; the carbon at position 11 and/or 12 is substituted with —NH$_2$, —NHR$^8$, or —NR$^8$R$^8$; the carbon at position 11 and/or 12 is substituted with —CN, —X, —OH, —NO$_2$, —SH, or —OR$^8$; the carbon at position 13 is substituted with —NH$_2$, —CONH$_2$, —COOH, —CN, —CHO, —OCHO, —X, —OH, —NO$_2$, —SH, —COX, —NHR$^8$, —NR$^8$R$^8$, —CONHR$^8$, —CONR$^8$R$^8$, —COOR$^8$, —COR$^8$, —OCOR$^8$, or —OR$^8$; the carbon at position 13 is substituted with —NH$_2$, —NHR$^8$, or —NR$^8$R$^8$; the carbon at position 13 is substituted with —CN, —X, —OH, —NO$_2$, —SH, or —OR$^8$; at least one carbon from positions 11, 12, and 13 is substituted with —R$^7$(W)$_n$;

In another aspect, only one of the carbons at positions 11, 12, and 13 is substituted with hydrogen. In another aspect, exactly two of the carbons at positions 11, 12, and 13 are substituted with hydrogen. In another aspect, none of the carbons at positions 11, 12, and 13 are substituted with hydrogen. In another aspect, no more than one of the carbons at positions 11, 12, and 13 are substituted with hydrogen.

In compounds of formula (4), and compositions comprising one or more compounds of formula (4) and a pharmaceutically acceptable carrier, diluent or excipient, the carbon at position 6 is preferably not substituted with either =O or =S; the carbon at position 4 is preferably not substituted with =O; the phenyl ring bonded to the carbon at position 5 is preferably substituted with no more than 4 hydrogen atoms; the phenyl ring bonded to the carbon at position 5 is preferably substituted with no more than 4 R$^7$(W)$_n$ groups, and/or the compounds of formula (4) preferably exclude massonianalactone.

Thus, in a preferred compound of formula (4), Q is O or NH, the carbon at position 6 is not substituted with either =O or =S; the carbon at position 4 is not substituted with =O; the phenyl ring bonded directly to carbon 5 is directly substituted in at least one position with an atom other than carbon or hydrogen; and massonianalactone is excluded. Massonianalactone, which has the CAS Registry No. of 150270-05-6, is also known as 2H-pyran-2-one, tetrahydro-3-hydroxy-5-(4-hydroxy-3-methoxyphenyl)-3-[(4-hydroxy-3-methoxyphenyl)methyl]-, (3R-trans)).

For example, the present invention provides a Δ-lactam compound, and in particular a γ-Phenyl-substituted Δ-lactam compound of the formula (4) wherein Q is N or substituted N, as follows:

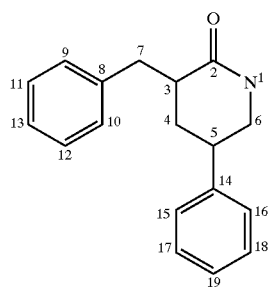

wherein each of the carbons at positions 3, 4, 5, 6, 7, 9, 10, 11, 12, 13, 15, 16, 17, 18, and 19, as well as the nitrogen at position 1, is independently substituted at each occurrence with H, —W or —R$^7$(W)$_n$, W is selected from —NH$_2$, —CONH$_2$, —COOH, —CN, —CHO, —OCHO, —X, —OH, —NO$_2$, —SH, —COX, —NHR$^8$, —NR$^8$R$^8$, —CONHR$^8$, —CONR$^8$R$^8$, —COOR$^8$, —COR$^8$, —OCOR$^8$, —OR$^8$, —BH$_2$, —BHR$^8$, —BR$^8$R$^8$, —BO$_2$H$_2$, —BO$_2$R$^8$R$^8$, —PH$_2$, —PHR$^8$, —PR$^8$R$^8$, —POR$^8$, —PO$_2$R$^8$, —PO$_3$R$^8$, —SR$^8$; —SOR$^8$, —SO$_2$R$^8$, —SONH$_2$, —SONHR$^8$, —SONR$^8$R$^8$, —SO$_2$NH$_2$, —SO$_2$NHR$^8$ and —SO$_2$NR$^8$R$^8$;

R$^7$ is a C$_1$–C$_{30}$ hydrocarbyl, halocarbyl or hydrohalocarbyl group wherein n of the hydrogen or halogen atoms of R$^7$ are substituted by an equal number of W groups independently selected at each location;

R$^8$ is a C$_1$–C$_{30}$ hydrocarbyl, halocarbyl or hydrohalocarbyl group;

n is selected from 0, 1, 2, 3, 4 and 5; and

X is selected from —Br, —Cl, —F, and —I.

In various embodiments of the aspect of the present invention that provides a γ-Phenyl-substituted Δ-lactam compound of the formula (4) wherein Q is N or substituted N, the following criteria may be used alone or in any combination in further describing the compound(s) of the invention, where these criteria are exemplary only and other criteria may be found elsewhere herein: positions 4 and 6 are substituted exclusively with hydrogen; position 19 is substituted with —W; position 19 is substituted with —CN, —X, —OH, —NO$_2$, —SH, or —OR$^8$; one carbon at positions 17 and 18 is substituted with hydrogen; at least one carbon at positions 17 and 18 is substituted with —W; at least one carbon at positions 17 and 18 is substituted with —NH$_2$, —CONH$_2$, —COOH, —CN, —CHO, —OCHO, —X, —OH, —NO$_2$, —SH, —COX, —NHR$^8$, —NR$^8$R$^8$, —CONHR$^8$, —CONR$^8$R$^8$, —COOR$^8$, —COR$^8$, —OCOR$^8$, or —OR$^8$; at least one carbon at positions 17 and 18 is substituted with —CN, —X, —OH, —NO$_2$, —SH, or —OR$^8$; only one of the carbons at positions 17, 18 and 19 is substituted with hydrogen; the carbon at position 7 is substituted exclusively with hydrogen; the carbon at position 3 is substituted with hydrogen, R$^8$ or X; the carbons at positions 9 and 10 are substituted with hydrogen; the carbons at positions 11, 12, and 13 are independently substituted with hydrogen and —W; only one of the carbons at positions 11 and 12 is substituted with hydrogen; a carbon selected from positions 11 and 12 is substituted with —CN, —X, —OH, —NO$_2$, —SH, or —OR$^8$; at least one carbon from positions 11, 12, and 13 is substituted with —R$^7$(W)$_n$; at least one carbon from positions 11, 12, and 13 is substituted with C$_1$–C$_6$hydrocarbyl, C$_1$–C$_6$halocarbyl or C$_1$–C$_6$hydrohalocarbyl; exactly two of the carbons at positions 11, 12 and 13 are substituted with hydrogen; W is selected from, —OCHO, —OH, —OCOR$^8$, and —OR$^8$; W is selected from —NH$_2$, —CN, —X, —OH, —NO$_2$, —SH, —NHR$^8$, —NR$^8$R$^8$, —OR$^8$, and —SR$^8$; W is —OR$^8$; R$^7$ is a C$_1$–C$_{10}$ hydrocarbyl group wherein n of the hydrogen or halogen atoms of R$^7$ are substituted by an equal number of W groups independently selected at each location; R$^7$ is selected from the group consisting of alkyl, alkenyl, alkynyl, aryl, aralkyl, alkylaryl, alkenyl-substituted aryl, aryl-substituted alkenyl, alkynyl-substituted aryl, aryl-substituted alkynyl, biaryl, cycloalkyl, cycloalkenyl, bicycloalkyl, bicycloalkenyl, alkylcycloalkyl, alkenylcycloalkyl, alkynylcycloalkyl, aryl-substituted cycloalkyl, cycloalkyl-substituted aryl, aryl-substituted cycloalkenyl, cycloalkenyl-substituted aryl, aryl-fused cycloalkyl and polycycloalkyl; R$^8$ is a C$_1$–C$_{10}$ hydrocarbyl group; R$^8$ is a C$_1$–C$_{10}$ cyclohydrocarbyl group; R$^8$ is selected from the group consisting of alkyl, alkenyl, alkynyl, aryl, aralkyl, alkylaryl, alkenyl-substituted aryl, aryl-substituted alkenyl, alkynyl-substituted aryl, aryl-substituted alkynyl, biaryl, cycloalkyl, cycloalkenyl, bicycloalkyl, bicycloalkenyl, alkylcycloalkyl, alkenylcycloalkyl, alkynylcycloalkyl, aryl-substituted cycloalkyl, cycloalkyl-substituted aryl, aryl-substituted cycloalkenyl, cycloalkenyl-substituted aryl, aryl-fused cycloalkyl and polycycloalkyl; n is 0; position 1 is substituted with hydrogen; carbon 3 has the S configuration; carbon 3 has the R configuration; carbon 5 has the S configuration; carbon 5 has the the R configuration; wherein positions 3, 4, 6, 7, 9 and 10 are substituted with hydrogen, one of positions 11 and 12 is substituted with hydrogen, and one of positions 17 and 18 is substituted with hydrogen; at least one carbon from positions 11, 12, and 13 is substituted with $C_1$–$C_6$ hydrocarbyl, $C_1$–$C_6$ halocarbyl or $C_1$–$C_6$ hydrohalocarbyl, and exactly two of the carbons at positions 11, 12 and 13 are substituted with hydrogen; position 19 is substituted with —CN, —X, —OH, —NO$_2$, —SH, or —OR$^8$ and one carbon at positions 17 and 18 is substituted with hydrogen and at least one carbon at positions 17 and 18 is substituted with —CN, —X, —OH, —NO$_2$, —SH, or —OR$^8$; positions 3, 4, 6, 7, 9 and 10 are substituted with hydrogen, and exactly two of the carbons at positions 11, 12 and 13 are substituted with hydrogen, and at least one carbon from positions 11, 12, and 13 is substituted with $C_1$–$C_6$ hydrocarbyl, $C_1$–$C_6$ halocarbyl or $C_1$–$C_6$ hydrohalocarbyl, and one of positions 17 and 18 is substituted with hydrogen, and position 19 is substituted with —CN, —X, —OH, —NO$_2$, —SH, or —OR$^8$, and at least one carbon at positions 17 and 18 is substituted with —CN, —X, —OH, —NO$_2$, —SH, or —OR$^8$, and one carbon at positions 17 and 18 is substituted with hydrogen; positions 1, 3, 4, 6, 7, 9, 10, 11 and 18 are substituted with hydrogen, and positions 17 and 19 are substituted with OR$^8$ where R$^8$ is a $C_{1-C10}$ hydrocarbyl group, and position 12 is substituted with $C_1$–$C_6$ hydrocarbyl, $C_1$–$C_6$ halocarbyl or $C_1$–$C_6$ hydrohalocarbyl; positions 1, 3, 4, 5, 6, 7, 9, 10, 11, 13, 15, 16, and 18 are substituted with hydrogen, and position 12 is substituted with $C_1$ hydrocarbyl, and position 17 is substituted with —O-cyclopentyl; and position 19 is substituted with —O-methyl, where optionally positions 3 and 5 both have the S stereochemistry. Any of these compounds may be in the form of a pharmaceutically acceptable salt or solvate according to the present invention.

In the γ-Phenyl-substituted Δ-lactam compounds of the formula (4) wherein Q is N or substituted N, the ring containing Q is monocyclic and saturated, as shown in the formula (4).

In compounds of formulae (1–4):

W may be selected from —NH$_2$, —CONH$_2$, —COOH, —CN, —CHO, —OCHO, —X, —OH, —NO$_2$, —SH, —COX, —NHR$^8$, —NR$^8$R$^8$, —CONHR$^8$, —CONR$^8$R$^8$, —COOR$^8$, —COR$^8$, —OCOR$^8$, —OR$^8$, —BH$_2$, —BHR$^8$, —BR$^8$R$^8$, —BO$_2$H$_2$, —BO$_2$R$^8$R$^8$, —PH$_2$, PHR$^8$, —PR$^8$R$^8$, —POR$^8$, —PO$_2$R$^8$, —PO$_3$R$^8$, —SR$^8$; —SOR$^8$, —SO$_2$R$^8$, —SONH$_2$, —SONHR$^8$, —SONR$^8$R$^8$, —SO$_2$NH$_2$, —SO$_2$NHR$^8$ and —SO$_2$NR$^8$R$^8$;

R$^7$ may be a $C_1$–$C_{30}$ hydrocarbyl, halocarbyl or hydrohalocarbyl group wherein n of the hydrogen or halogen atoms of R$^7$ are substituted by an equal number of W groups independently selected at each location;

R$^8$ may be a $C_1$–$C_{30}$ hydrocarbyl, halocarbyl or hydrohalocarbyl group;

n may be selected from 0, 1, 2, 3, 4 and 5; and

X may be selected from —Br, —Cl, —F, —I.

In preferred embodiments: W is selected from —NH$_2$, —NHR$^8$, and —NR$^8$R$^8$; W is selected from —CONH$_2$, —COOH, —CN, —CHO, —COX, —CONHR$^8$, —CONR$^8$R$^8$, —COOR$^8$, —COR$^8$; W is selected from, —OCHO, —OH, —OCOR$^8$, and —OR$^8$; W is selected from —BH$_2$, —BHR$^8$, —BR$^8$R$^8$, —BO$_2$H$_2$, —BO$_2$R$^8$R$^8$, —PH$_2$, —PHR$^8$, —PR$^8$R$^8$, —POR$^8$, —PO$_2$R$^8$, —PO$_3$R$^8$, —SR$^8$; —SOR$^8$, —SO$_2$R$^8$, —SONH$_2$, —SONHR$^8$, —SONR$^8$R$^8$, —SO$_2$NH$_2$, —SO$_2$NHR$^8$ and —SO$_2$NR$^8$R$^8$; W is selected from —NH$_2$, —CN, —X, —OH, —NO$_2$, —SH, —NHR$^8$, —NR$^8$R$^8$, —OR$^8$, and —SR$^8$; and W is —OR$^8$.

In preferred embodiments: R$^7$ is a $C_1$–$C_{30}$ hydrocarbyl group wherein n of the hydrogen or halogen atoms of R$^7$ are substituted by an equal number of W groups independently selected at each location; R$^7$ is a $C_1$–$C_{10}$ hydrocarbyl group wherein n of the hydrogen or halogen atoms of R$^7$ are substituted by an equal number of W groups independently selected at each location; and/or R$^7$ is selected from alkyl, alkenyl, alkynyl, aryl, aralkyl, alkylaryl, alkenyl-substituted aryl, aryl-substituted alkenyl, alkynyl-substituted aryl, aryl-substituted alkynyl, biaryl, cycloalkyl, cycloalkenyl, bicycloalkyl, bicycloalkenyl, alkylcycloalkyl, alkenylcycloalkyl, alkynylcycloalkyl, aryl-substituted cycloalkyl, cycloalkyl-substituted aryl, aryl-substituted cycloalkenyl, cycloalkenyl-substituted aryl, aryl-fused cycloalkyl and polycycloalkyl.

In preferred embodiments: R$^8$ is a $C_1$–$C_{30}$ hydrocarbyl group; R$^8$ is a $C_1$–$C_{10}$ hydrocarbyl group; and/or R$^8$ is selected from alkyl, alkenyl, alkynyl, aryl, aralkyl, alkylaryl, alkenyl-substituted aryl, aryl-substituted alkenyl, alkynyl-substituted aryl, aryl-substituted alkynyl, biaryl, cycloalkyl, cycloalkenyl, bicycloalkyl, bicycloalkenyl, alkylcycloalkyl, alkenylcycloalkyl, alkynylcycloalkyl, aryl-substituted cycloalkyl, cycloalkyl-substituted aryl, aryl-substituted cycloalkenyl, cycloalkenyl-substituted aryl, aryl-fused cycloalkyl and polycycloalkyl.

In preferred embodiments: n is 0; n is 1; n is 2; n is 3; n is 4; n is 5; n is greater than 0; n is 1 or 2; and n is 1 or 2 or 3.

In preferred embodiments, none of $H_a$ through $H_g$ is a heterocyclic ring.

In the above compounds, a pharmaceutically acceptable salt includes acid addition salts and base addition salts.

Acid addition salts refer to those salts formed from compounds of formulae (1–4) and inorganic acids such as hydrochloric acid, hydrobromic acid, sulfuric acid, nitric acid, phosphoric acid and the like, and/or organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

Base addition salts include those salts derived from compounds of formulae (1–4) and inorganic bases such as sodium, potassium, lithium, ammonium, calcium, magnesium, iron, zinc, copper, manganese, aluminum salts and the like. Suitable salts include the ammonium, potassium, sodium, calcium and magnesium salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, trimethamine, dicyclohexylamine, lysine, arginine, histidine, caffeine, procaines, hydrabamine, choline, betaine, ethylenediamine, glucosamine, methylglucamine, theobromine, purines, piperazine, piperidine, N-ethylpiperidine, and the like.

In the above compounds and compositions, a hydrocarbyl group is formed exclusively from carbon and hydrogen, and includes, for example, any of alkyl, alkenyl, alkynyl, aryl, aralkyl, alkylaryl, alkenyl-substituted aryl, aryl-substituted alkenyl, alkynyl-substituted aryl, aryl-substituted alkynyl, biaryl, cycloalkyl, cycloalkenyl, bicycloalkyl, bicycloalkenyl, alkylcycloalkyl, alkenylcycloalkyl, alkynylcycloalkyl, aryl-substituted cycloalkyl, cycloalkyl-substituted aryl, aryl-substituted cycloalkenyl, cycloalkenyl-substituted aryl, aryl-fused cycloalkyl and polycycloalkyl. A cyclohydrocarbyl group is also formed exclusively from carbon and hydrogen, and includes at least one ring, where exemplary cyclohydrocarbyl groups include any of aryl, aralkyl, alkylaryl, alkenyl-substituted aryl, aryl-substituted alkenyl, alkynyl-substituted aryl, aryl-substituted alkynyl, biaryl, cycloalkyl, cycloalkenyl, bicycloalkyl, bicycloalkenyl, alkylcycloalkyl, alkenylcycloalkyl, alkynylcycloalkyl, aryl-substituted cycloalkyl, cycloalkyl-substituted aryl, aryl-substituted cycloalkenyl, cycloalkenyl-substituted aryl, aryl-fused cycloalkyl and polycycloalkyl. In one aspect of the invention, the cyclohydrocarbyl group is selected from cyclopropyl, cyclobutyl, cyclopentyl and cyclohexyl. In another aspect, the cyclohydrocarbyl group is cyclopentyl.

A halocarbyl group is formed exclusively from carbon and halogen, and includes the hydrocarbyl groups identified above wherein each hydrogen is replaced with a halogen selected from fluorine, chlorine, bromine and iodine, preferably fluorine and chlorine. A hydrohalocarbyl group, which may also be referred to as a halohydrocarbyl group, is formed from exclusively from all of carbon, hydrogen and halogen, and includes the specific hydrocarbyl groups identified above wherein some, but not all, of the hydrogen atoms are replaced with halogen atoms selected from fluorine, chlorine, bromine and iodine, preferably fluorine and/or chlorine. Representative definitions of these hydrocarbyl groups (which may be substitued with halogen atoms to provide halocarbyl and hydrohalocarbyl derivatives thereof) are provided below.

"Alkyl" refers to an acyclic chain of carbon atoms which may be branched or unbranched (linear). Methyl, ethyl, propyl (including n-propyl and iso-propyl) butyl (including n-butyl, iso-butyl, sec-butyl, and t-butyl), pentyl (including numerous isomers) and hexyl (including numerous isomers) are alkyl groups having 1 to 6 carbon atoms (commonly referred to as lower alkyl groups), and are exemplary of alkyl groups of the invention.

"Alkenyl" refers to an unsaturated aliphatic group having at least one double bond.

"Alkynyl" refers to an unsaturated hydrocarbon which may be either straight- or branched-chain and have one or more triple bonds. Preferred groups have no more than about 12 carbons atoms and may be ethyl, propynyl, 4-methylpentynl and so on, and structure isomers thereof.

"Aralkyl" refers to an alkyl group substituted by an aryl radical. For example, benzyl.

"Aralkynyl" refers to an alkynyl group substituted by an aryl ring. For example, ArC≡C—, ArCH$_2$CH$_2$CH$_2$C≡C— and so on.

"Cyloalkyl" refers to a cyclic arrangement of carbon atoms, where cyclopropyl, cyclobutyl, cyclopentyl, cyclohexyl are cycloalkyl groups of the invention having 3–6 carbon atoms. Additional groups within the scope of "cycloalkyl" as defined herein are polycycloalkyl groups, defined below.

"Cycloalkenyl" refers to a cyclic alkenyl group. Suitable cycloalkenyl groups include, for example, cyclopentenyl and cyclohexenyl.

A polycycloalkyl group is an arrangement of carbon atoms wherein at least one carbon atom is a part of at least two separately identifiable rings. The polycycloalkyl group may contain bridging between two carbon atoms, where bicyclo[1.1.0]butyl, bicyclo[3.2.1]octyl, bicyclo[5.2.0]nonyl, tricycl[2.2.1.0$^1$]heptyl, norbornyl and pinanyl are representative examples. The polycycloalkyl group may contain one or more fused ring systems, where decalinyl (radical from decalin) and perhydroanthracenyl are representative examples. The polycycloalkyl group may contain a spiro union, in which a single atom is the only common member of two rings. Spiro[3.4]octyl, spiro[3.3]heptyl and spiro[4.5]decyl are representative examples.

"Halogen" refers to fluorine, chlorine, bromine and iodine.

As used herein, the following abbreviations have the indicated meanings:

| Abbreviation | Full name |
|---|---|
| 5-ASA | 5-aminosalicylic acid |
| Ab | Antibody |
| ABTS | 2,2'-azino-di-[3-ethylbenzthiazoline sulphonate] |
| ACD | Acid citrate dextrose |
| AcOH | Acetic Acid |
| ACVP | American College of Veterinary Practice |
| ANOVA | Analysis of Variance |
| Ar | Argon |
| BCR-ABL | Oncogene in chromosome 9:22 translocation in CML |
| BINAP | 2,2'-Bis(diphenylphosphino)-1,1'-binaphthyl |
| Bn | Benzyl |
| BnBr | Benzyl Bromide |
| BOC | tert-Butoxycarbonyl |
| cAMP | Cyclic adenosine 3'-5'-monophosphate |
| cat | Catalytic |
| CD | Cluster designation |
| CFA | Complete Freund's adjuvant |
| cGMP | Cyclic guanosine 3'-5'-monophosphate |
| CIA | Collagen Induced Arthritis |
| CLL | Chronic lymphocytic leukemia |
| CML | Chronic myelogenous leukemia |
| CNS | Central Nervous System |
| Con A | Concanavalin A |
| COX | Cyclooxygenase |
| cPent | Cyclopentyl |
| cPentBr | Cyclopentyl bromide |
| CRE | cAMP response element |
| CsA | Cyclosporin A |
| DMAP | 4-Dimethylaminopyridine |
| DMARD | Disease modifying anti-rheumatic drug |
| DMF | N,N-Dimethylformamide |
| DMSO | dimethylsulfoxide |
| DNA | Deoxyriboneucleic acid |
| dppf | 1,1'-Bis(diphenylphosphino)ferrocene |
| dppp | 1,3-Bis(diphenylphosphino)propane |
| EC$_{50}$ | Concentration at which a 50% of maximum observable effect is noted |
| EDTA | Ethylenediaminotetraacetic acid |
| ELISA | Enzyme-linked immunosorbent assay |
| EtOAc | Ethyl acetate |
| EtOH | Ethyl alcohol |
| FBS | Fetal bovine serum |
| FCS | Fetal calf serum |
| fMLP | Formyl-methionyl leucine phenylalanine |
| g.i. | Gastrointestinal |
| H & E | Haematoxylin and eosin |
| HARBS | High affinity rolipram binding site |
| HBSS | Hanks Balanced Salt Solution |
| HMPA | Hexamethylphosphoramide |
| HPLC | High pressure liquid chromatography |
| i.p. | intraperitoneal |
| IBD | Inflammatory bowel disease |
| IBMX | 3-isobutyl-1-methylxanthine |
| IC | Inhibitory concentration |
| IC$_{50}$ | Concentration at which 50% inhibition is observed |
| IFA | Incomplete Freund's adjuvant |
| IFN-γ | Interferon gamma |
| IL | Interleukin |
| LAH | Lithium aluminum hydride |
| LDA | Lithium diisopropylamide |
| LN | Lymph node |
| LPS | lipopolysaccharide |
| LTB4 | Leukotriene B4 |
| luc | luciferase |

-continued

| Abbreviation | Full name |
|---|---|
| Me | Methyl |
| MeOH | Methyl alcohol |
| MHC | Major histocompatibility class |
| MLR | Mixed lymphocyte reaction |
| MPO | myeloperoxidase |
| Ms | Methanesulfonyl |
| MsCl | Methanesulfonyl chloride |
| NBS | N-Bromosuccinimide |
| n-BuLi | n-Butyllithium |
| n-BuSH | n-Butanethiol |
| NF-κB | Nuclear factor kappa B |
| NSAID | Non-steroidal anti-inflammatory drug |
| p.t. | Post-transplant |
| PBS | Phosphate buffered saline |
| Pcc | Pigeon cytochrome C |
| PDE | Phosphodiesterase |
| PEG | Polyethylene glycol |
| PG | Prostaglandin |
| PMS | Phenazine methosulfate |
| PMSF | Phenyl methyl sulfonyl fluoride |
| pTsOH | p-Toluenesulfonic acid monohydrate |
| Py | Pyridine |
| RA | Rheumatoid arthritis |
| RF | Rheumatoid factor |
| $R_f$ | Retardation factor |
| ROS | Reactive oxygen species |
| RPMI | Rosewell Park Memorial Institute |
| RTX | Resiniferitoxin |
| SAR | Structure activity relationship |
| TBAF | Tetrabutylammonium fluoride |
| TBDMS | tert-Butyldimethylsilyl |
| TBDMSCI | tert-Butyldimethylsilyl chloride |
| TCR | T-cell receptor |
| TEA | Triethylamine |
| Tf | Trifluoromethanesulfonyl |
| TFA | Trifluoroacetic acid |
| Th | T helper |
| THF | Tetrahydrofuran |
| TNBS | Trinitrobenzene sulfonic acid |
| TNF-α | Tumour necrosis factor alpha |
| Trolox ® | 6-hydroxy-2.5.7.8-tetramethylchroman-2-carboxylic acid |
| TsOH | p-Toluenesulfonic acid monohydrate |
| XTT | 2,3-bis[2-methoxy-4-nitro-5-sulfo-phenyl]-2H-tetrazolium 5-carboxanilide inner salt |
| $\mu M$ | Micro molar |

When any variable occurs more than one time in any constituent or in compounds of formulae (1–4), its definition on each occurrence is independent of its definition at every other occurrence. Combinations of substituents and/or variables are permissible only if such combinations result in stable compounds. The compounds useful in the methods and compositions of the present invention, as well as the compounds of the present invention, may have asymmetric centers and occur as racemates, racemic mixtures and as individual diastereomers, or enantiomers with all isomeric forms being included in the present invention. A racemate or racemic mixture does not imply a 50:50 mixture of stereoisomers.

In another embodiment, the present invention provides pharmaceutical compositions containing a compound of formulae (1–4) as set forth above, in combination with a pharmaceutically-acceptable carrier, diluent or excipient. These compositions may be used for the treatment inflammation or other conditions as disclosed herein. These compositions may also be formed into a medicament, which may used in the treatment of, for example, inflammation.

These compositions are useful as, for example, assay standards, convenient means of making bulk shipments, or pharmaceutical compositions. An assayable amount of a compound of the invention is an amount which is readily measurable by standard assay procedures and techniques as are well known and appreciated by those skilled in the art. Assayable amounts of a compound of the invention will generally vary from about 0.001 wt % to about 80 wt % of the entire weight of the composition. Inert carriers include any material which does not degrade or otherwise covalently react with a compound of formulae (1–4). Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers.

"Pharmaceutically acceptable carriers" for therapeutic use are well known in the pharmaceutical art, and are described, for example, in Remingtons Pharmaceutical Sciences, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

Thus, the present invention provides a pharmaceutical or veterinary composition (hereinafter, simply referred to as a pharmaceutical composition) containing a compound of formulae (1–4) as described above, in admixture with a pharmaceutically acceptable carrier. The invention further provides a composition, preferably a pharmaceutical composition, containing an effective amount of a compound of (1–4) as described above, in association with a pharmaceutically acceptable carrier.

The pharmaceutical compositions of the present invention may be in any form which allows for the composition to be administered to a patient. For example, the composition may be in the form of a solid, liquid or gas (aerosol). Typical routes of administration include, without limitation, oral, topical, parenteral, sublingual, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a patient take the form of one or more dosage units, where for example, a tablet may be a single dosage unit, and a container of a compound of formulae (1–4) in aerosol form may hold a plurality of dosage units.

Materials used in preparing the pharmaceutical compositions should be pharmaceutically pure and non-toxic in the amounts used. It will be evident to those of ordinary skill in the art that the optimal dosage of the active ingredient(s) in the pharmaceutical composition will depend on a variety of factors. Relevant factors include, without limitation, the type of subject (e.g., human), the particular form of the active ingredient, the manner of administration and the composition employed.

In general, the pharmaceutical composition includes an (where "a" and "an" refers here, and throughout this specification, as one or more) active compound of formulae (1–4) as described herein, in admixture with one or more carriers. The carrier(s) may be particulate, so that the compositions are, for example, in tablet or powder form. The carrier(s) may be liquid, with the compositions being, for example, an oral syrup or injectable liquid. In addition, the carrier(s) may be gaseous, so as to provide an aerosol composition useful in, e.g., inhalatory administration.

When intended for oral administration, the composition is preferably in either solid or liquid form, where semi-solid, semi-liquid, suspension and gel forms are included within the forms considered herein as either solid or liquid.

As a solid composition for oral administration, the composition may be formulated into a powder, granule, compressed tablet, pill, capsule, chewing gum, wafer or the like form. Such a solid composition will typically contain one or more inert diluents or edible carriers. In addition, one or more of the following adjuvants may be present: binders such as carboxymethylcellulose, ethyl cellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When the composition is in the form of a capsule, e.g., a gelatin capsule, it may contain, in addition to materials of the above type, a liquid carrier such as polyethylene glycol, cyclodextrin or a fatty oil.

The composition may be in the form of a liquid, e.g., an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or digylcerides which may serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid composition intended for either parenteral or oral administration should contain an amount of a compound of formulae (1–4) such that a suitable dosage will be obtained. Typically, this amount is at least 0.01% of a compound of the invention in the composition. When intended for oral administration, this amount may be varied to be between 0.1% and about 70% of the weight of the composition. Preferred oral compositions contain between about 4% and about 50% of the active compound of formulae (1–4). Preferred compositions and preparations according to the present invention are prepared so that a parenteral dosage unit contains between 0.01% to 1% by weight of active compound.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, beeswax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of formulae (1–4) of from about 0.1% to about 10% w/v (weight per unit volume).

The composition may be intended for rectal administration, in the form, e.g., of a suppository which will melt in the rectum and release the drug. The composition for rectal administration may contain an oleaginous base as a suitable nonirritating excipient. Such bases include, without limitation, lanolin, cocoa butter and polyethylene glycol.

The composition may include various materials which modify the physical form of a solid or liquid dosage unit. For example, the composition may include materials that form a coating shell around the active ingredients. The materials which form the coating shell are typically inert, and may be selected from, for example, sugar, shellac, and other enteric coating agents. Alternatively, the active ingredients may be encased in a gelatin capsule.

The composition in solid or liquid form may include an agent which binds to the active component(s) and thereby assists in the delivery of the active components. Suitable agents which may act in this capacity include a monoclonal or polyclonal antibody, a protein or a liposome.

The pharmaceutical composition of the present invention may consist of gaseous dosage units, e.g., it may be in the form of an aerosol. The term aerosol is used to denote a variety of systems ranging from those of colloidal nature to systems consisting of pressurized packages. Delivery may be by a liquefied or compressed gas or by a suitable pump system which dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, spacers and the like, which together may form a kit. Preferred aerosols may be determined by one skilled in the art, without undue experimentation.

Whether in solid, liquid or gaseous form, the pharmaceutical composition of the present invention may contain one or more known pharmacological agents used in the treatment of inflammation (including arthritis).

The pharmaceutical compositions may be prepared by methodology well known in the pharmaceutical art.

A composition intended to be administered by injection can be prepared by combining the compound of formulae (1–4) with water so as to form a solution. A surfactant may be added to facilitate the formation of a homogeneous solution or suspension. Surfactants are compounds that non-covalently interact with the compound of formulae (1–4) so as to facilitate dissolution or homogeneous suspension of the active compound in the aqueous delivery system.

The compounds disclosed herein of formulae 1, 2, 3 or 4 (i.e., compounds of formulae (1–4), or compounds of the present invention), or compositions comprising one of more of these compounds and a pharmaceutically acceptable carrier, diluent or excipient, may be used in a method for treating or preventing an inflammatory condition or disease in a patient, where the method comprises administering to the patient in need thereof an amount of a compound or composition according to the present invention, where the amount is effective to treat or prevent the inflammatory condition or disease of the patient.

The inflammatory condition or disease may be an autoimmune condition or disease; the inflammatory condition or disease may involve acute or chronic inflammation of bone and/or cartilage compartments of joints; the inflammatory condition or disease may be an arthritis selected from rheumatoid arthritis, gouty arthritis or juvenile rheumatoid arthritis; the inflammatory condition or disease may be asthma; the condition or disease may be associated with the disregulation of T-cells; the condition or disease may be associated with elevated levels of inflammatory cytokines (e.g., wherein the inflammatory cytokine is IL-2, or wherein the inflammatory cytokine is IFN-γ, or wherein the inflammatory cytokine is TNF-α); the inflammatory condition or disease may be multiple sclerosis; the inflammatory condition or disease may be pulmonary sarcadosis; the inflammatory condition or disease may be ocular inflammation or allergy; the inflammatory condition or disease may be an inflammatory bowel disease (e.g., Crohn's disease or ulcerative colitis); and the inflammatory condition or disease may be an inflammatory cutaneous disease (e.g., psoriasis or dermatitis).

Furthermore, the present invention provides a method for modulating intracellular cyclic adenosine 5'-monophosphate levels within a patient, comprising administering to a patient in need thereof an amount of a compound or composition according to the present invention, wherein the amount is effective to modulate the intracellular cyclic adenosine 5'-monophosphate levels of the patient. The patient may have an inflammatory condition or disease.

Furthermore, the present invention provides a method for treating or preventing a disease or condition in a patient, where the disease or condition is associated with pathological conditions that are modulated by inhibiting enzymes associated with secondary cellular messengers, the method comprising administering to a patient in need thereof an amount of a compound or a composition of the present invention, wherein the amount is effective to treat or prevent a disease or condition associated with pathological conditions that are modulated by inhibiting enzymes associated with secondary cellular messengers. The enzyme may be a cyclic AMP phosphodiesterase; or the enzyme may be a phosphodiesterase 4; or the enzyme may be a phosphodiesterase 3; or the enzymes may be both of phosphodiesterase 4 and phosphodiesterase 3; or the enzyme may be a cyclic GMP phosphodiesterase.

Furthermore, the present invention provides a method of treating or preventing transplant rejection in a patient, comprising administering to a patient in need thereof an amount of a compound or composition of the present invention, where the amount is effective to treat or prevent transplant rejection in the patient. The rejection may be due to graft versus host disease.

Furthermore, the present invention provides a method of treating or preventing uncontrolled cellular proliferation in a patient, comprising administering to a patient in need thereof an amount of a compound or composition according to the present invention, where the amount is effective to treat or prevent uncontrolled cellular proliferation in the patient. The uncontrolled cellular proliferation may be caused by a cancer selected from leukemia and solid tumors.

Furthermore, the present invention provides a method of treating or preventing conditions associated with the central nervous system (CNS) in a patient, comprising administering to a patient in need thereof an amount of a compound or composition according to the present invention, where the amount is effective to treat or prevent conditions associated with the central nervous system (CNS) in the patient. The condition associated with the central nervous system (CNS) may be depression.

In a method of the present invention, a compound of formulae (1–4), or a composition comprising one or more compounds of formulae (1–4) and a pharmaceutically acceptable carrier, diluent or excipient, may, although need not, achieve one or more of the following desired results in the subject to whom has been administered a compound of formulae (1–4) as defined above, or a composition containing one of these compounds and a pharmaceutically acceptable carrier, diluent or excipient:

1. Inhibition of reactive oxygen species generation from primary neutrophils;
2. Inhibition of neutrophil chemotaxis;
3. Inhibition of TNF-α production;
4. Inhibition of edema;
5. Oxygen radical scavenging;
6. Inhibition of cyclic-AMP phosphodiesterases 1, 3 and/or 4, and related PDEs such as PDE7;
7. Potentiate induction of CRE-mediated transcription activity in human monocytic cells;
8. Inhibition of PDE, preferably PDE4, PDE3, or PDE3 and PDE4;
9. Inhibition of cytokine production by activated T-cell subsets;
10. Inhibition of neutrophil myeloperoxidase release;
11. Low ratio of $IC_{50}PDE4(cat):IC_{50}PDE4(HARBS)$;
12. Inhibition of graft rejection;
13. Inhibition of clinical and histopathological parameters of disease in inflammatory bowel disease; and
14. Inhibition of clinical and histopathological parameters of arthritis in a murine collage-induced arthritis model.

Thus, the inventive method may be used to treat inflammation, including both acute and chronic inflammation as well as certain proliferative disorders (cancers). As used herein, inflammation includes, without limitation, ankylosing spondylitis, arthritis (where this term encompasses over 100 kinds of rheumatic diseases), asthma, Crohn's disease, fibromyalgia syndrome, gout, inflammations of the brain (including multiple sclerosis, AIDS dementia, Lyme encephalopathy, herpes encephalitis, Creutzfeld-Jakob disease, and cerebral toxoplasmosis), emphysema, inflammatory bowel disease, irritable bowel syndrome, ischemia-reperfusion injury juvenile erythematosus pulmonary sarcoidosis, Kawasaki disease, osteoarthritis, pelvic inflammatory disease, psoriatic arthritis (psoriasis), rheumatoid arthritis, psoriasis, tissue/organ transplant, scleroderma, spondyloarthropathies, systemic lupus erythematosus, pulmonary sarcoidosis, and ulcerative colitis. As used herein, proliferative disorders includes, without limitation, all leukemias and solid tumors that are susceptible to undergoing differentiation or apoptosis upon interruption of their cell cycle.

The inventive method provides for administering a therapeutically effective amount of a compound of formulae (1–4), including salts, compositions etc. thereof. As used herein, the actual amount encompassed by the term "therapeutically effective amount" will depend on the route of administration, the type of warm-blooded animal being treated, and the physical characteristics of the specific warm-blooded animal under consideration. These factors and their relationship to determining this amount are well known to skilled practitioners in the medical arts. This amount and the method of administration can be tailored to achieve optimal efficacy but will depend on such factors as weight, diet, concurrent medication and other factors which those skilled in the medical arts will recognize.

An effective amount of a compound or composition of the present invention will be sufficient to treat inflammation in a warm-blooded animal, such as a human. Methods of administering effective amounts of anti-inflammatory agents are well known in the art and include the administration of inhalation, oral or parenteral forms. Such dosage forms include, but are not limited to, parenteral solutions, tablets, capsules, sustained release implants and transdermal delivery systems; or inhalation dosage systems employing dry powder inhalers or pressurized multi-dose inhalation devices.

The dosage amount and frequency are selected to create an effective level of the agent without harmful effects. It will generally range from a dosage of about 0.01 to 100 mg/Kg/day, and typically from about 0.1 to 10 mg/Kg/day where administered orally or intravenously. Also, the dosage range will be typically from about 0.01 to 1 mg/Kg/day where administered intranasally or by inhalation.

The compounds of formulae (1–4) including the compounds used in the methods and compositions set forth above, may be prepared according to the Schemes set forth in the following examples. The following examples are offered by way of illustration and not by way of limitation.

Unless otherwise stated, flash chromatography and column chromatography may be accomplished using Merck silica gel 60 (230–400 mesh). Flash chromatography may be carried out according to the procedure set forth in: "Purification of Laboratory Chemicals", 3rd. edition, Butterworth-Heinemann Ltd., Oxford (1988), Eds. D. D. Perrin and W. L. F. Armarego, page 23. Column chromatography refers to the process whereby the flow rate of eluent through a packing material is determined by gravity. In all cases flash chromatography and radial chromatography may be used interchangeably. Radial chromatography is performed using silica gel on a Chromatotron Model #7924T (Harrison Research, Palo Alto, Calif.). Unless otherwise stated, quoted $R_f$ values are obtained by thin layer chromatography using Silica Gel 60 $F_{254}$ (Merck KGaA, 64271, Darmstadt, Germany).

Also, unless otherwise stated, chemical reactants and reagents were obtained from standard chemical supply houses, such as Aldrich (Milwaukee, Wis.; www.aldrich.sial.com); EM Industries, Inc. (Hawthorne, N.Y.; www.emscience.com); Fisher Scientific Co. (Hampton, N.H.; www.fischer1.com); and Lancaster Synthesis, Inc. (Windham, N.H.; www.lancaster.co.uk). Gases were obtained from Praxair (Vancouver, B.C.). Cell lines, unless otherwise stated, where obtained from public or commercial sources, e.g., American Tissue Culture Collection (ATCC, Rockville, Md.).

EXAMPLES

Compound 12, a representative compound of the invention, is prepared according to Schemes 1 and 2. Any number of compounds related to compound 12 could be produced using similar methodology but starting with different cinnamic acids. Compound 12 has the S-configuration at carbon 3 (C3) which is directed by the configuration of the chiral auxiliary (which has the S-configuration) in compound 4. Alternatively the R-configuration at C3 in compound 12 is generated using the chiral auxiliary with the opposite configuration (R). In the compounds generated using methodology in Schemes 1 and 2, the products have an isomeric mixture at C5. Alternatively, compounds with fixed configurations at this center (C5) are generated according to Schemes 3 and 4. Thus all of the diastereoisomers can be prepared using the appropriate methodology described in the following four Scheme s.

Focusing on compound 12, hydrogenation of the double bond in the commercially available starting material para-hydroxy-meta-methoxy cinnamic acid (1) is accomplished using $H_2$ in the presence of catalyst 10% Pd/C. Protection of the para-hydroxy functionality in compound 2 is followed by the addition of the (S)-(−)-4-benzyl-2-oxazolidinone moiety to form compound 4. The use of this chiral auxiliary to direct the stereochemistry at positions α to carbonyls has been well documented. Alkylation of compound 4 with a substituted aryl bromide prepared according to Scheme 2 stereoselectively affords compound 5. Lithium aluminum hydride reduction of compound 5 gives compound 6 containing the primary alcohol. Protection of the primary alcohol as the silyl ether is followed by hydroboration of the double bond to afford compound 8. Benzylation then desilylation gives compound 10 which is oxidized using Jones' conditions to give the carboxylic acid 11. Hydrogenation in acetic acid affords the desired cyclized product 12.

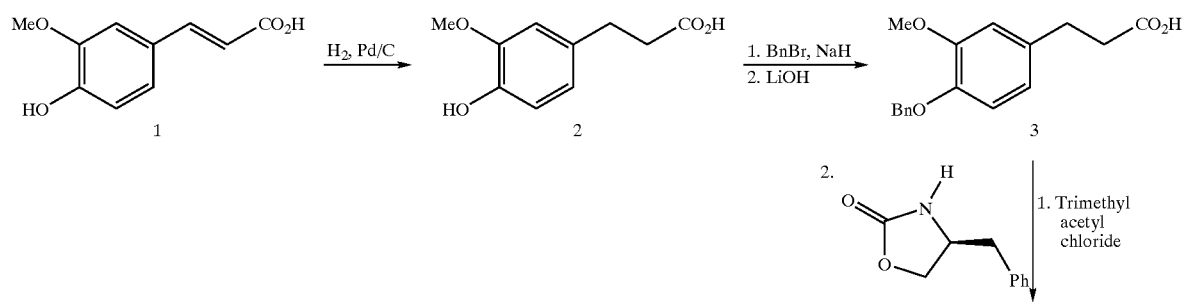

Scheme 1

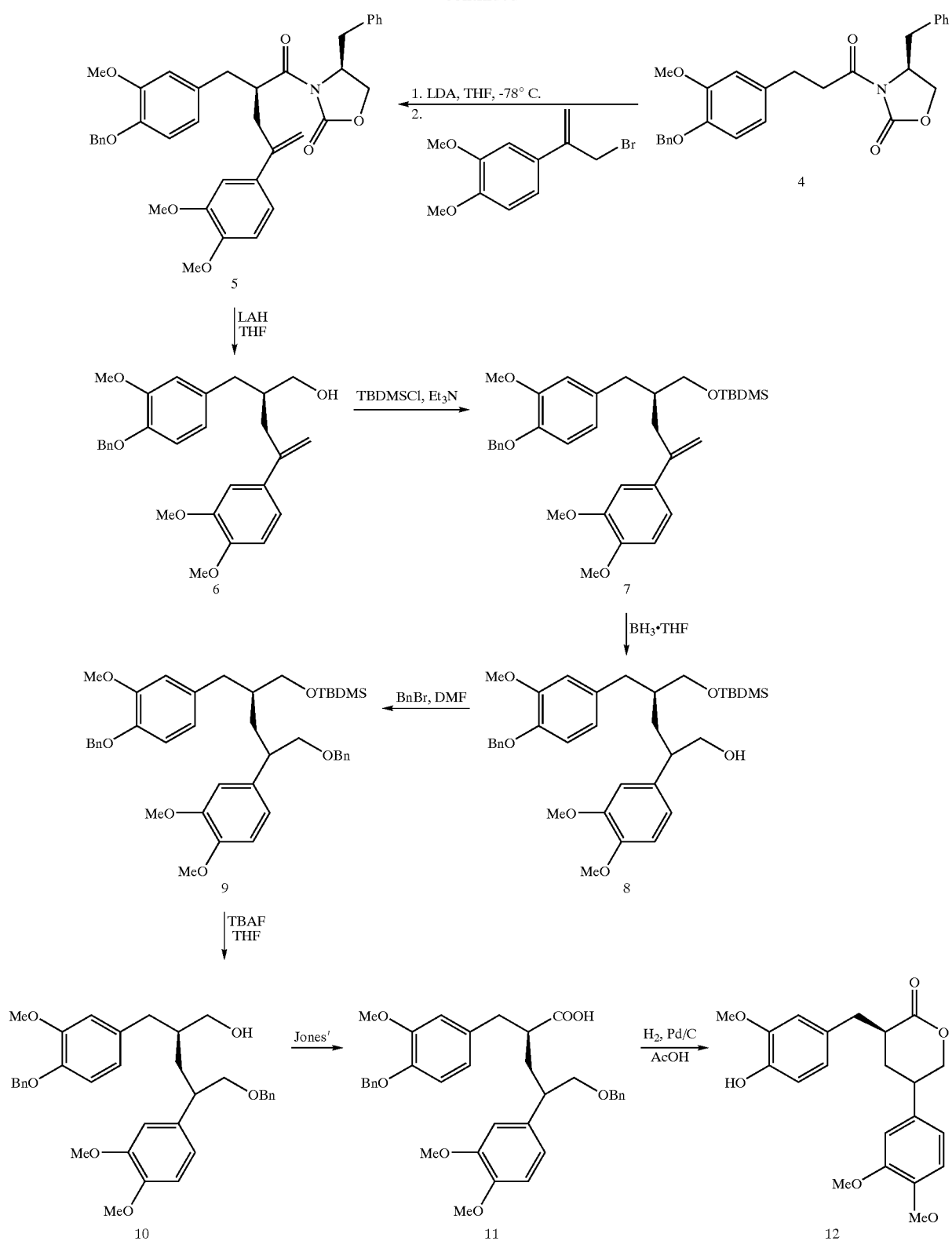

Scheme 2

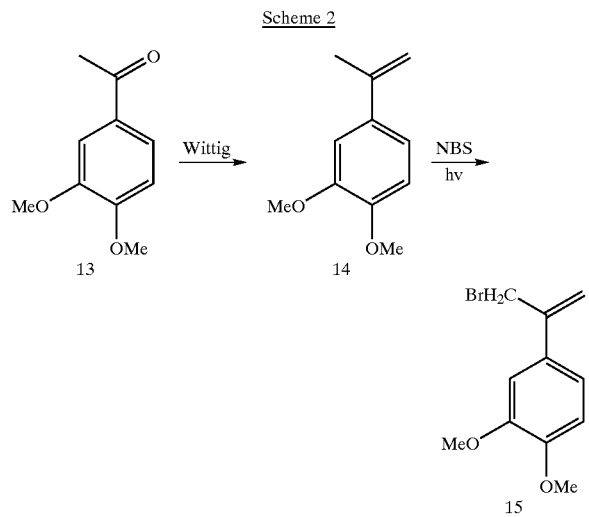

Synthesis of Compound 2

A mixture of compound 1 (3.0 g, 0.0155 moles) and 10% Pd/C (150 mg) in AcOH/EtOAc (30 mL, 2:1) was stirred under $H_2$ (balloon) for 14 hours. After filtering through a celite plug, the solvent was evaporated under reduced pressure to provide compound 2 (2.98 g, 98%) as a white solid which was used without further purification.

Synthesis of Compound 3

Compound 2 (2.71 g, 13.8 mmol) was dissolved in dry DMF (25 mL) and the solution was cooled to 0° C. NaH (2.21 g, 60% in mineral oil, 55.2 mmol) was added. After one hour, benzyl bromide (BnBr) (8.21 mL, 69.0 mmol) was added and the resulting mixture was stirred at room temperature for another 16 hours. The mixture was diluted with diethyl ether (200 mL) and washed with saturated $NaHCO_3$ solution (2×75 mL) then $H_2O$ (2×75 mL). The organic phase was dried with $MgSO_4$ and the solvent was evaporated to dryness to afford the crude benzyl ether compound. This crude mixture, which contained an amount of the corresponding benzyl ester, was dissolved in THF/MeOH/$H_2O$ (50 mL, 2:1:1). $LiOH \cdot H_2O$ (1.74 g, 41.4 mmol) was added and the reaction mixture was stirred at room temperature for 20 hours. After evaporation of the solvent to a small volume, the mixture was extracted with $CH_2Cl_2$ (3×100 mL). The combined organic layer was washed with $H_2O$ (2×75 mL), dried over $MgSO_4$, filtered, and the filtrate was evaporated to dryness. The residue was purified by column chromatography on silica gel (hexanes/EtOAc, 2:1) to afford compound 3 (3.2 g, 81%) as a white solid.

Synthesis of Compound 4

Solution 1: Triethylamine (2.9 mL, 21.0 mmol) followed by trimethyl acetyl chloride (2.4 mL, 19.3 mmol) were added to a solution of compound 3 (5.0 g, 17.5 mmol) in THF (40 mL) at 0° C. The mixture was stirred at 0° C. for one hour.

Solution 2: In a second flask, n-butlyllithium (7.7 mL, 19.3 mmol) was added to a solution of (S)-(−)-4-benzyl-2-oxazolidinone (3.4 g, 19.3 mmol) in dry THF (25 mL) at −78° C. This mixture was stirred for one hour and then added to the above anhydride (solution 1) via cannula. The mixture was warmed from 0° C. to room temperature then stirred for 24 hours. The solution was diluted with saturated $NaHCO_3$ solution (150 mL), and extracted with $CH_2Cl_2$ (4×100 mL). The combined organic layer was washed with $H_2O$ (2×100 mL), dried over $MgSO_4$, filtered, and the filtrate was evaporated to dryness. The residue was purified by column chromatography on silica gel (hexanes/EtOAc, 4:1) to afford compound 4 (7.05 g, 91%) as a white crystalline solid.

Synthesis of Compound 5

Compound 4 (3.0 g, 6.73 mmol) was dissolved in dry THF (25 mL), cooled to −78° C. and 2.0 M LDA (in THF, 3.5 mL, 7.0 mmol) was added slowly. After one hour, a solution of compound 15 (3.2 g, 13.5 mmol) in THF (10 mL) was added in one portion to the reaction solution, and the resulting mixture was warmed to 0° C. and stirred for an additional 2 hours. The excess base was quenched at 0° C. with saturated aqueous NaCl (100 mL), and the resulting solution was extracted with $CH_2Cl_2$ (3×100 mL). The combined organic layer was washed with saturated $NaHCO_3$ (2×100 mL), $H_2O$ (2×100 mL), dried over $MgSO_4$, filtered, and the filtrate was evaporated to dryness. The residue was purified by column chromatography on silica gel (hexanes/EtOAc, 3:1) to give compound 5 (2.63 g, 63%) as a colorless oil.

Synthesis of Compound 6

Compound 5 (2.4 g, 3.86 mmol) in THF (5 mL) was added to a suspension of $LiAlH_4$ (154.2 mg, 3.86 mmol) in THF (15 mL) at 0° C. The mixture was stirred for 2 hours at 0° C. and quenched with saturated $NaHCO_3$ (1 mL) and 10% NaOH (1 mL). The resulting mixture was filtered, the filtrate was diluted with diethyl ether (150 mL), and washed with saturated NaCl (2×50 mL). The organic layer was dried over $MgSO_4$, filtered, and the filtrate evaporated to dryness. The crude product was purified by flash column chromatography, eluted with 2:1 hexanes/EtOAc to afford compound 6 (1.47 g, 85%) as a colorless oil.

Synthesis of Compound 7

Compound 6 (1.50 g, 3.34 mmol) was stirred in dry $CH_2Cl_2$ (25 mL), then $Et_3N$ (0.56 mL, 4.01 mmol) was added followed by TBDMSCl (554.5 mg, 3.68 mmol). The mixture was stirred at room temperature for 6 hours, diluted with EtOAc (200 mL) and washed with saturated $NaHCO_3$ solution (2×75 mL) and saturated NaCl solution (2×75 mL). The organic layer was dried over $MgSO_4$, filtered, and the filtrate evaporated to dryness. The residue was purified by column chromatography on silica gel (hexanes/EtOAc, 5:1) to give compound 7 (1.74 g, 93%) as a colorless oil.

Synthesis of Compound 8

Compound 7 (560.0 mg, 0.995 mmol) was dissolved in THF (5 mL) and cooled to 0° C. $BH_3$-THF (1.0 M in THF, 1.0 mL, 1.0 mmol) was added dropwise. After the mixture was stirred at 0° C. for 5 hours, 10 N NaOH (1 mL) was added followed by 30% $H_2O_2$ (1 mL) and the mixture was stirred for another 16 hours at room temperature. THF was evaporated, the mixture was diluted with EtOAc (120 mL) and washed with saturated NaCl solution (2×30 mL). The organic layer was dried over $MgSO_4$, filtered and the filtrate was evaporated to dryness. The residue was purified by column chromatography on silica gel (hexanes/EtOAc, 2:1) to afford compound 8 (435.5 mg, 75%) as a colorless oil.

Synthesis of Compound 9

Compound 8 (900.4 mg, 1.72 mmol) was dissolved in DMF (10 mL) and cooled to 0° C., and NaH (137.7 mg, 60% in mineral oil, 3.44 mmol) was added. After one hour, benzyl bromide (BnBr) (0.41 mL, 3.44 mmol) was added and the resulting mixture was stirred at room temperature for another 16 hours. The mixture was diluted with diethyl ether (150 mL) and washed with $H_2O$ (2×30 mL). The organic phase was then dried with $MgSO_4$, filtered and the filtrate was evaporated to dryness. The residue was purified by column chromatography on silica gel (hexanes/EtOAc, 10:1) to afford compound 9 (915.1 mg, 88%) as a colorless oil.

Synthesis of Compound 10

Compound 9 (899.8 mg, 1.34 mmol) was dissolved in THF (10 mL), 1.0 M tetrabutylammonium fluoride (in THF, 2.7 mL, 2.7 mmol) was added and the resulting mixture was stirred at room temperature for 8 hours. The solvent was evaporated, then the mixture was dissolved in EtOAc (100 mL) and washed with $H_2O$ (2×40 mL). The organic phase was dried with $MgSO_4$, filtered and the filtrate was evaporated to dryness. The residue was purified by column chromatography on silica gel (hexanes/EtOAc, 2:1) to afford compound 10 (731.6 mg, 98%) as a colorless oil.

Synthesis of Compound 11

Compound 10 (570.7 mg, 1.03 mmol) was dissolved in acetone (12 mL) and cooled to 0° C. Jones' reagent (aqueous 1N $CrO_3$ in 25% $H_2SO_4$, 2.06 mL, 2.06 mmol) was added slowly over 5 minutes. The resulting dark green mixture was stirred for 40 minutes at room temperature, diluted with EtOAc (150 mL) and washed with 5% HCl (2×40 mL) and $H_2O$ (2×40 mL). The organic layer was then dried over $MgSO_4$, filtered, and the filtrate was evaporated to give crude compound 11 (547.0 mg) which was used without further purification.

Synthesis of Compound 12

A mixture of compound 11 (547.0 mg, 0.946 moles) and 10% Pd/C (78.0 mg) in AcOH (10 mL) was stirred under $H_2$ (balloon) for 48 hours. After filtering through a celite plug and evaporating the filtrate to dryness, the mixture was purified by reversed phase HPLC (column: Nova Pak HK $C_{18}$, M4063102 (Waters), 6µ, 19×300 mm) using 55% MeOH in water affording compound 12 (183.7 mg, 48% over two steps) as a colorless oil.

Synthesis of Compound 14

Potassium tert-butoxide (9.80 g, 0.0833 moles) was added to a suspension of $MePPh_3Br$ (29.8 g, 0.0833 moles) in dry toluene (180 mL) under argon. The mixture was stirred at room temperature for 2 hours. 3',4'-Dimethoxyacetophenone 13 (10.0 g, 0.0555 moles) was added as solid and the reaction mixture was stirred at room temperature for another 16 hours. Water (10 mL) was added slowly and the mixture was diluted with EtOAc (200 mL), washed with saturated $NaHCO_3$ (2×200 mL), then with $H_2O$ (2×200 mL). After drying over $MgSO_4$, the solution was filtered and the filtrate was concentrated in vacuo. The residue was purified by column chromatography on silica gel (hexanes/EtOAc, 19:1) to give compound 14 (9.31 g, 93%) as a colorless oil.

Synthesis of Compound 15

N-bromosuccinimide (4.93 g, 27.38 mmol) and benzoyl peroxide (80.0 mg, 0.330 mmol) were added to a solution of compound 14 (4.88 g, 27.38 mmol) in $CHCl_3$ (60 mL). The reaction mixture was stirred at room temperature for 30 minutes. The mixture was then diluted with EtOAc (200 mL), washed with saturated sodium chloride (100 mL), dried ($MgSO_4$), filtered and the filtrate was concentrated in vacuo. The resulting residue was purified using silica gel column chromatography (hexanes/EtOAc, 97:3) to yield compound 15 (2.44 g, 37%) as a light yellow oil.

Compounds with defined stereochemistry at C5 can be synthesized according to Scheme 3. Thus, the mixed anhydride, obtained from commercially available (3,4-dimethoxyphenyl) acetic acid 16 (Aldrich) and trimethylacetyl chloride, is reacted with the lithium anion of (S)-(−)-4-benzyl-2-oxazolidinone to afford compound 17. Enantioselective Michael addition of the titanium enolate of the chiral oxazolidinone 17 to tert-butyl acrylate provided compound 18 having the carboxylate functionality with a suitable protecting group. Hydrolysis of the chiral auxiliary with lithium hydroxide and hydrogen peroxide yields the carboxylic acid 19. Selective reduction of compound 19 with $BH_3$-THF gives compound 20 containing the primary alcohol. Removal of the t-butyl ester linkage with pTsOH.$H_2O$ in toluene gives the corresponding hydroxyl acid which is lactonized spontaneous to produce compound 21. Alkylation of the lithium anion of compound 21 with 4-(benzyloxy)-3-methoxybenzyl bromide affords compound 22 as a mixture of diastereomers (~1:1). Hydrogenation of compound 22 yields the desired product 23. Accordingly, any number of substituted benzyl bromides can be used to prepare compounds related to compound 23 with different substitution patterns about the benzyl ring.

Synthesis of Compound 17

Solution 1: Triethylamine (12.8 mL, 91.7 mmol) followed by trimethyl acetyl chloride (10.4 mL, 84.2 mmol) were added to a solution of (3,4-dimethoxyphenyl) acetic acid 16 (15.0 g, 76.5 mmol) in THF (120 mL) at 0° C. and the mixture was stirred for one hour.

Solution 2: In a second flask, n-bulyllithium (2.5 M in hexanes, 33.7 mL, 84.2 mmol) was added to a solution of (S)-(−)-4-benzyl-2-oxazolidinone (14.9 g, 84.2 mmol) in dry THF (75 mL) at −78° C. This solution was stirred for one hour and then added to solution 1 at 0° C. via cannula. The resultant mixture was warmed from 0° C. to room temperature, stirred for 24 hours, then diluted with saturated $NaHCO_3$ solution (300 mL), and extracted with $CH_2Cl_2$ (3×200 mL). The combined organic layer was washed with saturated NaCl (2×150 mL), dried over $MgSO_4$, filtered and the filtrate concentrated under reduced pressure. The residue was purified by column chromatography on silica gel (hexanes/EtOAc, 4:1) to afford compound 17 (19.04 g, 70%) as a white solid.

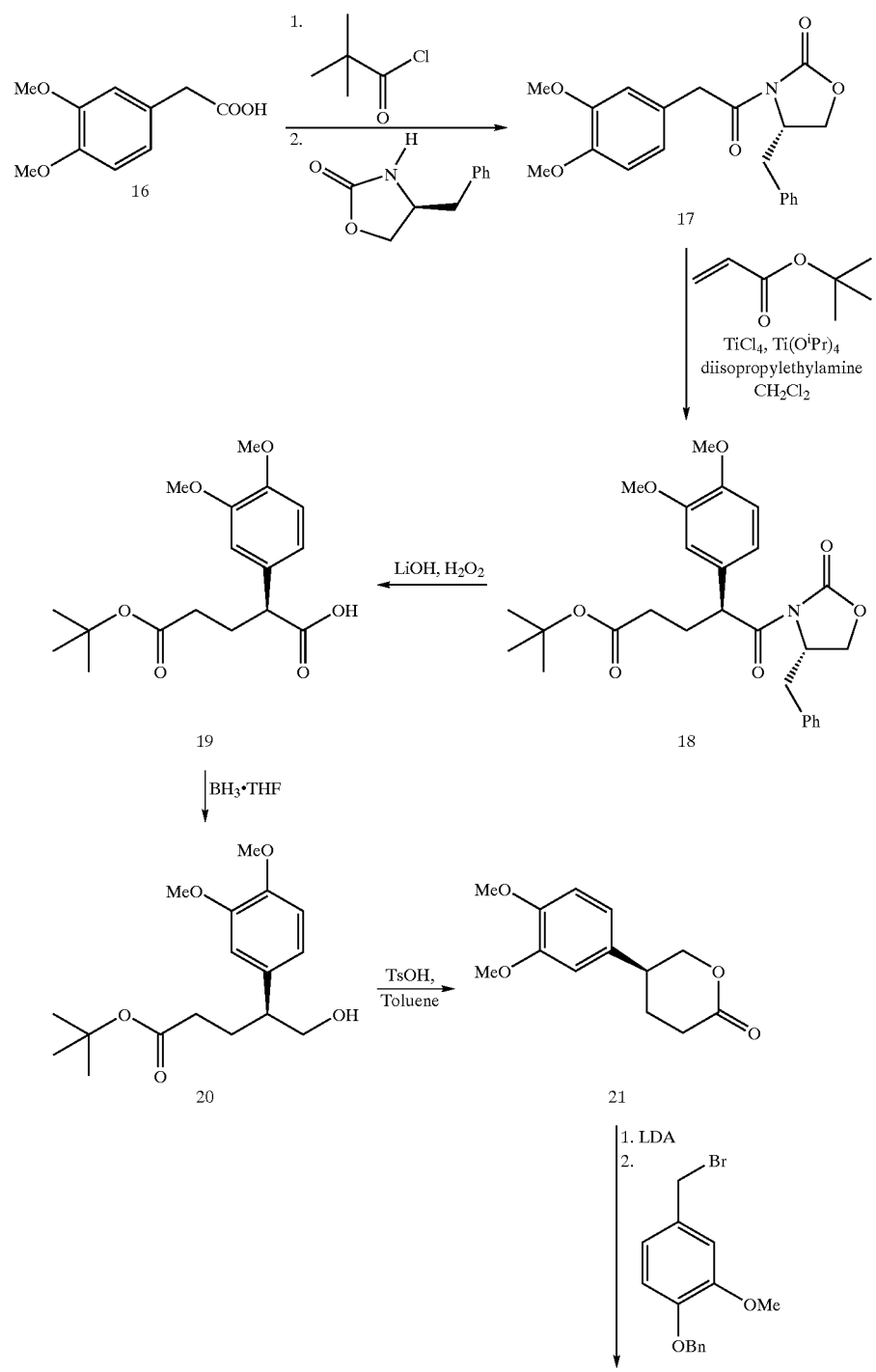

-continued

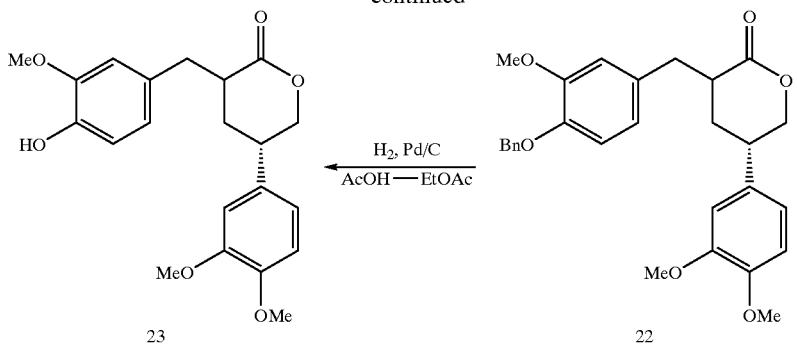

Synthesis of Compound 19

Titanium isopropoxide (0.42 mL, 1.41 mmol) was added slowly into a solution of titanium tetrachloride (0.50 mL, 4.50 mmol) in dry dichloromethane (10 mL) at 0° C. The resulting mixture was stirred at 0° C. for 5 minutes then diisopropylethylamine (1.04 mL, 5.91 mmol) was added. After 15 minutes, a solution of compound 17 (2.0 g, 5.63 mmol) in dichloromethane (10 mL) was added. The mixture was stirred for 90 minutes at 0° C., then tert-butyl acrylate (1.24 mL, 8.45 mmol) was added. The reaction mixture was warmed to room temperature and stirred for 36 hours and then diluted with saturated ammonium chloride (50 mL). The aqueous layer was extracted with dichloromethane (3×50 mL) and the combined organic layers were washed with 1 N HCl (2×75), water (2×75 mL) and saturated NaCl (2×75 mL). After drying over $MgSO_4$, filtration and evaporation of the filtrate in vacuo gave crude compound 18 (2.69 g) which was used without further purification.

Crude compound 18 (2.69 g) was dissolved in a mixture of 3:1 THF/water (85 mL) and cooled to 0° C. Lithium hydroxide monohydrate (466.6 mg, 11.12 mmol) and 30% hydrogen peroxide (2.5 mL, 22.25 mmol) were added and the mixture was stirred at 0° C. for 3 hours. A solution of sodium sulfite (3.06 g, 24.46 mmol) was added followed by 0.5 N sodium bicarbonate (41 mL). The mixture was stirred at room temperature for 2 hours and then concentrated in vacuo. The aqueous phase was diluted with 5% HCl to pH=2 and then extracted with EtOAc (3×75 mL). The combined organic layers were dried over $MgSO_4$, filtered and the filtrate concentrated in vacuo. The crude product was purified by column chromatography over silica gel using 0.2% acetic acid in 20% ethyl acetate/hexanes to afford compound 19 (1.09 g, 60% over two steps) as a light yellow oil.

Synthesis of Compound 20

$BH_3$-THF (1.0 M solution in THF, 37.6 mL, 0.0376 moles) was added dropwise over 20 minutes to a solution of compound 19 (12.18 g, 0.0376 moles) in dry THF (50 mL) at −18° C. The cooling bath was then removed, and the reaction mixture was stirred at room temperature for 16 hours. Saturated $NaHCO_3$ solution (50 mL) was added, and the aqueous phase was extracted with EtOAc (3×75 mL). The combined organic phase was washed with saturated NaCl (2×75 mL). The organic phase was dried over $MgSO_4$, filtered and the filtrate evaporated in vacuo. The residue was purified by column chromatography, eluting with 50% EtOAc in hexanes to afford compound 20 (10.52 g, 91%) as a colorless oil.

Synthesis of Compound 21

A solution of compound 20 (482.1 mg, 1.57 mmol) and p-toluenesulfonic acid monohydrate (44.9 mg, 0.236 mmol) in toluene (20 mL) was heated at 80° C. for 30 minutes. The reaction mixture was diluted with EtOAc (100 mL) and washed with saturated $NaHCO_3$ solution (2×40 mL). After drying with $MgSO_4$, the mixture was filtered, and the filtrate concentrated to give compound 21 (342.1 mg, 92%) as a white solid.

Synthesis of Compound 22

Preparation of 4-(benzyloxy)-3-methoxybenzyl bromide: To a solution of 4-(benzyloxy)-3-methoxybenzyl alcohol (9.0 g, 36.84 mmol) in anhydrous diethyl ether (150 mL) was slowly added $PBr_3$ (4.99 g, 18.42 mmol) via syringe, and the resulting mixture was stirred at room temperature for 3 hours. The mixture was diluted with diethyl ether (100 mL) and washed with saturated aqueous $NaHCO_3$ (2×75 mL) and brine (2×75 mL). The organic layer was dried over anhydrous $MgSO_4$, and the solvent was removed under reduced pressure to afford 4-(benzyloxy)-3-methoxybenzyl bromide (10.9 g, 96%) as a white solid.

n-Butyllithium (2.5 M solution in hexanes, 0.42 mL, 1.06 mmol) was added to a solution of diisopropylamine (0.15 mL) in dry THF (10 mL) at −78° C. The mixture was stirred at −78° C. for 1 hour, then a solution of compound 21 (226.8 mg, 0.96 mmol) in THF (5 mL) was added. After 1 hour, a solution of 4-(benzyloxy)-3-methoxybenzyl bromide (248.5 mg, 0.80 mmol, made according to literature procedures found in J. Org. Chem. 1996, 61, 9146–9155) in THF (1 mL) was added in one portion to the reaction, and the resulting mixture was stirred at −78° C. for an additional 4 hours. The excess base was quenched at 0° C. with saturated aqueous NaCl (10 mL), and the resulting solution was extracted with EtOAc (3×20 mL). The combined organic layer was washed with saturated NaCl (2×30 mL), dried over $MgSO_4$, filtered and the filtrate evaporated to dryness. The residue was purified by column chromatography on silica gel (hexanes/EtOAc, 2:1) to give compound 22 (152.1 mg, 41%) as a colorless oil.

Synthesis of Compound 23

A mixture of compound 22 (150.0 mg, 0.324 mmol) and 10% Pd/C (22.5 mg) in EtOAc/AcOH (4:1, 5 mL) was stirred under $H_2$ (balloon) for 2 hours. The mixture was then filtered through a celite plug and the filtrate was evaporated to dryness. The residue was purified by column chromatography on silica gel (hexanes/EtOAc, 3:2) to give compound 23 (106.3 mg, 88%) as a colorless syrup.

Certain compounds of the present invention contain two asymmetric carbon atoms and thus there are four possible diastereomers for these compounds. An examplary synthetic sequence to prepare a specific stereoisomer is summarized in Scheme 4 below. Thus, protection of the primary alcohol in compound 20 (Scheme 3) is accomplished using benzyl bromide (BnBr) and sodium hydride in DMF to yield benzyloxy derivative 24. Compound 24 is then converted to its corresponding acid 25 by reacting compound 24 with TFA. Synthesis of N-acyloxazolidinone derivative 26 from compound 25 is achieved using the same type of the reaction describe in previous sections. Stereoselective alkylation of compound 26 with 4-(benzyloxy)-3-methoxybenzyl bromide affords compound 27. Hydrolysis of the chiral auxiliary with lithium hydroxide and hydrogen peroxide yields the carboxylic acid 28. Hydrogenation of compound 28 in acetic acid and lactonization with pTsOH.H$_2$O in toluene gives the desired cyclized product 29 which has the 3R, 5S configuration. Accordingly, the three other diastereoisomers can be synthesized similarly but starting with different chiral oxazolidinones. For example, compound 30 which has the 3S, 5S configuration is synthesized using the intermediate analogous to compound 26 with the oxazolidinone containing the opposite (R) configuration.

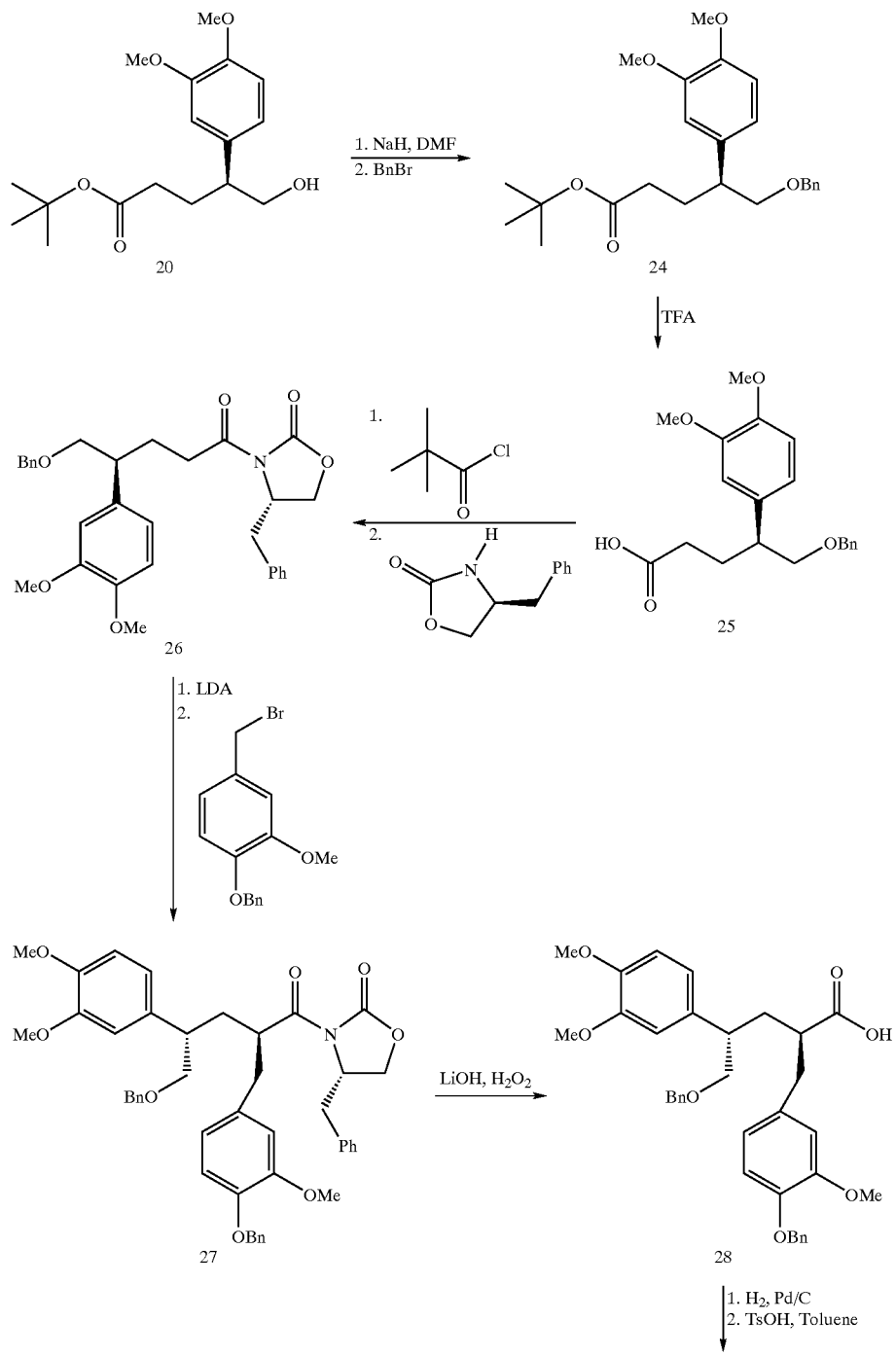

Scheme 4

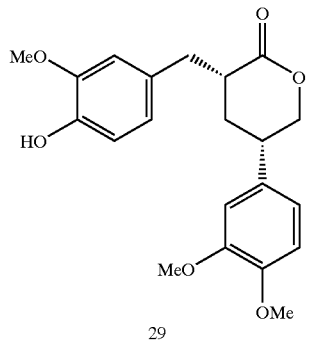

29

Synthesis of Compound 24

Compound 20 (9.45 g, 30.45 mmol) was dissolved in DMF (100 mL) and cooled to 0° C., NaH (2.43 g, 60% in mineral oil, 60.90 mmol) was added. After one hour, BnBr (7.2 mL, 60.90 mmol) was slowly added and the resulting mixture was stirred at room temperature for another 16 hours. The mixture was diluted with diethyl ether (600 mL) and washed with $H_2O$ (2×200 mL). The organic phase was dried over $MgSO_4$, filtered and the filtrate was concentrated in vacuo. The residue was purified by column chromatography on silica gel to afford compound 24 (10.73 g, 88%) as a colorless oil.

Synthesis of Compound 25

Trifluoroacetic acid (TFA) (25 mL) was added to a solution of compound 24 (10.0 g, 29.00 mmol) in dichloromethane (100 mL) at room temperature. This mixture was stirred for 16 hours and then concentrated in vacuo. The resulting oil was purified using silica gel column chromatography eluting with hexane-EtOAc-AcOH (75:23:2) to afford compound 25 (8.49 g, 85%) as a colorless oil.

Synthesis of Compound 26

Solution 1: Triethylamine (0.98 mL, 6.82 mmol) followed by trimethyl acetyl chloride (0.78 mL, 6.38 mmol) were added to a solution of compound 25 (2.00 g, 5.80 mmol) in THF (20 mL) at 0° C., and the mixture was stirred for one hour.

Solution 2: In a second flask, n-bulyllithium (2.6 mL, 6.38 mmol) was added to a solution of (S)-(−)-4-benzyl-2-oxazolidinone (1.13 g, 6.38 mmol) in dry THF (15 mL) at −78° C. This solution was stirred for one hour and then added to the above mixed anhydride (solution 1) via cannula. The resultant mixture at 0° C. was allowed to warm to room temperature. After stirring at room temperature for 24 hours, the mixture was diluted with a saturated $NaHCO_3$ solution (150 mL), and extracted with $CH_2Cl_2$ (4×60 mL). The combined organic layer was washed with $H_2O$ (2×50 mL), dried over $MgSO_4$, filtered and the filtrate concentrated in vacuo. The residue was purified by column chromatography on silica gel (hexanes/EtOAc, 4:1) to afford compound 26 (2.38 g, 81%) as a pale yellow oil.

Synthesis of Compound 27 n-BuLi (2.84 mL, 2.5 M solution in hexane, 7.10 mmol) was slowly added to a solution of diisopropylamine (1.08 mL, 7.70 mmol) in dry THF (55 mL) at −78° C. The reaction mixture was stirred at −78° C. under argon for 1 hour at −78° C. Compound 26 in THF (35 mL) at −78° C. was added and the reaction mixture was stirred for 1 hour. A solution of 4-(benzyloxy)-3-methoxybenzyl bromide (2.73 g, 8.88 mmol) in THF (10 mL) was then added in one portion to the reaction. The resulting mixture was warmed to 0° C. and stirred for an additional 2 hours. The excess base was quenched at 0° C. with saturated aqueous $NH_4Cl$ (100 mL), and the resulting solution was extracted with $CH_2Cl_2$ (3×100 mL). The combined organic layer was washed with saturated $NaHCO_3$ (2×50 mL), $H_2O$ (2×50 mL), dried over $MgSO_4$, filtered and the filtrate was evaporated to dryness. The residue was purified by column chromatography on silica gel (hexanes/EtOAc, 3:1) to give compound 27 (3.30 g, 76%) as a white foam.

Synthesis of Compound 28

$LiOH.H_2O$ (0.404 g, 9.60 mmol) and $H_2O_2$ (30% in $H_2O$, 2.2 mL, 19.20 mmol) were added to a solution of compound 27 (3.50 g, 4.80 mmol) in $THF/H_2O$ (3:1, 67 mL) at 0° C. The reaction mixture was stirred at 0° C. for 3 hours. A solution of $Na_2SO_3$ (2.66 g, 21.1 mmol, in water (30 mL)) was then added followed by a solution of 0.5 N $NaHCO_3$ (40 mL). The mixture was stirred for 2 hours, and then the THF was evaporated in vacuo. This aqueous solution was diluted with 2N HCl to pH=2 and then extracted with EtOAc (3×250 mL). The combined organic layers were dried over $MgSO_4$, filtered and the filtrate was evaporated to dryness. The resulting oil was purified using silica gel column chromatography eluting with hexane-EtOAc-AcOH (75:23:2) to afford compound 28 (2.23 g, 84%) as a colorless oil.

Synthesis of Compound 29

A mixture of compound 28 (1.86 g, 3.37 moles) and 10% Pd/C (180 mg) in AcOH (150 mL) was stirred under $H_2$ (balloon) 16 hours. The catalyst was removed by filtering the reaction mixture through a celite plug. The filtrate was evaporated to dryness and the residue was stirred with $pTsOH.H_2O$ (200 mg) in toluene (100 mL) at 80° C. for 30 minutes. The toluene was removed in vacuo and the residue was purified by column chromatography on silica gel (hexanes/EtOAc, 1:1) to afford compound 29 (1.06 g, 85%) as a white foam.

Compounds with different alkoxy groups on the phenyl ring can be synthesized according to Scheme 5. For example, compound 43 can be synthesized as follows. Commercially available 3-hydroxy-4-methoxybenzyl alcohol 31 is selectively protected as the benzyloxy derivative 32 by treatment of 31 with benzyl bromide and potassium carbonate in refluxing toluene to yield 89% of the desired product after crystallization. Compound 32 is then reacted with methanesulfonyl chloride in the presence of triethylamine and $CH_2Cl_2$ to afford compound 33, which is used without further purification. The crude product 33 is then placed in DMF and treated with potassium cyanide in the presence of 18-crown-6. After work-up and purification, the nitrile 34 is isolated in 91% yield over two steps. Hydrolysis of nitrile 34 with potassium hydroxide is then achieved to afford the desire carboxylic acid 35 in 95% yield. Treatment of compound 35 with trimethylacetyl chloride gives a mixed anhydride which is reacted with the lithium anion of (S)-(−)-4-benzyl-2-oxazolidinone to furnish compound 36 in 75% yield. Enantioselective Michael addition of the titanium enolate of the chiral oxazolidinone 36 to tert-butyl acrylate provides compound 37 having the carboxylate functionality with a suitable protecting group. Hydrogenation of compound 37 gave the alcohol in quantitative yield, which is converted to the cyclopentyloxy derivative 38 in 64% yield by treatment with cyclopentyl bromide, potassium carbonate and potassium iodide in DMF. Accordingly, any number of alkoxy derivatives on the phenyl ring can be made using the corresponding alkyl bromide or functionalized alkyl bromide. Hydrolysis of the chiral auxiliary with lithium hydroxide and hydrogen peroxide gives the carboxylic acid 39 in 91% yield. Selective reduction of compound 39 with $BH_3$-THF affords compound 40 (89% yield) containing the primary alcohol. The lactone 41 is obtained in 94% yield by treatment of compound 40 with pTsOH.$H_2O$ in toluene. Alkylation of compound 41 with 4-(benzyloxy)-3-methoxybenzyl bromide affords compound 42 in 70% yield. Hydrogenation of compound 42 in acetic acid gives the desired product 43 in 83% yield.

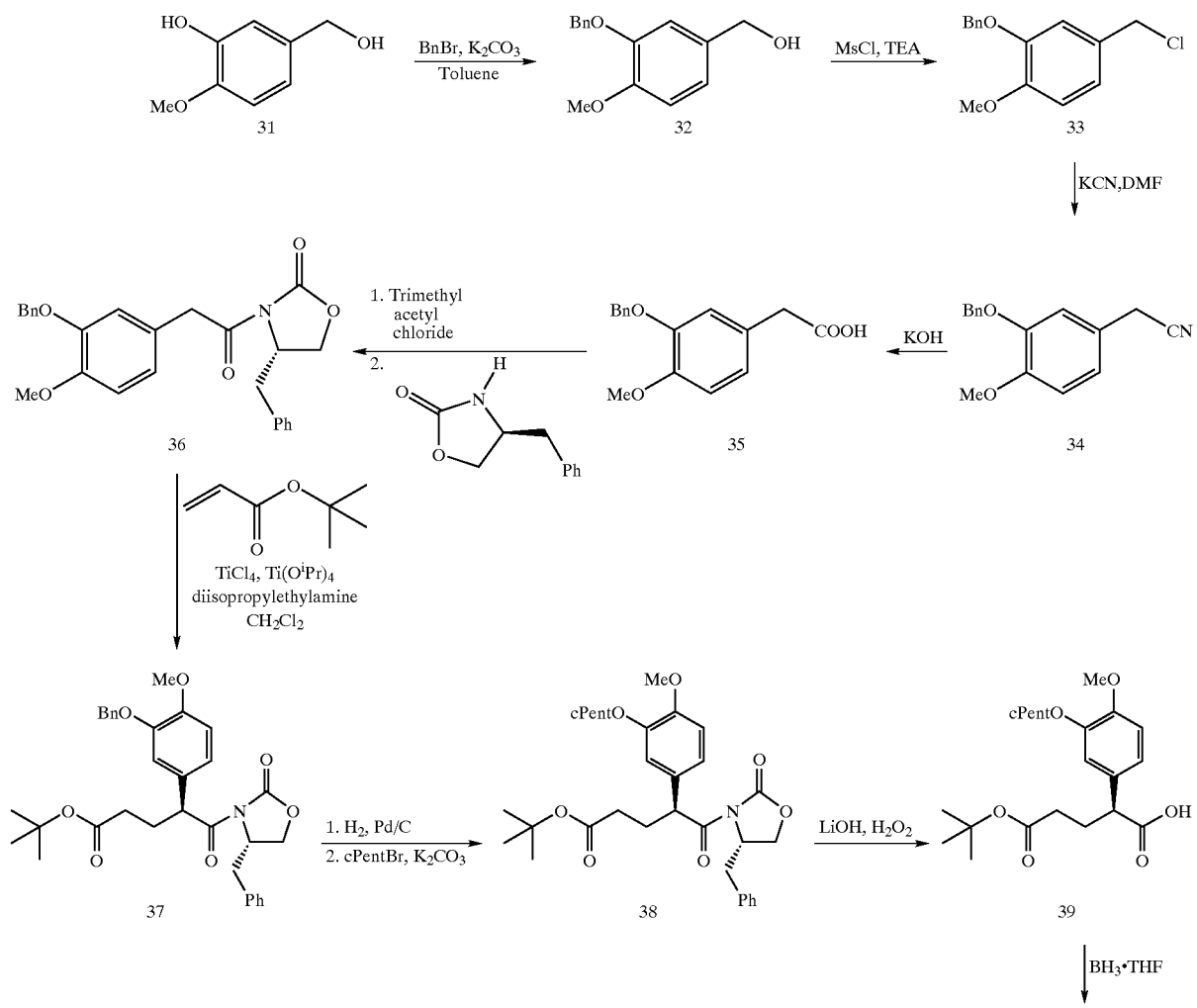

Scheme 5

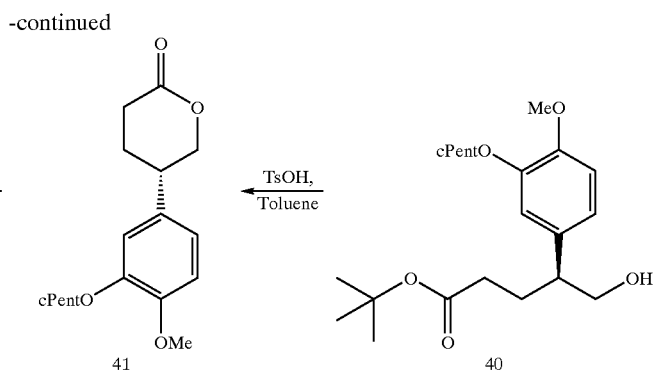
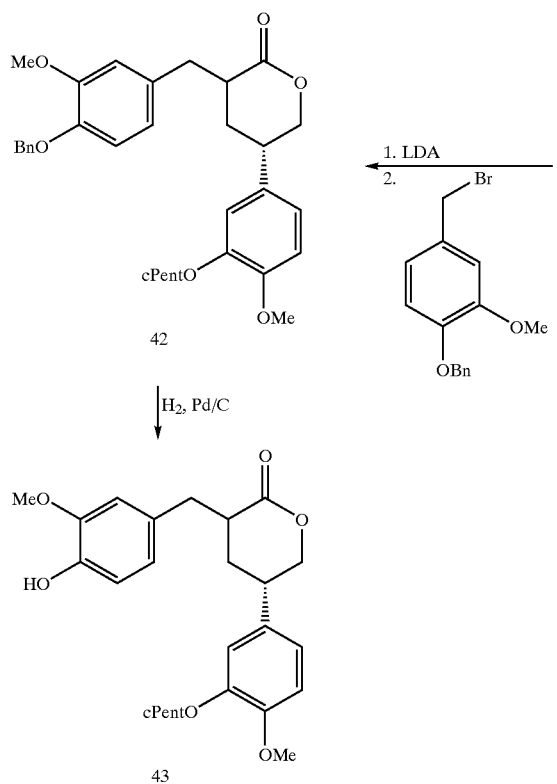

Synthesis of Compound 32

To a rapidly stirred slurry of 3-hydroxy-4-methoxybenzyl alcohol 31 (30.0 g, 195 mmol), potassium carbonate (62.2 g, 450 mmol), and 18-crown-6 (0.40 g, 1 mol %) in toluene (350 mL) was added a solution of benzyl bromide (25.6 g, 150 mmol) in toluene (150 mL) over 20 min. The reaction mixture was refluxed for 16 hours, after which the mixture was diluted with diethyl ether (400 mL) and washed successively with NaOH (1 N, 2×250 mL), saturated aqueous NaHCO$_3$ (2×250 mL), and brine (2×300 mL). The diethyl ether layer was dried over anhydrous MgSO$_4$, and the solvent was removed to provide a pale yellow solid (42.1 g) which was crystallized with EtOAc and hexanes to give compound 32 (32.7 g, 89%) as a white crystalline solid.

Synthesis of Compound 33

Compound 32 (30.0 g, 122.8 mmol) was dissolved in dichloromethane (300 mL) and cooled to 0° C., and then Et$_3$N (20.4 mL, 147.36 mmol) and methanesulfonyl chloride (11.40 mL, 147.36 mmol) were added. The ice bath was removed, and the solution was stirred at room temperature for 2 hours. The mixture was then diluted with dichloromethane (700 mL), washed successively with saturated aqueous NaHCO$_3$ (2×300 mL) and H$_2$O (2×300 mL). The organic phase was dried over MgSO$_4$, filtered and the filtrate was concentrated to afford compound 33 (33.08 g) as a pale yellow solid which was used for next step without further purification.

Synthesis of Compound 34

To a solution of crude 33 (33.08 g) in dry DMF (200 mL) were added KCN (15.99 g, 245.6 mmol) and 18-crown-6 (5.19 g, 19.65 mmol). The reaction mixture was stirred at room temperature for 18 hours, then poured into water (1.5 L). The precipitate was collected and dissolved in EtOAc (600 mL), washed with H$_2$O (2×200 mL) and brine (2×200 mL). The organic phase was dried over MgSO$_4$, filtered and the filtrate was concentrated to afford compound 34 (28.5 g, 91% yield over two steps) as an off-white solid.

Synthesis of Compound 35

A mixture of compound 34 (28.0 g, 110.5 mmol) and KOH (94.0 g, 167.5 mmol) in H$_2$O (170 mL) was heated at reflux for 12 hours. After the reaction mixture was cooled to room temperature, it was diluted with H$_2$O (1.6 L) and acidified with 12 N HCl to pH=2. The resulting precipitate was collected and dried over P$_2$O$_5$ to give compound 35 (28.8 g, 95%) as a white solid.

Synthesis of Compound 36

Solution 1: Triethylamine (17.7 mL, 126.92 mmol) followed by trimethyl acetyl chloride (14.3 mL, 116.35 mmol) were added to a solution of compound 35 (28.8 g, 105.77 mmol) in THF (250 mL) at 0° C. and the mixture was stirred for one hour.

Solution 2: In a second flask, n-butyllithium (2.5 M in hexanes, 46.5 mL, 116.35 mmol) was added to a solution of (S)-(−)-4-benzyl-2-oxazolidinone (20.6 g, 116.35 mmol) in dry THF (145 mL) at −78° C. This solution was stirred for one hour and then added to solution 1 at 0° C. The resultant mixture was warmed from 0° C. to room temperature, stirred for 24 hours, then diluted with saturated NaHCO$_3$ solution (400 mL), and extracted with CH$_2$Cl$_2$ (4×300 mL). The combined organic layer was washed with brine (200 mL), dried over MgSO$_4$, filtered and the filtrate concentrated under reduced pressure. The residue was purified by column chromatography on silica gel (hexanes/EtOAc, 4:1) to afford starting material (15.93 g) and compound 36 (15.30 g, 75% based on recovery of starting material) as a white solid.

Synthesis of Compound 37

Titanium isopropoxide (2.6 mL, 8.69 mmol) was added slowly into a solution of titanium tetrachloride (3.1 mL, 27.8 mmol) in dry dichloromethane (100 mL) at 0° C. The resulting mixture was stirred at 0° C. for 5 minutes then diisopropylethylamine (6.7 mL, 38.24 mmol) was added. After 15 minutes, a solution of compound 36 (15 g, 34.76 mmol) in dichloromethane (100 mL) was added. The mixture was stirred for 90 minutes at 0° C., then tert-butyl acrylate (15.3 mL, 104.28 mmol) was added. The reaction mixture was stirred for 3 days at 0° C. and then diluted with saturated ammonium chloride (300 mL). The aqueous layer was extracted with dichloromethane (3×300 mL) and the combined organic layers were washed with 5% HCl (2×400 mL), water (2×300 mL) and saturated NaCl (400 mL). After drying over MgSO$_4$, filtration and evaporation of the filtrate in vacuo gave crude compound 37 (21.0 g). A portion of crude 37 (2.1 g) was purified by silica gel column chromatography eluted with EtOAc/Hexanes (1:2) to furnish the pure compound 37 (1.55 g) as a syrup.

Synthesis of Compound 38

A mixture of compound 37 (1.55 g, 2.77 mmol) and 10% Pd/C (150 mg) in EtOAc/AcOH (5:1, 60 mL) was stirred under H$_2$ (balloon) for 18 hours. The mixture was filtered on celite and the filtrate was evaporated to dryness to provide the intermediate phenolic compound (1.30 g, 100%).

A suspension of the phenolic compound (0.30 g, 0.639 mmol), anhydrous K$_2$CO$_3$ (0.132 g, 0.958 mmol), and KI (5 mg) in dry DMF (1.5 mL) was stirred and heated to 65° C., and then cyclopentyl bromide (0.10 mL, 0.958 mmol) was added dropwise. The stirred mixture was heated at 65° C. for a further 21 hours. After cooling to room temperature, the reaction mixture was diluted with Et$_2$O (50 mL) and washed with H$_2$O (2×25 mL). The organic layer was dried with MgSO$_4$ and the solvent was evaporated. The residue was purified by silica gel column chromatography with hexanes/EtOAc (4:1) as eluent to yield compound 38 (0.22 g, 64%) as a colorless syrup.

Synthesis of Compound 39

Compound 38 (3.5 g, 6.51 mmol) was dissolved in THF/H$_2$O (3:1, 60 mL) and cooled to 0° C. Lithium hydroxide monohydrate (0.546 g, 13.02 mmol) and 30% hydrogen peroxide (2.98 mL, 26.04 mmol) were added and the mixture was stirred at 0° C. for 3 hours. A solution of sodium sulfite (3.61 g, 28.64 mmol) in water (19 mL) was added, followed by 0.5 N sodium bicarbonate (35 mL). The mixture was stirred at room temperature for 2 hours and then concentrated in vacuo. The aqueous phase was diluted with 5% HCl to pH=2 and then extracted with EtOAc (3×75 mL). The combined organic layers were dried over MgSO$_4$, filtered and the filtrate concentrated in vacuo. The crude product was purified by column chromatography over silica gel using 0.2% acetic acid in ethyl acetate/hexanes (1:4) as eluent to afford compound 39 (2.24 g, 91%) as a white solid.

Synthesis of Compound 40

BH$_3$-THF (1.0 M solution in THF, 2.70 mL, 2.70 mmol) was added dropwise over 40 minutes to a solution of compound 39 (2.23 g, 2.64 mmol) in dry THF (15 mL) at −18° C. The cooling bath was then removed, and the reaction mixture was stirred at room temperature for 18 hours. Saturated aqueous NaHCO$_3$ solution (15 mL) was added, and the aqueous phase was extracted with EtOAc (3×50 mL). The combined organic phase was washed with saturated NaCl (2×50 mL). The organic phase was dried over MgSO$_4$, filtered and the filtrate evaporated in vacuo. The residue was purified by silica gel column chromatography, eluting with 25% EtOAc in hexanes to afford compound 40 (1.91 g, 89%) as a colorless oil.

Synthesis of Compound 41

A solution of compound 40 (0.39 g, 1.07 mmol) and p-toluenesulfonic acid monohydrate (29 mg) in toluene (25 mL) was heated at 85° C. for 30 minutes. The toluene was removed in vacuo, and the residue was dissolved in dichloromethane (60 mL) and washed successively with saturated aqueous NaHCO$_3$ (20 mL) and brine (20 mL). The organic phase was dried over MgSO$_4$, filtered and the filtrate was concentrated to give compound 41 (0.293 g, 94%) as a white solid.

Synthesis of Compound 42

To a solution of compound 41 (0.29 g, 1.0 mmol) in dry THF (5 mL) under argon was slowly added LDA [1.20 mmol, prepared from n-BuLi (0.48 mL, 2.5 M solution in hexane, 1.20 mmol) and diisopropylamine (0.17 mL, 1.20 mmol)] in THF (2.5 mL) at −78° C. The mixture was stirred at −78° C. for one hour, and then HMPA (0.26 mL, 1.5 mmol) was added to the above mixture via syringe. After 15 minutes, 4-(benzyloxy)-3-methoxybenzyl bromide (0.614 g, 2.00 moles) in THF (1 mL) was added. The resulting mixture was slowly warmed to 0° C. and stirred for an additional 2 hours. The excess base was quenched at 0° C. with saturated aqueous NH$_4$Cl (15 mL), and the resulting solution was extracted with CH$_2$Cl$_2$ (3×50 mL). The combined organic layer was washed with brine (2×50 mL), dried over MgSO$_4$, filtered and the filtrate was evaporated to dryness. The residue was purified by column chromatography on silica gel (hexanes/EtOAc, 3:1) to give compound 42 (0.362 g, 70%) as a white foam.

Synthesis of Compound 43

A mixture of compound 42 (0.30 g, 0.581 mmol) and 10% Pd/C (30 mg) in EtOAc/AcOH (4:1, 10 mL) was stirred under H$_2$ (balloon) for 18 hours. The mixture was filtered on celite and the filtrate was evaporated to dryness. The residue was purified by column chromatography on silica gel eluted with hexanes/EtOAc (4:1) to afford compound 43 (0.205 g, 83%) as a white foam.

Synthesis of Lactam Compounds 51 and Related Analogues

δ-Lactams analogous to the δ-lactones can be synthesized according to Scheme 6. For example, conversion of compound 20 into the key intermediate 46 was achieved in a five steps sequence as follows. Treatment of compound 20 with zinc azide/bis-pyridine complex, triphenylphosphine and diisopropyl azodicarboxylate in toluene smoothly affords the corresponding azide 44 in 91% yield. Compound 44 is then hydrogenated in the presence of 10% Pd—C and the resulting amine 45 is converted into compound 46 (63% over two steps) by treatment with NaOH in DMF.

THF and alkylated with 4-(benzyloxy)-3-methoxybenzyl bromide to give the desired coupling products 48 and 49 in a ratio of 7.2:1 in 86% yield. These two isomers can be separated by silica gel column chromatography. De-O-benzylation of compound 49 using 10% Pd/C as catalyst proceeds readily and the phenol 50 is isolated in 98% yield. Further hydrogenolysis under high pressure can then afford compound 51.

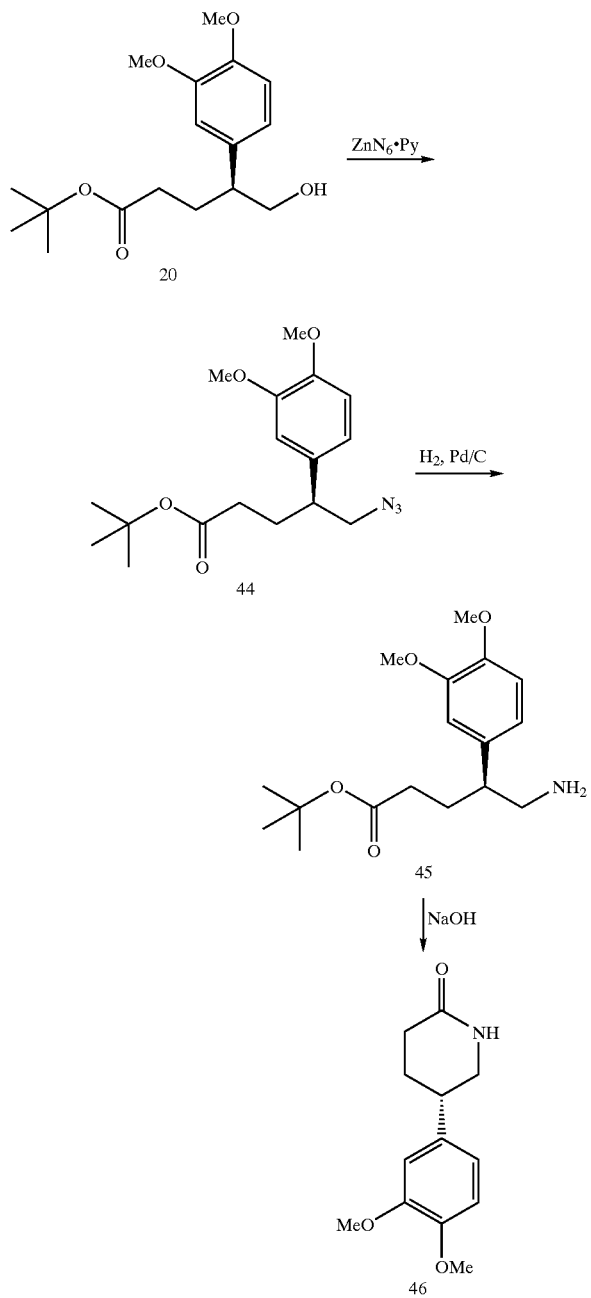

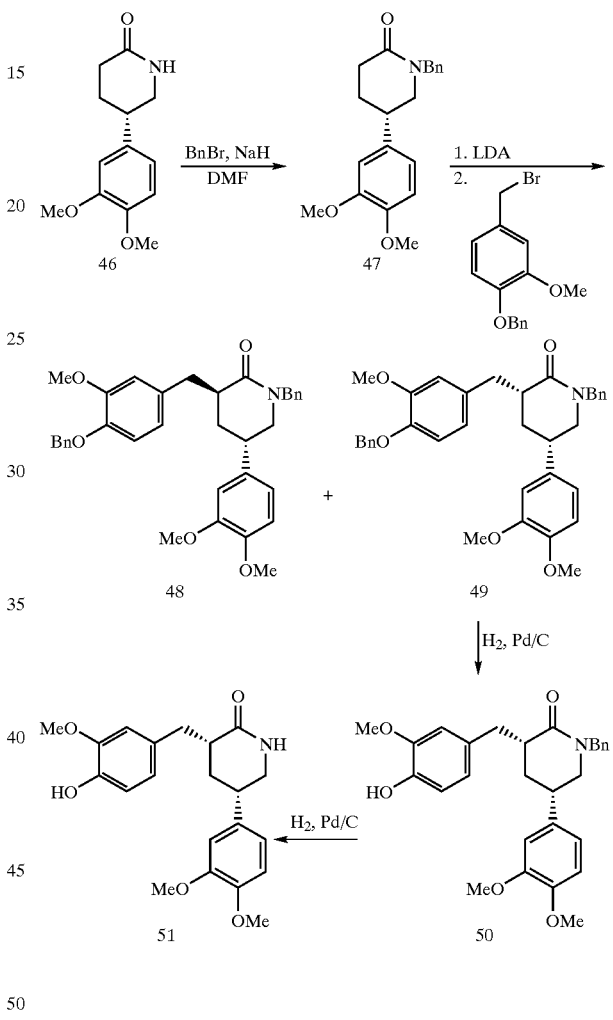

Towards the synthesis of compound 51, the first approach is depicted in Scheme 7. In this approach, compound 46 is treated with NaH and benzyl bromide in DMF to afford compound 47 in 80% yield. Compound 47 is then placed in Alternative methods to protect the lactam nitrogen can also be used as depicted in Scheme 8. For example, N-protection of 46 as the N-t-butoxycarbonylamide can be achieved using di-tert-butyldicarbonate and triethylamine in dichloromethane to give derivative 52 in 95% yield. Alkylation of compound 52 with 4-(benzyloxy)-3-methoxybenzyl bromide affords compound 53 in 67% yield. Compound 53 is a diasteromeric mixture. Removal of the N-BOC protecting group in compound 53 with trifluoroacetic acid in dichloromethane gives the product 54 in 74% yield. Hydrogenolysis of compound 54 using 10% Pd/C as catalyst provides the diastereomeric mixture 55 in 81% yield.

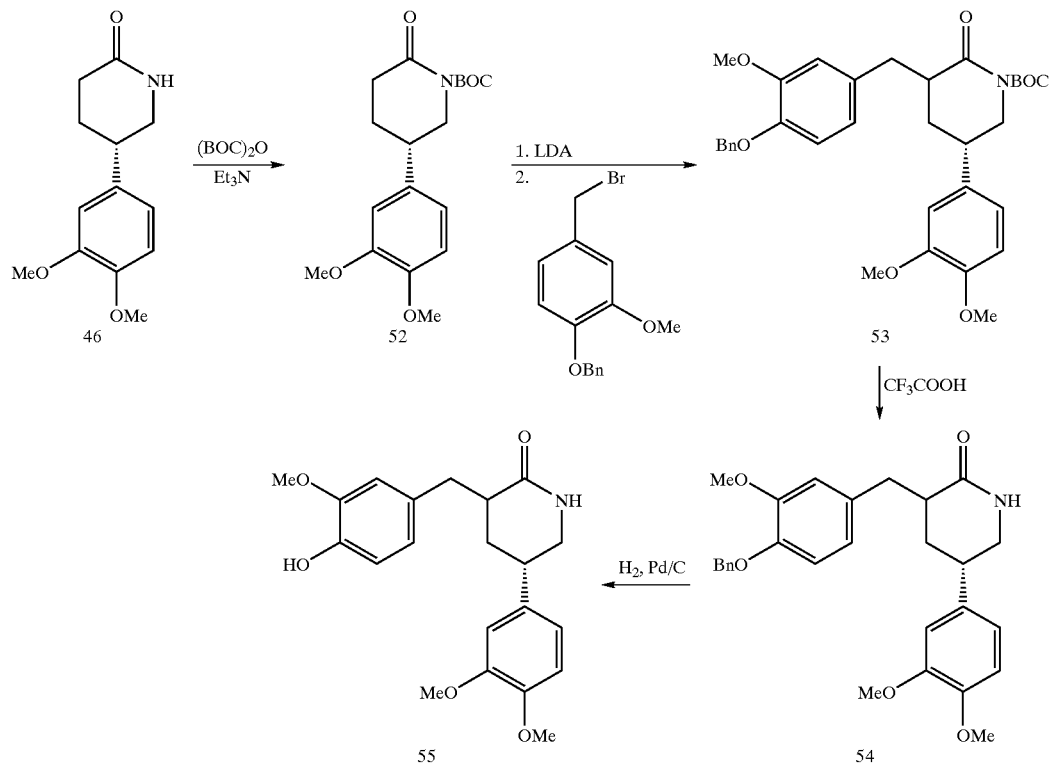

Synthesis of Lactam Compounds 61 and 62

In another example of preparing lactams, the synthesis of compounds 61 and 62 is achieved by the procedure depicted in Scheme 9. Treatment of compound 40 with zinc azide/bis-pyridine complex, triphenylphosphine and diisopropyl azodicarboxylate in toluene affords the corresponding azide 56. The crude compound 56 is then hydrogenated in the presence of 10% Pd—C to give compound 57 in 76% yield over two steps. The lactam cyclilization step involves a one-pot three-step reaction sequence employing tert-butyl ester solvolysis with p-toluenesulfonic acid monohydrate, esterification in methanol, and lactam cyclization upon addition of triethyl amine to provide compound 58 in a yield of 96% over the three steps. N-protection of the resulting 58 with di-tert-butyl dicarbonate and triethylamine in dichloromethane provides N-t-butoxycarbonylamide derivative 59 in 84% yield. Alkylation of compound 59 with LDA and 4-(benzyloxy)-3-methoxybenzyl bromide affords compound 60 in 74% yield. Compound 60 is a diasteromeric mixture with a R/S ratio of 1:1. Removal of the N-BOC protecting group in compound 60 with trifluoroacetic acid in dichloromethane gives the target product 61 in 74% yield. Hydrogenolysis of compound 61 using 10% Pd/C as catalyst provides the final product 62 in 81% yield.

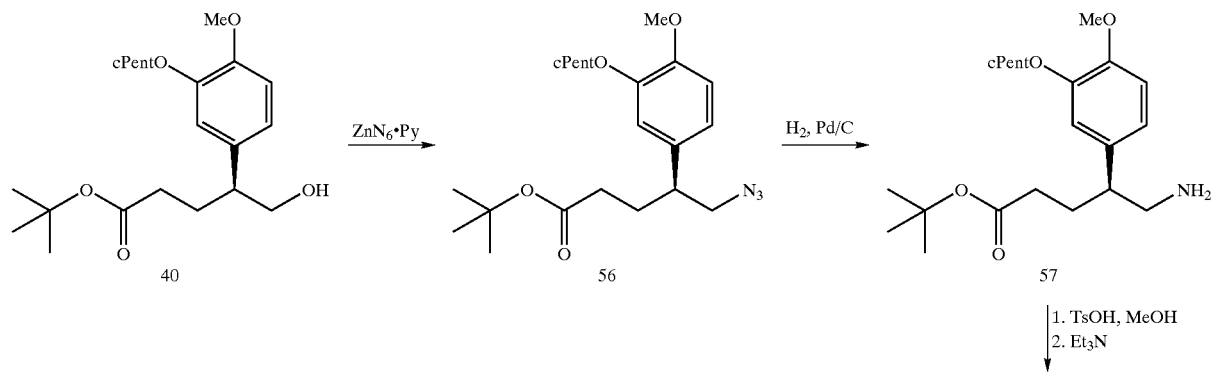

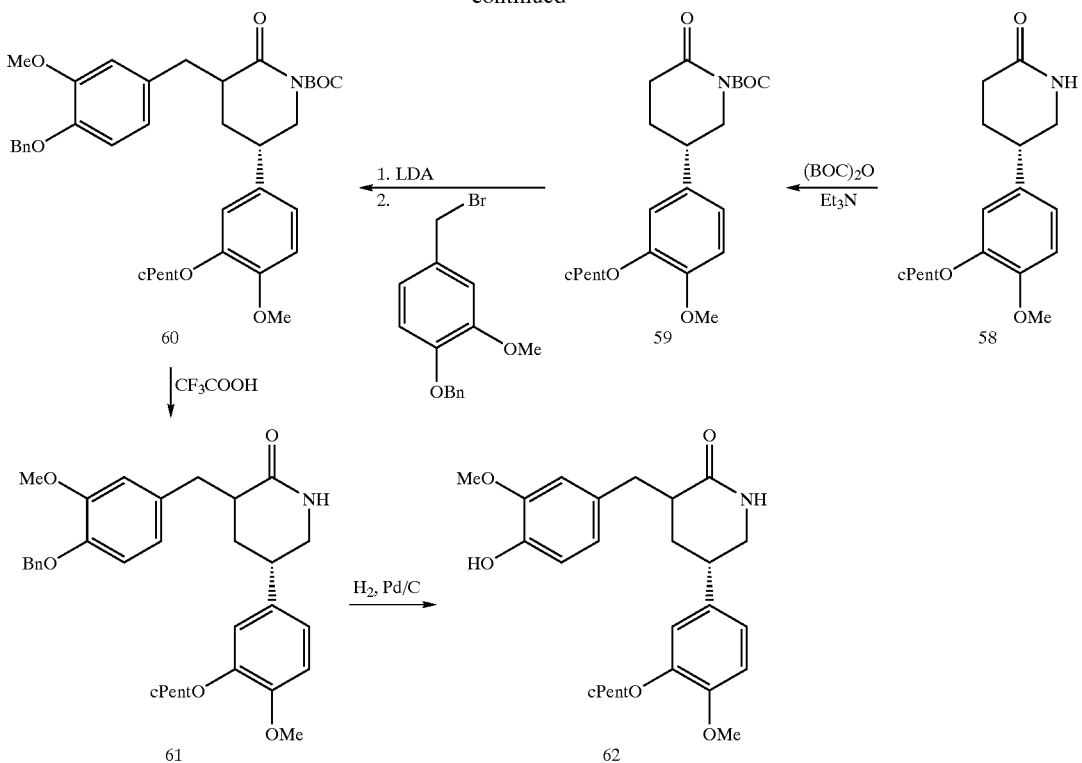

Synthesis of Compound 44

Preparation of ZnN$_6$.2Py complex: To a stirred solution of Zn(NO$_3$)$_2$.6H$_2$O (3.57 g, 12.0 mmol) in H$_2$O (6 mL) was added dropwise a solution of NaN$_3$ (1.56 g, 24.0 mmol) in H$_2$O (12 mL). The white suspension was brought to 50° C. in an oil bath, then pyridine (2.0 mL, 24.7 mmol) was added dropwise forming a dense white precipitate. Stirring was continued while the mixture was slowly cooled to room temperature. The salt was filtered, washed with ice cold water and dried in vacuo to give ZnN$_6$.2Py (2.99 g, 81%) as a white solid.

Diisopropyl azodicarboxylate (1.30 mL, 6.59 mmol) was added to a suspension of compound 20 (1.0 g, 3.30 mmol), ZnN$_6$.2Py (0.76 g, 2.47 mmol) and Ph$_3$P (1.73 g, 6.59 mmol) in anhydrous toluene (20 mL). The mixture was stirred at room temperature for 18 hours. The mixture was concentrated, and the residue was purified by column chromatography on silica gel eluted with hexanes/EtOAc (9:1) to afford compound 44 (1.01 g, 91%) as a colorless oil.

Synthesis of Compound 45

A mixture of compound 44 (1.00 g, 2.98 mmol) and 10% Pd/C (100 mg) in EtOAc (30 mL) was stirred under H$_2$ (balloon) for 18 hours. The mixture was filtered on celite and the filtrate was evaporated to dryness to give compound 45 (0.923 g, 100%) as a colorless syrup.

Synthesis of Compound 46

Sodium hydroxide (5 N, 0.14 mL, 0.70 mmol) was added to a solution of compound 45 (0.21 g, 0.68 mmol) in THF (1 mL) and MeOH (1 mL). The mixture was stirred at room temperature for 18 hours. The mixture was concentrated, and the residue was purified by column chromatography on silica gel eluted with hexanes/EtOAc (9:1) to afford compound 46 (0.091 g, 63%) as a white solid.

Synthesis of Compound 47

Compound 46 (0.184 g, 0.782 mmol) was dissolved in DMF (5 mL) and cooled to 0° C., NaH (0.0344 g, 60% in mineral oil, 0.860 mmol) was added. After two hours, benzyl bromide (0.14 mL, 1.173 mmol) was slowly added and the resulting mixture was stirred at room temperature for another 18 hours. The solvent was evaporated and the resulting residue was purified by column chromatography on silica gel eluted with EtOAc to afford compound 47 (0.203 g, 80%) as a white solid.

Synthesis of Compounds 48, 49

To a solution of compound 47 (0.23 g, 0.707 mmol) in dry THF (4 mL) under argon was slowly added LDA [0.85 mmol, prepared from n-BuLi (0.34 mL, 2.5 M solution in hexane, 0.85 mmol) and diisopropylamine (0.12 mL, 0.85 mmol)] in THF (2 mL) at −78° C. The mixture was stirred at −78° C. for one hour, and then HMPA (0.18 mL, 1.06 mmol) was added to the above mixture via syringe. After 15 minutes, 4-(benzyloxy)-3-methoxybenzyl bromide (0.434 g, 1.41 mmol) in THF (1 mL) was added. The resulting mixture was stirred for an additional 2 hours at −78° C. The excess base was quenched at 0° C. with saturated aqueous NH$_4$Cl (10 mL), and the resulting solution was extracted with EtOAc (3×30 mL). The combined organic layers were washed with brine (2×40 mL), dried over MgSO$_4$, filtered and the filtrate was evaporated to dryness. The residue was purified by column chromatography on silica gel eluted with hexanes/EtOAc (3:2) to give compounds 49 (0.295 g, 75.6%) and 48 (0.041 mg, 10.5%) as white foams.

Synthesis of Compound 50

A mixture of compound 49 (0.25 g, 0.453 mmol) and 10% Pd/C (50 mg) in EtOAc (20 mL) was stirred under H$_2$ (balloon) for 48 hours. The mixture was filtered on celite and the filtrate was evaporated to dryness to give compound 50 (0.204 g, 98%) as a white foam.

Synthesis of Compound 52

Di-tert-butyl dicarbonate (0.724 g, 3.32 mmol) was added to a solution of compound 46 (0.39 g, 1.66 mmol), $Et_3N$ (0.46 mL, 3.22 mmol) and DMAP (0.040 g) in $CH_2Cl_2$ (12 mL). The mixture was stirred at room temperature for 4 hours. The mixture was concentrated, and the residue was purified by column chromatography on silica gel eluted with hexanes/EtOAc (2:1) to afford compound 52 (0.543 g, 98%) as a white solid.

Synthesis of Compound 53

To a solution of compound 52 (0.54 g, 1.61 mmol) in dry THF (7 mL) under argon was slowly added LDA [1.93 mmol, prepared from n-BuLi (0.77 mL, 2.5 M solution in hexane, 1.93 mmol) and diisopropylamine (0.27 mL, 1.93 mmol)] in THF (4 mL) at −78° C. The mixture was stirred at −78° C. for one hour, and then HMPA (0.42 mL, 2.42 mmol) was added to the above mixture via syringe. After 15 minutes, 4-(benzyloxy)-3-methoxybenzyl bromide (0.989 g, 3.22 moles) in THF (2 mL) was added. The resulting mixture was stirred for an additional 4 hours at −78° C. The excess base was quenched at 0° C. with saturated aqueous $NH_4Cl$ (20 mL), and the resulting solution was extracted with EtOAc (4×50 mL). The combined organic layer was washed with saturated brine (2×50 mL), dried over $MgSO_4$, filtered and the filtrate was evaporated to dryness. The residue was purified by column chromatography on silica gel eluted with hexanes/EtOAc (4:1) to give compound 53 (0.604 g, 67%) as a white foam.

Synthesis of Compound 54

Trifluoroacetic acid (10 mL) was added to a solution of compound 53 (0.557 g, 0.990 mmol) in $CH_2Cl_2$ (10 mL). The mixture was stirred at room temperature for 2 hours and then concentrated in vacuo. The residue was dissolved in $CH_2Cl_2$ (100 mL) and washed with saturated $NaHCO_3$ (3×20 mL). The organic layer was dried over $MgSO_4$, filtered and the filtrate concentrated in vacuo. The crude product was purified by column chromatography over silica gel using 5% MeOH in ethyl acetate as eluent to afford compound 54 (0.349 g, 76%) as a white foam.

Synthesis of Compound 55

A mixture of compound 54 (0.30 g, 0.65 mmol) and 10% Pd/C (30 mg) in EtOAc/AcOH (1:1, 10 mL) was stirred under $H_2$ (balloon) for 5 hours. The mixture was filtered on celite and the filtrate was evaporated to dryness. The residue was purified by column chromatography on silica gel eluted with EtOAc/MeOH (9:1) to afford compounds 55 (0.195 g, 81%) as a white solid.

Synthesis of Compound 56

Diisopropyl azodicarboxylate (1.62 mL, 8.24 mmol) was added to a suspension of compound 40 (1.5 g, 4.12 mmol), $ZnN_6 \cdot 2Py$ (0.95 g, 3.09 mmol) and $Ph_3P$ (2.16 g, 8.24 mmol) in anhydrous toluene (20 mL). The mixture was stirred at room temperature for 18 hours. The mixture was then concentrated, and the residue was purified by column chromatography on silica gel eluted with 15% of EtOAc in hexanes to afford compound 56 (1.59 g) as a colorless oil.

Synthesis of Compound 57

A mixture of crude compound 56 (1.59 g) and 10% Pd/C (80 mg) in EtOAc (20 mL) was stirred under $H_2$ (balloon) for 20 hours. The mixture was filtered on celite and the filtrate was evaporated to dryness. The residue was purified by column chromatography on silica gel eluted with EtOAc/MeOH/$Et_3N$ (85:14:1) to afford compound 57 (1.14 g, 76% over two steps) as a colorless oil.

Synthesis of Compound 58

Compound 57 (0.301 g, 0.825 mmol) was dissolved in toluene (18 mL) and MeOH (2 mL) and treated with pTsOH·$H_2O$ (0.472 g, 2.48 mmol). The solution was heated at reflux for 1.5 hours using a Dean-Stark apparatus. The Dean-Stark apparatus was then removed and $Et_3N$ (0.35 mL, 2.48 mmol) was added to the solution, which was heated at reflux for a further 4 hours. The solvent was evaporated and the residue was purified by silica gel column chromatography eluted with 2% AcOH in EtOAc to provide compound 58 (0.228 g, 96%) as a white solid.

Synthesis of Compound 59

Di-tert-butyl dicarbonate (0.935 g, 4.28 mmol) was added to a solution of compound 58 (0.62 g, 2.14 mmol), $Et_3N$ (0.60 mL, 4.28 mmol) and DMAP (0.060 g) in $CH_2Cl_2$ (20 mL). The mixture was stirred at room temperature for 5 hours. The mixture was concentrated, and the residue was purified by column chromatography on silica gel eluted with hexanes/EtOAc (3:1) to afford compound 59 (0.696 g, 84%) as a white solid.

Synthesis of Compound 60

To a solution of compound 59 (0.60 g, 1.54 mmol) in dry THF (5 mL) under argon was slowly added LDA [1.85 mmol, prepared from n-BuLi (0.74 mL, 2.5 M solution in hexane, 1.85 mmol) and diisopropylamine (0.26 mL, 1.85 mmol)] in THF (2 mL) at −78° C. The mixture was stirred at −78° C. for one hour, and then HMPA (0.40 mL, 2.30 mmol) was added to the above mixture via syringe. After 15 minutes, 4-(benzyloxy)-3-methoxybenzyl bromide (0.71 g, 2.30 mmol) in THF (2 mL) was added. The resulting mixture was stirred for an additional 4 hours at −78° C. The excess base was quenched at 0° C. with saturated aqueous $NH_4Cl$ (20 mL), and the resulting solution was extracted with EtOAc (3×60 mL). The combined organic layer was washed with saturated brine (2×50 mL), dried over $MgSO_4$, filtered and the filtrate was evaporated to dryness. The residue was purified by column chromatography on silica gel eluted with hexanes/EtOAc (7:3) to give compound 60 (0.693 g, 74%) as a white foam.

Synthesis of Compound 61

Trifluoroacetic acid (3 mL) was added to a solution of compound 60 (0.63 g, 1.02 mmol) in $CH_2Cl_2$ (3 mL). The mixture was stirred at room temperature for 4 hours, diluted with toluene (20 mL) and then concentrated in vacuo. The residue was purified by column chromatography over silica gel using 5% MeOH in ethyl acetate as eluent to afford compound 61 (0.39 g, 74%) as a white solid.

Synthesis of Compound 62

A mixture of compound 61 (0.28 g, 0.54 mmol) and 10% Pd/C (27 mg) in EtOAc/AcOH (1:1, 6 mL) was stirred under $H_2$ (balloon) for 5 hours. The mixture was filtered on celite and the filtrate was evaporated to dryness. The residue was purified by column chromatography on silica gel eluted with EtOAc/MeOH (97:3) to afford compound 62 (0.20 g, 84%) as a white foam.

Preparation of Substituted Benzyl Bromides; Substituted Phenyl δ-Lactone Intermediates; and Final Products Scheme 10 depicts general synthetic methodology that may be used for the synthesis of δ-lactones C. Exemplary synthetic methodology to provide compounds A, B, and C is provided below.

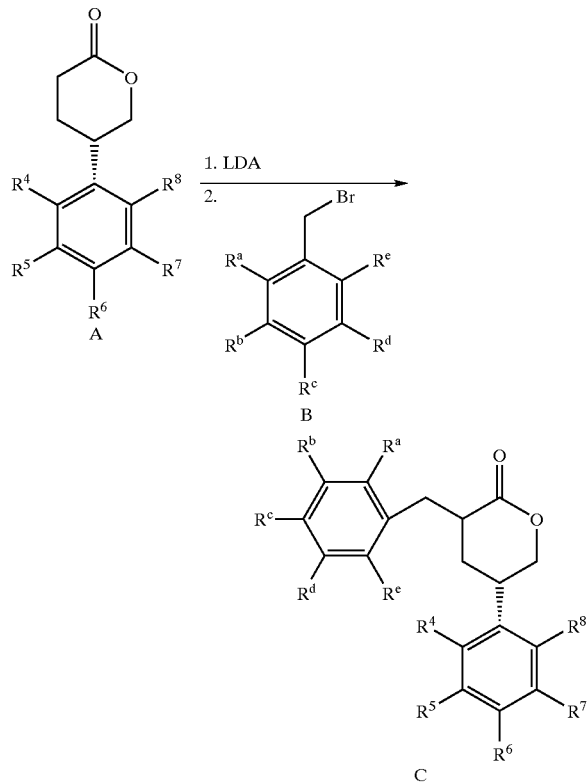

Any number of substituted benzyl halides can be used to generate an end product of structure C with different substitution patterns on the benzyl ring. Substituted benzyl bromides are available commercially or may be generated from the corresponding substituted benzyl alcohol, benzaldehyde, benzoic acid or benzoic ester.

For example, substituted benzyl bromides can be prepared as outlined in Scheme 11. Any number of compounds related to compound 63 could be produced using similar methodology but starting with a different substituted benzyl alcohol. Thus, treatment of commercially available starting material compound 31 with benzyl bromide and potassium carbonate in toluene gives the corresponding benzyloxy derivative 32, which is treated, without purification, with PBr₃ in diethyl ether to give desired bromide compound 63 in quantitative yield.

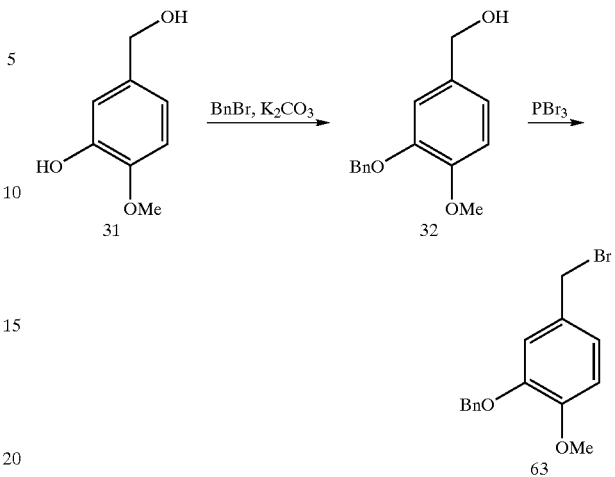

Synthesis of Compound 63

To a solution of alcohol 32 (3.20 g, 13.1 mmol) in anhydrous diethyl ether (15 mL) was added PBr₃ (1.77 g, 6.55 mmol) in one portion, and the resulting mixture was stirred at room temperature for 3 hours. The mixture was diluted with diethyl ether (40 mL) and washed with H₂O (2×30 mL), saturated NaHCO₃ (2×30 mL), and brine (2×30 mL). The ether layer was dried over anhydrous MgSO₄, and the solvent was removed under reduced pressure to afford compound 63 (4.02 g, 100%) as a light yellow solid.

Substituted benzyl bromide compounds can also be prepared from commercially available substituted benzaldehydes, benzoic acids and benzoic esters by first converting these compounds to the corresponding alcohol. Exemplary synthetic methodology to provide substituted benzyl bromide from benzyl aldehyde is described below. For example, as illustrated in Scheme 12, treatment of 4-hydroxy-3-nitro-benzaldehyde 73 with benzyl bromide in the presence of K₂CO₃ in DMF at 65° C. gives 4-benzyloxy-3-nitro-benzaldehyde 74. Reduction of compound 74 in methanol with NaBH₄ affords the alcohol 75 and subsequent bromination using PBr₃ in diethyl ether provides the desired bromide compound 76.

Scheme 12 also shows how other representative benzyl bromide compounds may be made.

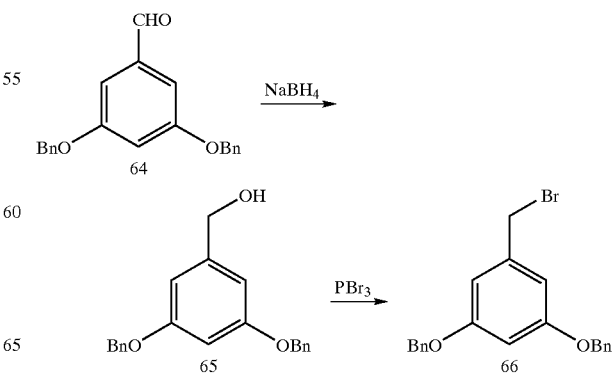

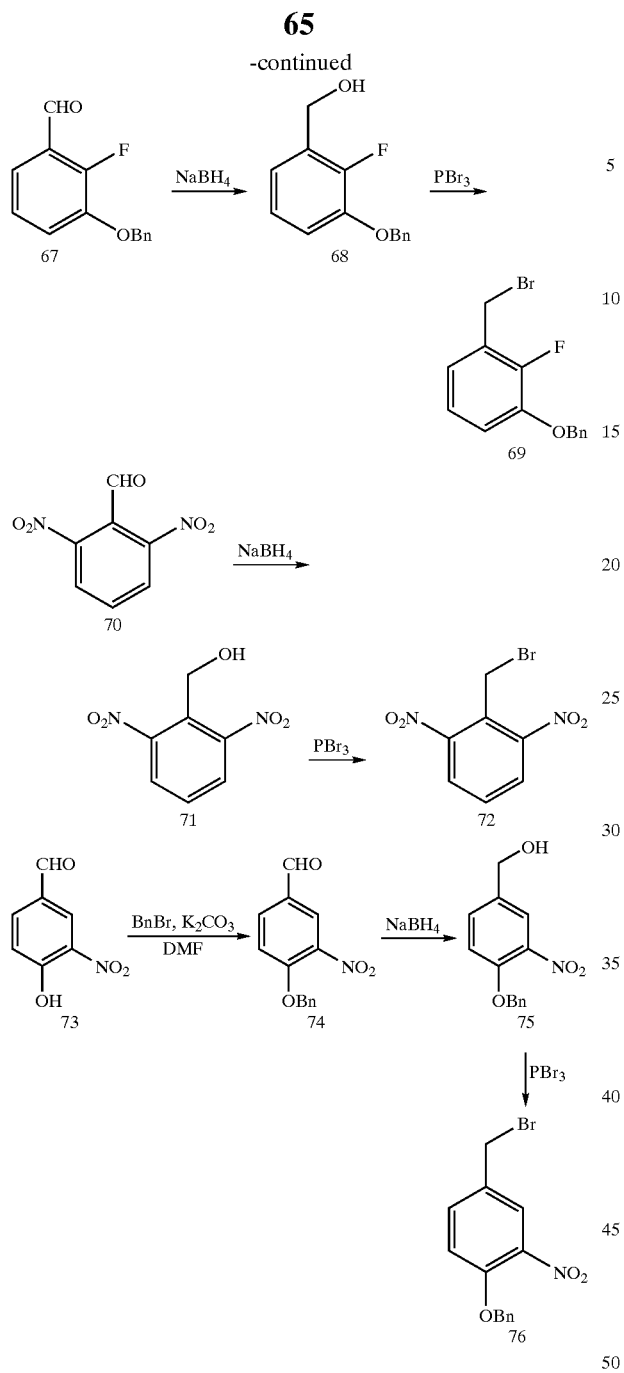

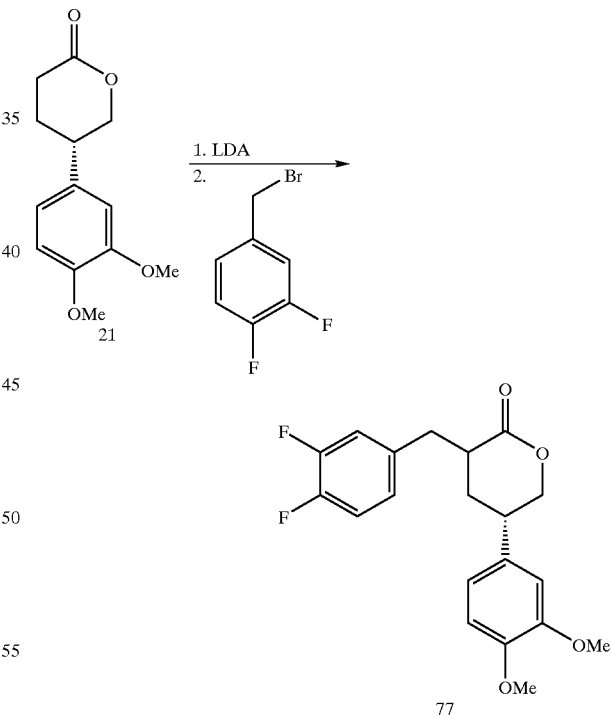

(0.63 g, 16.72 mmol) was added portionwise. After the addition was completed, the ice-water bath was removed and the reaction mixture was stirred at room temperature for 2 hours. Water (40 mL) was added and the mixture was extracted with $CH_2Cl_2$ (3×60 mL). The combined organic layers were washed with brine (50 mL) and dried over anhydrous $MgSO_4$. Removal of the solvent gave a pale yellow solid which was purified by silica gel column chromatography (hexanes/EtOAc, 1:1) to give compound 75 (4.31 g, 99%) as a pale yellow solid.

Synthesis of Compound 76

To a solution of compound 75 (4.30 g, 16.59 mmol) in anhydrous diethyl ether (40 mL) was slowly added $PBr_3$ (0.79 mL, 8.30 mmol) via syringe, and the resulting mixture was stirred at room temperature for 3 hours. The mixture was diluted with EtOAc (100 mL) and washed with saturated aqueous $NaHCO_3$ (2×50 mL) and brine (2×50 mL). The organic layer was dried over anhydrous $MgSO_4$, and the solvent was removed under reduced pressure to afford compound 76 (5.07 g, 95%) as a pale yellow solid.

Alkylation using various halide compounds to provide the desired products 77, 80, 89, 92, 94, 95 and 96 is depicted in Schemes 13, 14, 15, 16, 17, 18 and 19, respectively. In Scheme 13, compound 21 is alkylated with commercially available 3,4-difluorobenzyl bromide to give the desired compound 77 in 59% yield.

Synthesis of Compound 74

To a suspension of 4-hydroxy-3-nitrobenzaldehyde 73 (3.00 g, 17.95 mmol), potassium carbonate (3.73 g, 26.93 mmol) in DMF (300 mL) was slowly added benzyl bromide (2.85 mL, 23.96 mmol). The reaction mixture was stirred at 65° C. for 18 hours. After cooling to room temperature, the mixture was diluted with water (140 mL) and extracted with diethyl ether (3×150 mL). The combined organic layers were washed with water (150 mL) and brine (150 mL). After drying over anhydrous $MgSO_4$, filtration and evaporation of the filtrate in vacuo gave crude compound 74 (4.393 g, 95%) which was used for the next reaction without further purification.

Synthesis of Compound 75

Compound 74 (4.30 g, 16.72 mmol) was dissolved in EtOH/$CH_2Cl_2$ (1:1, 50 mL) and cooled to 0° C. $NaBH_4$ Synthesis of Compound 77 n-Butyllithium (2.5 M solution in hexanes, 0.56 mL, 1.40 mmol) was added to a solution of diisopropylamine (0.20 mL) in dry THF (10 mL) at −78° C. The mixture was stirred at −78° C. for 1 hour, then HMPA (0.33 mL, 1.91 mmol) was added, followed by addition of a solution of compound 21 (0.30 g, 1.27 mmol) in THF (3 mL). After 1 hour, a solution of 3,4-difluoro benzyl bromide (purchased from Aldrich Chemical Company, Inc., 0.32 mL, 2.54 mmol)) was added in one portion to the reaction, and the resulting mixture was stirred at −78° C. for an additional 4 hours. The excess base was quenched with saturated aqueous NH$_4$Cl (10 mL), and the resulting solution was extracted with EtOAc (3×20 mL). The combined organic layer was washed with saturated NaCl (2×30 mL), dried over MgSO$_4$, filtered and the filtrate evaporated to dryness. The residue was purified by column chromatography on silica gel (hexanes/EtOAc, 2:1) to give compound 77 (0.27 g, 59%) as a white solid.

In Scheme 14, compound 21 is alkylated with 3,4-dibenzyloxy benzyl bromide (prepared by treatment the corresponding alcohol with PBr$_3$), followed by hydrogenation using 10% Pd/C as catalyst to give the desired compound 80 in good yield.

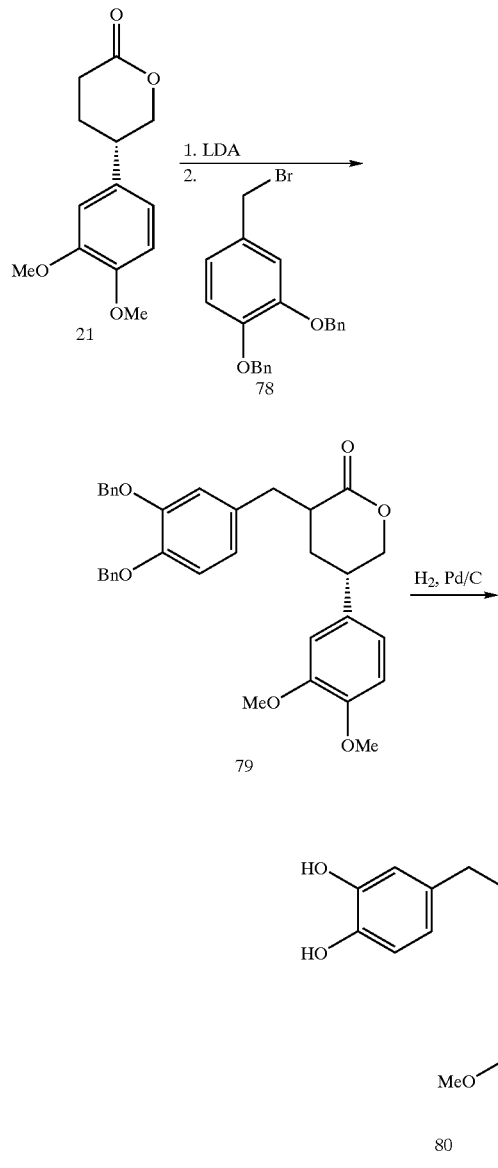

Scheme 14

Synthesis of Compound 78

To a solution of 3,4-dibenzyloxybenzyl alcohol (1.35 g, 4.21 mmol) in anhydrous diethyl ether (25 mL) was added PBr$_3$ (0.20 mL, 2.11 mmol) in one portion, and the resulting mixture was stirred at room temperature for 3 hours. The mixture was diluted with diethyl ether (50 mL) and washed with H$_2$O (2×30 mL), saturated NaHCO$_3$ (2×30 mL), and brine (2×30 mL). The ether layer was dried over anhydrous MgSO$_4$, and the solvent was removed under reduced pressure to afford compound 78 (1.47 g, 91%) as a light yellow oil.

Synthesis of Compound 79 n-Butyllithium (2.5 M solution in hexanes, 0.38 mL, 0.931 mmol) was added to a solution of diisopropylamine (0.14 mL 0.999 mmol) in dry THF (3 mL) at −78° C. The mixture was stirred at −78° C. for 1 hour, then HMPA (0.22 mL, 1.27 mmol) was added, followed by adding a solution of compound 21 (200.0 mg, 0.846 mmol) in THF (3 mL). After 1 hour, a solution of 3,4-dibenzyloxy benzyl bromide (compound 78, 248.5 mg, 0.80 mmol) in THF (1 mL) was added in one portion to the reaction, and the resulting mixture was stirred at −78° C. for an additional 4 hours. The excess base was quenched with saturated aqueous NH$_4$Cl (10 mL), and the resulting solution was extracted with EtOAc (3×20 mL). The combined organic layer was washed with saturated NaCl (2×30 mL), dried over MgSO$_4$, filtered and the filtrate evaporated to dryness. The residue was purified by column chromatography on silica gel (hexanes/EtOAc, 2:1) to give compound 79 (0.31 g, 67%) as a colorless oil.

Synthesis of Compound 80

A mixture of compound 79 (0.20 g, 0.37 mmol) and 10% Pd/C (25 mg) in EtOAc/AcOH (4:1, 5 mL) was stirred under H$_2$ (balloon) for 2 hours. The mixture was then filtered through a celite plug and the filtrate was evaporated to dryness. The residue was purified by column chromatography on silica gel (hexanes/EtOAc, 3:2) to give compound 80 (0.093 mg, 70%) as a colorless syrup.

Schemes 15 and 16 illustrate the preparation of compounds 89 and 92, two representative compounds of the substituted phenyl δ-lactone intermediates, using synthetic methodology similar to that described in previous examples but using the appropriate benzyl alcohol to generate compounds 89 and 92 (e.g., synthesis of compound 41 in Scheme 5).

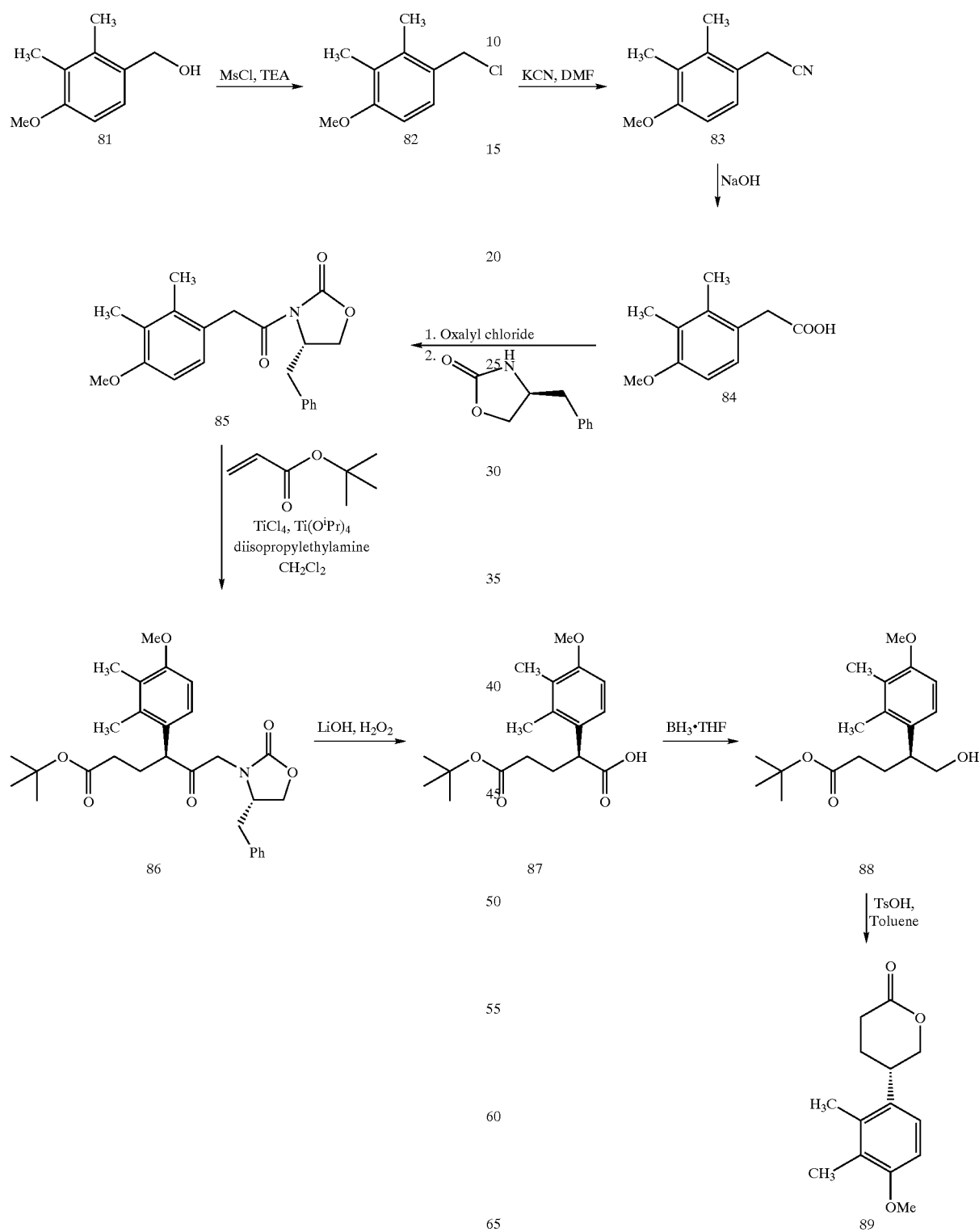
Scheme 15

Scheme 16

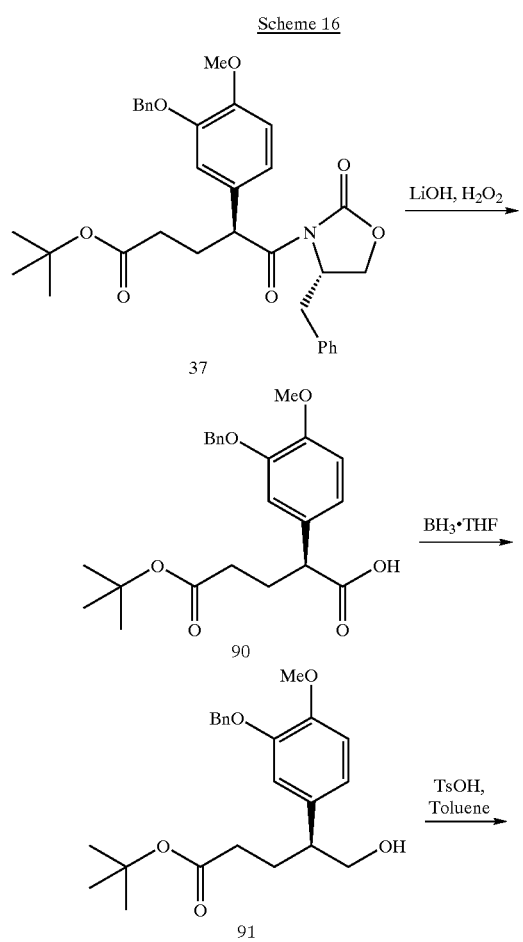

Synthesis of Compound (90)

Lithium hydroxide monohydrate (3.21 g, 76.5 mmol) and H₂O₂ (30% in H₂O, 17.5 mL, 152.8 mmol) were added a solution of compound 37 (21.4 g, 38.2 mmol) in THF/H₂O (3:1, 350 mL) at 0° C. The reaction mixture was stirred at 0° C. for 3 hours. A solution of sodium sulfite (21.2 g, 168.1 mmol) in water (100 mL) was then added, followed by a solution of 0.5 N sodium bicarbonate (200 mL). The mixture was stirred at room temperature for 2 hours and then concentrated in vacuo. The aqueous phase was diluted with 10% HCl to pH=2 and then extracted with EtOAc (3×700 mL). The combined organic layers were dried over MgSO₄, filtered and the filtrate concentrated in vacuo. The resulting oil was purified using silica gel column chromatography eluting with 0.2% acetic acid in ethyl acetate/hexanes (1:3) to afford compound 90 (12.6 g, 82%) as a white solid.

Synthesis of Compound (91)

BH₃-THF (1.0 M solution in THF, 13.8 mL, 13.8 mmol) was added dropwise over 20 minutes to a solution of compound 90 (5.53 g, 13.8 mmol) in dry THF (40 mL) at −15° C. The cooling bath was then removed, and the reaction mixture was stirred at room temperature for 4 hours. Saturated aqueous NaHCO₃ solution (20 mL) was added, and the aqueous phase was extracted with EtOAc (3×20 mL). The combined organic phase was washed with saturated NaCl (2×40 mL). The organic phase was dried over MgSO₄, filtered and the filtrate evaporated in vacuo. The residue was purified by silica gel column chromatography, eluting with EtOAc/hexanes (1:2) to afford compound 91 (5.22 g, 98%) as a colorless wax.

Synthesis of Compound (92)

A solution of Compound 91 (1.5 g, 3.88 mmol) and p-toluenesulfonic acid monohydrate (86.0 mg) in toluene (30 mL) was heated at 80° C. for 30 minutes. The toluene was removed in vacuo, and the residue was purified by silica gel column chromatography, eluting with EtOAc/hexanes (1:1) to afford compound 92 (1.11 g, 91%) as a colorless oil.

In Scheme 17, compound 41 is alkylated with compound 76 and subsequent catalytic hydrogenation of the resulting compound 93 affords the desired compound 94 in good yield.

Scheme 17

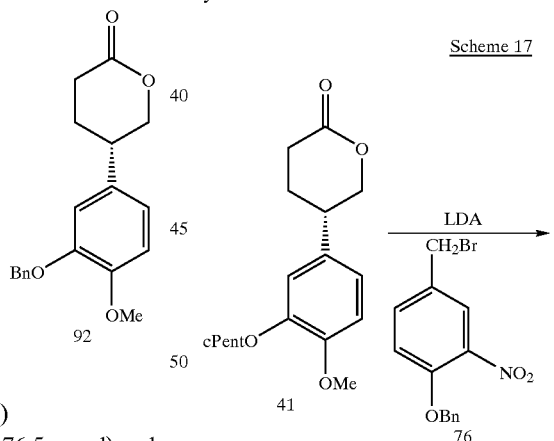

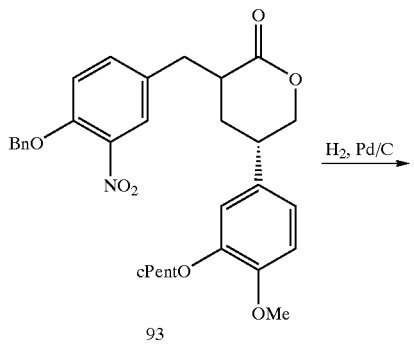

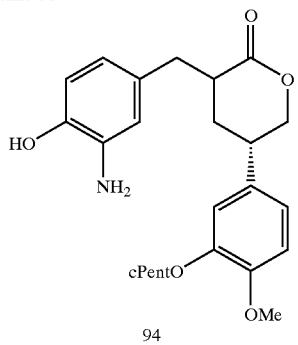

94

Synthesis of Compound 93

To a solution of compound 41 (0.20 g, 0.688 mmol) in dry THF (4 mL) under argon was slowly added LDA (1.16 mL, 0.826 mmol, freshly prepared from n-BuLi and diisopropylamine in THF at −78° C.). The mixture was stirred at −78° C. for one hour, and then HMPA (0.20 mL, 1.03 mmol) was added to the mixture via syringe. After 15 minutes, compound 76 (0.332 g, 1.03 mmol) was added. The resulting mixture was stirred at −78° C. for an additional 4 hours. Then reaction was quenched with saturated aqueous NH$_4$Cl (10 mL), and the resulting solution was extracted with EtOAc (3×20 mL). The combined organic layers were washed with brine (30 mL), dried over MgSO$_4$, and filtered, and the filtrate was evaporated to dryness. The residue was purified by silica gel column chromatography (benzene/EtOAc, 95:5) to give compound 93 (0.264 g, 72%) as a white foam.

Synthesis of Compound 94

A mixture of compound 93 (0.20 g, 0.376 mmol) and 10% Pd/C (30 mg) in EtOAc (7 mL) was stirred under H$_2$ (balloon) overnight. Catalyst was removed by filtration and the filtrate was evaporated to dryness. The residue was purified by silica gel column chromatography (hexanes/EtOAc, 7:3) to afford compound 94 (0.111 g, 72%) as a pale yellow solid. (The silica gel was pretreated with 1% triethylamine).

Similarly, in Scheme 18 and Scheme 19, compound 41 is alkylated with commercially available methyl iodide and allyl iodide, respectively, to provide the desired compound 95 and compound 96.

Scheme 18

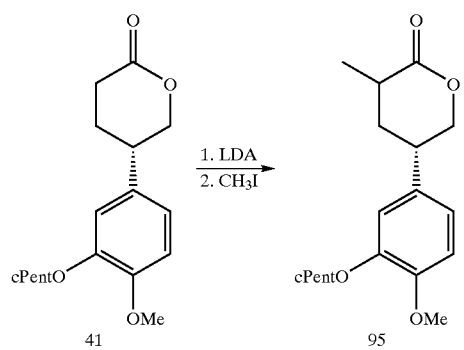

Synthesis of Compound 95

To a solution of compound 41 (0.20 g, 0.688 mmol) in dry THF (3 mL) under argon was slowly added LDA (1.16 mL, 0.826 mmol, freshly prepared from n-BuLi and diisopropylamine in THF at −78° C.). The mixture was stirred at −78° C. for one hour, and then HMPA (0.2 mL, 1.03 mmol) was added to the above mixture via syringe. After 15 minutes, methyl iodide (0.064 mL, 1.03 mmol) was added. The resulting mixture was stirred at −78° C. for an additional 4 hours. Then reaction was quenched with saturated aqueous NH$_4$Cl (5 mL), and the resulting solution was extracted with EtOAc (3×15 mL). The combined organic layers were washed with brine (15 mL), dried over MgSO$_4$, and filtered, and the filtrate was evaporated to dryness. The residue was purified by silica gel column chromatography (benzene/EtOAc, 95:5) to afford compound 95 (0.168 g, 80%) as a white solid.

Scheme 19

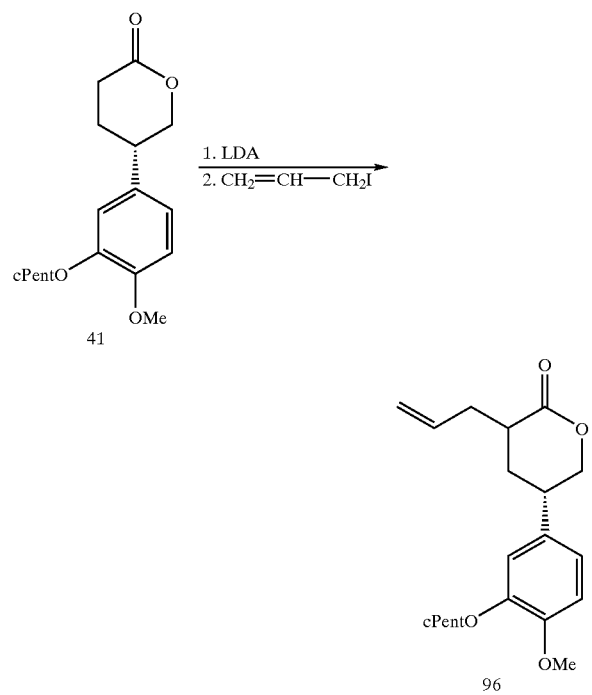

Synthesis of Compound 96

To a solution of compound 41 (0.40 g, 1.38 mmol) in dry THF (4 mL) under argon was slowly added LDA (2.32 mL, 1.66 mmol, freshly prepared from n-BuLi and diisopropylamine in THF at −78° C.). The mixture was stirred at −78° C. for one hour, and then HMPA (0.4 mL, 2.07 mmol) was added to the mixture via syringe. After 15 minutes, allyl iodide (0.19 mL, 2.07 mmol) was added. The resulting mixture was stirred at −78° C. for an additional 4 hours. Then the reaction was quenched with saturated aqueous NH$_4$Cl (10 mL), and the resulting solution was extracted with EtOAc (3×30 mL). The combined organic layers were washed with brine (30 mL), dried over MgSO$_4$, and filtered, and the filtrate was evaporated to dryness. The residue was purified by silica gel column chromatography (benzene/EtOAc, 95:5) to afford compound 96 (0.33 g, 72%) as a white solid.

Compounds of formulae (1–4) with higher carbon number alkyloxy chains attached to a phenyl ring, and particularly the phenyl ring at the 5 position of the lactone or analog ring, have been prepared. For example, compound 101 can be produced in 5 steps from compound 91, as illustrated in Scheme 20. It should be recognized that the same or analogous synthetic methodology can be applied to provide hydrocarbyloxy substitution on a phenyl ring for any compound of or related to compounds of formulae (1–4).

Thus, deprotection of compound 91 using $H_2$ and 10% palladium on carbon gives the corresponding phenol derivative 97. Treatment of compound 97 with 1-bromobutane, potassium carbonate and potassium iodide in DMF gives the butyloxy derivative 98. Removal of the t-butyl ester linkage in compound 98 with p-toluenesulfonic acid monohydrate in toluene produces the corresponding hydroxyl acid, which is lactonized spontaneously to afford compound 99. Alkylation of the lithium anion of compound 99 with compound 76 yields compound 100. Hydrogenation of compound 100 provides the desired compound 101.

Synthesis of Compound 99

A mixture of compound 98 (0.834 g, 2.37 mmol) and p-toluenesulfonic acid monohydrate (80.0 mg) in toluene (20.0 mL) was heated at 75° C. for 30 minutes. Toluene was removed in vacuo, and the residue was purified by silica gel column chromatography (hexanes/EtOAc, 7:3) to afford compound 99 (0.422 g, 64%) as a colorless syrup.

Synthesis of Compound 100

To a solution of the lactone 99 (0.30 g, 1.08 mmol) in dry THF (4 mL) under argon was slowly added LDA (0.58 mL, 0.412 mmol, freshly prepared from n-BuLi and diisopropylamine in THF at −78° C.). The mixture was stirred at −78° C. for one hour, and then HMPA (0.18 mL, 1.30 mmol) was added to the mixture via syringe. After 15 minutes, com-

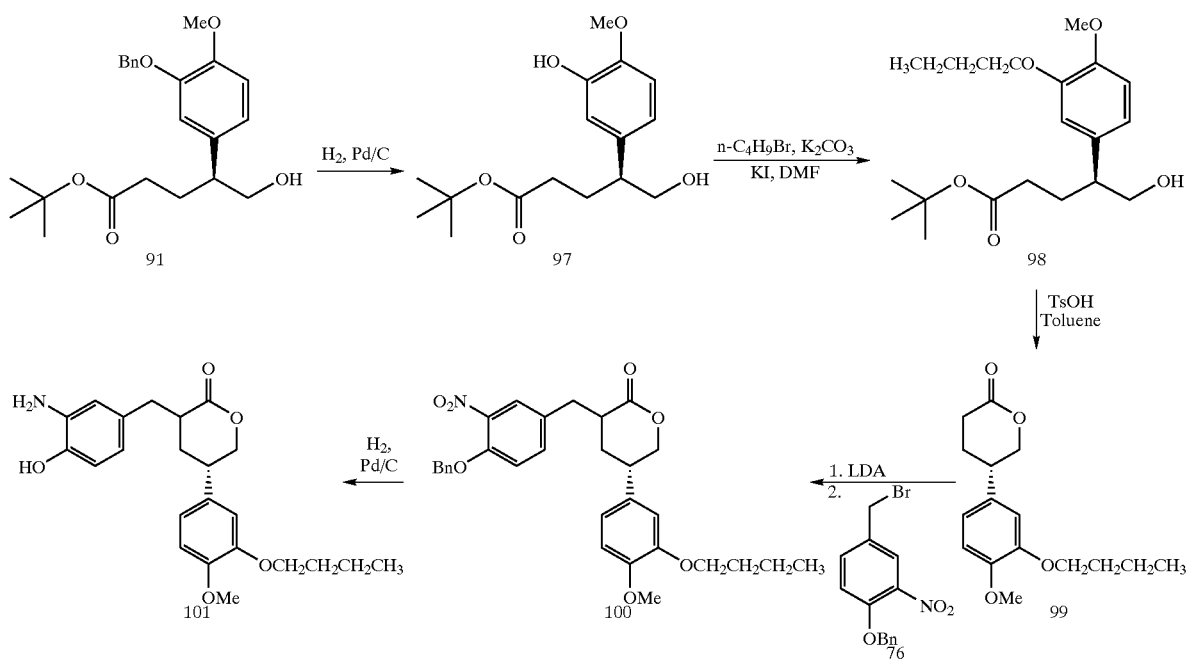

Scheme 20

Synthesis of Compound 97

A mixture of compound 91 (3.0 g, 7.76 mmol) and 10% Pd/C (0.30 mg) in EtOAc/AcOH (1:1, 40 mL) was stirred under $H_2$ (balloon) overnight. Catalyst was removed by filtration and the filtrate was evaporated to dryness. The residue was purified by silica gel column chromatography (hexanes/EtOAc, 3:2) to afford compound 97 (1.82 g, 79%) as a white solid.

Synthesis of Compound 98

To a suspension of compound 97 (0.80 g, 2.70 mmol), potassium carbonate (0.746 g, 5.40 mmol) and KI (30 mg) in anhydrous DMF (7 mL) was added 1-bromobutane (0.58 mL, 5.40 mmol) via syringe. Then the reaction mixture was stirred at 65° C. overnight. After cooling, the mixture was diluted with water (30 mL) and extracted with diethyl ether (3×50 mL). The combined organic layers were washed with brine (2×50 mL), dried over anhydrous $MgSO_4$, and concentrated to dryness. The residue was purified by silica gel column chromatography (hexanes/EtOAc, 7:3) to afford compound 98 (0.834 g, 88%) as a white solid.

pound 76 (0.52 g, 1.62 mmol) was added. The resulting mixture was stirred at −78° C. for an additional 4 hours. Then reaction was quenched with saturated aqueous $NH_4Cl$ (10 mL), and the resulting solution was extracted with EtOAc (3×20 mL). The combined organic layers were washed with brine (15 mL), dried over $MgSO_4$, and filtered, and the filtrate was evaporated to dryness. The residue was purified by silica gel column chromatography (benzene/EtOAc, 95:5) to afford compound 100 (0.443 g, 79%) as a light yellow solid.

Synthesis of Compound 101

A mixture of compound 100 (0.40 g, 0.77 mmol) and 10% Pd/C (40 mg) in EtOAc (5 mL) was stirred under $H_2$ (balloon) overnight. Catalyst was removed by filtration and the filtrate was evaporated to dryness. The residue was purified by silica gel column chromatography (benzene/EtOAc, 3:2) to afford compound 101 (0.215 g, 70%) as a pale yellow foam.

Compounds of formulae (1–4) containing hydrocarbyloxycarbonyl substitutions at a phenyl ring, and particularly the phenyl ring at C5 of the lactone or analog ring, can be prepared according to Scheme 21. For example, compound 103 can be synthesized as follows. Lactonization of compound 97 using p-toluenesulfonic acid monohydrate in toluene gives compound 102. Reaction of compound 102 with acetyl chloride and triethylamine in dichloromethane provides compound 103 with the ester linkage on phenyl ring.

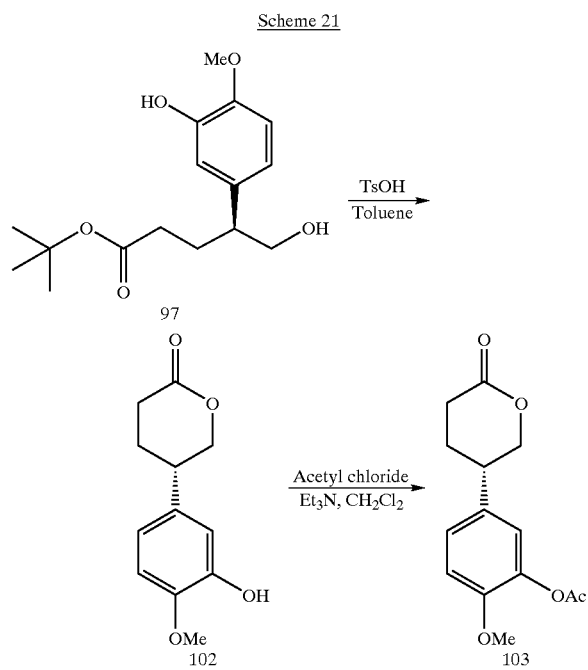

Synthesis of Compound 102

A mixture of compound 97 (1.01 g, 3.41 mmol) and p-toluenesulfonic acid monohydrate (100 mg) in toluene (30 mL) was heated at 75° C. for 30 minutes. Toluene was removed in vacuo, and the residue was purified by silica gel column chromatography (CH$_2$Cl$_2$/EtOAc, 70:30) to give compound 102 (0.71 g, 94%) as a white solid.

Synthesis of Compound 103

To a solution of compound 102 (0.100 g, 0.45 mmol) in CH$_2$Cl$_2$ (2 mL) at 0° C. were added triethylamine (0.125 mL, 0.9 mmol) and acetyl chloride (0.048 mL, 0.675 mmol). The reaction mixture was warmed to room temperature and stirred for 4 hours and then quenched with water (5 mL). The mixture was extracted with ethyl acetate (3×10 mL), and the combined organic layers were washed with brine (15 mL) and dried over MgSO$_4$. Solvent was removed and the resulting residue was purified by silica gel column chromatography (benzene/EtOAc, 90:10) to give compound 103 (0.103 g, 87%) as a colorless syrup.

Compounds of formulae (1–4) containing hydrocarbyl group substitution on a phenyl ring, and particularly the phenyl ring at position 5 of the lactone or analog ring, can be synthesized according to the reaction sequence depicted in Scheme 22. The same or analogous synthetic methodology can be applied to provide hydrocarbon substitutions on a phenyl ring for any compound of, or compound related to, formulae (1–4).

As depicted in Scheme 22, protection of the hydroxyl group in compound 91 is achieved using t-butyldimethylsilyl chloride and imidazole in N,N-dimethylformamide to give compound 104. Removal of the benzyl protecting group using hydrogen and palladium on carbon in ethyl acetate yields compound 105. Compound 105 is then converted to its corresponding aryl triflate 106 by reacting compound 105 with trifluoromethanesulfonic anhydride in pyridine. Palladium-catalyzed cross-coupling of compound 106 with phenyl boronic acid affords compound 107. Lactonization followed by alkylation furnishes compound 109. Finally, catalytic hydrogenation provides compound 110.

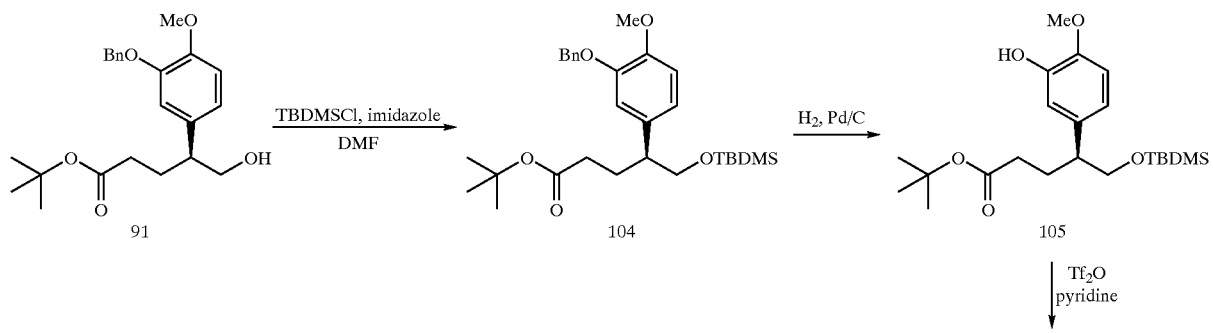

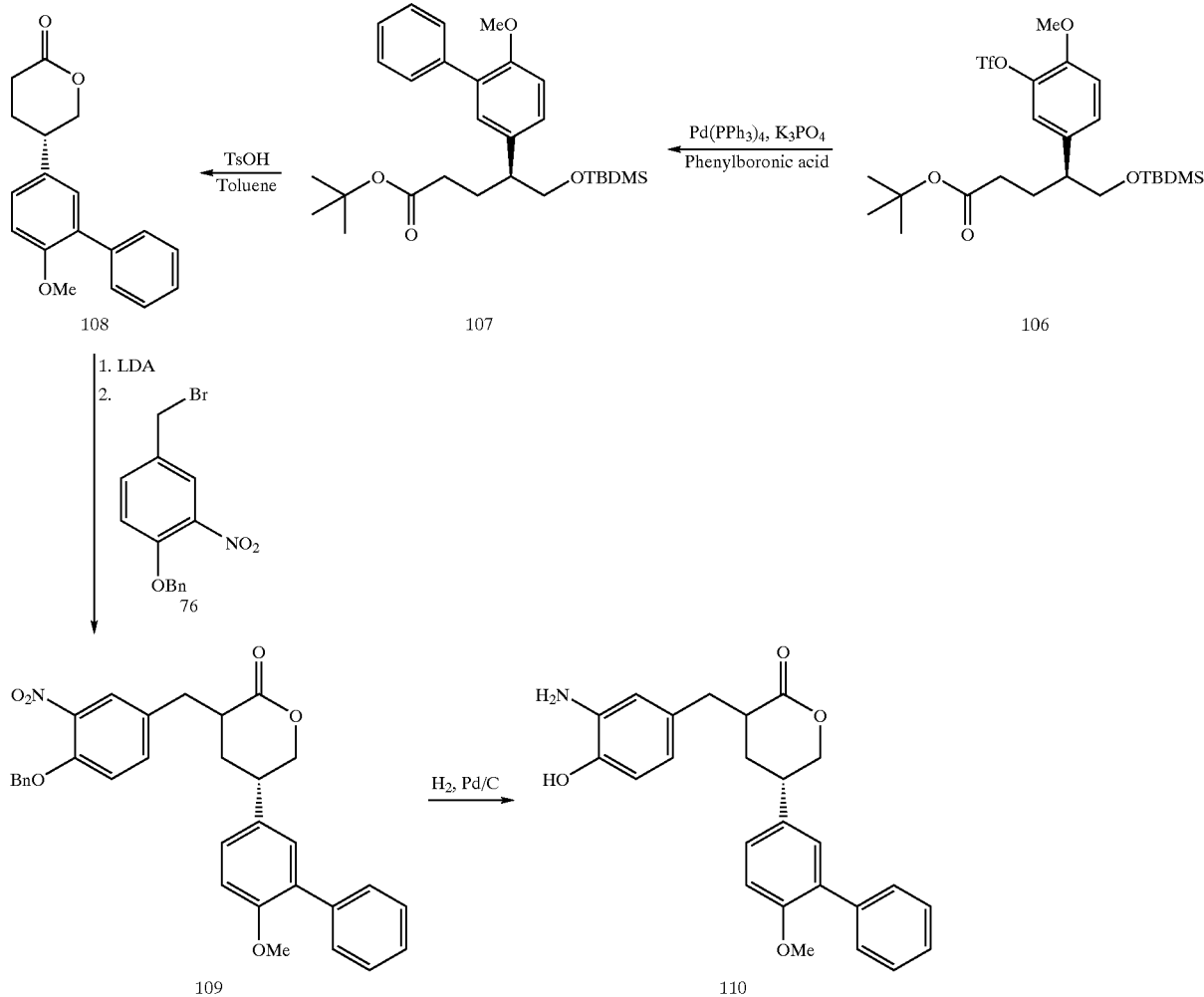

Synthesis of Compound 104

Compound 91 (2.50 g, 6.50 mmol) was dissolved in dry DMF (20 mL), then imidazole (0.664 g, 9.75 mmol) was added followed by TBDMSCl (1.47 g, 9.75 mmol). The mixture was stirred at room temperature for 2 hours, diluted with diethyl ether (150 mL) and washed with saturated aqueous NaHCO$_3$ solution (2×50 mL) and water (2×50 mL). The organic layer was dried over MgSO$_4$, filtered, and the filtrate was evaporated to dryness to give compound 104 (3.43 g) as a colorless oil which was used without further purification.

Synthesis of Compound 105

To a solution of compound 104 (3.43 g) in ethyl acetate (20 mL) was added 10% Pd on activated carbon (0.172 g). The flask was flushed with hydrogen and the mixture was stirred vigorously under an atmosphere of hydrogen for a period of 16 hours. The mixture was filtered and the solvent was evaporated. The residue was purified by silica gel column chromatography (hexanes/ethyl acetate, 3:1) to afford compound 105 (2.72 g, 85% over two steps) as a colorless oil.

Synthesis of Compound 106

To a solution of compound 105 (0.50 g, 1.22 mmol) in anhydrous pyridine (5 mL) at 0° C. was slowly added trifluoromethanesulfonic anhydride (0.23 mL, 1.34 mmol) via syringe, and the resulting mixture was stirred at 0° C. for 1 hour. The mixture was diluted with EtOAc (100 mL) and washed with saturated aqueous brine (2×50 mL). The organic layer was dried over anhydrous MgSO$_4$, and the solvent was removed under reduced pressure to afford compound 106 (0.623 g, 94%) as a pale yellow oil.

Synthesis of Compound 107

To a mixture of a solution of phenylboronic acid (0.0247 g, 0.202 mmol), compound 106 (0.10 g, 0.184 mmol), K$_3$PO$_4$ (0.0586 g, 0.276 mmol), and dry 1,4-dioxane (2 mL) in a dry, Ar-flushed flask was added Pd(PPh$_3$)$_4$ (5.3 mg, 0.00461 mmol). The mixture was stirred and heated in an 80° C. oil bath for a period of 16 hours. The cooled mixture was diluted with ethyl acetate (75 mL) and washed with brine (2×25 mL). The organic layer was then dried with MgSO$_4$, filtered and the filtrate was evaporated to dryness. The residue was purified by column chromatography on silica gel (hexanes/EtOAc, 30:1) to give compound 107 (0.0666 g, 87%) as a colorless oil.

Synthesis of Compound 108

A solution of compound 107 (0.060 g, 0.128 mmol) and p-toluenesulfonic acid monohydrate (12.2 mg, 0.064 mmol)

in dry toluene (1 mL) was stirred under an atmosphere of dry argon and heated to 80° C. for 2 hours. The cooled solution was filtered through a column of flash silica gel and the column was washed with hexanes/ethyl acetate (2:1, 150 mL). Evaporation of the solvent gave compound 108 (32.7 mg, 91%) as a colorless syrup.

Synthesis of Compound 109

To a solution of compound 108 in dry THF under argon was slowly added LDA. The mixture was stirred at −78° C. for one hour, and then HMPA was added to the mixture via syringe. After 15 minutes, compound 76 was added. The The synthesis of compound 114 is accomplished by the procedure depicted in Scheme 23. The synthetic methodology is similar to the synthesis of compound 110. Palladium-catalyzed cross-coupling of compound 106 with commercially available B-benzyl-9-BBN (Aldrich Chemical Co., Milwaukee, Wis.) provides compound 111. Lactonization of compound 111 using p-toluenesulfonic acid monohydrate in toluene affords compound 112. Akylation followed by catalytic hydrogenation gives the desired compound 114.

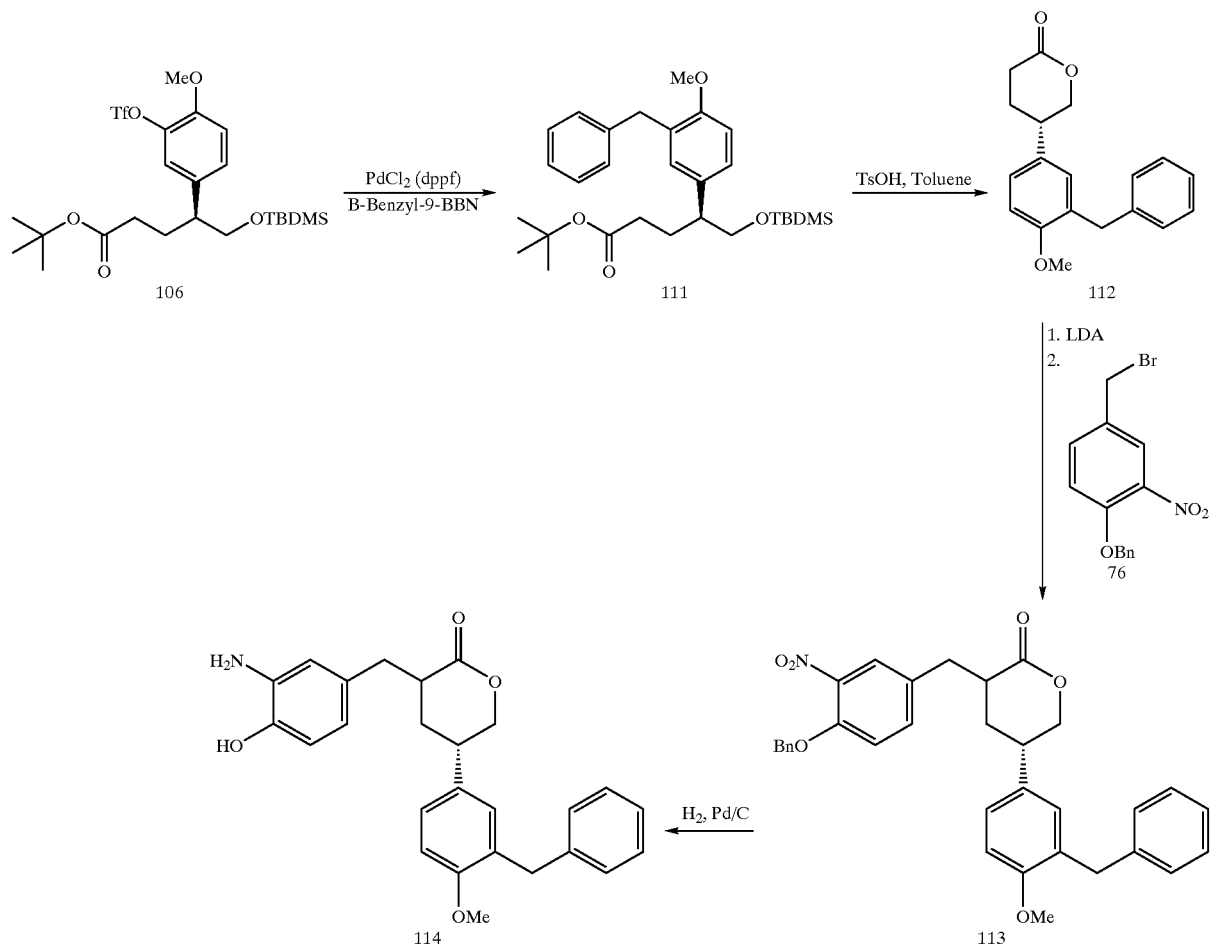

Scheme 23 resulting mixture was stirred at −78° C. for an additional 4 hours. The reaction was quenched with saturated aqueous NH$_4$Cl and the resulting solution was extracted with EtOAc. The combined organic layers were washed with brine, dried over MgSO$_4$, and filtered, and the filtrate was evaporated to dryness. The residue was purified by silica gel column chromatography to afford compound 109.

Synthesis of Compound 110

A mixture of compound 109 and 10% Pd/C in EtOAc was stirred under H$_2$ (balloon) overnight. Catalyst was removed by filtration and the filtrate was evaporated to dryness. The residue was purified by silica gel column chromatography to give compound 110.

Synthesis of Compound 111

To a mixture of a solution of B-benzyl-9-BBN (0.5 M, 1.32 mmol), compound 106 (0.650 g, 1.20 mmol), K$_3$PO$_4$ (0.382 g, 1.80 mmol), and dry 1,4-dioxane (4 mL) in a dry, Ar-flushed flask was added (diphenylphosphino-ferrocene) palladium(II) chloride. The mixture was stirred and heated in an 80° C. oil bath for a period of 18 hours. The cooled mixture was diluted with ethyl acetate (20 mL), treated with 10% KOH (aq) and 30% H$_2$O$_2$ (aq, 1.0 mL each) and allowed to stir for 2 hours. The layers were separated and the organic phase was washed with brine (2×20 mL) before being dried (MgSO$_4$). The solution was filtered and evaporated to yield the crude product. This material was separated by column chromatography (30:1 hexanes/ethyl acetate, 35 g of flash silica gel, 2.5 cm column). The fraction containing the spot at $R_f$=0.35 (19:1 hexanes/ethyl acetate, uv 254 nm, phosphomolybdic acid, heat) was isolated. Evaporation of the solvent gave compound 111 (0.295 g, 52%) as a colorless oil.

Synthesis of Compound 112

A solution of compound 111 (0.285 g, 0.603 mmol) and p-toluenesulfonic acid monohydrate (40.0 mg, 0.211 mmol) in dry toluene (5 mL) was stirred under an atmosphere of dry Ar and heated to 80° C. for 3 hours. The cooled solution was filtered though a column of flash silica gel (10 g in a 2 cm column) and the column was washed with hexanes/ethyl acetate (1:1, 150 mL). Evaporation of the solvent gave compound 112 (0.105 g, 59%) as a colorless oil which slowly solidified on standing.

Synthesis of Compound 113

To a solution of diisopropylamine (56 μL, 0.40 mmol) in dry THF (6 mL) in a dry, Ar-flushed flask at −78° C. was added a solution of tert-butyllithium (1.7 M, 0.40 mmol). The solution was stirred for 15 min and then compound 112 (0.100 g, 0.337 mmol) and dry THF (3 mL) were added by cannula. The reaction mixture was stirred for 1 h and then briefly warmed in an ice-water bath. Dry HMPA (88 μL, 0.51 mmol) was added and the solution was cooled to −78° C. Compound 76 (0.163 g, 0.506 mmol) was added and the mixture was allowed to stir at −78° C. for a period of 3 h. The mixture was warmed to room temperature and then opened to the air. The solvent was evaporated and the crude product was immediately purified by column chromatography (2:1 hexanes/ethyl acetate, 20 g of flash silica gel, 2 cm column). The fraction containing the spot at $R_f$=0.65 (1:1 hexanes/ethyl acetate, uv 254 nm, phosphomolybdic acid, heat) was isolated. Evaporation of the solvent gave compound 113 (0.103 g, 57%) as a colorless oil.

Synthesis of Compound 114

To a solution of compound 113 (0.100 g, 0.186 mmol) in 4:1 methanol/ethyl acetate (5 mL) was added 10% Pd on activated carbon (25 mg, 0.023 mmol). The flask was flushed with hydrogen and the mixture was stirred vigorously under an atmosphere of hydrogen for a period of 48 hours. The mixture was filtered and the solvent was evaporated. The residue was purified by column chromatography (1:1 hexanes/ethyl acetate, 15 g of flash silica gel, 2 cm column). The fraction containing the spot at $R_f$=0.35 (1:1 hexanes/ethyl acetate, uv 254 nm, phosphomolybdic acid, heat) was isolated. Evaporation of the solvent gave compound 114 (24.9 mg, 32%) as an off-white solid foam.

Compounds of formulae (1–4) may have boron substituent(s) on a phenyl ring, and particularly the phenyl ring that is attached at position 5 of the lactone or analog ring. Exemplary synthetic methodology to provide boron substitution is provided below. It should be recognized that the same or analogous synthetic methodology can be applied to provide the same or analogous substitution on a phenyl ring for any compound of, or related to, compounds of formulae (1–4).

For example, introduction of a boron functionality on a phenyl ring of compounds of formulae (1–4), and particularly on a phenyl ring at position 5 of the lactone or analog of formulae (1–4), may be accomplished as depicted in Scheme 24. Thus compound 115 could be produced by palladium-catalyzed cross-coupling of compound 106 with bis(pinacolato)diboron using [1,1'-bis(diphenylphosphio) ferrocene]dichloropalladium(II) [PdCl$_2$(dppf)] as catalyst and 1-1'-bis(diphenylphosphio)ferrocene (dppf) as ligand. Lactonization of compound 115 using p-toluenesulfonic acid monohydrate in toluene may afford compound 116. Alkylation of compound 116 with compound 76 may provide compound 117. Catalytic hydrogenation of compound 117 using hydrogen and palladium on carbon may provide the desired compound 118.

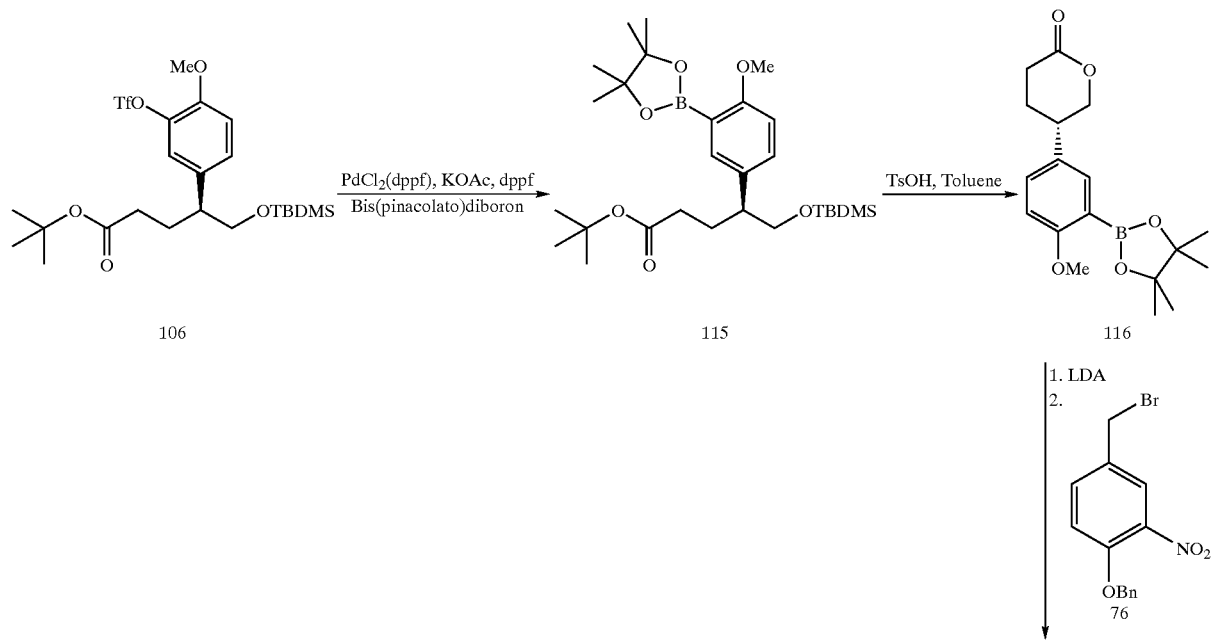

Scheme 24

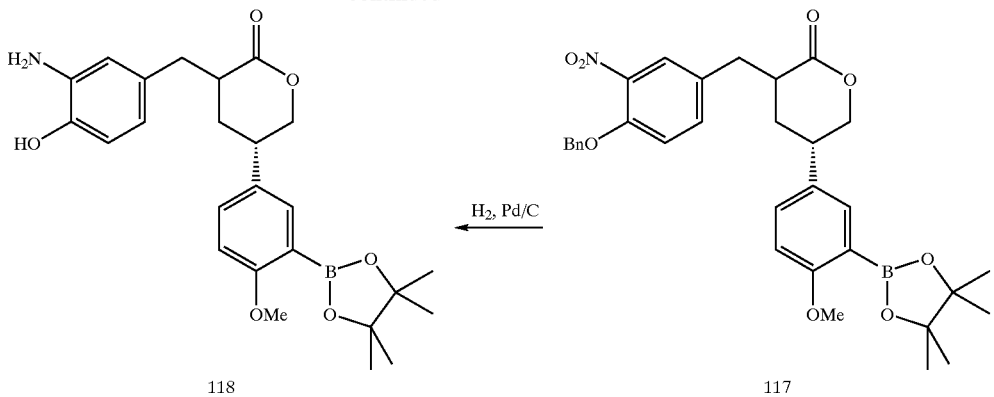

Compounds of formulae (1–4) may have nitrogen substitution(s) on a phenyl ring, and particularly a phenyl ring at position 5 of the lactone or analog ring. Exemplary synthetic methodology to provide nitrogen substitution is provided below. It should be recognized that the same or analogous synthetic methodology can be applied to provide the same or analogous substitution at a phenyl ring for any compound of, or related to, compounds of formulae (1–4).

For example, compound 122 could be prepared in a multi-step synthesis from compound 106, as depicted in Scheme 25. Thus, palladium-catalyzed amination of compound 106 using pyrrolidine, palladium acetate or palladium dibenzylideneacetone, bis(diphenylphosphono)binaphthyl and sodium tert-butoxide in toluene may give compound 119. Lactonization of compound 119 using p-toluenesulfonic acid monohydrate in toluene may afford compound 120. Alkylation of compound 120 with compound 76 may provide compound 121. Catalytic hydrogenation of compound 121 using hydrogen and palladium on carbon may provide the desired compound 122.

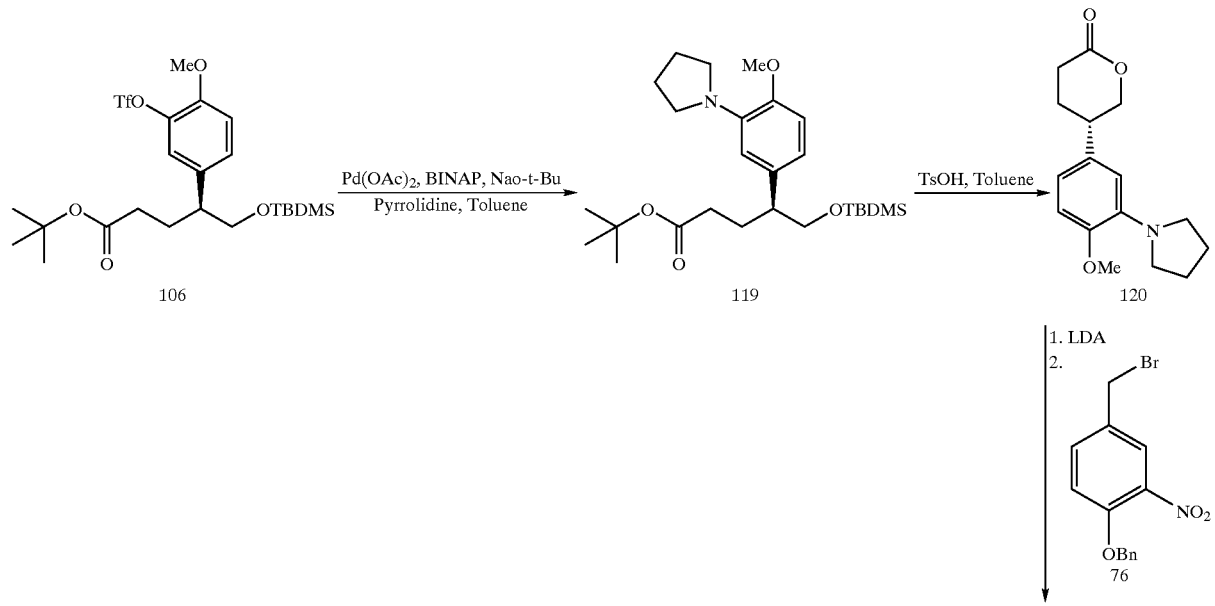

Scheme 25

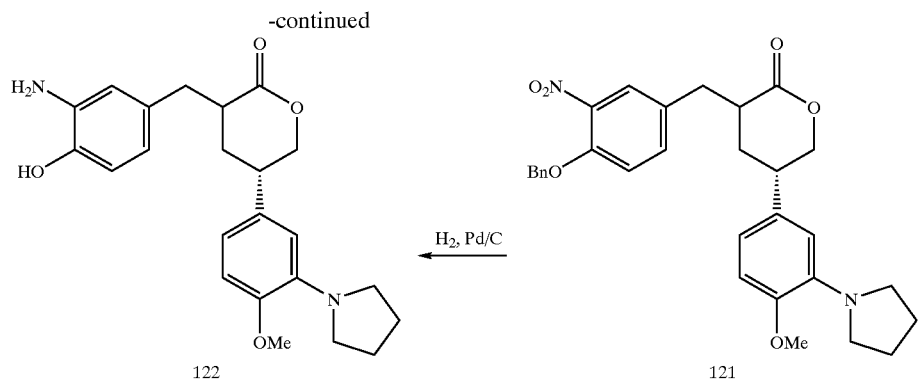

Compounds of formulae (1–4) may have sulphur substitution(s) on a phenyl ring, and particularly the phenyl ring at position 5 of the lactone or analog ring. Exemplary synthetic methodology to provide sulphur substitutions at a phenyl ring is provided below. It should be recognized that the same or analogous synthetic methodology can be applied to provide the same or analogous substitution at a phenyl ring of other compounds of formulae (1–4).

Placement of a sulphur-containing group on a phenyl ring may be achieved as depicted in Scheme 26.

Thus, an aryl triflate, such as compound 106, may be reacted with 1-butanethiol, palladium acetate or palladium dibenzylideneacetone, bis(diphenylphosphono)binaphthyl and sodium tert-butoxide in toluene to provide a compound, such as compound 123, with a carbon-sulphur bond. Lactonization may be achieved using p-toluenesulfonic acid monohydrate in toluene to give the corresponding compound 124. Alkylation of compound 124 may then be accomplished by treatment of compound 124 with LDA and compound 76 in THF. Subsequent catalytic hydrogenation of the resulting compound 125 using hydrogen and palladium on carbon may provide the desired compound 126.

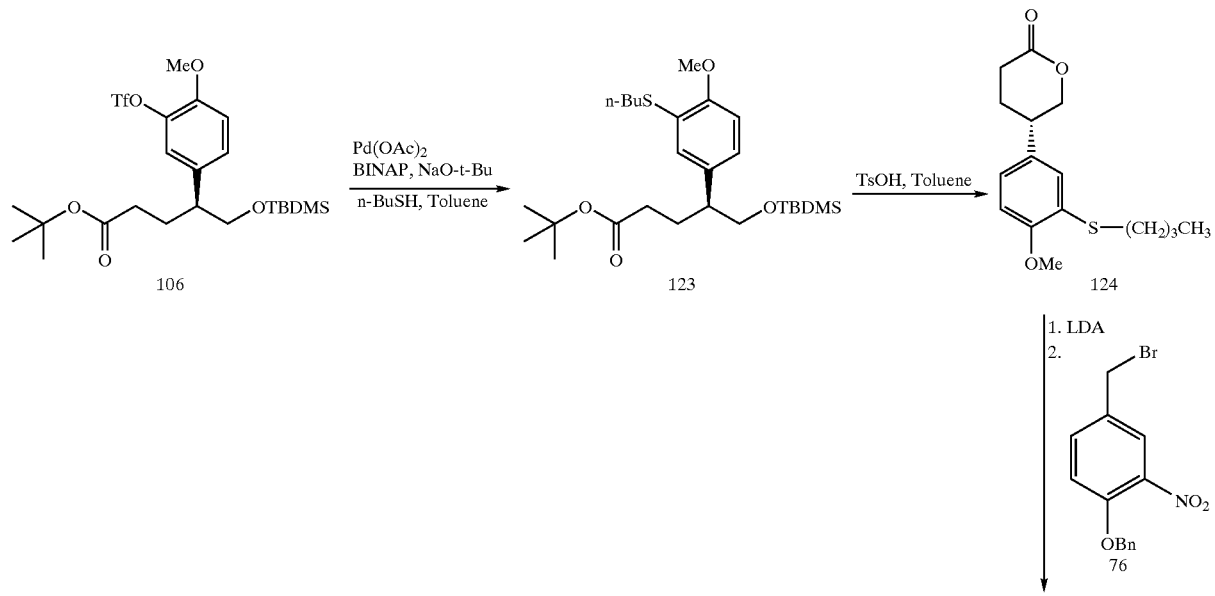

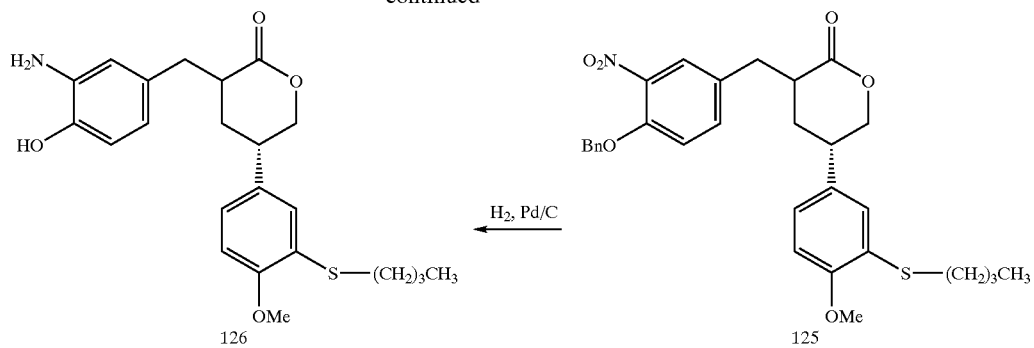

Compounds of formulae (1–4) may have phosphorus substitution(s) on a phenyl ring, and particularly the phenyl ring at carbon number 5 of the lactone or analog ring. Exemplary synthetic methodology to provide phosphorus substitution is provided below. It should be recognized that the same or analogous synthetic methodology can be applied to provide the same or analogous substitution at a phenyl ring for any compound of, or related to, compounds of formulae (1–4).

Phosphorous substituent at the phenyl ring may be introduced according to the pathway depicted in Scheme 27 below. Thus, conversion of compound 106 to compound 127 may be achieved by treatment of compound 106 with $PdCl_2(PPh_3)_2$, diethylphosphine, 1,3-bis(diphenylphosphino)propane (dppp) and diisopropylethylamine in DMF. Lactonization of compound 127 using p-toluenesulfonic acid monohydrate in toluene may then provide the desired compound 128.

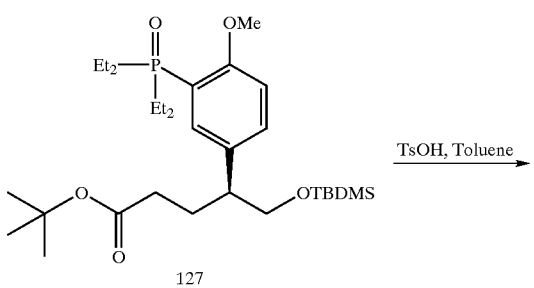

Scheme 27

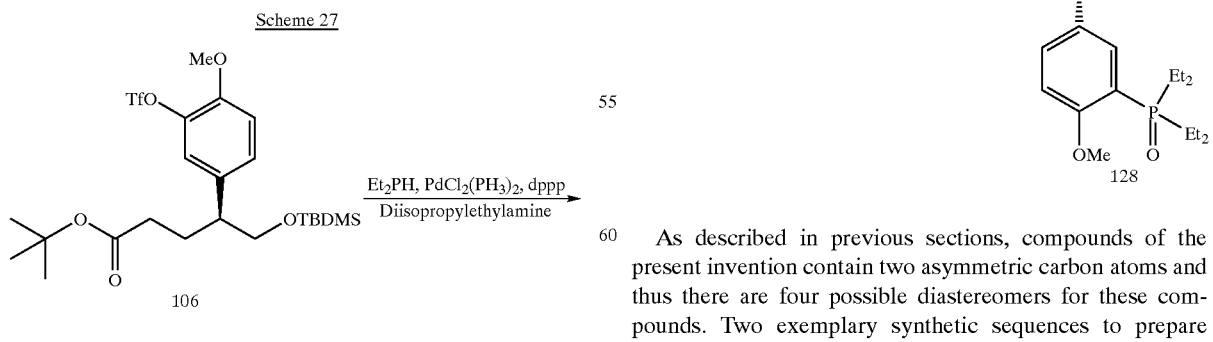

As described in previous sections, compounds of the present invention contain two asymmetric carbon atoms and thus there are four possible diastereomers for these compounds. Two exemplary synthetic sequences to prepare specific stereoisomers are depicted in Schemes 28 and 29, respectively, using methodology described in previous examples.

Scheme 28
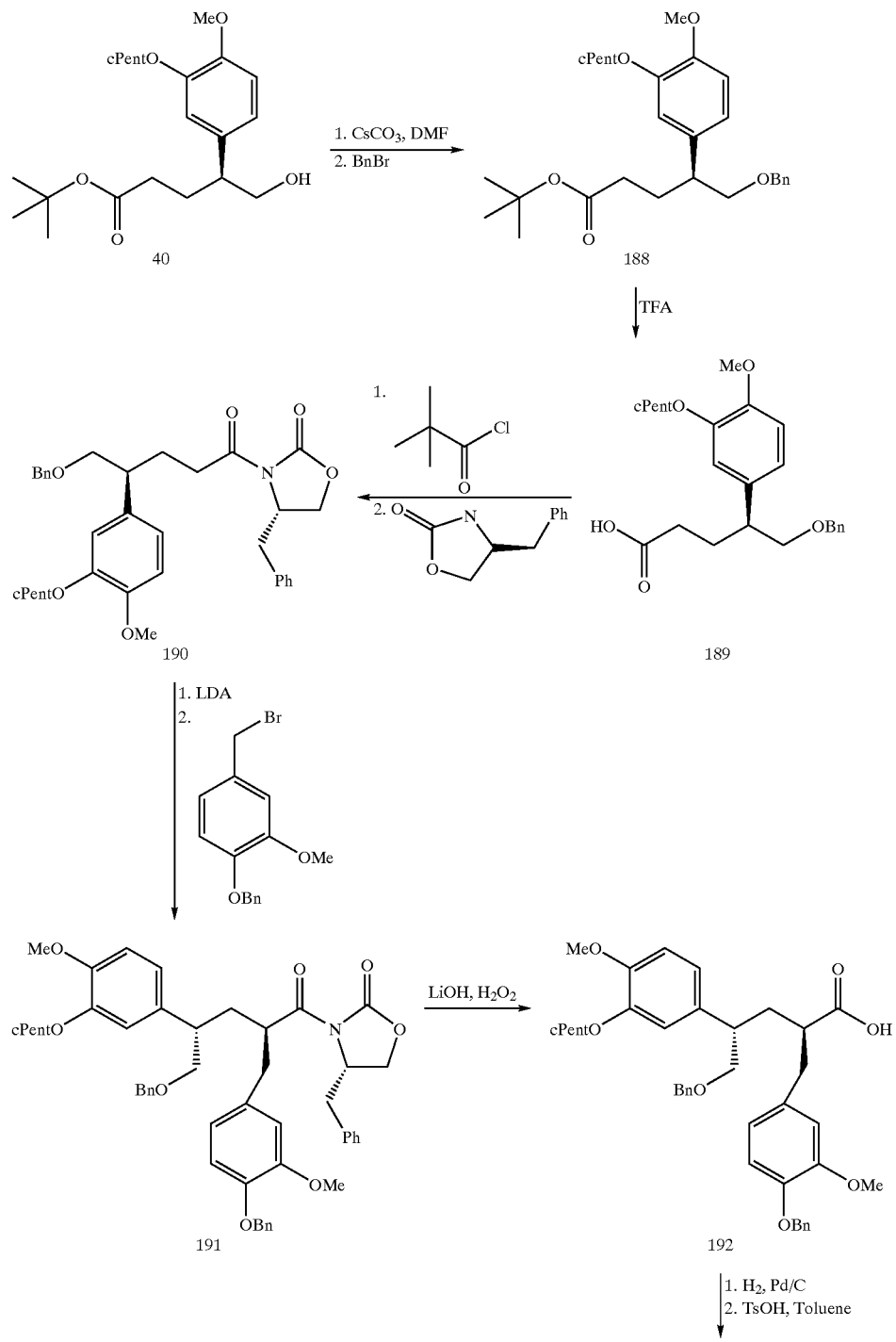

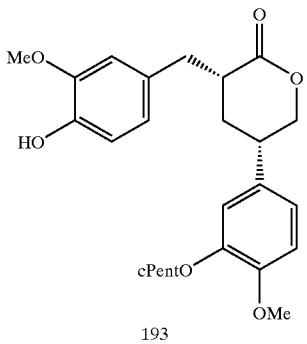

193

In Scheme 28, protection of the primary alcohol in compound 40 may be achieved using benzyl bromide (BnBr) and cesium carbonate in DMF to yield benzyloxy derivative 188, Compound 188 may then be converted to its corresponding acid 189 by reacting compound 188 with trifluoroacetic acid. Synthesis of N-acyloxazolidinone derivative 190 from compound 189 may be accomplished using the same type of the reaction describe in previous sections (for example, Scheme 4). Stereoselective alkylation of compound 190 with 4-(benzyloxy)-3-methoxybenzyl bromide may afford compound 191. Hydrolysis of the chiral auxiliary with lithium hydroxide and hydrogen peroxide may yield the carboxylic acid 192. Hydrogenation of compound 192 in acetic acid and lactonization with p-toluenesulfonic acid monohydrate in toluene may give the desired cyclized product 193 which has the 3R, 5S configuration.

Scheme 30) may afford compound 194. Hydrolysis of the chiral auxiliary with lithium hydroxide and hydrogen peroxide may yield the carboxylic acid 195. Hydrogenation of compound 195 in acetic acid and lactonization with p-toluenesulfonic acid monohydrate in toluene may give the desired cyclized product 196 which has the 3R, 5S configuration. Accordingly, the three other diastereoisomers related to compound 193 or compound 196 can be synthesized similarly but starting with different chiral oxazolidinones. For example, compounds containing 3S, 5S configuration may be synthesized using the intermediate analogous to compound 26 or compound 190 with the oxazolidinone containing the opposite (R) configuration.

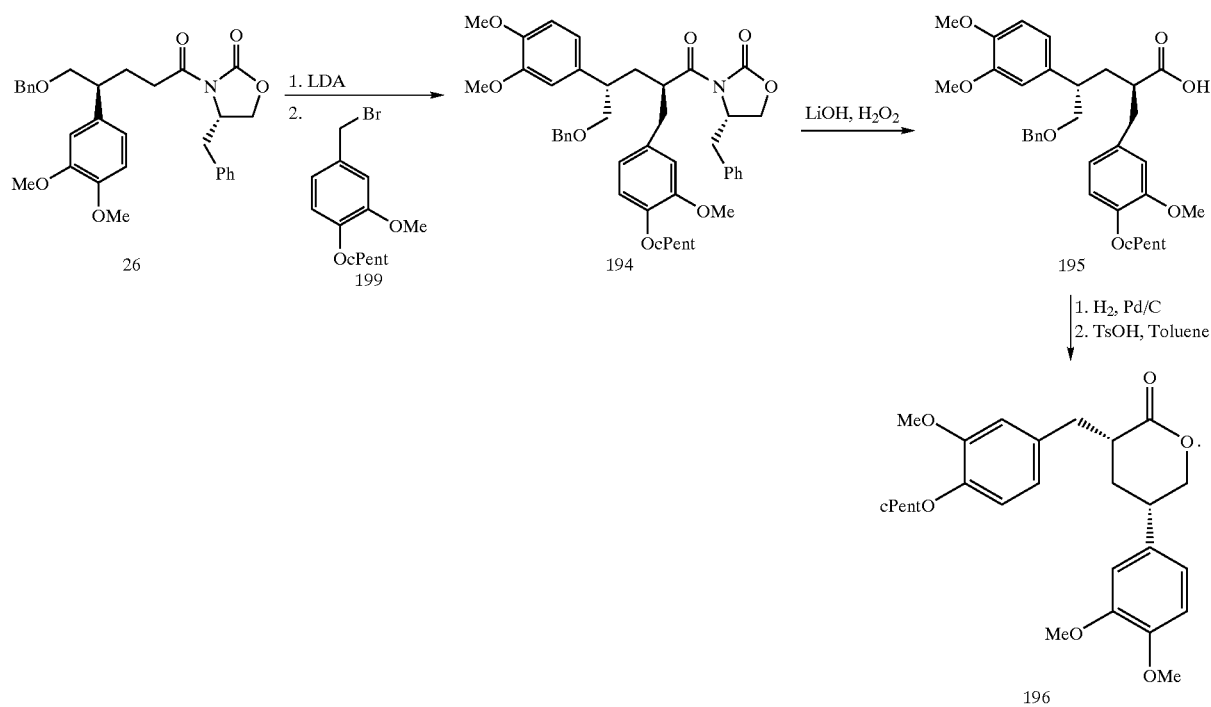

Scheme 29

Similarly, in Scheme 29, stereoselective alkylation of compound 26 with 4-(cyclopentyloxy)-3-methoxybenzyl bromide (preparation of compound 199 is described in Scheme 30 and 31 illustrate the preparation of compound 199 and 203, two intermediates using to generate compounds 134, 136 and 194.

Thus, in Scheme 30, treatment of compound 197 with cyclopentyl bromide, potassium iodide and potassium carbonate in DMF gives the corresponding cyclopentyloxy derivative 198, which is treated with PBr$_3$ in diethyl ether to give desired bromide compound 199.

Scheme 30

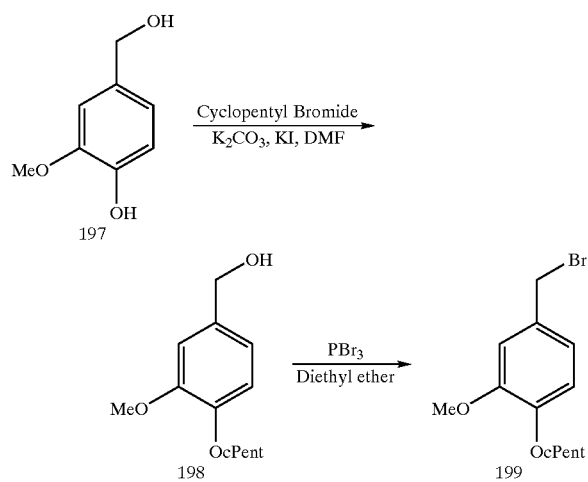

Synthesis of Compound 198

To a suspension of 4-hydroxy-3-methoxybenzyl alcohol 197 (1.00 g, 6.49 mmol), potassium carbonate (1.79 g, 12.98 mmol) and potassium iodide (29.1 mg, 0.175 mmol) in DMF (10 mL) was slowly added cyclopentyl bromide (0.91 mL, 8.44 mmol). The reaction mixture was stirred at 65° C. for 24 hours. After cooling to room temperature, the mixture was diluted with diethyl ether (50 mL) and washed with water (2×25 mL). After drying over anhydrous MgSO$_4$, filtration and evaporation of the filtrate in vacuo gave crude yellow, solid which was purified by silica gel column chromatography (hexanes/EtOAc, 3:1) to give compound 198 (0.502 g, 35%) as a pale yellow solid.

Synthesis of Compound 199

To a solution of compound 198 (0.48 g, 2.17 mmol) in anhydrous diethyl ether (8 mL) was slowly added PBr$_3$ (0.10 mL, 1.09 mmol) via syringe, and the resulting mixture was stirred at room temperature for 2 hours. The mixture was diluted with diethyl ether (50 mL) and washed with saturated aqueous NaHCO$_3$ (2×25 mL) and brine (2×25 mL). The organic layer was dried over anhydrous MgSO$_4$, and the solvent was removed under reduced pressure to afford compound 199 (0.577 g, 93%) as a white solid.

In Scheme 31, treatment of compound 200 with cyclopentyl bromide, potassium iodide and potassium carbonate in DMF gives the corresponding cyclopentyloxy derivative 201. Reduction of compound 201 with NaBH$_4$ affords the alcohol 202 and subsequent bromination using PBr$_3$ in diethyl ether provides the desired bromide compound 203.

Scheme 31

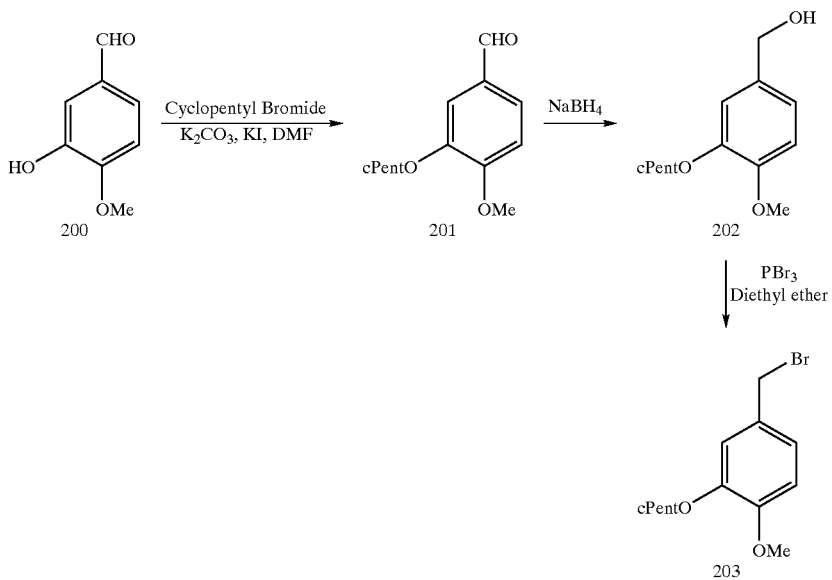

Synthesis of Compound 201

To a suspension of 3-hydroxy-4-methoxybenzaldehyde 200 (2.00 g, 13.2 mmol), potassium carbonate (2.74 g, 19.8 mmol) and potassium iodide (60.0 mg, 0.361 mmol) in DMF (13 mL) was slowly added cyclopentyl bromide (1.84 mL, 17.2 mmol). The reaction mixture was stirred at 65° C. for 21 hours. After cooling to room temperature, the mixture was diluted with toluene (100 mL), and the organic phase was washed with 1N NaOH (2×30 mL) and water (2×30 mL). After drying over anhydrous $MgSO_4$, filtration and evaporation of the filtrate in vacuo gave crude compound 201 (2.70 g) which was used in the next step without further purification.

Synthesis of Compound 202

Compound 201 (2.7 g) was dissolved in $MeOH/CH_2Cl_2$ (2:1, 15 mL) and cooled to 0° C. $NaBH_4$ (0.464 g, 12.26 mmol) was added portionwise. The reaction mixture was stirred at 0° C. for 30 minutes. Water (100 mL) was added and the mixture was extracted with $CH_2Cl_2$ (3×30 mL). The combined organic layers were washed with brine (50 mL) and dried over anhydrous $MgSO_4$. Removal of the solvent gave a pale yellow solid which was purified by silica gel column chromatography (hexanes/EtOAc, 1:1) to give compound 202 (2.65 g, 91% over two steps) as a colorless oil.

Synthesis of Compound 203

To a solution of compound 202 (0.50 g, 2.26 mmol) in anhydrous diethyl ether (9 mL) was slowly added $PBr_3$ (0.11 mL, 1.13 mmol) via syringe, and the resulting mixture was stirred at room temperature for 2 hours. The mixture was diluted with diethyl ether (50 mL) and washed with saturated aqueous $NaHCO_3$ (2×25 mL) and brine (2×25 mL). The organic layer was dried over anhydrous $MgSO_4$, and the solvent was removed under reduced pressure to afford compound 203 (0.604 g, 94%) as a light yellow oil.

p-Substitution on Phenyl Ring

Compounds with different alkoxy groups substituted at the para position on the phenyl ring may be synthesized according to Scheme 32 using methodology analogous to that described in previous sections. For example, compound 216 can be synthesized as follows. Commercially available 4-hydroxy-3-methoxybenzyl alcohol 204 (Aldrich, Milwaukee, Wis.) may be selectively protected as the benzyloxy derivative 205 by treatment of 204 with benzyl bromide and potassium carbonate in refluxing toluene. Compound 205 may then be reacted with methanesulfonyl chloride in the presence of triethylamine and $CH_2Cl_2$ to afford compound 206. Compound 206 may then be placed in DMF and treated with potassium cyanide in the presence of 18-crown-6 to give the nitrile 207. Hydrolysis of nitrile 207 with 1 N aqueous potassium hydroxide may then be used to afford the desire carboxylic acid 208. Treatment of compound 208 with trimethylacetyl chloride may give a mixed anhydride, which may be reacted with the lithium anion of (S)-(−)-4-benzyl-2-oxazolidinone to furnish compound 209. Enantioselective Michael addition of the titanium enolate of the chiral oxazolidinone 209 to tert-butyl acrylate may provide compound 210 having the carboxylate functionality with a suitable protecting group. Hydrogenation of compound 210 may give the phenolic group, which may be protected as the cyclopentyloxy derivative 211 by treatment with cyclopentyl bromide, potassium carbonate and potassium iodide in DMF. Hydrolysis of the chiral auxiliary with lithium hydroxide and hydrogen peroxide may give the carboxylic acid 212. Selective reduction of compound 212 with $BH_3$-THF may give compound 213 containing the primary alcohol. The lactone 214 may be obtained by treatment of compound 213 with pTsOH in toluene. Alkylation of compound 214 with 4-(benzyloxy)-3-methoxybenzyl bromide may be used to afford compound 215. Hydrogenation of compound 215 in acetic acid may be used to give the desired product 216.

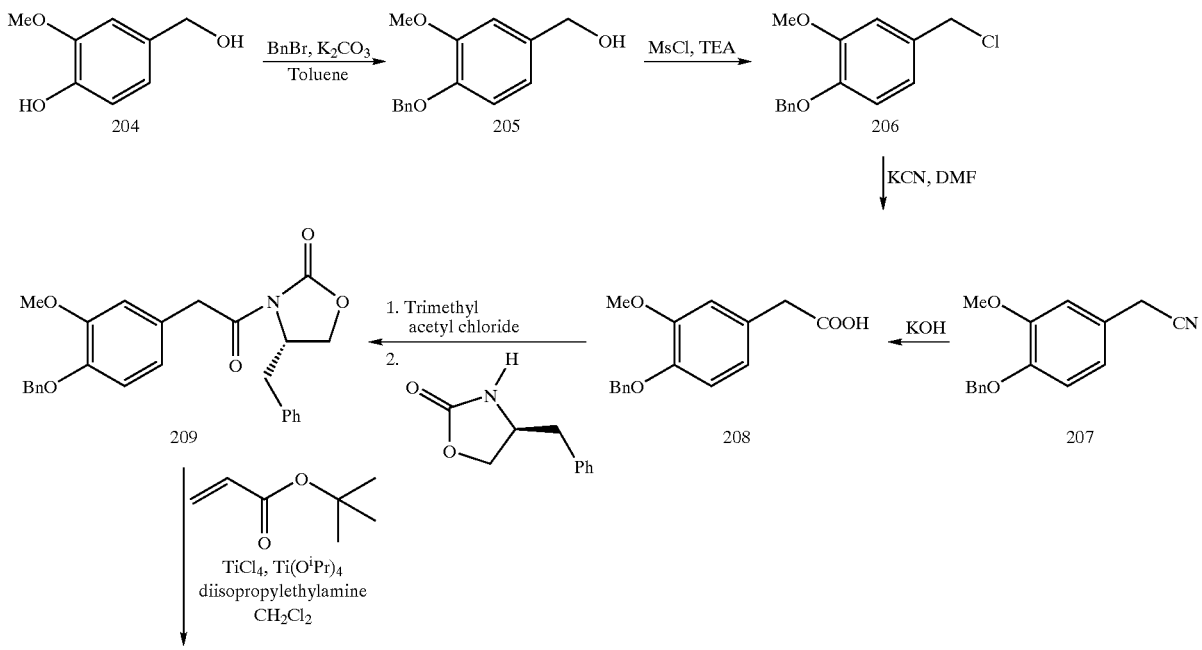

Scheme 32

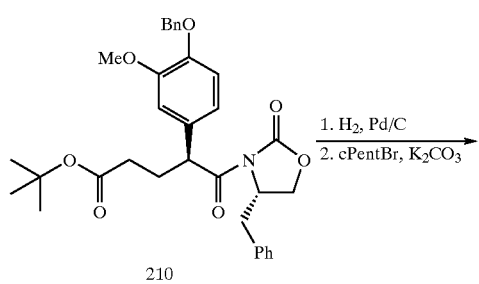
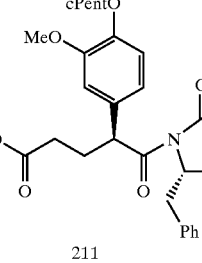
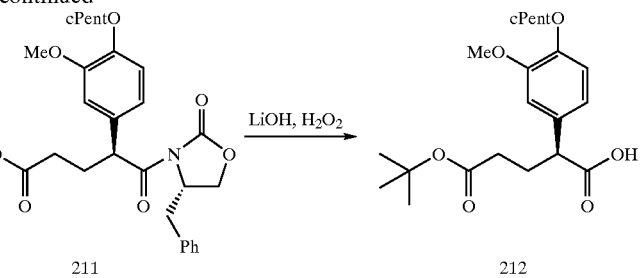
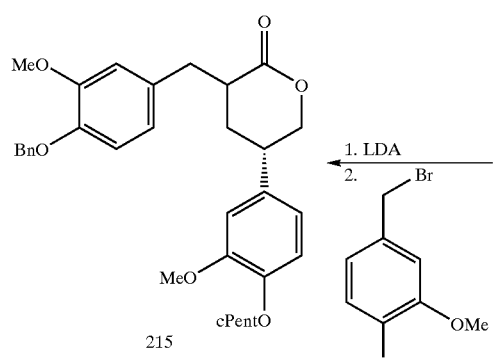
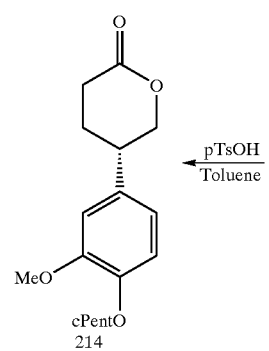
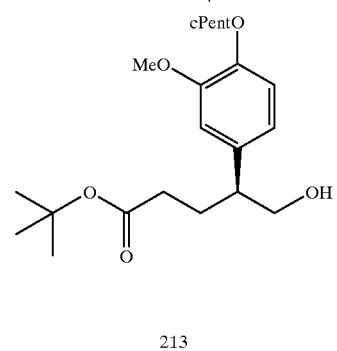
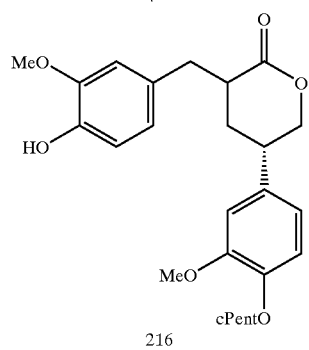
Scheme 33 illustrates the preparation of compound 218, using synthetic methodology similar to that described in Scheme 16.
Scheme 33
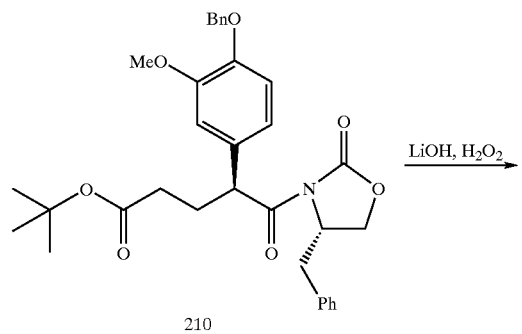
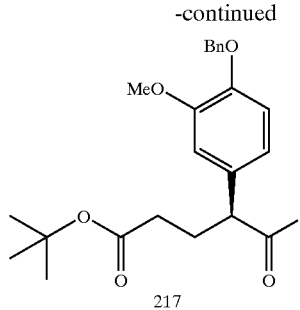

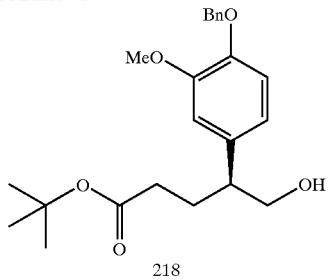

218

Compound 218 is a key intermediate which may be used to generate compounds containing higher carbon number alkyloxy substitutions, hydrocarbyloxycarbonyl substitutions, hydrocarbyl substitutions, boron substitutions, nitrogen substitutions, sulphur substitutions and phosphorus substitutions at the para position of the phenyl ring using the synthetic methodology similar to that described in Schemes 20, 21, 22, 23, 24, 25, 26, and 27 for functionalization of the meta position of the same phenyl ring.

Synthesis of Compound 142 n-Butyllithium (2.5 M solution in hexanes, 0.38 mL, 0.931 mmol) was added to a solution of diisopropylamine (0.14 mL, 0.999 mmol) in dry THF (3 mL) at −78° C. The mixture was stirred at −78° C. for 1 hour, then HMPA (0.22 mL, 1.27 mmol) was added, followed by adding a solution of compound 21 (0.20 g, 0.846 mmol) in THF (3 mL). After 1 hour, a solution of 3-benzyloxybenzyl bromide (0.469 g, 1.69 mmol) in THF (1 mL) was added in one portion to the reaction, and the resulting mixture was stirred at −78° C. for an additional 4 hours. The excess base was quenched with saturated aqueous $NH_4Cl$ (10 mL), and the resulting solution was extracted with EtOAc (3×20 mL). The combined organic layer was washed with saturated NaCl (2×30 mL), dried over $MgSO_4$, filtered and the filtrate evaporated to dryness. The residue was purified by column chromatography on silica gel (hexanes/EtOAc, 2:1) to give compound 142 (0.284 g, 78%) as a colorless oil.

Synthesis of Compound 131

A mixture of compound 142 (0.190 mg, 0.439 mmol) and 10% Pd/C (0.025 g) in EtOAc/AcOH (4:1, 5 mL) was stirred under $H_2$ (balloon) for 2 hours. The mixture was then filtered through a celite plug and the filtrate was evaporated to dryness. The residue was purified by column chromatography on silica gel (hexanes/EtOAc, 3:2) to give compound 131 (0.133 g, 89%) as a colorless syrup.

Synthesis of Compound 132 n-Butyllithium (2.5 M solution in hexanes, 0.38 mL, 0.931 mmol) was added to a solution of diisopropylamine (0.14 mL, 0.999 mmol) in dry THF (3 mL) at −78° C. The mixture was stirred at −78° C. for 1 hour, then HMPA (0.22 mL, 1.27 mmol) was added, followed by adding a solution of compound 21 (0.20 g, 0.846 mmol) in THF (3 mL). After 1 hour, a solution of 4-methoxybenzyl bromide (0.34 g, 1.69 mmol) in THF (1 mL) was added in one portion to the reaction, and the resulting mixture was stirred at −78° C. for an additional 4 hours. The excess base was quenched with saturated aqueous $NH_4Cl$ (10 mL), and the resulting solution was extracted with EtOAc (3×20 mL). The combined organic layer was washed with saturated NaCl (2×30 mL), dried over $MgSO_4$, filtered and the filtrate evaporated to dryness. The residue was purified by column chromatography on silica gel (hexanes/EtOAc, 2:1) to give compound 132 (0.221 g, 73%) as a colorless oil.

Synthesis of Compound 138 n-Butyllithium (2.5 M solution in hexanes, 0.38 mL, 0.931 mmol) was added to a solution of diisopropylamine (0.14 mL, 0.999 mmol) in dry THF (3 mL) at −78° C. The mixture was stirred at −78° C. for 1 hour, then HMPA (0.22 mL, 1.27 mmol) was added, followed by adding a solution of compound 21 (0.20 g, 0.846 mmol) in THF (3 mL). After 1 hour, a solution of 4-benzyloxybenzyl bromide (0.469 g, 1.692 mmol) in THF (1 mL) was added in one portion to the reaction, and the resulting mixture was stirred at −78° C. for an additional 4 hours. The excess base was quenched with saturated aqueous $NH_4Cl$ (10 mL), and the resulting solution was extracted with EtOAc (3×20 mL). The combined organic layer was washed with saturated NaCl (2×30 mL), dried over $MgSO_4$, filtered and the filtrate evaporated to dryness. The residue was purified by column chromatography on silica gel (hexanes/EtOAc, 2:1) to give compound 138 (0.29 g, 79%) as a colorless oil.

Synthesis of Compound 133

A mixture of compound 138 (190.0 mg, 0.324 mmol) and 10% Pd/C (25.0 mg) in EtOAc/AcOH (4:1, 5 mL) was stirred under $H_2$ (balloon) for 2 hours. The mixture was then filtered through a celite plug and the filtrate was evaporated to dryness. The residue was purified by column chromatography on silica gel (hexanes/EtOAc, 3:2) to give compound 133 (139.1 mg, 92%) as a colorless syrup.

Synthesis of Compound 134 n-Butyllithium (2.5 M solution in hexanes, 0.42 mL, 1.06 mmol) was added to a solution of diisopropylamine (0.15 mL, 1.07 mmol) in dry THF (10 mL) at −78° C. The mixture was stirred at −78° C. for 1 hour, then HMPA (0.22 mL, 1.27 mmol) was added, followed by adding a solution of compound 21 (226.8 mg, 0.96 mmol) in THF (5 mL). After 1 hour, a solution of 3-(cyclopentyloxy)-4-methoxybenzyl bromide (0.48 g, 1.68 mmol) in THF (1 mL) was added in one portion to the reaction, and the resulting mixture was stirred at −78° C. for an additional 4 hours. The excess base was quenched with saturated aqueous $NH_4Cl$ (10 mL), and the resulting solution was extracted with EtOAc (3×20 mL). The combined organic layer was washed with saturated NaCl (2×30 mL), dried over $MgSO_4$, filtered and the filtrate evaporated to dryness. The residue was purified by column chromatography on silica gel (hexanes/EtOAc, 2:1) to give compound 134 (0.224 g, 60%) as a colorless oil.

Synthesis of Compound 135 n-Butyllithium (2.5 M solution in hexanes, 4.47 mL, 11.18 mmol) was added to a solution of diisopropylamine (1.57 mL, 11.18 mmol) in dry THF (28 mL) at −78° C. The mixture was stirred at −78° C. for one hour, then HMPA (1.32 mL, 7.62 mmol) was added, followed by adding a solution of compound 21 (1.20 g, 5.08 mmol) in THF (27 mL). After 1 hour, a solution of 3-(benzyloxy)-4-methoxybenzyl bromide (63) (3.12 g, 10.16 mmol) in THF (5 mL) was added in one portion to the reaction, and the resulting mixture was stirred at −78° C. for an additional 4 hours. The excess base was quenched with saturated aqueous $NH_4Cl$ (100 mL), and the resulting solution was extracted with EtOAc (3×200 mL). The combined organic layer was washed with saturated NaCl (2×200 mL), dried over MgSO$_4$, filtered and the filtrate evaporated to dryness. The residue was purified by column chromatography on silica gel (hexanes/EtOAc, 2:1) to give compound 135 (1.16 g, 73%) as a white foam.

Synthesis of Compound 136 n-Butyllithium (2.5 M solution in hexanes, 0.38 mL, 0.931 mmol) was added to a solution of diisopropylamine (0.14 mL, 0.999 mmol) in dry THF (3 mL) at −78° C. The mixture was stirred at −78° C. for one hour, then HMPA (0.22 mL, 1.27 mmol) was added, followed by adding a solution of compound 21 (0.20 mg, 0.846 mmol) in THF (3 mL). After 1 hour, a solution of 4-(cyclopentyloxy)-3-methoxybenzyl bromide (199) (0.507 g, 1.78 mmol) in THF (1 mL) was added in one portion to the reaction, and the resulting mixture was stirred at −78° C. for an additional 4 hours. The excess base was quenched with saturated aqueous NH$_4$Cl (10 mL), and the resulting solution was extracted with EtOAc (3×20 mL). The combined organic layer was washed with saturated NaCl (2×30 mL), dried over MgSO$_4$, filtered and the filtrate evaporated to dryness. The residue was purified by column chromatography on silica gel (hexanes/EtOAc, 2:1) to give compound 136 (0.206 g, 55%) as a colorless oil.

Synthesis of Compound 137

Preparation of 4-(propyloxy)-3-methoxybenzyl bromide: To a suspension of vanillin (2.00 g, 13.2 mmol), potassium carbonate (2.74 g, 19.8 mmol) and potassium iodide (60.0 mg, 0.361 mmol) in DMF (15 mL) was slowly added 1-bromopropane (1.56 mL, 17.2 mmol) via syringe. The reaction mixture was stirred at 65° C. for 5 hours. After cooling to room temperature, the mixture was diluted with diethyl ether (100 mL), and the organic phase was washed with water (2×50 mL). After drying over anhydrous MgSO$_4$, filtration and evaporation of the filtrate in vacuo gave crude 4-(propyloxy)-3-methoxybenzaldehyde (2.55 g) which was used in the next step without further purification.

Crude 4-(propyloxy)-3-methoxybenzaldehyde (2.55 g) was dissolved in EtOH (30 mL) and cooled to 0° C. NaBH$_4$ (0.499 g, 13.2 mmol) was added portionwise. After the addition was completed, the ice-water bath was removed and the reaction mixture was stirred at room temperature for 2 hours. Water (50 mL) was added and the resulting mixture was extracted with diethyl ether (3×100 mL). The combined organic layers were dried over anhydrous MgSO$_4$. Removal of the solvent gave a pale yellow oil which was purified by silica gel column chromatography (hexanes/EtOAc, 4:1) to give 4-(propyloxy)-3-methoxybenzyl alcohol (2.38 g, 92% over two steps) as a colorless oil.

To a solution of 4-(propyloxy)-3-methoxybenzyl alcohol (2.28 g, 11.62 mmol) in anhydrous diethyl ether (30 mL) was slowly added PBr$_3$ (0.55 mL, 5.81 mmol) via syringe, and the resulting mixture was stirred at room temperature for 2 hours. The mixture was diluted with diethyl ether (150 mL) and washed with saturated aqueous NaHCO$_3$ (2×75 mL) and brine (2×75 mL). The organic layer was dried over anhydrous MgSO$_4$, and the solvent was removed under reduced pressure to afford 4-(propyloxy)-3-methoxybenzyl bromide (2.94 g, 98%) as a white solid.

n-Butyllithium (2.5 M solution in hexanes, 0.56 mL, 1.40 mmol) was added to a solution of diisopropylamine (0.20 mL, 1.42 mmol) in dry THF (4 mL) at −78° C. The mixture was stirred at −78° C. for one hour, then HMPA (0.33 mL, 1.91 mmol) was added, followed by adding a solution of compound 21 (0.30 g, 1.27 mmol) in THF (3 mL). After 1 hour, a solution of 4-(propyloxy)-3-methoxybenzyl bromide (0.658 g, 2.54 mmol) in THF (3 mL) was added in one portion to the reaction, and the resulting mixture was stirred at −78° C. for an additional 4 hours. The excess base was quenched with saturated aqueous NH$_4$Cl (15 mL), and the resulting solution was extracted with EtOAc (3×25 mL). The combined organic layer was washed with saturated NaCl (2×30 mL), dried over MgSO$_4$, filtered and the filtrate evaporated to dryness. The residue was purified by column chromatography on silica gel (hexanes/EtOAc, 2:1) to give compound 137 (0.302 g, 57%) as a white foam.

Synthesis of Compound 139 n-Butyllithium (2.5 M solution in hexanes, 0.38 mL, 0.931 mmol) was added to a solution of diisopropylamine (0.14 mL, 0.999 mmol) in dry THF (3 mL) at −78° C. The mixture was stirred at −78° C. for 1 hour, then HMPA (0.22 mL, 1.27 mmol) was added, followed by adding a solution of compound 21 (0.200 g, 0.846 mmol) in THF (3 mL). After 1 hour, a solution of benzyl bromide (0.10 mL, 0.846 mmol) was added in one portion to the reaction, and the resulting mixture was stirred at −78° C. for an additional 4 hours. The excess base was quenched with saturated aqueous NH$_4$Cl (10 mL), and the resulting solution was extracted with EtOAc (3×20 mL). The combined organic layer was washed with saturated NaCl (2×30 mL), dried over MgSO$_4$, filtered and the filtrate evaporated to dryness. The residue was purified by column chromatography on silica gel (hexanes/EtOAc, 2:1) to give compound 139 (53 mg, 38%) as a colorless oil.

Synthesis of Compound 140

Preparation of 3-(propyloxy)-4-methoxybenzyl bromide: To a suspension of 3-hydroxy-4-methoxybenzaldehyde (2.00 g, 13.2 mmol), potassium carbonate (2.74 g, 19.8 mmol) and potassium iodide (60.0 mg, 0.361 mmol) in DMF (15 mL) was slowly added 1-bromopropane (1.56 mL, 17.2 mmol) via syringe. The reaction mixture was stirred at 65° C. for 5 hours. After cooling to room temperature, the mixture was diluted with diethyl ether (100 mL), and the organic phase was washed with water (2×50 mL). After drying over anhydrous MgSO$_4$, filtration and evaporation of the filtrate in vacuo gave crude 3-(propyloxy)-4-methoxybenzaldehyde (2.60 g) which was used in the next step without further purification.

Crude 3-(propyloxy)-4-methoxybenzaldehyde (2.60 g) was dissolved in EtOH (30 mL) and cooled to 0° C. NaBH$_4$ (0.499 g, 13.2 mmol) was added portionwise. After the addition was completed, the ice-water bath was removed and the reaction mixture was stirred at room temperature for 2 hours. Water (50 mL) was added and the resulting mixture was extracted with diethyl ether (3×100 mL). The combined organic layers were dried over anhydrous MgSO$_4$. Removal of the solvent gave a pale yellow oil which was purified by silica gel column chromatography (hexanes/EtOAc, 4:1) to give 3-(propyloxy)-4-methoxybenzyl alcohol (2.29 g, 89% over two steps) as a colorless oil.

To a solution of 3-(propyloxy)-4-methoxybenzyl alcohol (2.28 g, 11.62 mmol) in anhydrous diethyl ether (30 mL) was slowly added PBr$_3$ (0.55 mL, 5.81 mmol) via syringe, and the resulting mixture was stirred at room temperature for 2 hours. The mixture was diluted with diethyl ether (150 mL) and washed with saturated aqueous NaHCO$_3$ (2×75 mL) and brine (2×75 mL). The organic layer was dried over anhydrous MgSO$_4$, and the solvent was removed under reduced pressure to afford 3-(propyloxy)-4-methoxybenzyl bromide (2.92 g, 97%) as a white solid.

n-Butyllithium (2.5 M solution in hexanes, 0.56 mL, 1.40 mmol) was added to a solution of diisopropylamine (0.20 mL, 1.42 mmol) in dry THF (4 mL) at −78° C. The mixture was stirred at −78° C. for one hour, then HMPA (0.33 mL, 1.91 mmol) was added, followed by adding a solution of compound 21 (0.30 g, 1.27 mmol) in THF (3 mL). After 1 hour, a solution of 3-(propyloxy)-4-methoxybenzyl bromide (0.658 g, 2.54 mmol) in THF (3 mL) was added in one portion to the reaction, and the resulting mixture was stirred at −78° C. for an additional 4 hours. The excess base was quenched with saturated aqueous $NH_4Cl$ (15 mL), and the resulting solution was extracted with EtOAc (3×25 mL). The combined organic layer was washed with saturated NaCl (2×30 mL), dried over $MgSO_4$, filtered and the filtrate evaporated to dryness. The residue was purified by column chromatography on silica gel (hexanes/EtOAc, 2:1) to give compound 140 (0.310 g, 59%) as a white foam.

Synthesis of Compound 141 n-Butyllithium (2.5 M solution in hexanes, 0.56 mL, 1.40 mmol) was added to a solution of diisopropylamine (0.20 mL, 1.42 mmol) in dry THF (4 mL) at −78° C. The mixture was stirred at −78° C. for one hour, then HMPA (0.33 mL, 1.91 mmol) was added, followed by adding a solution of compound 21 (0.30 g, 1.27 mmol) in THF (3 mL). After 1 hour, a solution of 4-fluoro benzyl bromide (0.32 mL, 2.54 mmol) was added in one portion to the reaction, and the resulting mixture was stirred at −78° C. for an additional 4 hours. The excess base was quenched with saturated aqueous $NH_4Cl$ (15 mL), and the resulting solution was extracted with EtOAc (3×25 mL). The combined organic layer was washed with saturated NaCl (2×30 mL), dried over $MgSO_4$, filtered and the filtrate evaporated to dryness. The residue was purified by column chromatography on silica gel (hexanes/EtOAc, 2:1) to give compound 141 (0.267 g, 61%) as a colorless syrup.

Synthesis of Compound 143

To a suspension of compound 97 (0.120 g, 0.41 mmol) and potassium carbonate (0.085 g, 0.615 mmol) in anhydrous DMF (2 mL) was added 1-iodoethane (0.049 mL, 0.615 mmol) via syringe. The reaction mixture was stirred at 65° C. overnight. After cooling, the mixture was diluted with water (10 mL) and extracted with diethyl ether (3×15 mL). The combined organic layers were washed with brine (10 mL), dried over anhydrous $MgSO_4$, and concentrated to dryness. The residue was purified by silica gel column chromatography (hexanes/EtOAc, 7:3) to afford compound 143 (0.096 g, 72%) as a colorless syrup.

Synthesis of Compound 144

To a suspension of compound 97 (0.21 g, 0.71 mmol), potassium carbonate (0.147 g, 1.06 mmol) and KI (0.02 g) in anhydrous DMF (2 mL) was added 1-bromopropane (0.077 mL, 0.85 mmol) via syringe. Then the reaction mixture was stirred at 65° C. overnight. After cooling, the mixture was diluted with water (10 mL) and extracted with diethyl ether (3×15 mL). The combined organic layers were washed with brine (10 mL), dried over anhydrous $MgSO_4$, and concentrated to dryness. The residue was purified by silica gel column chromatography (hexanes/EtOAc, 7:3) to afford compound 144 (0.185 g, 77%) as a colorless syrup.

Synthesis of Compound 145

To a suspension of compound 97 (0.15 g, 0.51 mmol) and potassium carbonate (0.105 g, 0.76 mmol) in anhydrous DMF (2 mL) was added 2-iodopropane (0.18 mL, 1.02 mmol) via syringe. Then the reaction mixture was stirred at 65° C. overnight. After cooling, the mixture was diluted with water (10 mL) and extracted with diethyl ether (3×15 mL). The combined organic layers were washed with brine (10 mL), dried over anhydrous $MgSO_4$, and concentrated to dryness. The residue was purified by silica gel column chromatography (hexanes/EtOAc, 7:3) to afford compound 145 (0.18 g, 86%) as a colorless syrup.

Synthesis of Compound 146

To a suspension of compound 97 (0.15 g, 0.51 mmol) and potassium carbonate (0.105 g, 0.76 mmol in anhydrous DMF (2 mL) was added 3-bromo-2-methylpropene (0.077 mL, 0.76 mmol) via syringe. Then the reaction mixture was stirred at 65° C. overnight. After cooling, the mixture was diluted with water (10 mL) and extracted with diethyl ether (3×15 mL). The combined organic layers were washed with brine (10 mL), dried over anhydrous $MgSO_4$, and concentrated to dryness. The residue was purified by silica gel column chromatography (hexanes/EtOAc, 7:3) to afford compound 146 (0.118 g, 66%) as a colorless syrup.

Synthesis of Compound 147

To a suspension of compound 97 (0.15 g, 0.51 mmol), potassium carbonate (0.105 g, 0.76 mmol) and KI (5.0 mg) in anhydrous DMF (2 mL) was added (bromomethyl)cyclobutane (0.085 mL, 0.76 mmol) via syringe. Then the reaction mixture was stirred at 65° C. overnight. After cooling, the mixture was diluted with water (10 mL) and extracted with diethyl ether (3×15 mL). The combined organic layers were washed with brine (10 mL), dried over anhydrous $MgSO_4$, and concentrated to dryness. The residue was purified by silica gel column chromatography (hexanes/EtOAc, 7:3) to afford compound 147 (0.132 g, 71%) as a white solid.

Synthesis of Compound 148

To a suspension of compound 97 (0.15 g, 0.51 mmol), potassium carbonate (0.105 g, 0.76 mmol) and KI (10 mg, cat.) in anhydrous DMF (2 mL) was added (bromomethyl)cyclohexane (0.077 mL, 0.76 mmol) via syringe. Then the reaction mixture was stirred at 65° C. overnight. After cooling, the mixture was diluted with water (10 mL) and extracted with diethyl ether (3×15 mL). The combined organic layers were washed with brine (10 mL), dried over anhydrous $MgSO_4$, and concentrated to dryness. The residue was purified by silica gel column chromatography (hexanes/EtOAc, 7:3) to afford compound 148 (0.124 g, 62%) as a colorless syrup.

Synthesis of Compound 149

To a suspension of compound 97 (0.15 g, 0.51 mmol) and potassium carbonate (0.105 g, 0.76 mmol) in anhydrous DMF (2 mL) was added 1-iodopentane (0.099 mL, 0.76 mmol) via syringe. Then the reaction mixture was stirred at 65° C. overnight. After cooling, the mixture was diluted with water (10 mL) and extracted with diethyl ether (3×15 mL). The combined organic layers were washed with brine (10 mL), dried over anhydrous $MgSO_4$, and concentrated to dryness. The residue was purified by silica gel column chromatography (hexanes/EtOAc, 7:3) to afford compound 149 (0.143 g, 77%) as a white solid.

Synthesis of Compound 150

To a suspension of compound 97 (0.15 g, 0.51 mmol) and potassium carbonate (0.105 g, 0.76 mmol) in anhydrous DMF (2 mL) was added 1-iodohexane (0.11 mL, 0.76 mmol) via syringe. Then the reaction mixture was stirred at 65° C. overnight. After cooling, the mixture was diluted with water (10 mL) and extracted with diethyl ether (3×15 mL). The combined organic layers were washed with brine (10 mL), dried over anhydrous $MgSO_4$, and concentrated to dryness. The residue was purified by silica gel column chromatography (hexanes/EtOAc, 7:3) to afford compound 150 (0.148 g, 77%) as a white solid.

Synthesis of Compound 151

To a suspension of compound 97 (0.15 g, 0.51 mmol) and potassium carbonate (0.105 g, 0.76 mmol) in anhydrous DMF (2 mL) was added 1-iodoheptane (0.13 mL, 0.76 mmol) via syringe. Then the reaction mixture was stirred at 65° C. overnight. After cooling, the mixture was diluted with water (10 mL) and extracted with diethyl ether (3×15 mL). The combined organic layers were washed with brine (10 mL), dried over anhydrous $MgSO_4$, and concentrated to dryness. The residue was purified by silica gel column chromatography (hexanes/EtOAc, 7:3) to afford compound 151 (0.160 g, 80%) as a colorless syrup.

Synthesis of Compound 152

To a suspension of compound 97 (0.15 g, 0.51 mmol) and potassium carbonate (0.105 g, 0.76 mmol) in anhydrous DMF (2 mL) was added 1-iodooctane (0.18 mL, 1.02 mmol) via syringe. Then the reaction mixture was stirred at 65° C. overnight. After cooling, the mixture was diluted with water (10 mL) and extracted with diethyl ether (3×15 mL). The combined organic layers were washed with brine (10 mL), dried over anhydrous $MgSO_4$, and concentrated to dryness. The residue was purified by silica gel column chromatography (hexanes/EtOAc, 7:3) to afford compound 152 (0.18 g, 86%) as a colorless syrup.

Synthesis of Compound 153

A mixture of compound 143 (0.096 g, 0.38 mmol) and p-toluenesulfonic acid monohydrate (10 mg, cat.) in toluene (5 mL) was heated at 75° C. for 30 minutes. Toluene was removed in vacuo, and the residue was purified by silica gel column chromatography (hexanes/EtOAc, 65:35) to give compound 153 (0.060 g, 63%) as a white solid.

Synthesis of Compound 154

A mixture of compound 144 (0.179 g, 0.53 mmol) and p-toluenesulfonic acid monohydrate (20 mg, cat.) in toluene (5 mL) was heated at 75° C. for 30 minutes. Toluene was removed in vacuo, and the residue was purified by silica gel column chromatography (hexanes/EtOAc, 65:35) to give compound 154 (0.086 g, 61%) as a colorless syrup.

Synthesis of Compound 155

A mixture of compound 145 (0.094 g, 0.278 mmol) and p-toluenesulfonic acid monohydrate (9 mg, cat.) in toluene (5 mL) was heated at 75° C. for 30 minutes. Toluene was removed in vacuo, and the residue was purified by silica gel column chromatography (hexanes/EtOAc, 65:35) to give compound 155 (0.069 g, 94%) as a colorless syrup.

Synthesis of Compound 156

A mixture of compound 146 (118 mg, 0.337 mmol) and p-toluenesulfonic acid monohydrate (10 mg, cat.) in toluene (5 mL) was heated at 75° C. for 30 minutes. Toluene was removed in vacuo, and the residue was purified by silica gel column chromatography (hexanes/EtOAc, 65:35) to give compound 156 (0.092 g, 100%) as a colorless syrup.

Synthesis of Compound 157

A mixture of compound 147 (0.132 g, 0.362 mmol) and p-toluenesulfonic acid monohydrate (15 mg, cat.) in toluene (5 mL) was heated at 75° C. for 30 minutes. Toluene was removed in vacuo, and the residue was purified by silica gel column chromatography (hexanes/EtOAc, 65:35) to give compound 157 (0.101 g, 96%) as a colorless syrup.

Synthesis of Compound 158

A mixture of compound 148 (0.124 g, 0.389 mmol) and p-toluenesulfonic acid monohydrate (15 mg, cat.) in toluene (5 mL) was heated at 75° C. for 30 minutes. Toluene was removed in vacuo, and the residue was purified by silica gel column chromatography (hexanes/EtOAc, 65:35) to give compound 158 (0.09 g, 73%) as a white solid.

Synthesis of Compound 159

A mixture of compound 149 (0.143 g, 0.39 mmol) and p-toluenesulfonic acid monohydrate (20 mg, cat.) in toluene (5 mL) was heated at 75° C. for 30 minutes. Toluene was removed in vacuo, and the residue was purified by silica gel column chromatography (hexanes/EtOAc, 65:35) to give compound 159 (0.112 g, 98%) as a colorless syrup.

Synthesis of Compound 160

A mixture of compound 150 (0.148 g, 0.389 mmol) and p-toluenesulfonic acid monohydrate (20 mg, cat.) in toluene (5 mL) was heated at 75° C. for 30 minutes. Toluene was removed in vacuo, and the residue was purified by silica gel column chromatography (hexanes/EtOAc, 65:35) to give compound 160 (0.112 g, 94%) as a colorless syrup.

Synthesis of Compound 161

A mixture of compound 151 (0.148 g, 0.389 mmol) and p-toluenesulfonic acid monohydrate (30 mg, cat.) in toluene (5 mL) was heated at 75° C. for 30 minutes. Toluene was removed in vacuo, and the residue was purified by silica gel column chromatography (hexanes/EtOAc, 65:35) to give compound 161 (0.12 g, 100%) as a colorless syrup.

Synthesis of Compound 162

A mixture of compound 152 (0.180 g, 0.44 mmol) and p-toluenesulfonic acid monohydrate (30 mg, cat.) in toluene (5 mL) was heated at 75° C. for 30 minutes. Toluene was removed in vacuo, and the residue was purified by silica gel column chromatography (hexanes/EtOAc, 65:35) to give compound 162 (0.13 g, 88%) as a colorless syrup.

Synthesis of Compound 163

To a solution of compound 99 (0.11 g, 0.40 mmol) in dry THF (2 mL) under argon was slowly added LDA (0.67 mL, 0.48 mmol, freshly prepared from n-BuLi and diisopropylamine in THF at −78° C.). The mixture was stirred at −78° C. for one hour, and then HMPA (0.1 mL, 0.60 mmol) was added to the mixture via syringe. After 15 minutes, 4-(benzyloxy)-3-methoxybenzyl bromide (0.184 g, 0.60 mmol) was added. The resulting mixture was stirred at −78° C. for an additional 4 hours. The excess base was quenched with saturated aqueous $NH_4Cl$ (5 mL), and the resulting solution was extracted with EtOAc (3×15 mL). The combined organic layers were washed with brine (15 mL), dried over MgSO$_4$, and filtered, and the filtrate was evaporated to dryness. The residue was purified by silica gel column chromatography (benzene/EtOAc, 95:5) to afford compound 163 (0.136 g, 67%) as a colorless syrup.

Synthesis of Compound 164

A mixture of compound 163 (0.136 g, 0.27 mmol) and 10% Pd/C (15 mg) in EtOAc (3 mL) was stirred under H$_2$ (balloon) overnight. The catalyst was removed by filtration and the filtrate was evaporated to dryness. The residue was purified by silica gel column chromatography (bezene/EtOAc, 19:1) to afford compound 164 (0.082 g, 73%) as a colorless syrup.

Synthesis of Compound 165

To a solution of compound 99 (0.30 g, 1.08 mmol) in dry THF (4 mL) under argon was slowly added LDA (1.8, mL, 1.3 mmol, freshly prepared from n-BuLi and diisopropylamine in THF at −78° C.). The mixture was stirred at −78° C. for one hour, and then HMPA (0.28 mL, 1.62 mmol) was added via syringe. After 15 minutes, compound 76 (0.52 g, 1.62 mmol) was added. The resulting mixture was stirred at −78° C. for an additional 4 hours. The excess base was quenched with saturated aqueous NH$_4$Cl (5 mL), and the resulting solution was extracted with EtOAc (3×15 mL). The combined organic layers were washed with brine (15 mL), dried over MgSO$_4$, and filtered, and the filtrate was evaporated to dryness. The residue was purified by silica gel column chromatography (benzene/EtOAc, 95:5) to afford compound 165 (0.443 g, 79%) as a bright yellow solid.

Synthesis of Compound 166

A mixture of compound 165 (0.136 mg, 0.27 mmol) and 10% Pd/C (15 mg) in EtOAc (3 mL) was stirred under H$_2$ (balloon) overnight. The catalyst was removed by filtration and the filtrate was evaporated to dryness. The residue was purified by silica gel column chromatography (bezene/EtOAc, 3:2) to afford compound 166 (0.215 g, 70%, R$_f$=0.29, benzene/EtOAc, 9:4) as a pale yellow foam.

Synthesis of Compound 167

Preparation of (3,4-dibenzyloxy)benzyl bromide: To a solution of (3,4-dibenzyloxy)benzyl alcohol (1.35 g, 4.21 mmol) in anhydrous diethyl ether (25 mL) was added PBr$_3$ (0.20 mL, 2.11 mmol) in one portion, and the resulting mixture was stirred at room temperature for 3 hours. The mixture was diluted with diethyl ether (50 mL) and washed with H$_2$O (2×30 mL), saturated NaHCO$_3$ (2×30 mL), and brine (2×30 mL). The ether layer was dried over anhydrous MgSO$_4$, and the solvent was removed under reduced pressure to afford (3,4-dibenzyloxy)benzyl bromide (1.47 g, 91%) as a white solid.

To a solution of compound 41 (0.10 g, 0.344 mmol) in dry THF (2 mL) under argon was slowly added LDA (0.53 mL, 0.379 mmol, freshly prepared from n-BuLi and diisopropylamine in THF at −78° C.). The mixture was stirred at −78° C. for one hour, and then HMPA (0.09 mL, 0.517 mmol) was added via syringe. After 15 minutes, (3,4-dibenzyloxy) benzyl bromide (0.198 g, 0.517 mmol) was added. The resulting mixture was stirred at −78° C. for two hours and then allowed to warm up to room temperature over a period of two hours. The excess base was quenched with saturated aqueous NH$_4$Cl (5 mL), and the resulting solution was extracted with EtOAc (3×15 mL). The combined organic layers were washed with brine (15 mL) dried over MgSO$_4$, and filtered, and the filtrate was evaporated to dryness. The residue was purified by silica gel column chromatography (benzene/EtOAc, 95:5) to afford compound 167 (0.061 g, 30%) as a colorless syrup.

Synthesis of Compound 168

To a solution of compound 41 (0.10 g, 0.344 mmol) in dry THF (2 mL) under argon was slowly added LDA (0.53 mL, 0.379 mmol, freshly prepared from n-BuLi and diisopropylamine in THF at −78° C.). The mixture was stirred at −78° C. for one hour, and then HMPA (0.09 mL, 0.517 mmol) was added via syringe. After 15 minutes, benzyl bromide (0.062 mL, 0.517 mmol) was added. The resulting mixture was stirred at −78° C. for two hours and then allowed to warm up to room temperature over a period of two hours. The excess base was quenched with saturated aqueous NH$_4$Cl (5 mL), and the resulting solution was extracted with EtOAc (3×15 mL). The combined organic layers were washed with brine (15 mL), dried over MgSO$_4$, and filtered, and the filtrate was evaporated to dryness. The residue was purified by silica gel column chromatography (benzene/EtOAc, 95:5) to afford compound 168 (0.051 g, 39%) as a colorless syrup.

Synthesis of Compound 169

To a solution of compound 41 (0.10 g, 0.344 mmol) in dry THF (2 mL) under argon was slowly added LDA (0.53 mL, 0.379 mmol, freshly prepared from n-BuLi and diisopropylamine in THF at −78° C.). The mixture was stirred at −78° C. for one hour, and then HMPA (0.09 mL, 0.517 mmol) was added via syringe. After 15 minutes, commercially available (3-trifluoromethyl)benzyl bromide (Aldrich Chemical Co., Milwaukee, Wis., 0.079 mL, 0.517 mmol) was added. The resulting mixture was stirred at −78° C. for an additional 4 hours. The excess base was quenched with saturated aqueous NH$_4$Cl (5 mL), and the resulting solution was extracted with EtOAc (3×15 mL). The combined organic layers were washed with brine (15 mL), dried over MgSO$_4$, and filtered, and the filtrate was evaporated to dryness. The residue was purified by silica gel column chromatography (benzene/ EtOAc, 95:5) to afford compound 169 (0.126 g, 82%) as a colorless syrup.

Synthesis of Compound 170

To a solution of compound 41 (0.283 g, 0.975 mmol) in dry THF (2 mL) under argon was slowly added LDA (1.64 mL, 1.17 mmol, freshly prepared from n-BuLi and diisopropylamine in THF at −78° C.). The mixture was stirred at −78° C. for one hour, and then HMPA (0.254 mL, 1.46 mmol) was added via syringe. After 15 minutes, compound 63 (0.45 g, 1.46 mmol) was added. The resulting mixture was stirred at −78° C. for an additional 4 hours. The excess base was quenched with saturated aqueous NH$_4$Cl (5 mL), and the resulting solution was extracted with EtOAc (3×15 mL). The combined organic layers were washed with brine (15 mL), dried over MgSO$_4$, and filtered, and the filtrate was evaporated to dryness. The residue was purified by silica gel column chromatography (hexanes/EtOAc, 4:1) to afford compound 170 (0.211 g) containing a small amount of disubstituted product as a colorless syrup.

Synthesis of Compound 171

Preparation of piperonyl bromide: To a solution of piperonyl alcohol (5.0 g, 32.86 mmol) in anhydrous diethyl ether (80 mL) was added PBr$_3$ (1.56 mL, 16.43 mmol) in one portion, and the resulting mixture was stirred at room temperature for 3 hours. The mixture was diluted with diethyl ether (100 mL) and washed with H$_2$O (2×50 mL), saturated NaHCO$_3$ (2×50 mL), and brine (2×50 mL). The ether layer was dried over anhydrous MgSO$_4$, and the solvent was removed under reduced pressure to afford piperonyl bromide (6.43 g, 91%) as a yellow-grey solid.

To a solution of compound 41 (0.154 g, 0.53 mmol) in dry THF (2 mL) under argon was slowly added LDA (0.89 mL, 0.636 mmol, freshly prepared from n-BuLi and diisopropylamine in THF at −78° C.). The mixture was stirred at −78° C. for one hour, and then HMPA (0.14 mL, 0.795 mmol) was added via syringe. After 15 minutes, piperonyl bromide (0.22 g, 1.02 mmol) was added. The resulting mixture was stirred at −78° C. for an additional 5 hours. The excess base was quenched with saturated aqueous NH$_4$Cl (5 mL), and the resulting solution was extracted with EtOAc (3×15 mL). The combined organic layers were washed with brine (15 mL), dried over MgSO$_4$, and filtered, and the filtrate was evaporated to dryness. The residue was purified by silica gel column chromatography (hexanes/EtOAc, 4:1) to afford compound 171 (0.101 g, 45%) as a colorless syrup.

Synthesis of Compound 172

Preparation of (3-benzyloxy)benzyl bromide: To a solution of (3-benzyloxy)benzyl alcohol (3.0 g, 14.0 mmol) in anhydrous diethyl ether (50 mL) was added PBr$_3$ (0.66 mL, 7.0 mmol) in one portion, and the resulting mixture was stirred at room temperature for 3 hours. The mixture was diluted with diethyl ether (60 mL) and washed with H$_2$O (2×40 mL), saturated NaHCO$_3$ (2×40 mL), and brine (2×40 mL). The ether layer was dried over anhydrous MgSO$_4$, and the solvent was removed under reduced pressure to afford (3-benzyloxy)benzyl bromide (3.76 g, 97%) as a pale yellow solid.

To a solution of compound 41 (0.10 g, 0.344 mmol) in dry THF (2 mL) under argon was slowly added LDA (0.53 mL, 0.379 mmol, freshly prepared from n-BuLi and diisopropylamine in THF at −78° C.). The mixture was stirred at −78° C. for one hour, and then HMPA (0.09 mL, 0.517 mmol) was added via syringe. After 15 minutes, (3-benzyloxy)benzyl bromide (0.143 g, 0.517 mmol) was added. The resulting mixture was stirred at −78° C. for two hours and then allowed to warm up to room temperature over a period of two hours. The excess base was quenched with saturated aqueous NH$_4$Cl (5 mL), and the resulting solution was extracted with EtOAc (3×15 mL). The combined organic layers were washed with brine (15 mL), dried over MgSO$_4$, and filtered, and the filtrate was evaporated to dryness. The residue was purified by silica gel column chromatography (benzene/EtOAc, 95:5) to afford compound 172 (0.054 g, 32%) as a colorless syrup.

Synthesis of Compound 173

Preparation of (4-benzyloxy)benzyl bromide: To a solution of (4-benzyloxy)benzyl alcohol (1.00 g, 4.67 mmol) in anhydrous diethyl ether (20 mL) was added PBr$_3$ (0.22 mL, 2.34 mmol) in one portion, and the resulting mixture was stirred at room temperature for 3 hours. The mixture was diluted with diethyl ether (30 mL) and washed with H$_2$O (2×20 mL), saturated NaHCO$_3$ (2×20 mL); and brine (2×20 mL). The ether layer was dried over anhydrous MgSO$_4$, and the solvent was removed under reduced pressure to afford (4-benzyloxy)benzyl bromide (1.10 g, 85%) as a white solid.

To a solution of compound 41 (0.276 g, 0.95 mmol) in dry THF (2 mL) under argon was slowly added LDA (1.6 mL, 1.14 mmol, freshly prepared from n-BuLi and diisopropylamine in THF at −78° C.). The mixture was stirred at −78° C. for one hour, and then HMPA (0.25 mL, 1.425 mmol) was added via syringe. After 15 minutes, (4-benzyloxy)benzyl bromide (0.306 g, 1.10 mmol) was added. The resulting mixture was stirred at −78° C. for an additional 4 hours. The excess base was quenched with saturated aqueous NH$_4$Cl (5 mL), and the resulting solution was extracted with EtOAc (3×15 mL). The combined organic layers were washed with brine (15 mL) dried over MgSO$_4$, and filtered, and the filtrate was evaporated to dryness. The residue was purified by silica gel column chromatography (hexanes/EtOAc, 4:1) to afford compound 173 (0.121 g, 26%) as a colorless syrup.

Synthesis of Compound 174

To a solution of compound 41 (0.10 g, 0.344 mmol) in dry THF (2 mL) under argon was slowly added LDA (0.58 mL, 0.412 mmol, freshly prepared from n-BuLi and diisopropylamine in THF at −78° C.). The mixture was stirred at −78° C. for one hour, and then HMPA (0.1 mL, 0.516 mmol) was added via syringe. After 15 minutes, 2-nitrobenzyl bromide (0.112 g, 0.516 mmol) was added. The resulting mixture was stirred at −78° C. for an additional 4 hours. The excess base was quenched with saturated aqueous NH$_4$Cl (5 mL), and the resulting solution was extracted with EtOAc (3×15 mL). The combined organic layers were washed with brine (15 mL), dried over MgSO$_4$, and filtered, and the filtrate was evaporated to dryness. The residue was purified by silica gel column chromatography (benzene:EtOAc, 95:5) to afford compound 174 (0.126 g, 86%) as a colorless syrup.

Synthesis of Compound 175

To a solution of compound 41 (0.10 g, 0.344 mmol) in dry THF (2 mL) under argon was slowly added LDA (0.58 mL, 0.412 mmol, freshly prepared from n-BuLi and diisopropylamine in THF at −78° C.). The mixture was stirred at −78° C. for one hour, and then HMPA (0.1 mL, 0.516 mmol) was added via syringe. After 15 minutes, 3-nitrobenzyl bromide (0.112 g, 0.516 mmol) was added. The resulting mixture was stirred at −78° C. for an additional 4 hours. The excess base was quenched with saturated aqueous NH$_4$Cl (5 mL), and the resulting solution was extracted with EtOAc (3×15 mL). The combined organic layers were washed with brine (15 mL), dried over MgSO$_4$, and filtered, and the filtrate was evaporated to dryness. The residue was purified by silica gel column chromatography (benzene/EtOAc, 95:5) to afford compound 175 (0.118 g, 81%) as a colorless syrup.

Synthesis of Compound 176

To a solution of compound 41 (0.10 g, 0.344 mmol) in dry THF (2 mL) under argon was slowly added LDA (0.58 mL, 0.412 mmol, freshly prepared from n-BuLi and diisopropylamine in THF at −78° C.). The mixture was stirred at −78° C. for one hour, and then HMPA (0.1 mL, 0.516 mmol) was added via syringe. After 15 minutes, 4-methyl-3-nitrobenzyl chloride (96 mg, 0.516 mmol) was added. The resulting mixture was stirred at −78° C. for an additional 4 hours. The excess base was quenched with saturated aqueous NH$_4$Cl (5 mL), and the resulting solution was extracted with EtOAc (3×15 mL). The combined organic layers were washed with brine (15 mL), dried over MgSO$_4$, and filtered, and the filtrate was evaporated to dryness. The residue was purified by silica gel column chromatography (benzene/EtOAc, 95:5) to afford compound 176 (0.049 g, 32%) as a colorless syrup.

Synthesis of Compound 177

To a solution of compound 41 (0.10 g, 0.344 mmol) in dry THF (2 mL) under argon was slowly added LDA (0.58 mL, 0.412 mmol, freshly prepared from n-BuLi and diisopropylamine in THF at −78° C.). The mixture was stirred at −78° C. for one hour, and then HMPA (0.1 mL, 0.516 mmol) was added via syringe. After 15 minutes, 4-nitrobenzyl bromide (0.112 g, 0.516 mmol) was added. The resulting mixture was stirred at −78° C. for an additional 4 hours. The excess base was quenched with saturated aqueous $NH_4Cl$ (5 mL), and the resulting solution was extracted with EtOAc (3×15 mL). The combined organic layers were washed with brine (15 mL), dried over $MgSO_4$, and filtered, and the filtrate was evaporated to dryness. The residue was purified by silica gel column chromatography (benzene/EtOAc, 95:5) to afford compound 177 (0.107 g, 73%) as a colorless syrup.

Synthesis of Compound 178

To a solution of compound 41 (0.15 g, 0.516 mmol) in dry THF (3 mL) under argon was slowly added LDA (0.72 mL, 0.62 mmol, freshly prepared from n-BuLi and diisopropylamine in THF at −78° C.). The mixture was stirred at −78° C. for one hour, and then HMPA (0.15 mL, 0.77 mmol) was added via syringe. After 15 minutes, 2-methoxy-5-nitrobenzyl bromide (0.19 g, 0.77 mmol) was added. The resulting mixture was stirred at −78° C. for an additional 4 hours. The excess base was quenched with saturated aqueous $NH_4Cl$ (5 mL), and the resulting solution was extracted with EtOAc (3×15 mL). The combined organic layers were washed with brine (15 mL), dried over $MgSO_4$, and filtered, and the filtrate was evaporated to dryness. The residue was purified by silica gel column chromatography (benzene/EtOAc, 95:5) to afford compound 178 (0.191 g, 81%) as a white foam.

Synthesis of Compound 179

A mixture of compound 167 (0.055 g, 0.084 mmol) and 10% Pd/C (55 mg) in HOAc/EtOAc (1:1, 4 mL) was stirred under $H_2$ (balloon) overnight. Catalyst was removed by filtration and the filtrate was evaporated to dryness. The residue was purified by silica gel column chromatography (hexanes/EtOAc, 3:2) to afford compound 179 (0.033 g, 95%) as a pale yellow syrup.

Synthesis of Compounds 180 and 181

A mixture of compound 170 (0.16 g, −0.31 mmol) containing a small amount of disubstituted product from previous reaction and 10% Pd/C (20 mg) in HOAc/EtOAc (1:1, 6 mL) was stirred under $H_2$ (balloon) overnight. Catalyst was removed by filtration and the filtrate was evaporated to dryness. The residue was purified by silica gel column chromatography (hexanes/EtOAc, 2:3) to afford compounds 180 (0.084 g) and 181 (0.020 g) as a colorless syrup.

Synthesis of Compound 182

A mixture of compound 172 (0.04 g, 0.082 mmol) and 10% Pd/C (5 mg) in HOAc/EtOAc (1:1, 4 mL) was stirred under $H_2$ (balloon) overnight. Catalyst was removed by filtration and the filtrate was evaporated to dryness. The residue was purified by silica gel column chromatography (hexanes/EtOAc, 7:3) to afford compound 182 (0.021 g, 65%) as a colorless syrup.

Synthesis of Compound 183

A mixture of compound 173 (0.095 g, 0.195 mmol) and 10% Pd/C (15 mg) in HOAc/EtOAc (1:1, 4 mL) was stirred under $H_2$ (balloon) overnight. Catalyst was removed by filtration and the filtrate was evaporated to dryness. The residue was purified by silica gel column chromatography (hexanes/EtOAc, 3:2) to afford compound 183 (0.069 g, 89%) as a colorless syrup.

Synthesis of Compound 184

A mixture of compound 175 (0.098 g, 0.23 mmol) and 10% Pd/C (15 mg) in EtOAc (3 mL) was stirred under $H_2$ (balloon) overnight. Catalyst was removed by filtration and the filtrate was evaporated to dryness. The residue was purified by silica gel column chromatography (hexanes/EtOAc, 3:7) to afford compound 184 (0.074 g, 81%) as a white solid.

Synthesis of Compound 185

A mixture of compound 177 (0.087 g, 0.205 mmol) and 10% Pd/C (10 mg) in EtOAc (3 mL) was stirred under $H_2$ (balloon) overnight. Catalyst was removed by filtration and the filtrate was evaporated to dryness. The residue was purified by silica gel column chromatography (hexanes/EtOAc, 3:7) to afford compound 185 (0.073 g, 84%) as a pale yellow syrup.

Synthesis of Compound 186

A mixture of compound 178 (0.161 g, 0.353 mmol) and 10% Pd/C (20 mg) in EtOAc (4 mL) was stirred under $H_2$ (balloon) overnight. Catalyst was removed by filtration and the filtrate was evaporated to dryness. The residue was purified by silica gel column chromatography (hexanes/EtOAc, 3:7) to afford compound 186 (0.084 g, 56%) as a white foam.

Synthesis of Compound 187

A mixture of compound 176 (0.043 g, 0.098 mmol) and 10% Pd/C (10 mg) in EtOAc (2 mL) was stirred under $H_2$ (balloon) overnight. Catalyst was removed by filtration and the filtrate was evaporated to dryness. The residue was purified by silica gel column chromatography (hexanes/EtOAc, 3:7) to afford compound 187 (0.017 g, 42%) as a light red syrup.

The following Scheme 34 illustrates a method of the present invention that may be employed to prepare compound 227. More specific details regarding this synthesis are provided after the Scheme.

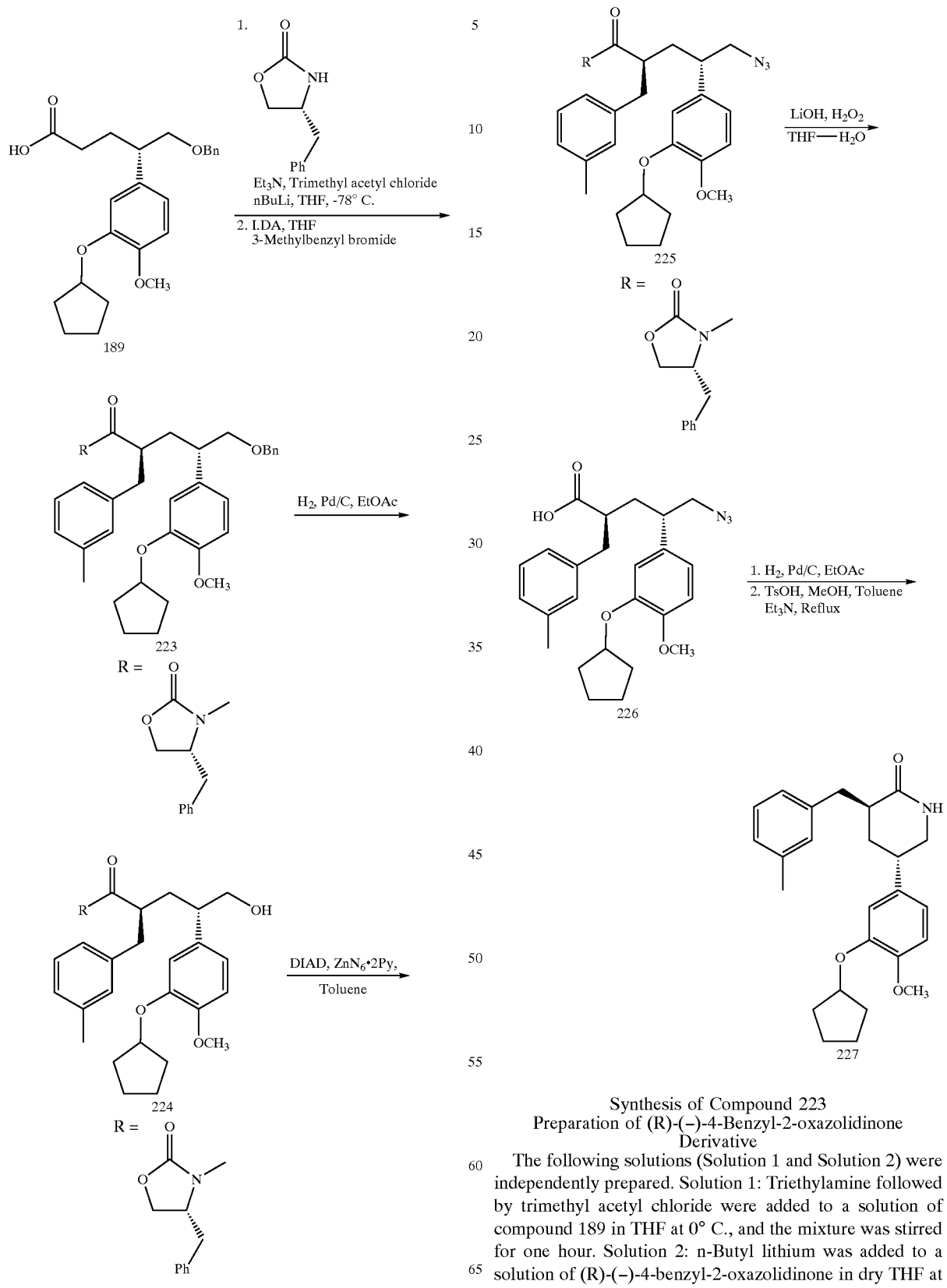

Synthesis of Compound 223
Preparation of (R)-(−)-4-Benzyl-2-oxazolidinone Derivative The following solutions (Solution 1 and Solution 2) were independently prepared. Solution 1: Triethylamine followed by trimethyl acetyl chloride were added to a solution of compound 189 in THF at 0° C., and the mixture was stirred for one hour. Solution 2: n-Butyl lithium was added to a solution of (R)-(−)-4-benzyl-2-oxazolidinone in dry THF at −78° C., and the mixture was stirred for one hour.

Solution 2 was added to Solution 1 via cannula. The resultant mixture at 0° C. was allowed to warm to room temperature. After stirring at room temperature for 24 hours, the mixture was diluted with a saturated NaHCO$_3$ solution, and extracted with CH$_2$Cl$_2$. The organic layers were combined, washed with H$_2$O, dried over MgSO$_4$, filtered, and the filtrate concentrated in vacuo. The residue was purified by column chromatography on silica gel to afford the desired (R)-(–)-4-benzyl-2-oxazolidinone derivative.

n-BuLi was slowly added to a solution of diisopropylamine in dry THF at –78° C. The reaction mixture was stirred at –78° C. under argon for 1 hour at –78° C. The (R)-(–)-4-benzyl-2-oxazolidinone derivative in THF at –78° C. was added and the reaction mixture was stirred for 1 hour. A solution of 3-methylbenzyl bromides in THF was then added in one portion to the reaction mixture. The resulting mixture was warmed to 0° C. and stirred for an additional 2 hours. The excess base was quenched at 0° C. with saturated aqueous NH$_4$Cl, and the resulting solution was extracted with CH$_2$Cl$_2$. The organic layers were combined, washed successively with saturated NaHCO$_3$ and H$_2$O, dried over MgSO$_4$, filtered, and the filtrate was concentrated in vacuo. The residue was purified by column chromatography on silica gel to give compound 223.

Synthesis of Compound 224

Compound 223 and 10% Pd/C in EtOAc was stirred under H$_2$ (balloon) for 20 hours. The mixture was filtered through Celite and the filtrate was concentrated in vacuo. The residue was purified by column chromatography on silica gel to give compound 224.

Synthesis of Compound 225

Diisopropyl azodicarboxylate was added to a suspension of compound 224 in admixture with ZnN$_6$.2Py and Ph$_3$P in anhydrous toluene. The mixture was stirred at room temperature for 18 hours. The mixture was concentrated in vacuo, and the residue was purified by column chromatography on silica gel to give compound 225.

Synthesis of Compound 226

LiOH.H$_2$O and H$_2$O$_2$ (30% in H$_2$O) were added to a solution of compound 225 in THF/H$_2$O (3:1) at 0° C. The reaction mixture was stirred at 0° C. for 3 hours. A solution of Na$_2$SO$_3$ in water was then added followed by a solution of 0.5 N NaHCO$_3$. The mixture was stirred for 2 hours, and then the THF was evaporated in vacuo. This aqueous solution was diluted with 2N HCl to pH=2 and then extracted with EtOAc. The combined organic layers were dried over MgSO$_4$, filtered and the filtrate was evaporated to dryness. The resulting oil was purified using silica gel column chromatography to give compound 226.

Synthesis of Compound 227

Compound 226 and 10% Pd/C in EtOAc were stirred under H$_2$ (balloon) for 20 hours. The mixture was filtered through Celite and the filtrate was evaporated to dryness. The residue was purified by column chromatography on silica gel to give the desired acid compound.

The acid compound was dissolved in toluene and MeOH and treated with pTsOH.H$_2$O. The solution was heated at reflux for 1.5 hours using a Dean-Stark apparatus. The Dean-Stark apparatus was then removed and Et$_3$N was added to the solution, which was heated at reflux for a further 4 hours. The solvent was evaporated and the residue was purified by silica gel column chromatography to give the desired compound 227.

The following tables are provided to define compound structures listed in the utility examples. All of the compounds in these tables were prepared using methodology described herein or methodology described for similar compounds as provided herein.

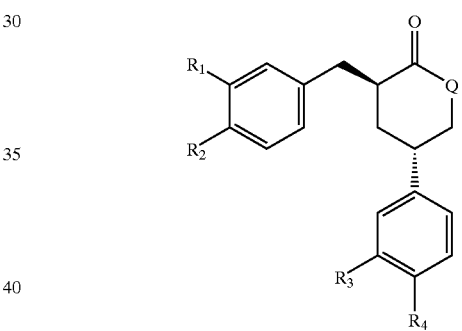

| Structure | Compound No. |
|---|---|
| R$_1$ = OMe, R$_2$ = OH, R$_3$ = OMe, R$_4$ = OMe, Q = O | 30 |

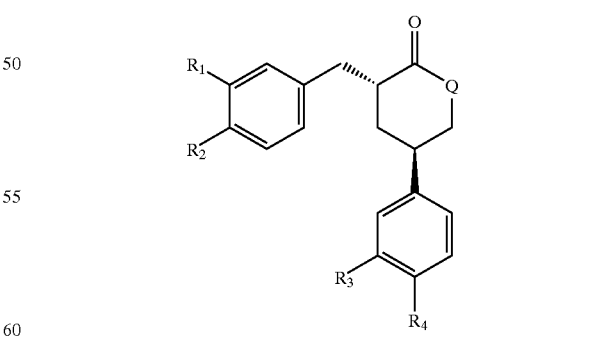

| Structure | Compound No. |
|---|---|
| R$_1$ = OMe, R$_2$ = OH, R$_3$ = OMe, R$_4$ = OMe, Q = O | 129 |

-continued

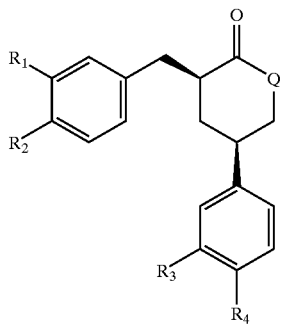

| Structure | Compound No. |
|---|---|
| $R_1$ = Ome, $R_2$ = OH, $R_3$ = Ome, $R_4$ = OMe, Q = O | 130 |

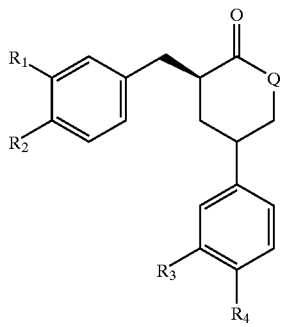

| Structure | Compound No. |
|---|---|
| $R_1$ = OMe, $R_2$ = OH, $R_3$ = OMe, $R_4$ = OMe, Q = O | 12 |

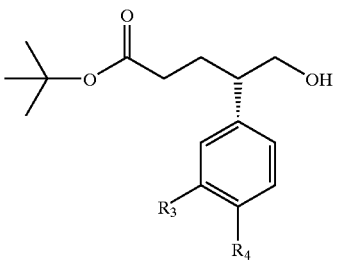

| Structure | Compound No. |
|---|---|
| $R_3$ = $OC_2H_5$, $R_4$ = OMe | 143 |
| $R_3$ = $OCH_2CH_2CH_3$, $R_4$ = OMe | 144 |
| $R_3$ = $OCH(CH_3)_2$, $R_4$ = OMe | 145 |
| $R_3$ = $OCH_2C(CH_3)$ = $CH_2$, $R_4$ = OMe | 146 |
| $R_3$ = (Cyclobutyl)methoxy, $R_4$ = OMe | 147 |
| $R_3$ = (Cyclohexyl)methoxy, $R_4$ = OMe | 148 |
| $R_3$ = $OCH_2(CH_2)_3CH_3$, $R_4$ = OMe | 149 |
| $R_3$ = $OCH_2(CH_2)_4CH_3$, $R_4$ = OMe | 150 |
| $R_3$ = $OCH_2(CH_2)_5CH_3$, $R_4$ = OMe | 151 |
| $R_3$ = $OCH_2(CH_2)_6CH_3$, $R_4$ = OMe | 152 |

-continued

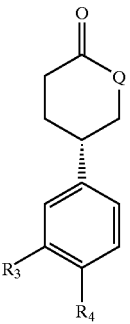

| Structure | Compound No. |
|---|---|
| $R_3$ = OMe, $R_4$ = OMe, Q = O | 21 |
| $R_3$ = OcPent, $R_4$ = OMe, Q = O | 41 |
| $R_3$ = OMe, $R_4$ = OMe, Q = NH | 46 |
| $R_3$ = OMe, $R_4$ = OMe, Q = NBn | 47 |
| $R_3$ = OMe, $R_4$ = OMe, Q = NBOC | 52 |
| $R_3$ = OcPent, $R_4$ = OMe, Q = NH | 58 |
| $R_3$ = OcPent, $R_4$ = OMe, Q = NBOC | 59 |
| $R_3$ = OBn, $R_4$ = OMe, Q = O | 92 |
| $R_3$ = $OC_2H_5$, $R_4$ = OMe, Q = O | 153 |
| $R_3$ = $OCH_2CH_2CH_3$, $R_4$ = OMe, Q = O | 154 |
| $R_3$ = $OCH(CH_3)_2$, $R_4$ = OMe, Q = O | 155 |
| $R_3$ = $OCH_2C(CH_3)$ = $CH_2$, $R_4$ = OMe, Q = O | 156 |
| $R_3$ = (Cyclobutyl)methoxy, $R_4$ = OMe, Q = O | 157 |
| $R_3$ = (Cyclohexyl)methoxy, $R_4$ = OMe, Q = O | 158 |
| $R_3$ = $OCH_2(CH_2)_3CH_3$, $R_4$ = OMe, Q = O | 159 |
| $R_3$ = $OCH_2(CH_2)_4CH_3$, $R_4$ = OMe, Q = O | 160 |
| $R_3$ = $OCH_2(CH_2)_5CH_3$, $R_4$ = OMe, Q = O | 161 |
| $R_3$ = $OCH_2(CH_2)_6CH_3$, $R_4$ = OMe, Q = O | 162 |

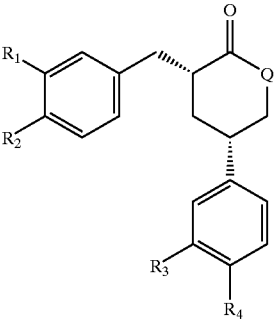

| Structure | Compound No. |
|---|---|
| $R_1$ = OMe, $R_2$ = OH, $R_3$ = OMe, $R_4$ = OMe, Q = O | 29 |
| $R_1$ = OMe, $R_2$ = OBn, $R_3$ = OMe, $R_4$ = OMe, Q = NBn | 49 |
| $R_1$ = OMe, $R_2$ = OH, $R_3$ = OMe, $R_4$ = OMe, Q = NBn | 50 |

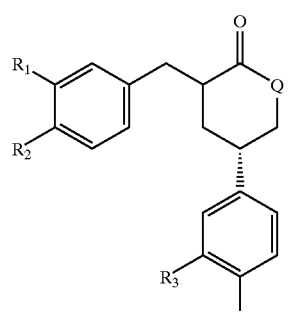

| Structure | Compound No. |
|---|---|
| $R_1$ = OMe, $R_2$ = OBn, $R_3$ = OMe, $R_4$ = OMe, Q = O | 22 |

-continued

| Structure | Compound No. |
|---|---|
| $R_1$ = OMe, $R_2$ = OBn, $R_3$ = OcPent, $R_4$ = OMe, Q = O | 42 |
| $R_1$ = OMe, $R_2$ = OH, $R_3$ = OcPent, $R_4$ = OMe, Q = O | 43 |
| $R_1$ = OMe, $R_2$ = OBn, $R_3$ = OMe, $R_4$ = OMe, Q = NBOC | 53 |
| $R_1$ = OMe, $R_2$ = OBn, $R_3$ = OMe, $R_4$ = OMe, Q = NH | 54 |
| $R_1$ = OMe, $R_2$ = OH, $R_3$ = OMe, $R_4$ = OMe, Q = NH | 55 |
| $R_1$ = OMe, $R_2$ = OBn, $R_3$ = OcPent, $R_4$ = OMe, Q = NBOC | 60 |
| $R_1$ = OMe, $R_2$ = OBn, $R_3$ = OcPent, $R_4$ = OMe, Q = NH | 61 |
| $R_1$ = OMe, $R_2$ = OH, $R_3$ = OcPent, $R_4$ = OMe, Q = NH | 62 |
| $R_1$ = F, $R_2$ = F, $R_3$ = OMe, $R_4$ = OMe, Q = O | 77 |
| $R_1$ = OBn, $R_2$ = OBn, $R_3$ = OMe, $R_4$ = OMe, Q = O | 79 |
| $R_1$ = OH, $R_2$ = OH, $R_3$ = OMe, $R_4$ = OMe, Q = O | 80 |
| $R_1$ = OH, $R_2$ = H, $R_3$ = OMe, $R_4$ = OMe, Q = O | 131 |
| $R_1$ = H, $R_2$ = OMe, $R_3$ = OMe, $R_4$ = OMe, Q = O | 132 |
| $R_1$ = H, $R_2$ = OH, $R_3$ = OMe, $R_4$ = OMe, Q = O | 133 |
| $R_1$ = OcPent, $R_2$ = OMe, $R_3$OMe, $R_4$ = OMe, Q = O | 134 |
| $R_1$ = OBn, $R_2$ = OMe, $R_3$ = OMe, $R_4$ = OMe, Q = O | 135 |
| $R_1$ = OMe, $R_2$ = OcPent, $R_3$ = OMe, $R_4$ = OMe, Q = O | 136 |
| $R_1$ = OMe, $R_2$ = OPr, $R_3$ = OMe, $R_4$ = OMe, Q = O | 137 |
| $R_1$ = H, $R_2$ = OBn, $R_3$ = OMe, $R_4$ = OMe, Q = O | 138 |
| $R_1$ = H, $R_2$ = H, $R_3$ = OMe, $R_4$ = OMe, Q = O | 139 |
| $R_1$ = OPr, $R_2$ = OMe, $R_3$ = OMe, $R_4$ = OMe, Q = O | 140 |
| $R_1$ = H, $R_2$ = F, $R_3$ = OMe, $R_4$ = OMe, Q = O | 141 |
| $R_1$ = OBn, $R_2$ = H, $R_3$ = OMe, $R_4$ = OMe, Q = O | 142 |
| $R_1$ = OMe, $R_2$ = OBn, $R_3$ = OCH$_2$(CH$_2$)$_2$CH$_3$, $R_4$ = OMe, Q = O | 163 |
| $R_1$ = OMe, $R_2$ = OH, $R_3$ = OCH$_2$(CH$_2$)$_2$CH$_3$, $R_4$ = OMe, Q = O | 164 |
| $R_1$ = NO$_2$, $R_2$ = OBn, $R_3$ = OCH$_2$(CH$_2$)$_2$CH$_3$, $R_4$ = OMe, Q = O | 165 |
| $R_1$ = NH$_2$, $R_2$ = OH, $R_3$ = OCH$_2$(CH$_2$)$_2$CH$_3$, $R_4$ = OMe, Q = O | 166 |
| $R_1$ = OBn, $R_2$ = OBn, $R_3$ = OcPent, $R_4$ = OMe, Q = O | 167 |
| $R_1$ = H, $R_2$ = H, $R_3$ = OcPent, $R_4$ = OMe, Q = O | 168 |
| $R_1$ = CF$_3$, $R_2$ = H, $R_3$ = OcPent, $R_4$ = OMe, Q = O | 169 |
| $R_1$ = OBn, $R_2$ = OMe, $R_3$ = OcPent, $R_4$ = OMe, Q = O | 170 |
| $R_1$, $R_2$ = OCH$_2$O, $R_3$ = OcPent, $R_4$ = OMe, Q = O | 171 |
| $R_1$ = OBn, $R_2$ = H, $R_3$ = OcPent, $R_4$ = OMe, Q = O | 172 |
| $R_1$ = H, $R_2$ = OBn, $R_3$ = OcPent, $R_4$ = OMe, Q = O | 173 |
| $R_1$ = NO$_2$, $R_2$ = H, $R_3$ = OcPent, $R_4$ = OMe, Q = O | 175 |
| $R_1$ = NO$_2$, $R_2$ = Me, $R_3$ = OcPent, $R_4$ = OMe, Q = O | 176 |
| $R_1$ = H, $R_2$ = NO$_2$, $R_3$ = OcPent, $R_4$ = OMe, Q = O | 177 |
| $R_1$ = NO$_2$, $R_2$ = OBn, $R_3$ = OcPent, $R_4$ = OMe, Q = O | 93 |
| $R_1$ = OH, $R_2$ = OH, $R_3$ = OcPent, $R_4$ = OMe, Q = O | 179 |
| $R_1$ = OH, $R_2$ = OMe, $R_3$ = OcPent, $R_4$ = OMe, Q = O | 180 |
| $R_1$ = NH$_2$, $R_2$ = OH, $R_3$ = OcPent, $R_4$ = OMe, Q = O | 94 |
| $R_1$ = OH, $R_2$ = H, $R_3$ = OcPent, $R_4$ = OMe, Q = O | 182 |
| $R_1$ = H, $R_2$ = OH, $R_3$ = OcPent, $R_4$ = OMe, Q = O | 183 |
| $R_1$ = NH$_2$, $R_2$ = H, $R_3$ = OcPent, $R_4$ = OMe, Q = O | 184 |
| $R_1$ = H, $R_2$ = NH$_2$, $R_3$ = OcPent, $R_4$ = OMe, Q = O | 185 |
| $R_1$ = NH$_2$, $R_2$ = Me, $R_3$ = OcPent, $R_4$ = OMe, Q = O | 187 |

-continued

| Structure | Compound No. |
|---|---|
| $R_1$ = NO$_2$, $R_2$ = H, $R_3$ = OcPent, $R_4$ = OMe, Q = O | 174 |
| $R_1$ = OMe, $R_2$ = NO$_2$, $R_3$ = OcPent, $R_4$ = OMe, Q = O | 178 |
| $R_1$ = OMe, $R_2$ = NH$_2$, $R_3$ = OcPent, $R_4$ = OMe, Q = O | 186 |

| Structure | Compound No. |
|---|---|
| $R_1$ = OH, $R_2$ = OMe, $R_3$ = OcPent, $R_4$ = OMe, Q = O | 181 |

Utility Examples

In vitro and in vivo biological testing showed that the lactone and lactam components of the present invention exhibit an array of potent biological activities against targets relevant to rheumatoid arthritis, other inflammatory diseases and non-inflammation related diseases as described below.

As used herein, "treating inflammation" refers to both therapy for inflammation, and for the prevention of the development of the inflammatory response. An effective amount of a compound or composition of the present invention is used to treat inflammation in a warm-blooded animal, such as a human. Methods of administering effective amounts of anti-inflammatory agents are well known in the art and include the administration of inhalation, oral or parenteral forms. Such dosage forms include, but are not limited to, parenteral solutions, tablets, capsules, sustained release implants and transdermal delivery systems; or inhalation dosage systems employing fry powder inhalers or pressurized multi-dose inhalation devices. Generally, oral or topical administration is preferred for the treatment of inflammation. The dosage amount and frequency are selected to create an effective level of the agent without harmful effects. It will generally range from a dosage of about 0.01 to 10 mg/Kg/day where administered orally or intravenously. Also, the dosage range will be typically from about 0.01 to 1 mg/Kg/day where administered intranasally or by inhalation.

Administration of compounds or compositions of the present invention may be carried out in combination with the administration of other agents. For example, it may be desired to co-administer a glucocorticoid for its effect on arthritis.

Generation of Reactive Oxygen Species by Activated Neutrophils

Neutrophils comprise over 90% of the leukocytic infiltrate in synovial fluid of rheumatoid arthritis (RA) patients and are believed to contribute to both the acute and chronic phases of this and many other inflammatory diseases through release of pro-inflammatory mediators, matrix degradative enzymes and toxic oxygen radicals resulting in tissue injury. One proposed pathogenic mechanism is that the cells are unable to phagocytose large pro-inflammatory substances such as insoluble immune complexes or damaged endothelium present in the joint. Consequently, neutrophilic granules fuse with the plasma membrane at the site of activation, rather than internally with phagocyte vacuoles, allowing extracellular release of pro-inflammatory reactive oxygen species (ROS) and other toxic substances.

Neutrophil activation can be measured by quantitation of ROS generated in vitro. Measurement of ROS allows specific quantitation of a pro-inflammatory species and is also a general measure of neutrophil activation. The most sensitive method for measuring the production of ROS by neutrophils is luminol-enhanced chemiluminescence. Compounds and compositions of the present invention inhibit the generation of ROS. The assay system used to evaluate the ability of compounds to inhibit ROS generation in neutrophils is indicative of anti-inflammatory activity that may be efficacious in disease states including but not limited to rheumatoid arthritis and inflammatory bowel disease.

Freshly isolated primary human neutrophils ($5 \times 10^6$ cells/mL) were incubated with the required concentrations of compound or vehicle for 30 minutes at 37° C. in HBSS buffer (pH 7.4) containing $Ca^{2+}$. 100 nM wortmannin was used as a positive control. Aliquots of each sample were transferred to a microtitre plate to which luminol (1 $\mu$M); obtained from Sigma; Catalogue No. A8511 is added. Activation of the neutrophils was immediately initiated by addition of (1 $\mu$M) fMLP; obtained from Sigma, Catalogue No. F3506. Light output from each well was recorded for 30 minutes in a microplate luminometer. Total light output (integral of the time-course) was determined for each well. Inhibitory activities of test drugs against neutrophil ROS generation is expressed as percentage activity relative to a no drug control (100% activation or generation of ROS) containing 0.25% DMSO. Concentration of test compound required to inhibit the generation of ROS to 50% of control values ($IC_{50}$'s) were determined from concentration-response curves by non-linear regression analysis. The results are shown in Table 1.

TABLE 1

Inhibition Of Neutrophil Degranulation By Test Compounds As Measured By Ros Production

| COMPOUND NUMBER | $IC_{50}$ RANGE ($\mu$M) | | | |
|---|---|---|---|---|
| | <1 | 1–10 | 10–100 | >100 |
| 12 | X | | | |
| 21 | | X | | |
| 30 | | X | | |
| 29 | X | | | |
| 129 | X | | | |
| 130 | X | | | |
| 179 | X | | | |
| 131 | X | | | |
| 43 | X | | | |
| 168 | X | | | |
| 132 | | | | X |
| 133 | X | | | |
| 54 | | X | | |
| 61 | | | | X |
| 79 | | | | X |
| 47 | | X | | |
| 154 | X | | | |
| 135 | X | | | |
| 46 | | | X | |
| 169 | | | | X |
| 136 | | | | X |
| 153 | X | | | |
| 42 | | | X | |
| 58 | X | | | |
| 139 | | | | X |
| 41 | X | | | |
| 155 | | X | | |
| 181 | | X | | |
| 180 | X | | | |
| 77 | | | | X |
| 22 | | | | X |
| 171 | | X | | |
| 62 | | | X | |
| 94 | X | | | |
| 182 | | X | | |
| 99 | X | | | |
| 183 | X | | | |
| 172 | | | | X |
| 55 | | X | | |
| 80 | X | | | |
| 156 | X | | | |
| 186 | X | | | |
| 175 | | X | | |
| 108 | X | | | |
| 174 | | | | X |
| 185 | | X | | |
| 184 | X | | | |
| 176 | | X | | |
| 155 | | X | | |
| 157 | X | | | |

As shown in Table 1, numerous compounds of the present invention demonstrate $IC_{50}$'s in the range of 0.1–1 $\mu$M. This result shows that these compounds potently block generation of pro-inflammatory reactive oxygen species by neutrophils in vitro. This result may arise from inhibition of phosphodiesterase and/or chemical scavenging. This property is predictive of anti-inflammatory activity in vivo due to the established role of ROS-mediated tissue injury, e.g., in rheumatoid arthritis, inflammatory bowel disorders, and psoriasis.

Neutrophil Degranulation (Myeloperoxidase Release)

Neutrophilic granulocytes contain several type of organelles known as granules. These sub-cellular bodies contain a diverse array of bacteriocidal agents including proteases and other hydrolytic enzymes that are essential to the normal inflammatory response but contribute to acute tissue injury when neutrophils are chronically and/or inappropriately activated in disease. One of the characteristic granule enzymes is myeloperoxidase (MPO) which catalyses the conversion of hydrogen peroxide to hypohalide. MPO is released into the extracellular milieu on stimulation of degranulation and is a reliable index of neutrophil activation. Compounds of the present invention inhibited the release of neutrophil myeloperoxidase from primary human neutrophils stimulated with 100 $\mu$M fMLP. The assay system used to evaluate the ability of a compound to inhibit MPO release from neutrophils is indicative of anti-rheumatoid activity as well as other diseases where inappropriate neutrophil activation is implicated.

Two tubes of human blood (12 mL) were collected into ACD anti-coagulant tubes (Fisher; Catalogue No. 02-684-29). The blood was mixed with 4 mL of 6% dextran in saline. Blood mixture was collected into a 60 cc syringe. The syringe was tipped upright onto a bench top for 30 min. The upper serum layer was overlaid on 4 mL Histopaque (Sigma; Catalogue No. 1077-1) in a 15 mL centrifuge tube. The tube was centrifuged for 30 min at 2000 rpm. The supernatant was discarded. The pellet was mixed with 3 mL cold distilled $H_2O$, followed by 1 mL 6 N NaCl after 30 seconds. The tube was centrifuged for 5 min at 1100 rpm. The pellet in each tube was combined and washed twice with 10 mL (HBSS); Hank's Balance of Salt Solution (Stem Cell Ltd.; Catalogue No. LMC 75). The cells were counted and diluted to $2 \times 10^6$ cells/mL.

Cells (0.3 mL) were pipetted into pre-labelled microcentrifuge tubes. The cells were incubated with 5 $\mu$g/mL cytochalasin B, 10 nM $PGE_2$ and the desired concentration of test compound or vehicle (0.5% DMSO) for 5 min at 37° C. Wortmannnin or rolipram was used as a positive control. 100 nM fMLP was added into each tube except control. After 30 min incubation, cells were placed on ice and centrifuged at 13,000 rpm for 3 min. 50 $\mu$L of supernatant was pipetted into appropriate wells of a 96-well plate (triplicate). 100 $\mu$L of substrate was added into each well (0.53 mM o-dianisidin; Sigma, Catalogue No. D 3252, 0.147 mM $H_2O_2$ in phosphate buffer pH6.0). The plate was incubated for 30 min at 37° C. Reaction was terminated by addition of 50 $\mu$L 4N $H_2SO_4$ into each well. To prepare a standard curve, 200 $\mu$L of 1, 0.1, 0.01, and 0.001 mg/mL horseradish peroxidase was pipetted into the wells (triplicate). Plate was read by an ELISA reader at 405 nm. The maximum inhibition of myeloperoxidase routinely observed for standard compounds with similar mechanisms of action to the compounds of the invention (cAMP PDE inhibitor) was about 30–35%. Therefore inhibitory potencies from concentration response studies are quoted as $IC_{15}$ values determined from at least three separate experiments using triplicate determinations.

As shown in Table 2, compounds of the invention potently inhibited MPO release from stimulated human neutrophils with $IC_{15}$ values ranging from 0.1 to 1 $\mu$M. These compounds exhibited a maximum inhibition of neutrophil MPO release of about 40%, consistent with the effects of known PDE4 inhibitors such as rolipram (data not shown). This result shows that these compounds are able to concentration-dependently inhibit the degranulation response of human neutrophils stimulated with fMLP. Since neutrophil degranulation is considered a major effector of tissue injury mediated by this cell type in a number of inflammatory diseases (e.g., psoriasis, rheumatoid arthritis), inhibition of this response by these compounds indicates clinical utility of compounds for these and other related disease states.

TABLE 2

Inhibition Of Neutrophil Degranulation As Measured By Myeloperoxidase Release

| COMPOUND NUMBER | $IC_{15}$ RANGE ($\mu$M) | | |
|---|---|---|---|
| | .1–1 | 1–10 | 10–100 |
| 30 | X | | |
| 21 | X | | |
| 78 | X | | |
| 42 | X | | |

Neutrophil Chemotaxis

The process of chemotaxis (directed leukocyte migration up a chemokine gradient) is essential to the accumulation of high numbers of neutrophils associated with pathological manifestations of inflammation (e.g., deterioration in the rheumatoid joint). Chemotaxis is a primary mechanism whereby neutrophils migrate from the blood vessel lumen to the site of inflammation and therefore is a common process associated with neutrophil mediated tissue injury in many inflammatory diseases. Within the present invention it was discovered that the test compounds concentration-dependently inhibited chemotaxis of primary human neutrophils in response to fMLP. These compounds also inhibit interleukin 8 (IL-8) mediated chemotaxis (data not shown). Specific inhibition of neutrophil migration to the inflamed joint is a valid therapeutic target in rheumatoid arthritis and many inflammatory diseases. This in vitro assay system used to evaluate the ability of compounds to inhibit chemotaxis is indicative of in vivo anti-rheumatoid activity and activity against inflammatory diseases where neutrophils are implicated in the associated tissue injury.

Chemotaxis buffer containing the chemoattractant fMLP (10 $\mu$M) was added to each well of a chemotaxis plate and a filter was inserted ensuring contact between the filter and the chemotaxis buffer in the well. A submaximal concentration of chemoattractant was used which had been determined in previous experiments. For determination of spontaneous cell migration certain wells did not receive chemoattractant, but instead received buffer only. Freshly isolated neutrophils ($1 \times 10^6$) were incubated with vehicle (0.125% DMSO)±test compound for 1 hr at 37° C. Treatment and control cell suspensions were then gently resuspended and 20 $\mu$L of cells was added to the top side of the filter on each well. The plate was incubated for 1.5 hours at 37° C. under 5% $CO_2$. Cells were then removed from the top side of the filter by aspiration and the entire plate was centrifuged. The filter was removed and known concentrations of cells were added to unused wells to prepare a standard curve. XTT (Sigma; Catalogue No. X 4251)/PMS (Sigma; Catalogue No. P 7626) solution prepared in buffer was added to each well and the cells were further incubated 1–2 hours and measured for absorbance at 450 nm. Absorbance values were converted to cell numbers using the standard curve. $IC_{50}$ values are averages from at least three separate experiments with triplicate determinations.

Table 3 shows the inhibitory potency of compounds of the present invention against chemotaxis induced by 10 nM fMLP. Several of the compounds display $IC_{50}$'s of less than 10 $\mu$M in this assay system. The phosphodiesterase IV inhibitor Rolipram, used as a positive control, inhibited neutrophil chemotaxis by 85% at 12.5 $\mu$M under these assay conditions (data not shown). In control experiments it was found that the compounds did not significantly affect general neutrophil motility (in absence of chemoattractant). Thus, the compounds are effective in inhibiting directed migration of human neutrophils in response to a bacterially derived peptide, fMLP.

TABLE 3

Inhibition Of Fmlp-Induced Human Neutrophil Chemotaxis

| COMPOUND NUMBER | $IC_{15}$ RANGE ($\mu$M) | | |
|---|---|---|---|
| | .1–1 | 1–10 | 10–100 |
| 12 | | | X |
| 29 | | | X |
| 30 | | | X |
| 129 | | X | |
| 130 | | X | |
| 21 | | X | |

Inhibition of TNF-α Production in Concanavalin-A Stimulated Primary Human CD4+ T-Lymphocytes Activated T-lymphocytes are known to produce TNF-α and may constitute a significant source of this important inflammatory mediator in localized regions of inflammation such as the rheumatoid synovium or psoriatic lesions. Supernatants from conA-stimulated primary human CD4+ T-cells that had been incubated in the presence or absence of a test compound were analyzed for TNF-α using an ELISA system. (Pharingen; recommended anti-TNF antibody set 18631-D and 18642-D). Substantial quantities of TNF-α were induced in vehicle treated T-cells stimulated with conA. As shown in Table 4, compounds of the present invention were able to potently inhibit the production of T-cell derived TNF-α. This result contrasts with the lower potency of these compounds in the inhibition of LPS-induced TNF-α release in human whole blood. This may be due to the differing sensitivity of monocyte/macrophages versus T-lymphocytes to elevations in intracellular cAMP with respect to regulatory pathways impacting TNF-α production. This result suggests that compounds of the invention may be used in the treatment of diseases involving production of TNF-α.

TABLE 4

Effects Of Test Compounds On Tnf-Alpha Production In Con-A Stimulated Human Cd4 + T-Cells

| COMPOUND | TNF-alpha $IC_{50}$ RANGE ($\mu$M) | | |
|---|---|---|---|
| | <2 | 2.0–20 | >20 |
| 54 | X | | |
| 55 | | X | |
| 62 | X | | |
| 30 | | X | |
| 136 | X | | |
| 43 | | | X |
| ROLIPRAM | X | | |
| ZARDAVERINE | X | | |

Inhibition of Human T-Lymphocyte Helper Function

Introduction and Rational

Many inflammatory diseases with an autoimmune etiology including rheumatoid arthritis and psoriasis are characterized by an imbalance in the T-helper cell function of self-reactive T-lymphocyte subsets resulting in initiation and maintenance of a pro-inflammatory state. This imbalance is often manifested as excessive expression of a Th1 phenotype and/or suppression of a Th2 phenotype. T-cells secreting IL-2 and INF-γ are designated as Th1 or type 1 cells. These cells are involved through direct cell-mediated immunity by the activation of macrophages and cytotoxic cellular pathways. Cells producing IL-4, IL-5 and IL-10 are termed Th2 or type 2 cells and regulate the hummoral immune response. Several compounds of the present invention inhibited Th1 function more potently than Th2 function in vitro in concanavalin A stimulated primary human CD4+ T-cells. Thus, these compounds may have therapeutic value in being able to selectively suppress Th1 cells without affecting Th2 cells to any significant extent thus resulting in correction of an imbalance in autoimmune inflammatory disease characterized by elevated Th1 responses.

The assay on the primary human T-cells involves their activation by concanavalin A (conA); (Sigma, Catalogue No. C 5275), followed by ELISA detection for cytokines for either profile. In the case of Th1-profiles, IL-2 and INF-γ are used as benchmarks while IL-10 is the indicator for a Th2-profile. Biologically, these indicators are useful in that IL-2 is the major T-cell mitogen while IL-10 represents a powerful yet selective immunosuppressive agent.

Methods

Approximately 60 cc of whole human blood was collected into ACD anti-coagulant vacutainer tubes. 15 mL Ficoll Paque 1077 was aliquoted into 6 sterile 50 mL conical tubes. 10 mL of blood was slowly layered on top of the Ficoll Paque by holding the tube upright and resting the pipette tip at the inside edge of the tube and allowing the blood to slowly run down the side of the tube. Tubes were spun at 1700 rpm for 30 minutes at room temperature. The plasma layer above the leukocyte band was aspirated off and a pasteur pipette was used to lift off the leukocyte band and transfer it to a sterile 50 mL conical tube. Cells from each leukocyte gradiant tube were transferred to a separate 50 mL conical tube. Sterile PBS pH 7.4 was added to each 50 mL conical tube containing cells from leukocyte band to a volume of 50 mL. Tubes were spun at 1100 rpm for 10 minutes. Supernatant was aspirated off and the cells were resuspended in 50 mL PBS pH 7.4. Tubes were re-centrifuged at 1100 rpm for 10 minutes. Supernatant was aspirated off and the cells were resuspended in appropriate medium at a density of $5 \times 10^7$ cells/mL or $2 \times 10^6$ cells/mL.

Crude Lymphocyte Preparation: Cells from Leukocyte preparation were resuspended in BASAL media (AcitCyte™) or RPMI 1640 with 10% FBS+2 mM L-glutamine at a density of $1 \times 10^6$ cells/mL.

CD4+ T-cell Preparation: Cells from Leukocyte preparation were resuspended in sterile PBS pH 7.4 supplemented with 2–6% Fetal Bovine Serum (FBS) at a density of $5 \times 10^7$ cells/mL. Cells were then ready for isolation.

CD4+ T-Cell Isolation (StemSep™):
 I) Immunomagnetic Labeling:
  100 μL of antibody cocktail (Stem Cell Technologies, Catalogue No. 14062) was added for each mL of cells and mixed well. Cells+Ab cocktail was incubated on ice for 30 minutes. After 30 minute incubation, 60 μL of magnetic colloid was added for each mL of cells, and mixed well. Cells+Ab cocktail+magnetic colloid were incubated on ice for 30 minutes. After a final 30 minute incubation cells were ready for magnetic cell separation.
 II) Separation Procedure (Gravity Feed):
  Sample was loaded into the top of a column. The stopcock was turned to allow the flow of media down through the column, and the media was collected into a collection tube. PBS supplemented with 2–6% FBS was added to the column until three column volumes had been collected (not including the volume of the start sample). Cells were washed, counted, and resuspended in RPMI 1640 with 10% FBS+2 mM L-glutamine at a density of $1 \times 10^6$ cells/mL.

IL-2, IFN-γ, TNFα and IL-10 Assay Procedure

CD4+ T-cells were isolated as described above. Cells were suspended in RPMI 1640 media (Stem Cell Technologies Inc.; Catalogue No. 36750) with 10% FBS+2 mM L-glutamine at a density of $1 \times 10^6$ cells/mL. Cells were maintained on ice as test compounds were prepared. Test compounds were prepared in a sterile 96-well assay plate at 50× the final desired test concentration, all wells contained an equal amount of dimethylsulfoxide vehicle. 500 µL of CD4+ T-cells were added to each well of 24-well assay plate. 10 µL of each test compound working solution was added to the appropriate wells; two wells were left as stimulated and non-stimulated controls. 10 µL of concanavalin A (50× the final concentration) at 10 µg/mL was added to each well with the exception of the non-stimulated control wells. Cells were incubated at 37° C. for 48 hours. Conditioned media is then assessed by ELISA for the quantity of IL-2, FN-γ, TNFα and IL-10 present.

Results and Discussion

Tables 5A, 5B and 5C represent a synopsis of data across individuals with respects to the potency of compounds of the invention in their ability to inhibit cytokines that are likely to promote or depress a Th1 or Th2 response. In Tables 5A, 5B and 5C, the effect of components of the present invention on IL-2, IFN-gamma and IL-10 production in peripheral human CD4+ T-cells stimulated with 10 µg/mL Concanavalin A for 48 hours is seen. $IC_{50}$'s are averages from at least three separate experiments performed in triplicate. CD4+ T-cell isolation, incubation conditions and ELISA detection of lymphokines are discussed in the Methods section above.

Many members of this series of compounds (in particular those that inhibit both PDE4 and PDE3) elicit a cytokine profile of activated T-cells that can potentially redress the imbalance of Th1 over Th2 cells seen in rheumatoid arthritis and other inflammatory diseases such as psoriasis. Table 5A shows examples of some members of this series that have demonstrated a selective inhibition of a Th1 profile of the conA stimulated CD4+ selected cells; in particular, these compounds are numbered 136, 54 and 30.

While the absolute potency of these compounds vary depending on the analog used, the effect is clearly different from that shown by Rolipram (Sigma; Catalogue No. R 6520). Rolipram was seen to inhibit both IL-2 and IL-10 synthesis by 48 hrs. In contrast, con-A stimulation of IL-10 is not inhibited by several compounds of the invention whereas the same supernatants show reduced levels of IL-2. The depression of a Th1 cytokine profile will necessitate the enhancement of the Th2 cells at the site of inflammation. The added benefit of inhibiting IL-2 production might under the right circumstances render reactive T-cells anergic (i.e., T-cells that cannot respond to their usual mitogenic stimuli via the TCR in the context of MHC II). Alternatively, it could also cause apoptosis of self-reactive T-cells. Therefore, this Th1 inhibiting, Th2 sustaining property of compounds of the invention would provide the potential to effect therapeutic improvement in Th1-mediated diseases such as rheumatoid arthritis, psoriasis and inflammatory bowel disease, amongst other diseases.

TABLE 5A

Effects Of Test Compounds On Th1 Profiles In Concanavalin A Stimulated Primary Human Cd4 + T-Cells

| | IL-2 $IC_{50}$ RANGE (µM) | | | |
|---|---|---|---|---|
| COMPOUND | 0.02–0.2 | 0.2–2.0 | 2.0–20 | >20 |
| 54 | X | | | |
| 55 | | X | | |
| 62 | | X | | |
| 30 | X | | | |
| 136 | X | | | |
| 140 | | | X | |
| 43 | | X | | |
| ROLIPRAM | | | X | |
| ZARDAVERINE | | X | | |

TABLE 5B

Effects Of Test Compounds On Th1 Profiles In Concanavalin A Stimulated Primary Human Cd4 + T-Cells

| | INF-GAMMA $IC_{50}$ RANGE (µM) | | | |
|---|---|---|---|---|
| COMPOUND | 0.02–0.2 | 0.2–2.0 | 2.0–20 | >20 |
| 54 | | X | | |
| 55 | | X | | |
| 62 | | X | | |
| 30 | | X | | |
| 136 | | X | | |
| 140 | | X | | |
| 43 | | X | | |
| ROLIPRAM | | X | | |
| ZARDAVERINE | | X | | |

TABLE 5C

Effects Of Test Compounds On Th2 Profiles In Concanavalin A Stimulated Primary Human Cd4 + T-Cells

| | IL-10 $IC_{50}$ RANGE (µM) | | | |
|---|---|---|---|---|
| COMPOUND | 0.02–0.2 | 0.2–2.0 | 2.0–20 | >20 |
| 54 | | X | | |
| 55 | | X | | |
| 62 | X | | | |
| 30 | | | X | |
| 136 | | | X | |
| 140 | | | X | |
| 43 | | | X | |
| ROLIPRAM | | | X | |
| ZARDAVERINE | | X | | |

Oxygen Radical Scavenging

Oxidants and free radicals produced by neutrophils and other cells are believed to contribute to the pathogenesis of rheumatoid arthritis and other inflammatory diseases. Consistent with this involvement, compounds capable of inactivating free radicals (antioxidants) have anti-inflammatory activities in rheumatoid arthritis and other inflammatory diseases.

Compounds of the present invention inhibited the formation of free radicals in a standard in vitro assay used to measure anti-oxidant activity of biological materials. The basis of the assay (an assay kit from RANDOX: Total Anti-Oxidant status) is the ability of antioxidants in a sample to suppress color formation due to the stable radical cation, $ABTS^{*+}$. The chromogen ABTS (2,2'-Azino-di-[3- ethylbenzthiazoline sulphonate] (Sigma; Catalogue No. A 1888)) (610 µM) is incubated with substrate solution (peroxidase (metmyoglobin) (6.1 µM) and $H_2O_2$ (250 µM)) along with a compound of the invention dissolved in DMSO for exactly 3 minutes at 37° C. Production of the radical cation $ABTS^{*+}$ which has a relatively stable blue-green color was measured at 600 nM. Antioxidant activity of 100 µM test compound was determined as described above. The positive control used was a potent biological antioxidant, Trolox® (6-hydroxy-2.5.7.8-tetramethylchroman-2-carboxylic acid). Inhibition of color formation (antioxidant activity) by test compounds is expressed relative to the positive control, Trolox® (100% inhibition). The results are shown in Table 6. Color suppression in this assay may be due to inhibition of the production of, or quenching of, the $ABTS^{*+}$ radical.

TABLE 6

Anti-Oxidant Activity of Compounds

| Compound Number | Anti-oxidant activity range (% of control) | | | |
|---|---|---|---|---|
| | 1–25 | 25–50 | 50–75 | 75–100 |
| 43 | | | | X |
| 41 | X | | | |
| 136 | X | | | |
| 54 | | | X | |
| 12 | | | | X |
| 99 | X | | | |
| 94 | | | | X |
| 55 | | | | X |
| 42 | X | | | |

The anti-oxidant characteristics of these compounds could contribute to anti-inflammatory activities in vivo and be of therapeutic efficacy in inflammatory diseases involving oxygen radicals. Thus, the anti-oxidant activity of compounds of the invention could constitute an additional mechanism of anti-inflammatory action in addition to cAMP phosphodiesterase inhibition.

Resiniferitoxin-Induced Mouse Ear Edema-Acute Inflammation

One of the primary characteristics of inflammation is an increase in vascular dilation and permeability leading to the extravasation of, and collection of fluids in, the interstitium, resulting in redness and swelling. Rheumatoid arthritis in particular is characterized by pronounced edema of affected joints resulting in significant pain and stiffness. The mouse ear inflammation model is a standard in vivo assay for inflammation that is based on an increase in ear weight which is attributable to edema induced by inflammatory mediators. RTX (resiniferitoxin; Sigma; Catalogue No. R 8756)) is a diterpene isolated from the plant *Euphorbia poisonii* and is an ultrapotent analog of capsaicin. RTX acts by selectively stimulating nociceptive and thermal-sensitive nerve endings in tissue, eliciting neurogenic edema. Compounds of the present invention, whether administered topically, intraperitoneally or orally, inhibited development of edema induced by topical application of RTX. Edema as induced in this model is inhibited by PDE4 inhibitors and is thus a useful in vivo system for differentiating the efficacy of test compounds that possess comparable in vitro potencies.

Mice (CD1, Charles River Laboratories) were separated into groups (n=5–8) and tagged. Control mice had RTX (0.1 µg/ear) applied topically to the inner and outer sides of the left ear and vehicle applied to the right ear as a control. For topical administration, experimental/treatment mice received RTX+test compound solution (50 µg/ear) on the left ear and acetone on the right ear. For intraperitoneal (i.p.) administration, 100 mg/kg test compound dissolved in 100 µL PEG 200:saline (1:1) was injected followed by a 30 minute waiting period then the standard 30 minute RTX edema induction. For oral (p.o.) administration, 10 mg/kg test compound in 100 µL PEG-200 was given to animals, then edema induced using 0.1 µg/ear RTX after a 1.5 hour waiting period. After edema induction, mice were sacrificed, and a standard disc of ear tissue was removed. Each disk of tissue was immediately weighed to the nearest $\frac{1}{10}$th of a mg. Data were analyzed by taking the difference of each left ear from the right ear, calculating the mean+/–SEM. Statistical significance was tested by 2-sample t-test on the left/right ear weight differences of the control group vs. the experimental group.

Tables 7, 8 and 9 show the efficacy of compounds of the invention in the RTX-induced mouse ear edema model when administered via topical, intraperitoneal or oral routes of administration. It is apparent from these data that the compounds effectively inhibit RTX-mediated inflammation (edema) in the mouse when delivered through any of the tested routes. Efficacy via topical administration is the greatest followed by intraperitoneal then oral gavage. The differences in efficacy between the different routes of administration are not surprising as g.i. absorption and metabolism processes are important for i.p. and oral delivery of compound.

TABLE 7

Inhibition of Resiniferitoxin-Induced Mouse Ear Edema by Topical Administration of Test Compound

| Compound Number | % Inhibition of Edema |
|---|---|
| 12 | 85 |
| 29 | 76 |
| 30 | 98 |
| 91 | 27 |
| 92 | 93 |
| 21 | 32 |
| 78 | 93 |
| 99 | 98 |
| 103 | 94 |
| 43 | 98 |

TABLE 8

Inhibition of Resiniferitoxin-Induced Mouse Ear Edema by Intraperitoneal Administration of Test Compound

| Compound Number | % Inhibition of Edema |
|---|---|
| 12 | 61 |
| 30 | 28 |
| 99 | 88 |
| 43 | 72 |
| 42 | 38 |

TABLE 9

Inhibition of Resiniferitoxin-Induced Mouse Ear Edema by
Oral Administration of Test Compound

| Compound Number | % Inhibition of Edema |
|---|---|
| 43 | 45 |
| 42 | 41 |
| 62 | 30 |

Inhibition of Cyclic Nucleotide Phosphodiesterases

Inhibition of cAMP Phosphodiesterase 4

Elevation of cAMP in cells involved in inflammation such as neutrophils, endothelial cells, macrophages, eosinophils, basophils, T-lymphocytes etc. generally leads to the down-regulation of an inflammatory cytokine profile such as the inhibition of tumor-necrosis factor (TNF-α) expression. Expression of the anti-inflammatory cytokine interleukin-10 (IL-10) is positively regulated by cAMP in many cells at a site of inflammation. Since degradation of cAMP in the cell is effected by cAMP phosphodiesterases (PDEs), specific inhibitors to these enzymes are of interest. Such compounds would have the effect of elevating intracellular cAMP in the cells expressing the PDE isoenzymes they specifically inhibit. Although there are at least nine different families of cyclic nucleotide PDEs, the PDE 4 family is of particular interest. This is because many of the critical cell types effecting the inflammatory response express predominantly PDE 4 over the other PDEs. PDE 4 inhibitors such as rolipram have been shown to specifically elevate cAMP in inflammatory cells such as neutrophils and eosinophils and quench their inflammatory phenotype. A therapeutically-effective PDE4 inhibitor desirably has minimal side-effects, including induction of gastric acid secretion, emesis and CNS effects. PDE 4 inhibitors without harmful side-effects hold great promise as a new generation of anti-inflammatory therapeutics for diseases including asthma, inflammatory bowel disease, rheumatoid arthritis, psoriasis and allogeneic transplantation, among others.

Compound 12 was screened for activity against 5 of the major classes of mammalian cyclic nucleotide phosphodiesterase (termed PDE1 through 5). PDE's 1 through 4 utilize cAMP as substrate while PDE 5 uses cGMP. The broad specificity PDE inhibitor 3-isobutyl-1-methylxanthine (IBMX; Sigma; Catalogue No. 17018)) was used as a positive control in all assays. PDE's for the various assays were partially purified from the following cells/tissues; PDE 1 (bovine heart), PDE 2 (human platelets), PDE 3 (human platelets), PDE 4 (human promonocytic U937 cells) and PDE 5 (human platelets).

Compound 12 was found to inhibit PDE 1,3 and 4 with $IC_{50}$'s of 89, 45 and 5.9 μM respectively. There were no significant inhibitory effects on PDEs 2 and 5. Thus, compound 12 exhibited significant activity and selectivity toward PDE4, the cAMP phosphodiesterase predominant in inflammatory cells. Compounds of the invention may provide therapeutic utility in autoimmune disease, inflammatory diseases or any disease where elevation of intracellular cAMP in the PDE4 expressing inflammatory cells participating in the disease leads to down-regulation of the inflammatory phenotype.

U937 cytoplasmic extracts were prepared by sonicating U937 cells (ATCC: Catalogue No. CRL-159) in lysis buffer (20 mM Tris Cl, 1 mM EDTA, 5 mM β-mercaptoethanol, 1 μM pepstatin, 1 μg/mL leupeptin, 1 mM benzamidine and 0.1 mM PMSF). Sonicated cell extracts were then centrifuged at 70,000 g for 30 minutes and supernatants removed. Sucrose was added to a final concentration of 0.25 M, aliquoted and stored at −80° C.

PDE reactions were performed for 30 minutes at 37° C. in 20 μL volumes in 1 μM [³H] cAMP (Amersham website http://www.apbiotech.com), 0.5 U/mL 5' nucleotidase (Sigma), 50 mM Tris Cl, 10 mM MgCl pH 7.5. U937 extract was added such that less than 10% of substrate was consumed. Test compound or vehicle was added to the desired concentration. Typically, compounds were tested at six 10-fold dilutions ranging from 100 μM to 1 nM. Reactions were performed in duplicate. Reactions were terminated by addition of 200 μL Dowex 1-8 400 Cl⁻ anion exchange resin in a ratio of 1 resin:2 methanol:1 $H_2O$. Samples were mixed by inversion and then allowed to settle for 2–3 hours. An aliquot of 65 μL was removed, dried on a Lumaplate (Packard; Catalogue No. 6005165) and counted on a Packard Scintillation counter (TopCount™) for 1.5 minutes, to provide the data in Table 10.

TABLE 10

Inhibition of cAMP Phosphodiesterase 4 from Human U937 Cells

| Compound Number | $IC_{50}$ range (μM) 0.1–1 | $IC_{50}$ range (μM) 1–10 |
|---|---|---|
| 12 |  | X |
| 21 |  | X |
| 30 |  | X |
| 29 |  | X |
| 129 |  | X |
| 130 |  | X |
| 179 | X |  |
| 131 |  | X |
| 43 | X |  |
| 168 | X |  |
| 132 |  | X |
| 133 |  | X |
| 54 |  | X |
| 61 | X |  |
| 79 |  | X |
| 47 |  | X |
| 154 | X |  |
| 135 |  | X |
| 46 |  | X |
| 169 | X |  |
| 136 |  | X |
| 153 | X |  |
| 42 | X |  |
| 58 | X |  |
| 139 |  | X |
| 41 | X |  |
| 155 | X |  |
| 181 | X |  |
| 180 |  | X |
| 77 |  | X |
| 22 | X |  |
| 171 | X |  |
| 62 |  | X |
| 94 | X |  |
| 182 | X |  |
| 99 | X |  |
| 183 | X |  |
| 172 | X |  |
| 55 |  | X |
| 80 |  | X |
| 186 | X |  |
| 162 | X |  |
| 175 | X |  |
| 187 | X |  |
| 156 | X |  |
| 108 | X |  |

TABLE 10-continued

Inhibition of cAMP Phosphodiesterase 4 from Human U937 Cells

| Compound | IC$_{50}$ range ($\mu$M) | |
|---|---|---|
| Number | 0.1–1 | 1–10 |
| 174 | X | |
| 185 | X | |
| 163 | X | |
| 166 | X | |
| 158 | X | |
| 159 | X | |
| 155 | X | |
| 160 | X | |
| 163 | X | |
| 161 | X | |
| 184 | X | |
| 95 | X | |
| 96 | X | |
| 114 | | X |
| 176 | X | |
| 157 | X | |

Table 10 shows the inhibitory activity of compounds of the invention against PDE4 isolated from a human promonocytic cell line, U937. Utilizing the PDE4 assay conditions described here, typical PDE4 inhibitors such as Rolipram and Ro-20-1724 (Calbiochem: Catalogue No. 557502) give IC$_{50}$ values in agreement with those found in the literature (reviewed in Schudt et al., 1996). In addition, use of IBMX (Sigma; Catalogue No. 17018) which inhibits PDEs 1, 3 and 4 does not show any additional inhibition (data not shown) again consistent with the finding that the predominant PDE in U937 cells is PDE 4.

Inhibition of PDE 4 (or more accurately, specific isoforms of PDE 4) with subsequent elevation of intracellular cAMP and protein kinase A activation is a therapeutic target in inflammatory or autoimmune diseases where the causal cells or tissues involved predominantly express this PDE isoform. With respect to rheumatoid arthritis, the PDE 4 inhibitor rolipram has been shown to be active in animal models of the disease such as collagen-induced arthritis in the rat (Nyman et al., *Clin. Exp. Immunol.* 108(3), 415–419, 1997).

Inhibition of cAMP Phosohodiesterase 3

Compounds of the invention were evaluated for inhibitory activity against human platelet PDE3 to ascertain whether the PDE4 inhibition and PDE3 inhibition were separable and also the pharmacophore required for each. Combined PDE4/3 inhibitors may be especially efficacious as therapeutic agents in diseases where the causative/contributory cell types express both PDE4 and PDE3, for example T-cells in inflammatory diseases such as arthritis, inflammatory bowel disease, psoriasis and allogeneic transplantation. In such diseases, combined PDE3/4 inhibitors may have advantages over a selective PDE4 inhibitor such as rolipram.

Platelet cell extracts were prepared as described above for the U937 cells. The PDE3 assay was performed using platelet cell extract as described above for the PDE 4 assay. Platelets contain PDE 2, 3 and 5. However PDE2 and 5 preferentially utilize cGMP, so in an assay with cAMP as a substrate they are not detected. In addition, under the conditions used in this assay, rolipram is without effect and the known PDE3 inhibitor trequinsin (Calbiochem; Catalogue No.382425) is a potent inhibitor confirming that the assay is specific for PDE3.

Table 11 shows IC$_{50}$'s for compounds of the invention for the inhibition of PDE3. The PDE3 and PDE4 activities appear to be separable and the compounds exhibit a wide range of selectivity for PDE4 vs. PDE3. Some compounds are specific for PDE4, some compounds are more potent against PDE4 than PDE3, and some compounds are approximately equipotent against PDE4 and PDE3. Accordingly, compounds of the invention may be selected for their PDE4/3 selectivity to enable maximum potency against different cell types.

TABLE 11

Inhibition of cAMP phosphodiesterase 3 from human platelets

| Compound Number | IC$_{50}$ range ($\mu$M) | | | Compound Number | IC$_{50}$ range ($\mu$M) | | |
|---|---|---|---|---|---|---|---|
| | 1–10 | 10–100 | >100 | | 1–10 | 10–100 | >100 |
| 12 | | | | 62 | X | | |
| 21 | | X | | 94 | | | X |
| 30 | X | | | 182 | | | X |
| 29 | X | | | 99 | | | X |
| 129 | X | | | 183 | | X | |
| 130 | X | | | 172 | | | X |
| 179 | X | | | 55 | X | | |
| 131 | | X | | 80 | | X | |
| 43 | X | | | 186 | | | X |
| 168 | | X | | 162 | | | X |
| 132 | X | | | 175 | | | X |
| 133 | | X | | 187 | | | X |
| 54 | X | | | 156 | | | X |
| 61 | X | | | 108 | | | X |
| 79 | | X | | 174 | | | X |
| 47 | X | | | 185 | | | X |
| 135 | X | | | 163 | | | X |
| 46 | | X | | 166 | | | X |
| 136 | X | | | 158 | | | X |
| 42 | | X | | 159 | | | X |
| 58 | | X | | 155 | | | X |
| 139 | | X | | 160 | | | X |
| 41 | | X | | 163 | | X | |
| 155 | | X | | 161 | | | X |
| 181 | | X | | 184 | | | X |
| 180 | X | | | 95 | | | X |
| 77 | X | | | 96 | | | X |
| 22 | | X | | 114 | | | X |
| 171 | | X | | 176 | | | X |
| | | | | 157 | | | X |

PDE Isozyme Specificity

We then proceeded to demonstrate that PDE isozyme specificity is a characteristic of the class of compounds. Test compounds (at 100 $\mu$M) were screened for activity against PDE 1,2 and 5, using standard biochemical methods performed at MDS Panlabs (Bothell, Wash., USA). The broad specificity PDE inhibitor 3-isobutyl-1-methylxanthine (IBMX) was used as a positive control in all assays. PDE's for the various assays were partially purified from the following cells/tissues; PDE 1 (bovine heart), PDE 2 (human platelets) and PDE 5 (human platelets). The results are shown in Table 12. For purposes of comparison, the effects on PDE3 (human platelets) and PDE4 (human U937 monocytic cell line) described above are presented again in Table 12.

TABLE 12

PDE Isozyme Specificity

| Compound number | PDE Isozyme | % inhibition by 100 µM test compound | | | |
|---|---|---|---|---|---|
| | | 1–25 | 25–50 | 50–75 | 75–100 |
| 12 | PDE1 | | | X | |
| | PDE2 | | X | | |
| | PDE3 | | | X | |
| | PDB4 | | | | X |
| | PDE5 | X | | | |
| 43 | PDE1 | | | X | |
| | PDE2 | | | X | |
| | PDE3 | | | | X |
| | PDE4 | | | | X |
| | PDE5 | X | | | |
| 41 | PDE1 | X | | | |
| | PDE2 | | X | | |
| | PDE3 | | X | | |
| | PDE4 | | | | X |
| | PDE5 | X | | | |
| 136 | PDE1 | | | X | |
| | PDE2 | | | X | |
| | PDE3 | | | | X |
| | PDE4 | | | | X |
| | PDE5 | X | | | |

Displacement of Rolipram from its High Affinity Binding Site (HARBS) on cAMP Phosphodiesterase 4

There is a need for phosphodiesterase 4 inhibitors that do not have undesirable side effects including nausea and vomiting. Animal models have shown that this activity is highly correlated with a compound's ability to displace [$^3$H]-Rolipram from a high affinity binding site from cells within the brain and central nervous system (CNS) [Duplantier 1996, Barnette 1996]. We have used a High Affinity Rolipram Binding Site (HARBS) displacement assay to predict the emetic potential of a compound of the present invention. Compounds of the present invention displayed a low affinity for the HARBS conformer of PDE4 suggesting that these compounds are not likely to be plagued by mechanism-associated side-effects associated with first generation PDE4 inhibitors such as rolipram.

Female CD1 mice were sacrificed via the intraperitoneal injection of 100 µL euthanol, and the brain tissue homogenized in 5 mL of ice-cold Tris-HCl, pH 8.00 supplemented with 1.2 MM $MgCl_2$, 1 mM benzamidine (Sigma; Catalogue No. B 6506) and 0.1 mM PMSF (Sigma; Catalogue No. P 7626). Suspension was centrifuged twice at 30,000×G at 4° C. and the supernatant discarded. The pellet was resuspended in buffer, and adjusted to a protein concentration of 0.5 mg/mL. Drugs to be tested were dissolved in DMSO and pipetted in triplicate into a 96 well microplate at concentrations ranging from 1 to 30,000 nM. 10 mL of membrane preparation was supplemented with 100 µL of 0.235 µM [$^3$H]-Rolipram in DMSO, and 100 µL dispensed into each well of the microplate. The plate was incubated at 4° C. for 1 hour. Contents of the plate were aspirated through a Whatman GF/C filterplate, and rinsed with 4×200 µL ice-cold buffer. Plate was dried overnight, 30 µL of Microscint 20 (Packard; Catalogue No. 6013621) was added to each well, and plate was read in the scintillation counter with a sampling time of 2 minutes/well. Values representing non-specific binding (defined by counts obtained using 20 µM rolipram) were subtracted from all data points. Triplicate determinations were performed at each concentration.

Results are shown in Table 13. PDE4:HARBS indicates the ratio of the $IC_{50}$ concentration required to inhibited catalytic activity to the concentration required to displace 50% of rolipram from the high affinity binding site.

Under these assay conditions rolipram is able to displace $^3$H-rolipram from a high-affinity binding site in mouse brain with an $IC_{50}$ of about 10 nM (data not shown). Thus, rolipram binds with 20–40 fold greater affinity to its high affinity site than the concentration required for half-maximal inhibition of PDE4 catalytic activity. This preferential affinity for HARBS over the catalytic conformer has been correlated with the negative side effects of first generation PDE4 inhibitors; namely emesis and CNS effects.

The data shown in Table 13 indicates that the tested compounds are much less potent at binding to this site than rolipram. For instance, rolipram and compound 43 have very similar $IC_{50}$'s against the catalytic activity of PDE4 (280 and 260 nM respectively), however, their HARBS activities are 10 nM and 250 nM respectively. Thus compound 43 is approximately 28 times less potent than rolipram for interaction with the HARBS conformer of PDE4. The ratio of $IC_{50}$'s for $PDE4_{catalytic}$ to $PDE4_{HARBS}$ for rolipram and compound 43 is 28 and 1.04 respectively. This ratio for compound 43 compares very favorably with values reported for second-generation PDE4 inhibitors where HARBS activity has been reduced through SAR efforts. For example, the ratios reported for SB 207499 (Ariflo) and RP 73401 (piclamilast), two specific PDE4 inhibitors that have been tested in phase II trials for asthma are 1 and 3 respectively. Thus, compounds of the present invention may display in-vivo emetogenic effects that are much less than rolipram, Ro 20-1724 or other first generation PDE4 inhibitors.

TABLE 13

Affinity of Test Compounds for the High Affinity Rolipram Binding Site of PDE4 in Mouse Brain

| Compound Number | 50% displacement of rolipram (µM) | | | | PDE4:HARBS |
|---|---|---|---|---|---|
| | 0.01–0.1 | 0.1–1 | 1–10 | >10 | |
| 21 | | | X | | <1 |
| 30 | | | X | | <1 |
| 29 | | | | X | <1 |
| 129 | | | | X | <1 |
| 130 | | | X | | <1 |
| 179 | | X | | | <1 |
| 43 | | X | | | >1 |
| 168 | | X | | | <1 |
| 132 | | | X | | <1 |
| 133 | | | X | | <1 |
| 54 | | | X | | >1 |
| 61 | | | X | | <1 |
| 79 | | | | X | <1 |
| 154 | | X | | | >1 |
| 135 | | | X | | <1 |
| 46 | | | X | | >1 |
| 169 | | | | X | <1 |
| 136 | | | X | | <1 |
| 153 | | X | | | >1 |
| 42 | | X | | | <1 |
| 58 | X | | | | >1 |
| 41 | | X | | | >1 |
| 155 | | X | | | <1 |
| 181 | | | X | | <1 |
| 180 | | X | | | >1 |
| 77 | | | | | |
| 22 | | | X | | <1 |
| 171 | | X | | | <1 |
| 62 | | X | | | >1 |
| 94 | X | | | | >1 |

TABLE 13-continued

Affinity of Test Compounds for the High Affinity
Rolipram Binding Site of PDE4 in Mouse Brain

| Compound Number | 50% displacement of rolipram ($\mu$M) | | | | PDE4:HARBS |
|---|---|---|---|---|---|
| | 0.01–0.1 | 0.1–1 | 1–10 | >10 | |
| 182 | | | X | | <1 |
| 99 | X | | | | >1 |
| 183 | | X | | | <1 |
| 172 | | | X | | <1 |
| 55 | | X | | | >1 |
| 186 | | X | | | >1 |
| 175 | | | X | | <1 |
| 187 | | X | | | >1 |
| 156 | | X | | | 1 |
| 108 | | X | | | <1 |
| 174 | | | X | | <1 |
| 185 | | X | | | >1 |
| 163 | | | X | | <1 |
| 166 | | X | | | >1 |
| 158 | | | X | | <1 |
| 159 | | X | | | >1 |
| 155 | | X | | | <1 |
| 160 | | X | | | <1 |
| 163 | | | X | | <1 |
| 161 | | | X | | <1 |
| 184 | | X | | | >1 |
| 176 | | X | | | >1 |
| 157 | X | | | | >1 |

Potentiation of Forskolin-Induced cAMP Response Element Luciferase Activity in Human U937 Monocytic Cells In order to demonstrate the ability of compounds of the present invention to elevate cAMP in intact cells, transfection of cells with a plasmid construct containing a cAMP response element (CRE) in a promoter driving the expression of a luciferase reporter gene (Stratagene; Path Detect™: Catalogue No. 219076) was used to allow sensitive monitoring of intracellular cAMP levels through detection of light output in a luminometer. Pharmacological treatment of transfected cells with a compound providing a combination of PDE inhibitor and adenylyl cyclase agonist (receptor or intracellular activator) results in elevated intracellular cAMP levels detectable from increased light output. cAMP PDE 4 has been shown to be the predominant cyclic nucleotide phosphodieterase activity in U937 cells, and therefore this cell type transfected with the CRE-luciferase construct can serve as a convenient cellular screening assay for compounds with PDE 4 inhibitory activity. Compounds of the present invention were thereby shown to provide potentiated luciferase expression in U937 cells treated with the adenylyl cyclase activator forskolin.

Human pro-monocytic U937 cells were maintained in RPMI medium containing 10% FCS and 2 mM glutamate. U937 cells were transiently transfected as described in Biotechniques Vol. 17(6):1058, 1994. Briefly, cells were grown in medium containing serum to a density of $5 \times 10^6$ cells/mL and then resuspended in media containing serum at a density of approximately $1 \times 10^7$ cells/mL. 400 $\mu$L of cells were transferred into the electroporation cuvette containing 10 $\mu$g of the reporter vector (pCRE-luc) in a volume of 40 $\mu$L H$_2$O. Reporter vector DNA was prepared from DH5 $\alpha$ E. coli using the DNA endonuclease free kit (Qiagen) as per manufacturers instructions. U937 cells were electroporated at room temperature using a BIORAD electroporator. Capacitance was set to 1050 $\mu$F and voltage was 280 V. The time constant was noted after each electroporation. Cells were then diluted in 4 mL of media and serum and 200 $\mu$L of cells were plated per well. Cells were allowed to recover for 16–18 hours. Cells were then treated with a test compound or vehicle in the presence or absence of 10 $\mu$M forskolin for 4 hours at 37° C.

The luciferase assay was performed as per manufacturers instructions (Tropix). Briefly, cells were centrifuged for 4 minutes at 1200 rpm and media supernatant was removed. Cell pellets were lysed in 15 $\mu$L Lysis buffer (Tropix). Luciferase assay was performed using 10 $\mu$L of cell lysate with 10 $\mu$L of buffer A and 25 $\mu$L buffer B. Luciferase activity was obtained using a luminometer with a 5-second delay followed by a read time of 10 seconds.

As shown in Table 14, compounds of the invention potentiate the induction of luciferase activity in U937 cells treated with 10 $\mu$M forskolin. Eleven compounds within the series induce CRE-luciferase at concentrations between 0.1 and 1 $\mu$M. None of the test compounds on their own induced significant luciferase activity indicating a low basal adenylyl cyclase activity in these cells. This result demonstrates that these compounds are capable of elevating cAMP levels in a cell line predominantly expressing PDE 4 consistent with the observations in the enzymatic assays.

There is a broad correlation between in vitro PDE4 inhibitory activity and CRE luciferase induction potency.

The CRE luciferase assay or variants (different cell types or construct characteristics) thereof serves as a convenient cellular SAR backup/validation assay to in-vitro PDE 4 enzymatic assays for efficacy optimization for compounds of the present invention.

TABLE 14

Potentiation of CRE-Luciferase Activity by Test Compounds in U937 Cells Co-Incubated with the Adenylyl Cyclase Activator Forskolin

| Compound Number | IC$_{50}$ range ($\mu$M) | | | Compound Number | IC$_{50}$ range ($\mu$M) | | |
|---|---|---|---|---|---|---|---|
| | 0.1–1 | 1–25 | >25 | | 0.1–1 | 1–25 | >25 |
| 12 | | X | | 22 | | X | |
| 21 | | X | | 171 | | | X |
| 30 | | X | | 62 | | X | |
| 29 | | X | | 94 | X | | |
| 129 | | X | | 182 | | | X |
| 130 | | X | | 99 | X | | |
| 179 | | X | | 183 | | X | |
| 131 | | X | | 172 | | X | |
| 43 | X | | | 55 | | X | |
| 168 | | X | | 80 | | X | |
| 132 | | X | | 186 | | X | |
| 133 | | X | | 162 | | | X |
| 54 | | X | | 175 | | X | |
| 61 | | X | | 187 | | X | |
| 79 | X | | | 156 | | X | |
| 47 | | X | | 108 | | X | |
| 154 | | X | | 174 | | | X |
| 135 | | X | | 185 | | X | |
| 46 | | X | | 163 | | | X |
| 169 | | X | | 166 | X | | |
| 136 | | X | | 158 | X | | |
| 153 | | X | | 159 | | | X |
| 42 | | X | | 155 | X | | |
| 58 | X | | | 160 | | X | |
| 139 | | X | | 163 | | X | |
| 41 | X | | | 161 | | | X |
| 155 | | X | | 184 | | X | |
| 181 | | | X | 176 | | X | |
| 180 | | X | | 157 | | X | |
| 77 | | X | | | | | |

Effects of Compounds of the Invention on Growth of Transformed Cells—Potential Anti-cancer Activities

Introduction

The BCR-ABL transformed human myeloid leukemia derived cell line, K-562 (ATCC; Catalogue No. CRL 243) was used to determine how compounds of the present invention affect transformed cell growth. The elevation of intracellular cAMP is one way to cause cell-cycle arrest or apoptosis in a number of malignancies, in particular certain classes of leukemias (e.g., CLL). Such intracellular mechanisms (i.e., cAMP) have been reported to bring about differentiation of the un-differentiated leukemic clones. In particular, it has been shown that elevation of intracellular cAMP (using a cylic AMP analogue) in p210 BCR-ABL tranformed myleoid leukemia cells is anti-proliferative via inhibition of cyclin dependent kinase 4 and subsequent down-regulation of c-myc. Thus, the anti-proliferative capacity of compounds of the present invention in cultured K-562 cells was compared with several standard phosphodiesterase inhibitors using a 3H-thymidine uptake assay.

Methods

90 μL K562 cells (human chronic myelogenous leukemia cells) were seeded into sterile 96-well assay plates at a density of $1 \times 10^5$ cells/mL in RPMI 1640 supplemented with 10% FBS/2 mM L-glutamine. Samples to be tested were prepared in a sterile 96-well assay plate at 10× the final concentration desired. All sample dilutions contained equal amounts of DMSO to compensate for the % DMSO in the highest sample concentration used. Nine concentrations of test compound were examined for effects on growth up to a maximal concentration of 100 μM. 10 μL of the samples and controls (DMSO/normal growth control) were added to the aliquoted cells. The cells were incubated at 37° C./5% $CO_2$ for 48 hours. Following 48 hour incubation, 20 μL of $^3$H-thymidine was added to each well for a final concentration of 1 μCi/mL. The cells were then incubated at 37° C./5% $CO_2$ for 4 to 6 hours. Following 4–6 hour thymidine pulse, plates were wrapped in plastic and frozen in a −20° C. frost-free freezer overnight. Cells were harvested and $^3$H-thymidine counts determined. In order to distinguish between cytotoxicity and cytostatic activity, growth curves were prepared where the average CPM value of the seeding density of cells was plotted on the same curve as the average CPM value for the maximum proliferation attained after 48 hours (DMSO growth control cells). The cells were diluted 1:2 for a concentration range of $7.8 \times 10^3$ cells/mL to $2 \times 10^6$ cells/mL. 90 μL of each cell dilution was seeded in sterile 96-well assay plated and allowed to equilibrate for approximately 4 hours at 37° C./5% $CO_2$ prior to $^3$H-thymidine pulse. The data in Table 15 was obtained as described above, and more specifically, K562 cells were seeded into 96-well plates at $1 \times 10^5$ cells/mL in RPMI 1640 supplemented with 10% FBS/2 mM L-glutamine. Various concentrations of test compound or vehicle (DMSO) was added and the cells were incubated at 37° C./5 $CO_2$ for 48 hours. The cells were then pulsed at 37° C./5% $CO_2$ for 4 to 6 hours with 1 μCi/mL $^3$H-thymidine. Radioactivity incorporated into DNA was determined after harvesting onto glass fiber filters and scintillation counting.

Results and Discussion

The data in Table 15 demonstrates that compounds of the present invention are capable of causing cell cycle arrest (e.g., compound 179) and are likely therefore to promote cellular differentiation and/or apoptosis. In contrast, known PDE inhibitors (Rolipram, a PDE-4 inhibitor and Zadavarine, a PDE4/3 inhibitor) failed to have any effect upon the proliferative ability of the K-562 cells. While both the tested compounds of the invention and the known PDE inhibitors in this case all target PDE-4, only the inventive compounds show a dramatic effect on the growth properties of K-562 cells. This may well indicate a novel class of PDE-4 enzymes targeted by these compounds that are not affected by either rolipram or zardavarine. The ability of compound 179 to induce cell cycle arrest in the K-562 cell line whereas the canonical PDE4 or PDE4/3 inhibitors rolipram and zardaverine are unable to do so suggest the inventive compounds may be used in the treatment of myeloproliferative and lymphoproliferative disorders such as CML and CLL and potentially other malignancies.

TABLE 15

Anti-Proliferative Activity Of Test Compounds In K562 Chronic Myelogenous Leukemia Cells

| Compound | $IC_{50}$ range (μM) | |
|---|---|---|
| | <50 | >50 |
| 41 | | X |
| 179 | X | |
| ROLIPRAM | | X |
| ZARDAVERINE | | X |

Efficacy in Specific Animal Models of Inflammatory Disease and Autoimmunity

Proof of concept studies in specific disease models were undertaken in animals to further demonstrate the enzymatic, cellular and general anti-inflammatory activity of the lactone and lactam compounds of the present invention. Literature studies have shown that elevation of intracellular cAMP through administration of phosphodiesterase inhibitors, adenylyl cyclase activators, or both, can reduce established disease and/or prevent disease development in various animal models of inflammatory disease. The efficacy of compounds of the invention was demonstrated in animal models of Crohn's disease, rheumatoid arthritis and transplant rejection. With respect to Crohn's disease, an established preclinical model was used; trinitrobenzenesulfonic-acid (TNBS) induced colitis in the rat. For rheumatoid arthritis, collagen-induced arthritis (CIA) in the mouse was employed. To mimic human transplant rejection, a murine tail skin allograft transplantation model was used.

Inflammatory Bowel Disease (Crohn's Disease)

Inflammatory bowel disease (IBD) is an umbrella term for presently incurable, chronic, fluctuating inflammatory diseases of the gastrointestinal tract including Crohn's disease and ulcerative colitis. Symptoms of these disorders include abdominal pain (usually in the lower right side of the abdomen) and diarrhea with rectal bleeding, weight loss and fever as the condition progresses. The etiology of IBD is unknown, however epidemiological studies suggest an association between disease and viral infection (particularly measles) in utero or early in life. The Crohn's and Colitis Foundation of America (CCFA) estimates 1–2 million persons in the US suffer from Crohn's and related IBD's with those of European descent at greater risk. Incidence rates have increased significantly in the 60 years since it (Crohn's) was first described. In the United States alone, the economic costs of these diseases are estimated at U.S. $1.8–2.6 billion per year.

A common treatment for IBD consists of oral or intracolonic administration of 5-aminosalicylic acid (5-ASA), an NSAID derivative which is cleaved to ASA (the active drug) in the lower g.i. tract. Other mainstay treatments of IBD include corticosteroids and immunosuppressants (e.g., 6-mercaptopurine or azathioprine) or combinations thereof. Recently, an anti-TNF-α therapy was approved for the treatment of severe Crohn's disease that is resistant to conventional therapies. This therapeutic approach validates the importance of tumour necrosis factor in IBD. Even with the anti-TNFα approaches there is much room for improvement in current treatment modalities from both the point of view of side effects and efficacy.

Compounds of the present invention were tested in the trinitrobenzenesulfonic acid (TNBS) induced colitis model in rat (Morris et al., *Gastroenterology* 96:795–803, 1989; Kim, H.-S. and Berstad, A., *Scandinavian Journal of Gastroenterology* 27:529–537, 1992; Ward, *Lancet* ii:903–905, 1977; and Shorter et al., *Am. J. Dig. Dis.* 17:1024–1032, 1972)). Advantages of this particular IBD model include (a) disease development in the rat is immune-mediated with Th1 T-cells playing an important role as is thought to be the case in human disease, (b) single instillation of TNBS induces disease of consistent severity and persistence (c) the model is inexpensive, (d) long duration of inflammation (up to 8 weeks), (e) a variant of the model in which colitis is reactivated mimics the relapsing/remitting nature of the human disease, (f) lesions are histopathologically similar to those in humans (g) clinical pathology mimics the human disease including, necrosis, formation of ulcers, granulocytic infiltration, edema of the bowel, diarrhea and adhesions and (h) many drugs used to treat human IBD are active in the TNBS model.

Compound 43 was evaluated for its ability to attenuate the severity of colonic damage and inflammation using the TNBS model. For comparison, separate groups of rats with colitis were treated with 5-aminosalicylic acid, a drug commonly used to treat human inflammatory bowel disease, and NCX-456, a novel derivative of 5-aminosalicylic acid that has recently been shown to have markedly enhanced anti-inflammatory activity (Wallace et al., *Gastroenterology* 117: in press, 1999).

Methods

Colitis was induced by intracolonic instillation of the hapten TNBS (60 mg/mL) in 0.5 mL of 50% ethanol. Groups of 8 male, Wistar rats weighing 175–225 g received compound 43 (10 mg/kg), 5-aminosalicylic acid at 100 mg/kg, NCX-456 (100 mg/kg), or vehicle (1% carboxymethylcellulose) intracolonically 1 hour prior to induction of colitis, 1 h after induction of colitis and at 12 h intervals thereafter for one week. An additional group of rats received saline intracolonically in place of TNBS/ethanol and was treated with vehicle at the same times as outlined above. Body weights were recorded at the beginning of the study and at days 2 and 7.

The rats were sacrificed on the 7th day after the induction of colitis and the extent of damage and inflammation was assessed. After the rats were sacrificed, the distal colon was removed and pinned out on a wax platform. The presence or absence of diarrhea was noted, as well as the presence and severity of adhesions between the colon and other organs, and the severity and extent of colonic damage. The order of sacrifice of the rats was randomized, and the person scoring the injury was not aware of the treatment the rats had received. After scoring, a sample of colonic tissue was excised for measurement of myeloperoxidase activity as an index of granulocyte infiltration (see Wallace et al., *Gastroenterology* 117: in press, 1999; and Morris et al., *Gastroenterology* 96:795–803, 1989). This tissue sample was 1 cm long (along the axis of the colon) and 5 mm wide and was taken from a region of macroscopically visible damage (or the corresponding region in any rats in which there was no damage). The remainder of the tissue was fixed in neutral buffered formalin and processed by routine methods for subsequent evaluation by light microscopy. In a blinded manner, the sample of colonic tissue from each rat was examined for evidence of mucosal ulceration and inflammation. The percentage of the luminal surface of the section in which ulceration was present was calculated.

Results

One rat in the vehicle-treated group was excluded from analysis because the TNBS was rapidly excreted after its installation into the colon (i.e., colitis failed to develop). One vehicle-treated rat died on day 7 and one NCX-456-treated rat died on day 6. In each case, perforation of the distal colon was observed during necropsy. The various endpoints of this study are summarized in Table 16. In vehicle-treated rats, administration of TNBS resulted in extensive ulceration of the distal colon, diarrhea and adhesions between the colon and other visceral tissues. The bowel wall thickness was more than double that of healthy control rats. The global colitis score in the vehicle-treated group was 12±1. Colonic myeloperoxidase activity was increased approximately 10-fold over the levels in healthy control rats. Histologically, massive neutrophil infiltration was evident around sites of mucosal ulceration. In the vehicle-treated rats, almost the entire 1 cm segment of tissue exhibited mucosal ulceration extending to the depth of the muscularis propria. Vehicle-treated rats exhibited a significant loss of body weight (~12%) over the one-week period following TNBS administration (Table 16).

TABLE 16 effect of Compound 43 in a tnbs-induced model of inflammatory bowel disease in the rat

| Group | Mortality | Adhesion Score (Incidence) | Diarrhea | Damage Score | Bowel Thickness (mm) | Global Colitis Score | MPO Activity (U/mg) | Histology Score | Body Weight Change (%) |
|---|---|---|---|---|---|---|---|---|---|
| Vehicle | 1/7 | 1.4 ± 0.2 (6/6) | 5/6 | 6.9 ± 0.6 | 2.95 ± 0.35 | 12.04 ± 0.89 | 63.2 ± 4.9 | 96.7 ± 2.4 | −12.4 ± 0.6 |
| 5-ASA (100 mg/kg) | 0/8 | 1.4 ± 0.3 (7/8) | 1/8 | 6.3 ± 0.8 | 2.66 ± 0.69 | 10.41 ± 1.58 | 67.5 ± 8.8 | 91.4 ± 5.9 | −20.2 ± 3.4 |
| 43 (10 | 0/8 | 0.5 ± 0.3 | 3/8 | 3.4 ± 0.9* | 1.67 ± 0.28# | 5.86 ± 1.35** | 65.1 ± 8.6 | 50.6 ± 10.5## | +22.6 ± 1.8Ψ |

TABLE 16-continued effect of Compound 43 in a tnbs-induced model of inflammatory bowel disease in the rat

| Group | Mortality | Adhesion Score (Incidence) | Diarrhea | Damage Score | Bowel Thickness (mm) | Global Colitis Score | MPO Activity (U/mg) | Histology Score | Body Weight Change (%) |
|---|---|---|---|---|---|---|---|---|---|
| mg/kg) | | (3/8)$^{\zeta}$ | | | | | | | |
| NCX-456 (100 mg/kg) | 1/8 | 0.4 ± 0.3 (2/7)$^{\zeta}$ | 3/7 | 3.7 ± 0.9* | 2.02 ± 0.42 | 6.60 ± 1.67* | 57.8 ± 11.6 | 46.4 ± 4.1$^{\#\#}$ | −5.7 ± 0.3 |
| Healthy controls | 0/8 | 0 ± 0 (0/8)$^{\zeta\zeta\zeta}$ | 0/8 | 0 ± 0** | 1.13 ± 0.07$^{\#}$ | 1.13 ± 0.07$^{\#}$ | 5.8 ± 0.6** | 0 ± 0$^{\#\#}$ | 10.7 ± 0.3 |

$^{\zeta}$p < 0.05, $^{\zeta\zeta\zeta}$p < 0.001 versus the vehicle-treated group (Fisher Exact test)
*p < 0.05, **p < 0.01 versus the vehicle-treated group (Mann Whitney U test)
$^{\#}$p < 0.05, $^{\#\#}$p<0.01 versus the vehicle-treated group (ANOVA and Dunnett's Multiple Comparison test)
$^{\psi}$p < 0.05 versus the vehicle-treated group (ANOVA and Dunnett's Multiple Comparison test)

Treatment with 5-ASA over the course of one week did not significantly affect the incidence/severity of adhesions, colonic damage score, bowel wall thickness, myeloperoxidase activity or histological score (Table 16). However, 5-ASA did significantly reduce the incidence of diarrhea relative to the vehicle-treated group. Rats treated with 5-ASA exhibited similar loss of body weight (~20%) as the vehicle-treated group over the course of the one-week study (Table 16).

Treatment for one week with the nitric oxide-releasing derivative of 5-ASA, NCX-456, resulted in a significant (50%) reduction in the colonic damage score and a similar reduction in the histological score (Table 16). In the latter case, this reflected a reduction in the extent of ulceration of the 1 cm sample that had been fixed and processed for examination by light microscopy. NCX-456 also significantly reduced the incidence of adhesions relative to the vehicle-treated group. Mean body weights of the rats treated with NCX-456 did not differ significantly from those in the vehicle-treated group (Table 16).

Compound 43 significantly reduced the incidence of adhesions (36% of vehicle), the colonic damage score (49% of vehicle), the thickness of the bowel wall (30% of vehicle) and the histological score (52% of control) resulting in a total reduction in the global colitis score of 51% compared to vehicle treated animals. (Table 16). Compound 43 also reduced the incidence of diarrhea compared to vehicle treated animals although the effect was not statistically significant. Compound 43 was the only one of the various test compounds that prevented the decrease in body weight caused by administration of TNBS (Table 16). Increases in tissue myeloperoxidase (MPO) activity, a marker of tissue neutrophil infiltration in the colon were not prevented by any of the test compounds including compound 43.

Discussion

These studies demonstrate the effectiveness of compound 43 in the TNBS model of colitis in rats. Compound 43 markedly reduced colonic damage, as assessed both macroscopically and histologically, reduced bowel wall thickness, prevented the decrease in body weight normally observed following TNBS administration and reduced the incidence of adhesions between the colon and other visceral organs. 5-ASA, a drug commonly used for the treatment of inflammatory bowel disease in humans, was found to be ineffective in reducing colonic injury, adhesions, body weight changes and bowel wall thickness. 5-ASA is only effective in about 50% of the trials involving this model. On the other hand, NCX-456, which is a nitric oxide-releasing derivative of 5-ASA (Wallace et al., *Gastroenterology* 117: in press, 1999), exhibited actions in the TNBS model that were comparable to those of compound 43. However, while NCX-456 significantly reduced colonic damage and the incidence of adhesions, in contrast to compound 43, it did not significantly affect the changes in body weight following TNBS administration, nor did it significantly reduce bowel wall thickness. It is important to note that the effects of compound 43 reported herein correspond to a dosing level of 10 mg/kg. 5-ASA and NCX-456 were administered at 100 mg/kg. It has also been shown that the therapeutic effects of NCX-456 are lost when the dose is reduced to 50 mg/kg.

None of the tested compounds significantly affected colonic tissue myeloperoxidase activity. MPO is an enzyme found primarily in the azurophilic granules of neutrophils, thereby serving as a biochemical index of neutrophil infiltration. The lack of effect of any of the tested compounds on MPO activity, despite significant reductions in the severity/extent of colonic damage, may have been a consequence of the method of sampling of tissue. The tissue samples for MPO were taken from regions of macroscopically visible damage. The histological evaluation revealed that areas of damage were always associated with massive neutrophil infiltration. The large concentrations of neutrophils around sites of damage may therefore have "masked" any reduction in total neutrophil influx that occurred in tissues where damage was reduced by treatment with the test drugs.

The TNBS rat model of gastrointestinal inflammation is an accepted pre-clinical model for human IBD. The clinical and histopathological manifestations of disease show good similarity to human disease and many drugs currently used for treatment of IBD in humans have efficacy in this model. The efficacy of compound 43 in this model implies that this and other compounds of the invention may be used in therapy of human inflammatory disease including Crohn's disease and ulcerative colitis amongst others.

Rheumatoid Arthritis

Introduction and Rationale

The collagen-induced arthritis (CIA) model in mice is a suitable model for evaluating potential drugs active in human rheumatoid arthritis (Trentham, D. E., *Arthritis Rheum.* 25:911–916, 1982; Brahn, E., *Clin. Orthop.* 265:42–53, 1991; Holmdahl, R. et al., *Arthritis Rheum.* 29:106, 1986). It shares many of the molecular, cellular and histopathological changes identified as hallmarks of the human disease; these include (a) pronounced proliferation of cells comprising the joint synovial membrane, (b) formation of an invasive pannus-like tissue, (c) macrophage, granulocyte and lymphocytic infiltration and (d) destruction of bone and cartilage. Like rheumatoid arthritis, animals with CIA exhibit elevated serum levels of immunoglobulin complexes such as rheumatoid factor (RF) and anti-collagen antibodies and inflammatory cytokines in the synovium such as tumour necrosis factor (TNF-α). In addition, involvement of MHC class II-restricted T-helper cell activation/clonal expansion in the synovium has been demonstrated. Radiographs of affected joints often show erosive changes similar to those seen in human RA and the progressive arthritis often results in an RA-like joint deformity and dysfunction. In addition, many compounds which reduce the symptoms of human disease such as anti-TNF biologics, corticosteroids and DMARDS are efficacious in this animal model. The development/progression of disease in the CIA model occurs in both an immune (early) and inflammatory phase thus allowing the assessment of a wide range of drugs with diverse pharmacological modes of action.

Compound 43 was evaluated for its ability to affect the development or severity of arthritis in the murine CIA model when administered intraperitoneally (10 mg/kg, twice daily) in a prophylactic regime during developing disease. Effects of this treatment on disease severity were assessed by qualitative disease scores, quantitative determination of paw edema and detailed histopathological examination of affected joints. Dexamethasone, a powerful corticosteroid, was used as a positive control in the study.

Methods

Male DBA/1J mice (7–8 weeks of age) were immunized through a subcutaneous injection of 0.1 mL of a collagen-adjuvant emulsion (0.1 mg chick type II collagen in complete Freund's adjuvant) at the base of the tail. Mice were then randomly assigned to treatment or control groups in the following manner: Compound 43 (n=10); 45% 2-hydroxypropyl betacyclodextrin in 0.9% saline vehicle control (n=10); untreated (n=5) and dexamethasone positive control (n=5). After three weeks the animals were boosted with a second injection of chick type II collagen emulsified at 1.0 mg/mL in incomplete Freund's adjuvant. This second injection is required for reproducible induction of disease. In control animals, clinical signs of arthritis manifested as erythema and edema of the paws and tarsal/metatarsal joints usually appear within 1–2 weeks following the second immunization. Compounds were evaluated for their ability to delay the onset of or reduce the development of arthritis (prophylactic regime). Vehicle, dexamethasone positive control (0.075 mg/kg) and compound 43 (10 mg/kg) were administered twice daily (50 microliter per injection) by i.p. injection beginning on the day of the second collagen injection. The mice continued to receive doses until the last animal in the vehicle control group reached the seventh day of having established disease. In this particular case, this necessitated treatment for 25 days including the day of the booster injection.

The development of clinical arthritis (disease progression) was monitored daily after the second collagen injection. All four limbs were clinically evaluated by a trained observer unfamiliar (blinded) with the treatment group identity, and scored on a scale of 0–4 for disease severity (redness and swelling) according to the following criteria.

| Score | Condition |
| --- | --- |
| 0 | Normal |
| 1 | Some joints swollen and red, but not all |
| 2 | All joints swollen |
| 3 | Full inflammation of paw |
| 4 | Maximum inflammation, no further swelling possible |

Inflammation was defined as any redness or swelling (enlargement) of any part of any paw. Established disease was defined as a qualitative score of paw inflammation of 2 or greater, that persists for at least 24 hours. In addition, paw widths for all four limbs were measured by a blinded observer daily using precision, constant tension calipers.

At the end of the study each animal was euthanized by an overdose of halothane anesthesia. Joints both distal to the knee and including the knee were dissected and analyzed by histology. Limb joints were fixed in 10% formalin buffer and decalcified in 10% formic acid for 48 hours, then processed for paraffin embedding. Serial sections (5–7 micrometer thick) were stained with haematoxylin and eosin (H & E). Histopathological alterations of the tarsal and metatarsal joints were graded "blind" by a certified pathologist and a score assigned based on a ranking system.

Results and Discussion

Approximately 14–16 days after administration of the collagen booster injection in Incomplete Freund's Adjuvant (IFA) both mice in the untreated groups and in the vehicle treated groups began displaying overt signs of clinical arthritis. Clinical signs of arthritis included swelling, redness and disfigurement of the paws. Clinical disease was recorded quantitatively (using precision calipers to measure edema of the paw) and qualitatively (disease scores assigned based on the severity of paw inflammation) on a daily basis once signs were evident. As clinical disease progressed (the last 10 days of the study) in the untreated and vehicle treated groups of mice it became evident that in those mice treated with 10 mg/kg compound 43 (i.p., bid) the rate of disease progression as assessed by paw score was significantly reduced (data not shown).

Mice were sacrificed on the $25^{th}$ day after the second collagen injection corresponding to approximately the $10^{th}$ day of established disease. All four paws from each animal in the study were removed, fixed and processed for blinded histopathological examination by an ACVP board certified veterinary pathologist. Joint pathology for each foot was classified on a scale of 0 to 4, with 0 being normal and 4 the most severely affected. Lesion grades were assigned based on the most severe lesion(s) present in the paw according to the following scale:

| Histopathological Score | Description |
| --- | --- |
| 0 | Normal joint |
| 1 | Synovial hyperplasia |
| 2 | Synovial hyperplasia and leukocytic infiltration with pannus formation |
| 3 | Grade 2 with reabsorption of subchondral bone |
| 4 | Loss of joint integrity with massive leukocytic infiltration |

The individual paw scores were then summed to obtain a total for each animal with a maximum possible score for an animal being 16. Group values were obtained by averaging the individual animal scores.

Table 17 shows the average group values with respect to paw edema, clinical arthritis score and joint histopathological score for compound 43 treated animals compared to vehicle treated, dex treated and untreated mice on Day 25 after the collagen boost.

TABLE 17 effect of Compound 43 on clinical and histopathological parameters of disease in the murine collagen-induced arthritis model

| Compound | Paw Edema (1/100 in.) | Paw Arthritis Score | Histopathological Score (range) |
|---|---|---|---|
| 43 | 0.052 ± .0051 | 3.3 ± .64 | 7.7 (1–15) |
| Vehicle | 0.0891 ± .0088 | 5.1 ± .75 | 10.8 (3–16) |
| Untreated | 0.093 ± .0139 | 4.4 ± 1.2 | 9.0 (7–12) |
| dexamethasone | −0.0056 ± .0008 | 0.8 ± .36 | 5.4 (3–6) |

The data in Table 17 show that the vehicle employed in this study, 2-hydroxypropyl betacyclodextrin, does not affect the course of disease development whether assessed clinically or histopathologically. These data also show that on the final day of the study (day 25), disease severity (whether assessed clinically or histopathologically) was reduced in the compound 43 treated mice compared to the vehicle group. As shown in the Table, paw edema, arthritis score and histopathological score were reduced by 42%, 35% and 29% respectively in the compound 43 treated group compared to the vehicle group. A 2-way ANOVA analysis of data from the last 10 days of the study revealed that the arthritis scores of compound 43 treated animals were significantly lower than those of the vehicle treated animals (data not shown).

From examination of time courses for edema and arthritis scores it is clear that the effects of compound 43 become manifest more profoundly as disease progresses. This strongly suggests that compound effects at this dosage level would be statistically significant in all disease categories if the study had been continued for another week. Additionally, these results argue that compound 43 and other compounds of the invention may be more effective in treatment of existing disease (therapeutic regimen) rather than prophylactically. The modest effects of compound 43 in amelioration of CIA reported here may indicate that the dosage employed is on the cusp of efficacy and that higher doses would result in greater inhibition. It is also possible that bioavailability and metabolism parameters are playing important roles in the results seen.

The reduction in progression of collagen-induced arthritis in mice by compound 43 reported herein demonstrates that compound 43 may be used in the treatment of rheumatoid arthritis and other related inflammatory diseases. These results (in particular the histopathological scores) also indicate that these compounds may be used in the treatment of diseases involving perturbations in the bone and cartilage compartments of joints including osteoarthritis and osteopenia. The activity of compound 43 in this model supports the in-vitro data reported herein showing inhibitory effects of this compound and other compounds of the invention on neutrophil activation, monocyte/macrophage activation and T-cell Th1 responses.

Transplant Rejection

In Vitro Testing: CD4 T Cell Activation, Differentiation and Function

Methods

AND-TCR transgenic mice (Kaye J. et al., Nature 341:746–749, 1989) were used to provide a source of naive-antigen specific CD4+T cells. The AND-T cell antigen receptor recognizes a peptide derived from pigeon cytochrome C (pcc) in the context of the I-$E^k$ class II MHC molecule.

To examine the role of a test compound in naive CD4 T cell activation and proliferation, $1 \times 10^5$ AND-lymph node T cells were cultured with $1 \times 10^6$ irradiated B10.BR spleen cells in the presence of varying concentrations of pcc peptide (0–10 μM) in 96 well plates. Proliferation was assessed by $^3$H thymidine incorporation. All assay conditions were conducted in triplicate. Cell surface activation phenotype of T cells was assessed by flow cytometric analysis.

The differentiation of naive CD4 T cells toward Th1 and Th2 lineages was performed as follows: $1 \times 10^5$ AND-lymph node T cells were cultured with $10^7$ B10.BR irradiated spleen cells in 2 ml of culture media with the following supplements: for Th1 cell differentiation, 100 U/mL IFNγ, 25 U/mL IL2 and 10 ug/mL anti-IL4; for Th2 cell differentiation, 150 U/mL IL4, 25 U/mL IL2 and 10 ug/mL anti-IFNγ. After 3–4 days the wells were split 1:4 with the same additions. After 7 days the cells were harvested and washed 3 times to remove cytokines in the supernatents. $1 \times 10^5$ cultured cells were restimulated with $5 \times 10^5$ irradiated B10BR spleen cells+5 μM pcc peptide in 250 μl culture media without any added cytokines. The supernatents were harvested after 40 hrs and assessed for IL2, IL4 and IFNγ by ELISA. Test compounds were added throughout the differentiation of the culture.

Cultured Th1 and Th2 cells generated in the absence of test compounds were tested for proliferation and cytokine activity as described above during antigen stimulation in the presence of compound.

In Vitro Testing: CD8 T Cell Activation, Differentiation and Function

Methods

2C-TCR transgenic mice (Sha W. C. et al., Nature 335:271–274, 1988) were used to provide a source of naive antigen specific CD8+T cells. The 2C-T cell antigen receptor recognizes the 2C peptide derived from the mitochondrial alpha-ketoglutarate dehydrogenase enzyme in the context of the Db class I MHC molecule.

To test the efficacy of a test compound in naive CD8+ T cell activation and proliferation, single cell suspensions of 2C lymph node (LN) T cells were isolated from 2C-TCR transgenic mice. 2C-T cells were stimulated with irradiated TAP−/−H-$2^d$ splenocytes or $L^d$ transfected TAP−/−T2 cell line in the presence of varying concentrations of 2C peptide (0–10 uM). Proliferation was assessed by $^3$H thymidine incorporation. Cell surface activation phenotype of T cells was performed by flow cytometric analysis Cytotoxic T cells were generated by activation of 2C-T cells with irradiated H-$2^d$ splenocytes. Cells were cultured for 7–10 days in the presence of 25 U/mL IL2. Cytotoxic killer activity of culture cells was tested with a $Cr^{51}$ release assay using T2-$L^d$ target cells in the presence of varying concentrations of 2C peptide. The effect of test compounds on the differentiation of naive CD8 T cells into cytotoxic killer cells was assessed by addition of test compounds during the primary activation and culture period. The effect of the test compounds in cytotoxic CD8 T cell activation and effector function was measured using the $Cr^{51}$ release assay and $^3$H thymidine incorporation assay in the presence of the stated concentrations of compound.

Results and Discussion

Testing of compound 43 and 136 in both a one way and two way mixed-lymphocyte-reaction (MLR) demonstrated efficacy for both compounds (approx. 50% or greater inhibition of proliferation at 20 µM). Overall the best effect was shown for 136 with nearly 70% inhibition using either experimental regimen.

Inhibition of CD8+ T-cell proliferation was also demonstrated by these compounds with the stronger effect once again coming from 136 (approx. 40% inhibition at 5 µM). Both compounds were equipotent (i.e., approx. 50% inhibition at 5 µM), in inhibiting the cyto-toxic killer cell function of the same CD8+ T-cells.

Naive CD4+ T-cells proliferation was strongly inhibited by both compound 43 and 136 (greater than 70% inhibition @5 µM) while CD4+ T cells that were already differentiated into a Th1 or Th2 phenotype demonstrated lesser inhibition in the presence of these compounds. Both compounds however demonstrate a stronger inhibition of Th1 (approx. 30%) over Th2 cells (0 to 8%). This was also reflected somewhat in the extent of inhibition of Th1 cytokine (IFNγ) versus the Th2 cytokine (IL-4). This is likely to result over the long term in the down modulation/suppression of Th1 cytokines/phenotype in vivo due to their regulation by Th2 cytokines. This result thus further substantiates our finding of a preferential suppression of Th1 cytokine phenotype over a Th2 cytokine phenotype when compounds of the invention (e.g., 136 and compound 43) are used in gauging the activation of primary human CD4+ cells.

The results of the ex vivo studies discussed above indicate: (a) compound 136 and compound 43 preferentially inhibit CD4+ T-cells over CD8+ T-cells; (b) of the CD4+ T-cells, naive T-cells were strongly inhibited (>=80%), while committed T-cells (Th1/Th2) were not as strongly impacted; (c) some of the compounds however, notably compound 136, showed a preferential inhibition of the Th1 committed population over the Th2 committed population of T-cells; (d) also while inhibition of CD8+ T-cells was not profound, inhibition of their functional "killer" activity was observed for those compounds with dual PDE 4/3 activity; and (e) the control phosphodiesterase IV inhibitor, rolipram, was uniformly inhibitory to all T-cell populations with little to no differential activity.

In Vivo Testing: Murine Tail Skin Allograft Transplantation Model

Three compounds were evaluated in an in vivo transplant model, namely compounds 54, 41 and 136.

Methods

Tail skin from donor H-$2^b$ C57BL/6 mice was transplanted onto recipient female H-$2^d$ BALB/c mice (Lagodzinski, Z. et al., *Immunology* 71:148–150 (1990)). Five mice were included per group. Seven groups of mice consisting of four test groups treated with test compounds and three controls which include untreated, vehicle alone and Cyclosporin A (CsA; Sigma; Catalogue No. C 3662)-treated groups were included in the study. Test compounds and CsA were administered twice daily intraperitoneally at a dose of 10 mg/kg beginning at one day prior to transplantation and for 15 days after transplantation, including the day of transplantation. Mice were monitored and scored daily over 15 days post transplantation for graft rejection.

Results and Discussion

Skin allograft rejection is primarily mediated by T lymphocytes with little evidence for a major role of antibodies under most circumstances. Skin allograft rejection requires the activation of helper and cytotoxic effector T cell populations. Graft rejection was assessed by monitoring allograft necrosis. Because tail skin is visibly distinct from the surrounding trunk skin of the mouse, the course of rejection can be easily monitored. Fully intact grafts were scored as 100%. Complete graft rejection was defined as >90% graft necrosis. Acute graft rejection generally proceeds via a series of visually obvious events beginning with swelling and erythema of the graft. These events are followed by graft desiccation and scab formation over most or all of the graft, signaling the loss of the viable graft tissue. Scab formation is subsequently followed by shrinkage and scar formation.

All tested compounds of the present invention demonstrated significant enhancement of graft survival when compared to the control (carrier only; β-cyclodextrin; Sigma; Catalogue No. C 4767) group (Table 18).

TABLE 18

Effect Of Compounds On Graft Rejection In A Murine Tail Skin Allograft Transplantation Model

| Compound | Average graft survival (days) | Allograft survival rate (% at 9 days post-transplant) | # grafts surviving beyond 16 days p.t. |
|---|---|---|---|
| Untreated | 8 ± 1 | 0 | 0 |
| Vehicle | 8.5 ± 1 | 0 | 0 |
| Rolipram | 11.5 ± 3.7 | 50 | 1 |
| Cyclosporin | 13.5 ± 3.3 | 75 | 2 |
| 136 | 15.4 ± 1.3 | 100 | 3 |
| 41 | 11.6 ± 4.6 | 60 | 1 |
| 54 | 11.5 ± 3.3 | 75 | 0 |

The control group averaged an 8.5 day survival of the skin allografts while the groups treated with compounds 54 and 41 averaged 11 to 12 day survival. Compound 136 prolonged graft survival for an average of 15.4 days and in so doing exceeded the capacity of the positive control Cyclosporin A (13.5 days). Furthermore, the overall quality (% rejection of individual grafts) of the surviving grafts were similar to, if not better than, those obtained using Cyclosporin A.

By comparison to cyclosporin A, the compounds of the invention are also amenable for use in all indications where cyclosporin A is used. The differential activities of these compounds as well as their selectivity in cytokines inhibited argues for a mechanism that will not result in immunosuppression but instead immunomodulation. The ability of these compounds to suppress allograft rejection in this model implies that they may be of therapeutic utility in diseases such as multiple sclerosis, inflammatory bowel disease, rheumatoid arthritis, psoriasis, organ transplantation and all autoimmune disorders. For example, many drugs for the treatment of psoriasis are used in organ transplantation or have demonstrated efficacy in this setting. Thus, efficacy of immunomodulatory or immunosuppressive drugs in organ transplantation appears predictive of efficacy in psoriasis, boding well for this series of compounds as a therapeutic for psoriasis.

All publications, patents, and patent applications mentioned in this specification are incorporated herein by reference to the same extent as if each individual publication, patent, or patent application was specifically and individually incorporated by reference.

From the foregoing, it will be appreciated that, although specific embodiments of the invention have been described herein for purposes of illustration, various modifications may be made without deviating from the spirit and scope of the invention. Accordingly, the invention is not to be limited by the specific examples provided herein.

What is claimed is:

1. A compound of the formula

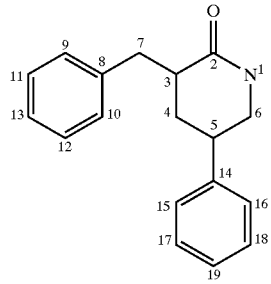

wherein,
each of the carbons at positions 3, 4, 5, 6, 7, 9, 10, 11, 12, 13, 15, 16, 17, 18, and 19, as well as the nitrogen at position 1, is independently substituted at each occurrence with H, —W or —R$^7$(W)$_n$, wherein
W is selected from —NH$_2$, —CONH$_2$, —COOH, —CN, —CHO, —OCHO, —X, —OH, —NO$_2$, —SH, —COX, —NHR$^8$, —NR$^8$R$^8$, —CONHR$^8$, —CONR$^8$R$^8$, —COOR$^8$, —COR$^8$, —OCOR$^8$, —OR$^8$, —BH$_2$, —BHR$^8$, —BR$^8$R$^8$, —BO$_2$H$_2$, —BO$_2$R$^8$R$^8$, —PH$_2$, —PHR$^8$, —PR$^8$R$^8$, —POR$^8$, —PO$_2$R$^8$, —PO$^3$R$^8$, —SR$^8$; —SOR$^8$, —SO$_2$R$^8$, —SONH$_2$, —SONHR$^8$, —SONR$^8$R$^8$, —SO$_2$NH$_2$, —SO$_2$NHR$^8$ and —SO$_2$NR$^8$R$^8$;
R$^7$ is a C$_1$–C$_{30}$ hydrocarbyl, halocarbyl or hydrohalocarbyl group wherein n of the hydrogen or halogen atoms of R$^7$ are substituted by an equal number of W groups independently selected at each location;
R$^8$ is a C$_1$–C$_{30}$ hydrocarbyl, halocarbyl or hydrohalocarbyl group;
n is selected from 0, 1, 2, 3, 4 and 5; and
X is selected from —Br, —Cl, —F, and —I; or
a pharmaceutically acceptable salt or solvate thereof, or as a single stereoisomer or a mixture thereof.

2. The compound of claim 1 wherein positions 4 and 6 are substituted exclusively with hydrogen.

3. The compound of claim 1 wherein position 19 is substituted with —W.

4. The compound of claim 1 wherein position 19 is substituted with —CN, —X, —OH, —NO$_2$, —SH, or —OR$^8$.

5. The compound of claim 1 wherein one carbon at positions 17 and 18 is substituted with hydrogen.

6. The compound of claim 1 wherein at least one carbon at positions 17 and 18 is substituted with —W.

7. The compound of claim 1 wherein at least one carbon at positions 17 and 18 is substituted with —NH$_2$, —CONH$_2$, —COOH, —CN, —CHO, —OCHO, —X, —OH, —NO$_2$, —SH, —COX, —NHR$^8$, —NR$^8$R$^8$, —CONHR$^8$, —CONR$^8$R$^8$, —COOR$^8$, —COR$^8$, —OCOR$^8$, or —OR$^8$.

8. The compound of claim 1 wherein at least one carbon at positions 17 and 18 is substituted with —CN, —X, —OH, —NO$_2$, —SH, or —OR$^8$.

9. The compound of claim 1 wherein only one of the carbons at positions 17, 18 and 19 is substituted with hydrogen.

10. The compound of claim 1 wherein the carbon at position 7 is substituted exclusively with hydrogen.

11. The compound of claim 1 wherein the carbon at position 3 is substituted with hydrogen, R$^8$ or X.

12. The compound of claim 1 wherein the carbons at positions 9 and 10 are substituted with hydrogen.

13. The compound of claim 1 wherein the carbons at positions 11, 12, and 13 are independently substituted with hydrogen and —W.

14. The compound of claim 1 wherein only one of the carbons at positions 11 and 12 is substituted with hydrogen.

15. The compound of claim 1 wherein a carbon selected from positions 11 and 12 is substituted with —CN, —X, —OH, —NO$_2$, —SH, or —OR$^8$.

16. The compound of claim 1 wherein at least one carbon from positions 11, 12, and 13 is substituted with —R$^7$(W)$_n$.

17. The compound of claim 1 wherein at least one carbon from positions 11, 12, and 13 is substituted with C$_1$–C$_6$hydrocarbyl, C$_1$–C$_6$halocarbyl or C$_1$–C$_6$hydrohalocarbyl.

18. The compound of claim 1 wherein exactly two of the carbons at positions 11, 12 and 13 are substituted with hydrogen.

19. The compound of claim 1 wherein W is selected from, —OCHO, —OH, —OCOR$^8$, and —OR$^8$.

20. The compound of claim 1 wherein W is selected from —NH$_2$, —CN, —X, —OH, —NO$_2$, —SH, —NHR$^8$, —NR$^8$R$^8$, —OR$^8$, and —SR$^8$.

21. The compound of claim 1 wherein W is —OR$^8$.

22. The compound of claim 1 wherein R$^7$ is a C$_1$–C$_{10}$ hydrocarbyl group wherein n of the hydrogen or halogen atoms of R$^7$ are substituted by an equal number of W groups independently selected at each location.

23. The compound of claim 1 wherein R$^7$ is selected from alkyl, alkenyl, alkynyl, aryl, aralkyl, alkylaryl, alkenyl-substituted aryl, aryl-substituted alkenyl, alkynyl-substituted aryl, aryl-substituted alkynyl, biaryl, cycloalkyl, cycloalkenyl, bicycloalkyl, bicycloalkenyl, alkylcycloalkyl, alkenylcycloalkyl, alkynylcycloalkyl, aryl-substituted cycloalkyl, cycloalkyl-substituted aryl, aryl-substituted cycloalkenyl, cycloalkenyl-substituted aryl, aryl-fused cycloalkyl and polycycloalkyl.

24. The compound of claim 1 wherein R$^8$ is a C$_1$–C$_{10}$ hydrocarbyl group.

25. The compound of claim 1 wherein R$^8$ is a C$_1$–C$_{10}$ cyclohydrocarbyl group.

26. The compound of claim 1 wherein R$^8$ is selected from alkyl, alkenyl, alkynyl, aryl, aralkyl, alkylaryl, alkenyl-substituted aryl, aryl-substituted alkenyl, alkynyl-substituted aryl, aryl-substituted alkynyl, biaryl, cycloalkyl, cycloalkenyl, bicycloalkyl, bicycloalkenyl, alkylcycloalkyl, alkenylcycloalkyl, alkynylcycloalkyl, aryl-substituted cycloalkyl, cycloalkyl-substituted aryl, aryl-substituted cycloalkenyl, cycloalkenyl-substituted aryl, aryl-fused cycloalkyl and polycycloalkyl.

27. The compound of claim 1 wherein n is 0.

28. The compound of claim 1 wherein position 1 is substituted with hydrogen.

29. The compound of claim 1 having the S configuration at carbon 3.

30. The compound of claim 1 having the R configuration at carbon 3.

31. The compound of claim 1 having the S configuration at carbon 5.

32. The compound of claim 1 having the R configuration at carbon 5.

33. The compound of claim 1 wherein positions 3, 4, 6, 7, 9 and 10 are substituted with hydrogen, one of positions 11 and 12 is substituted with hydrogen, and one of positions 17 and 18 is substituted with hydrogen.

34. The compound of claim 1 wherein at least one carbon from positions 11, 12, and 13 is substituted with $C_1$–$C_6$hydrocarbyl, $C_1$–$C_6$halocarbyl or $C_1$–$C_6$hydrohalocarbyl, and wherein exactly two of the carbons at positions 11, 12 and 13 are substituted with hydrogen.

35. The compound of claim 1 wherein position 19 is substituted with —CN, —X, —OH, —NO$_2$, —SH, or —OR$^8$; one carbon at positions 17 and 18 is substituted with hydrogen; and at least one carbon at positions 17 and 18 is substituted with —CN, —X, —OH, —NO$_2$, —SH, or —OR$^8$.

36. The compound of claim 1 wherein positions 3, 4, 6, 7, 9 and 10 are substituted with hydrogen; exactly two of the carbons at positions 11, 12 and 13 are substituted with hydrogen; at least one carbon from positions 11, 12, and 13 is substituted with $C_1$–$C_6$hydrocarbyl, $C_1$–$C_6$halocarbyl or $C_1$–$C_6$hydrohalocarbyl; one of positions 17 and 18 is substituted with hydrogen; position 19 is substituted with —CN, —X, —OH, —NO$_2$, —SH, or —OR$^8$; and at least one carbon at positions 17 and 18 is substituted with —CN, —X, —OH, —NO$_2$, —SH, or —OR$^8$; and one carbon at positions 17 and 18 is substituted with hydrogen.

37. The compound of claim 1 wherein positions 1, 3, 4, 6, 7, 9, 10, 11 and 18 are substituted with hydrogen; positions 17 and 19 are substituted with OR$^8$ where R$^8$ is a $C_1$–$C_{10}$ hydrocarbyl group; and position 12 is substituted with $C_1$–$C_6$hydrocarbyl, $C_1$–$C_6$halocarbyl or $C_1$–$C_6$hydrohalocarbyl.

38. The compound of claim 1 wherein positions 1, 3, 4, 5, 6, 7, 9, 10, 11, 13, 15, 16, and 18 are substituted with hydrogen; position 12 is substituted with $C_1$ hydrocarbyl; position 17 is substituted with —O-cyclopentyl; and position 19 is substituted with —O-methyl.

39. The compound of claim 38 wherein positions 3 and 5 both have the S stereochemistry.

40. The pharmaceutically acceptable salt or solvate of the compound of claim 1.

41. A pharmaceutical composition comprising a compound of the formula

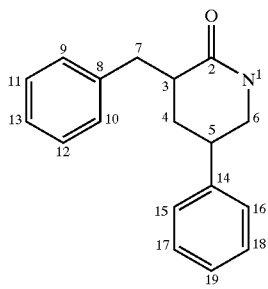

wherein,
each of the carbons at positions 3, 4, 5, 6, 7, 9, 10, 11, 12, 13, 15, 16, 17, 18, and 19, as well as the nitrogen at position 1, is independently substituted at each occurrence with H, —W or —R$^7$(W)$_n$, wherein
W is selected from —NH$_2$, —CONH$_2$, —COOH, —CN, —CHO, —OCHO, —X, —OH, —NO$_2$, —SH, —COX, —NHR$^8$, —NR$^8$R$^8$, —CONHR$^8$, —CONR$^8$R$^8$, —COOR$^8$, —COR$^8$, —OCOR$^8$, —OR$^8$, —BH$_2$, —BHR$^8$, —BR$^8$R$^8$, —BO$_2$H$_2$, —BO$_2$R$^8$R$^8$, —PH$_2$, —PHR$^8$, —PR$^8$R$^8$, —POR$^8$, —PO$_2$R$^8$, —PO$_3$R$^8$, —SR$^8$; —SOR$^8$, —SO$_2$R$^8$, —SONH$_2$, —SONHR$^8$, —SONR$^8$R$^8$, —SO$_2$NH$_2$, —SO$_2$NHR$^8$ and —SO$_2$NR$^8$R$^8$;
R$^7$ is a $C_1$–$C_{30}$ hydrocarbyl, halocarbyl or hydrohalocarbyl group wherein n of the hydrogen or halogen atoms of R$^7$ are substituted by an equal number of W groups independently selected at each location;
R$^8$ is a $C_1$–$C_{30}$ hydrocarbyl, halocarbyl or hydrohalocarbyl group;
n is selected from 0, 1, 2, 3, 4 and 5; and
X is selected from —Br, —Cl, —F, and —I; or
a pharmaceutically acceptable salt or solvate thereof, or as a single stereoisomer or a mixture thereof;
and a pharmaceutically acceptable carrier, diluent, or excipient.

42. The composition of claim 41 wherein the compound is a compound wherein positions 1, 3, 4, 5, 6, 7, 9, 10, 11, 13, 15, 16, and 18 are substituted with hydrogen; position 12 is substituted with $C_1$ hydrocarbyl; position 17 is substituted with —O-cyclopentyl; and position 19 is substituted with —O-methyl.

43. The pharmaceutical composition of claim 41 comprising a pharmaceutically acceptable salt or solvate of the compound of the formula and a pharmaceutically acceptable carrier, diluent or excipient.

44. A method for treating or preventing an inflammatory condition or disease in a patient, comprising administering to the patient in need thereof a therapeutically effective amount of a compound of the formula

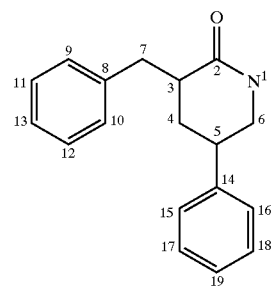

wherein,
each of the carbons at positions 3, 4, 5, 6, 7, 9, 10, 11, 12, 13, 15, 16, 17, 18, and 19, as well as the nitrogen at position 1, is independently substituted at each occurrence with H, —W or —R$^7$(W)$_n$, wherein
W is selected from —NH$_2$, —CONH$_2$, —COOH, —CN, —CHO, —OCHO, —X, —OH, —NO$_2$, —SH, —COX, —NHR$^8$, —NR$^8$R$^8$, —CONHR$^8$, —CONR$^8$R$^8$, —COOR$^8$, —COR$^8$, —OCOR$^8$, —OR$^8$, —BH$_2$, —BHR$^8$, —BR$^8$R$^8$, —BO$_2$H$_2$, —BO$_2$R$^8$R$^8$, —PH$_2$, —PHR$^8$, —PR$^8$R$^8$, —POR$^8$, —PO$_2$R$^8$, —PO$_3$R$^8$, —SR$^8$, —SOR$^8$, —SO$_2$R$^8$, —SONH$_2$, —SONHR$^8$, —SONR$^8$R$^8$, —SO$_2$NH$_2$, —SO$_2$NHR$^8$ and —SO$_2$NR$^8$R$^8$;
R$^7$ is a $C_1$–$C_{30}$ hydrocarbyl, halocarbyl or hydrohalocarbyl group wherein n of the hydrogen or halogen atoms of R$^7$ are substituted by an equal number of W groups independently selected at each location;
R$^8$ is a $C_1$–$C_{30}$ hydrocarbyl, halocarbyl or hydrohalocarbyl group;
n is selected from 0, 1, 2, 3, 4 and 5; and
X is selected from —Br, —Cl, —F, and —I; or
a pharmaceutically acceptable salt or solvate thereof, or as a single stereoisomer or a mixture thereof;
where the amount is effective to treat or prevent the inflammatory condition or disease of the patient.

45. A method for modulating intracellular cyclic adenosine 5'-monophosphate levels within a patient, comprising administering to a patient in need thereof a therapeutically effective amount of a compound of the formula

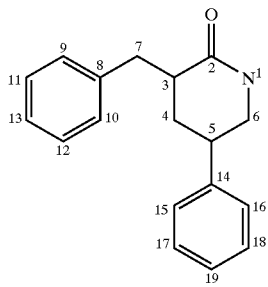

wherein,
each of the carbons at positions 3, 4, 5, 6, 7, 9, 10, 11, 12, 13, 15, 16, 17, 18, and 19, as well as the nitrogen at position 1, is independently substituted at each occurrence with H, —W or —$R^7(W)_n$, wherein
W is selected from —$NH_2$, —$CONH_2$, —COOH, —CN, —CHO, —OCHO, —X, —OH, —$NO_2$, —SH, —COX, —$NHR^8$, —$NR^8R^8$, —$CONHR^8$, —$CONR^8R^8$, —$COOR^8$, —$COR^8$, —$OCOR^8$, —$OR^8$, —$BH_2$, —$BHR^8$, —$BR^8R^8$, —$BO_2H_2$, —$BO_2R^8R^8$, —$PH_2$, —$PHR^8$, —$PR^8R^8$, —$POR^8$, —$PO_2R^8$, —$PO_3R^8$, —$SR^8$; —$SOR^8$, —$SO_2R^8$, —$SONH_2$, —$SONHR^8$, —$SONR^8R^8$, —$SO_2NH_2$, —$SO_2NHR^8$ and —$SO_2R^8R^8$;
$R^7$ is a $C_1$–$C_{30}$ hydrocarbyl, halocarbyl or hydrohalocarbyl group wherein n of the hydrogen or halogen atoms of $R^7$ are substituted by an equal number of W groups independently selected at each location;
$R^8$ is a $C_1$–$C_{30}$ hydrocarbyl, halocarbyl or hydrohalocarbyl group;
n is selected from 0, 1, 2, 3, 4 and 5; and
X is selected from —Br, —Cl, —F, and —I; or
a pharmaceutically acceptable salt or solvate thereof, or as a single stereoisomer or a mixture thereof;
wherein the amount is effective to modulate the intracellular cyclic adenosine 5'-monophosphate levels of the patient.

46. A method for treating or preventing a disease or condition in a patient, where the disease or condition is associated with pathological conditions that are modulated by inhibiting enzymes associated with secondary cellular messengers, the method comprising administering to a patient in need thereof a therapeutically effective amount of a compound of the formula

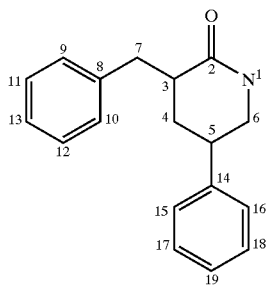

wherein,
each of the carbons at positions 3, 4, 5, 6, 7, 9, 10, 11, 12, 13, 15, 16, 17, 18, and 19, as well as the nitrogen at position 1, is independently substituted at each occurrence with H, —W or —$R^7(W)_n$, wherein
W is selected from —$NH_2$, —$CONH_2$, —COOH, —CN, —CHO, —OCHO, —X, —OH, —$NO_2$, —SH, —COX, —$NHR^8$, —$NR^8R^8$, —$CONHR^8$, —$CONR^8R^8$, —$COOR^8$, —$COR^8$, —$OCOR^8$, —$OR^8$, —$BH_2$, —$BHR^8$, —$BR^8R^8$, —$BO_2H_2$, —$BO_2R^8R^8$, —$PH_2$, —$PHR^8$, —$PR^8R^8$, —$POR^8$, —$PO_2R^8$, —$PO_3R^8$, —$SR^8$; —$SOR^8$, —$SO_2R^8$, —$SONH_2$, —$SONHR^8$, —$SONR^8R^8$, —$SO_2NH_2$, —$SO_2NHR^8$ and —$SO_2R^8R^8$;
$R^7$ is a $C_1$–$C_{30}$ hydrocarbyl, halocarbyl or hydrohalocarbyl group wherein n of the hydrogen or halogen atoms of $R^7$ are substituted by an equal number of W groups independently selected at each location;
$R^8$ is a $C_1$–$C_{30}$ hydrocarbyl, halocarbyl or hydrohalocarbyl group;
n is selected from 0, 1, 2, 3, 4 and 5; and
X is selected from —Br, —Cl, —F, and —I; or
a pharmaceutically acceptable salt or solvate thereof, or as a single stereoisomer or a mixture thereof;
wherein the amount is effective to treat or prevent a disease or condition associated with pathological conditions that are modulated by inhibiting enzymes associated with secondary cellular messengers.

47. A method of treating or preventing transplant rejection in a patient, comprising administering to a patient in need thereof a therapeutically effective amount of a compound of the formula

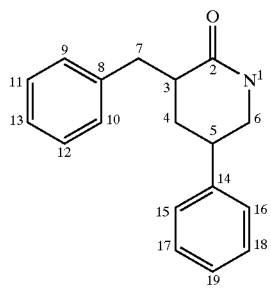

wherein,
each of the carbons at positions 3, 4, 5, 6, 7, 9, 10, 11, 12, 13, 15, 16, 17, 18, and 19, as well as the nitrogen at position 1, is independently substituted at each occurrence with H, —W or —$R^7(W)_n$, wherein
W is selected from —$NH_2$, —$CONH_2$, —COOH, —CN, —CHO, —OCHO, —X, —OH, —$NO_2$, —SH, —COX, —$NHR^8$, —$NR^8R^8$, —$CONHR^8$, —$CONR^8R^8$, —$COOR^8$, —$COR^8$, —$OCOR^8$, —$OR^8$, —$BH_2$, —$BHR^8$, —$BR^8R^8$, —$BO_2H_2$, —$BO_2R^8R^8$, —$PH_2$, —$PHR^8$, —$PR^8R^8$, —$POR^8$, —$PO_2R^8$, —$PO_3R^8$, —$SR^8$; —$SOR^8$, —$SO_2R^8$, —$SONH_2$, —$SONHR^8$, —$SONR^8R^8$, —$SO_2NH_2$, —$SO_2NHR^8$ and —$SO_2R^8R^8$;
$R^7$ is a $C_1$–$C_{30}$ hydrocarbyl, halocarbyl or hydrohalocarbyl group wherein n of the hydrogen or halogen atoms of $R^7$ are substituted by an equal number of W groups independently selected at each location;
$R^8$ is a $C_1$–$C_{30}$ hydrocarbyl, halocarbyl or hydrohalocarbyl group;
n is selected from 0, 1, 2, 3, 4 and 5; and
X is selected from —Br, —Cl, —F, and —I; or
a pharmaceutically acceptable salt or solvate thereof, or as a single stereoisomer or a mixture thereof;
where the amount is effective to treat or prevent transplant rejection in the patient.

48. A method of treating or preventing uncontrolled cellular proliferation in a patient, comprising administering to a patient in need thereof a therapeutically effective amount of a compound of the formula

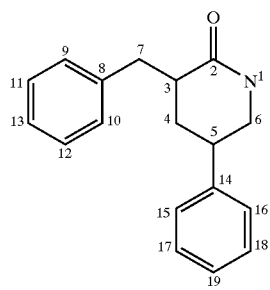

wherein, each of the carbons at positions 3, 4, 5, 6, 7, 9, 10, 11, 12, 13, 15, 16, 17, 18, and 19, as well as the nitrogen at position 1, is independently substituted at each occurrence with H, —W or —$R^7(W)_n$, wherein W is selected from —$NH_2$, —$CONH_2$, —COOH, —CN, —CHO, —OCHO, —X, —OH, —$NO_2$, —SH, —COX, —$NHR^8$, —$NR^8R^8$, —$CONHR^8$, —$CONR^8R^8$, —$COOR^8$, —$COR^8$, —$OCOR^8$, —$OR^8$, —$BH_2$, —$BHR^8$, —$BR^8R^8$, —$BO_2H_2$, —$BO_2R^8R^8$, —$PH_2$, —$PHR^8$, —$PR^8R^8$, —$POR^8$, —$PO_2R^8$, —$PO_3R^8$, —$SR^8$; —$SOR^8$, —$SO_2R^8$, —$SONH_2$, —$SONHR^8$, —$SONR^8R^8$, —$SO_2NH_2$, —$SO_2NHR^8$ and —$SO_2R^8R^8$;

$R^7$ is a $C_1$–$C_{30}$ hydrocarbyl, halocarbyl or hydrohalocarbyl group wherein n of the hydrogen or halogen atoms of $R^7$ are substituted by an equal number of W groups independently selected at each location;

$R^8$ is a $C_1$–$C_{30}$ hydrocarbyl, halocarbyl or hydrohalocarbyl group;

n is selected from 0, 1, 2, 3, 4 and 5; and

X is selected from —Br, —Cl, —F, and —I; or a pharmaceutically acceptable salt or solvate thereof, or as a single stereoisomer or a mixture thereof;

where the amount is effective to treat or prevent uncontrolled cellular proliferation in the patient.

49. A method of treating or preventing conditions associated with the central nervous system (CNS) in a patient, comprising administering to a patient in need thereof a therapeutically effective amount of a compound of the formula

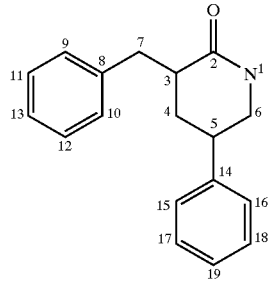

wherein, each of the carbons at positions 3, 4, 5, 6, 7, 9, 10, 11, 12, 13, 15, 16, 17, 18, and 19, as well as the nitrogen at position 1, is independently substituted at each occurrence with H, —W or —$R^7(W)_n$, wherein W is selected from —$NH_2$, —$CONH_2$, —COOH, —CN, —CHO, —OCHO, —X, —OH, —$NO_2$, —SH, —COX, —$NHR^8$, —$NR^8R^8$, —$CONHR^8$, —$CONR^8R^8$, —$COOR^8$, —$COR^8$, —$OCOR^8$, —$OR^8$, —$BH_2$, —$BHR^8$, —$BR^8R^8$, —$BO_2H_2$, —$BO_2R^8R^8$, —$PH_2$, —$PHR^8$, —$PR^8R^8$, —$POR^8$, —$PO_2R^8$, —$PO_3R^8$, —$SR^8$; —$SOR^8$, —$SO_2R^8$, —$SONH_2$, —$SONHR^8$, —$SONR^8R^8$, —$SO_2NH_2$, —$SO_2NHR^8$ and —$SO_2R^8R^8$;

$R^7$ is a $C_1$–$C_{30}$ hydrocarbyl, halocarbyl or hydrohalocarbyl group wherein n of the hydrogen or halogen atoms of $R^7$ are substituted by an equal number of W groups independently selected at each location;

$R^8$ is a $C_1$–$C_{30}$ hydrocarbyl, halocarbyl or hydrohalocarbyl group;

n is selected from 0, 1, 2, 3, 4 and 5; and

X is selected from —Br, —Cl, —F, and —I; or a pharmaceutically acceptable salt or solvate thereof, or as a single stereoisomer or a mixture thereof;

where the amount is effective to treat or prevent conditions associated with the central nervous system (CNS) in the patient.

50. The compound of claim 1 of the formula:

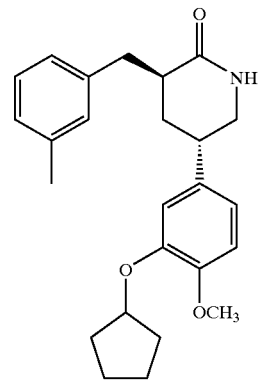

as a single stereoisomer or a mixture thereof, or a pharmaceutically acceptable salt or solvate thereof.

* * * * *